(12) United States Patent
Blum et al.

(10) Patent No.: US 9,512,147 B2
(45) Date of Patent: Dec. 6, 2016

(54) ORGANOBORON COMPOUNDS AND METHODS OF MAKING ORGANOBORON COMPOUNDS

(71) Applicant: The Regents of the University of California, Oakland, CA (US)

(72) Inventors: Suzanne A. Blum, Irvine, CA (US); Joshua J. Hirner, Irvine, CA (US); Darius J. Faizi, Oceanside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/941,880

(22) Filed: Nov. 16, 2015

(65) Prior Publication Data

US 2016/0083402 A1     Mar. 24, 2016

Related U.S. Application Data

(63) Continuation-in-part of application No. 14/303,684, filed on Jun. 13, 2014, now Pat. No. 9,238,661.

(60) Provisional application No. 61/836,391, filed on Jun. 18, 2013, provisional application No. 61/906,040, filed on Nov. 19, 2013, provisional application No. 62/198,410, filed on Jul. 29, 2015, provisional application No. 62/200,354, filed on Aug. 3, 2015.

(51) Int. Cl.
   *C07F 5/02*     (2006.01)
   *C07F 1/12*     (2006.01)

(52) U.S. Cl.
   CPC . *C07F 5/02* (2013.01); *C07F 1/12* (2013.01); *C07F 5/025* (2013.01); *C07F 5/027* (2013.01)

(58) Field of Classification Search
   CPC ........................................................ C07F 5/02
   USPC ........................................................ 549/471
   See application file for complete search history.

(56) References Cited

PUBLICATIONS

Ibraheem A. I. Mkhalid, et al.; "C—H Activation for the Construction of C—B Bonds"; Durham University, Department of Chemistry, South Road, Durham, DH1 3LE, United Kingdom; Chem. Rev. 2010, 110, 890-931.

Gary A. Molander, et al.; "Organotrifluoroborates: Protected Boronic Acids That Expand the Versatility of the Suzuki Coupling Reaction"; Roy and Diana Vagelos Laboratories, Department of Chemistry, University of Pennsylvania, 231 South 34th Street, Philadelphia, Pennsylvania 19104-6323; Acc. Chem. Res. 2007, 40, 275-286.

Tatsuo Ishiyama, et al.; "Palladium(0)-Catalyzed Thioboration of Terminal Alkynes with 9-(Alkylthio)-9-borabicyclo[3.3. Ilnonane Derivatives: Stereoselective Synthesis of Vinyl Sulfides via the Thioboration-Cross-Coupling Sequence"; Contribution from the Department of Applied Chemistry, Faculty of Engineering, Hokkaido University, Sapporo 060, Japan; J. Am. Chem. Soc. 1993, 115, 7219-7225.

Eric P. Gillis, et al.; "Multistep Synthesis of Complex Boronic Acids from Simple MIDA Boronates"; Roger Adams Laboratory, Department of Chemistry, UniVersity of Illinois at Urbana-Champaign, Urbana, Illinois 61801; 2 pages.

R.H. Cragg; et al.; "Chloroboration and Allied Reactions of Unsaturated Compounds. Part 111.1 Aminoboration and Alkoxyboration of Isocyanates and Isothiocyanates"; Jan. 1, 1964; University of California—Irvine; 8 pages.

Noriyoshi Matsumi, et al.; Alkoxyboration Polymerization. Synthesis of Novel Poly(boronic carbamate)s; Department of Polymer Chemistry, Graduate School of Engineering, Kyoto University, Yoshida, Sakyo-ku, Kyoto 606-8501, Japan; Macromolecules 1998, 31, 3802-3806.

*Primary Examiner* — Taofiq A Solola
(74) *Attorney, Agent, or Firm* — Thomas Horstemeyer, LLP

(57) ABSTRACT

Embodiments of the present disclosure provide for methods of making an organoboron compound, organoboron compounds, and the like.

2 Claims, 51 Drawing Sheets

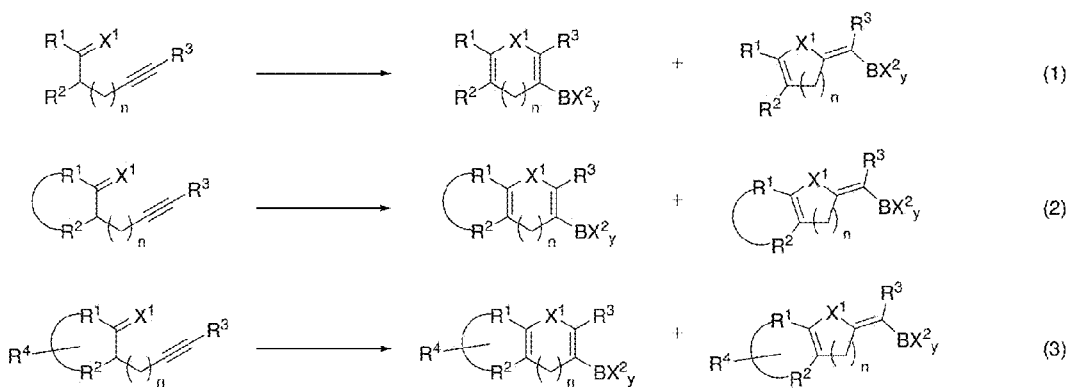
Fig. 1.1A
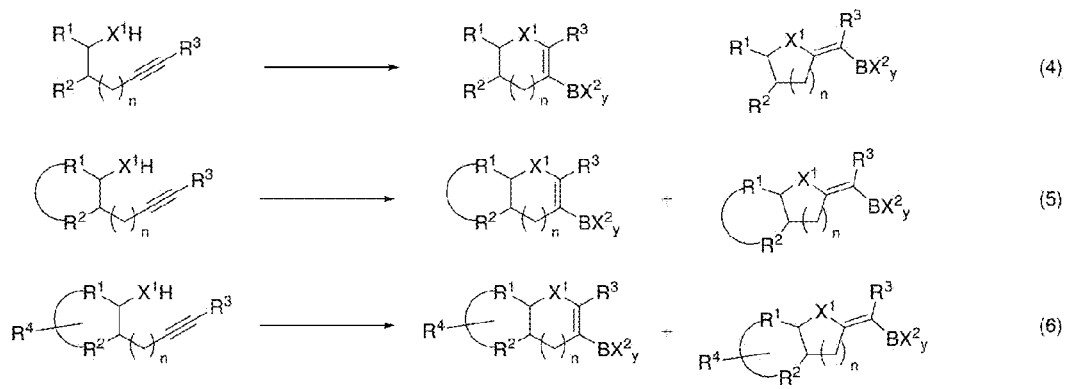
Fig. 1.1B

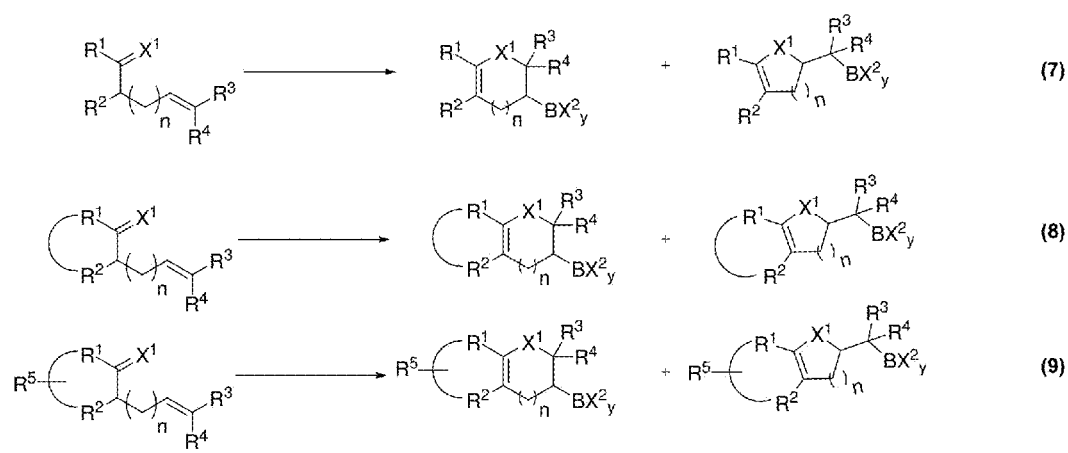
Fig. 1.1C
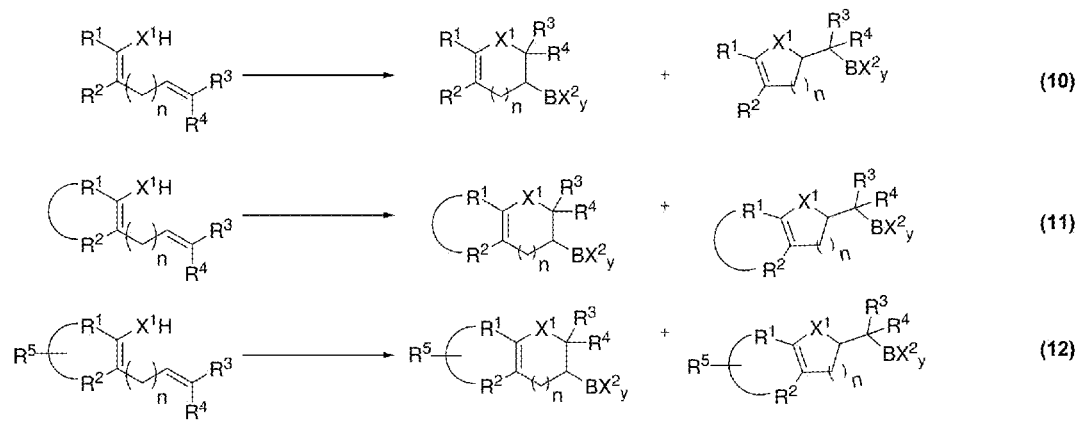
Fig. 1.1D

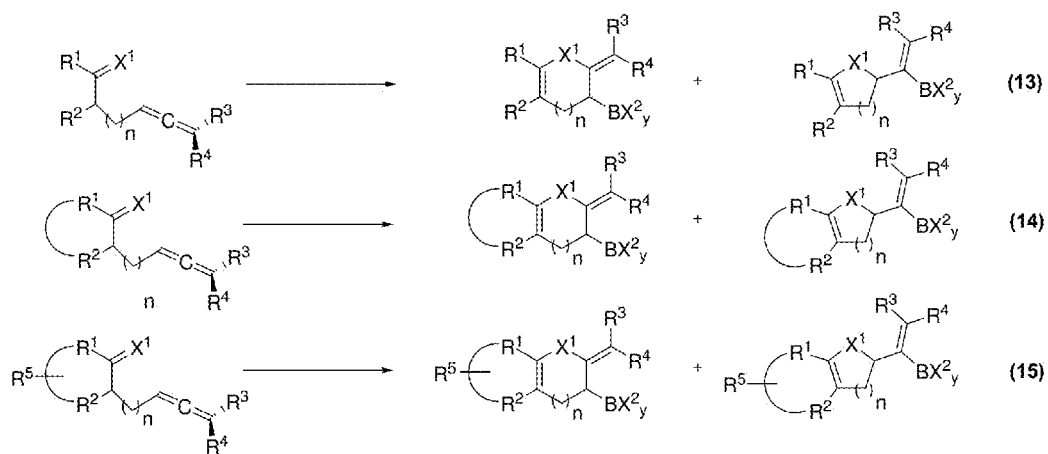
Fig. 1.1E
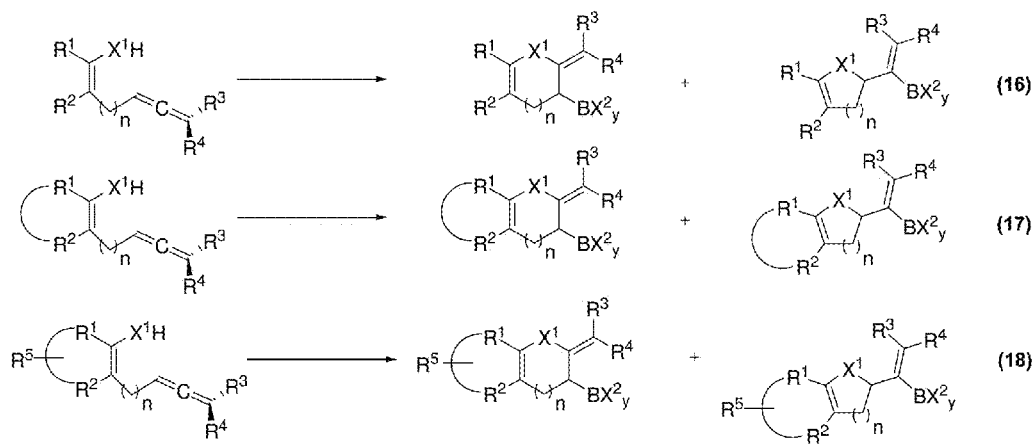
Fig. 1.1F

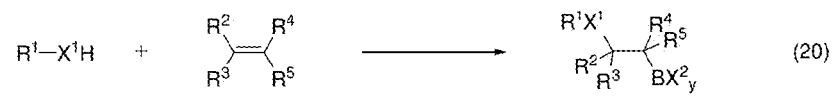
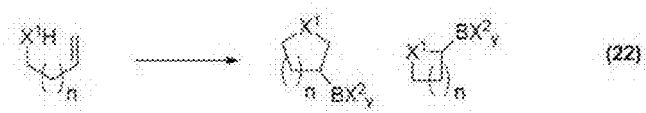
Fig. 1.1G
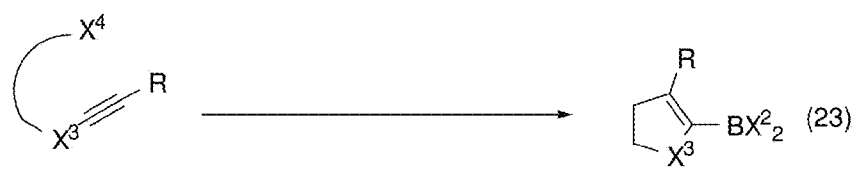
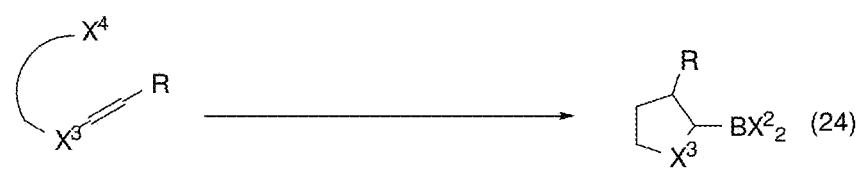
Fig. 1.1H

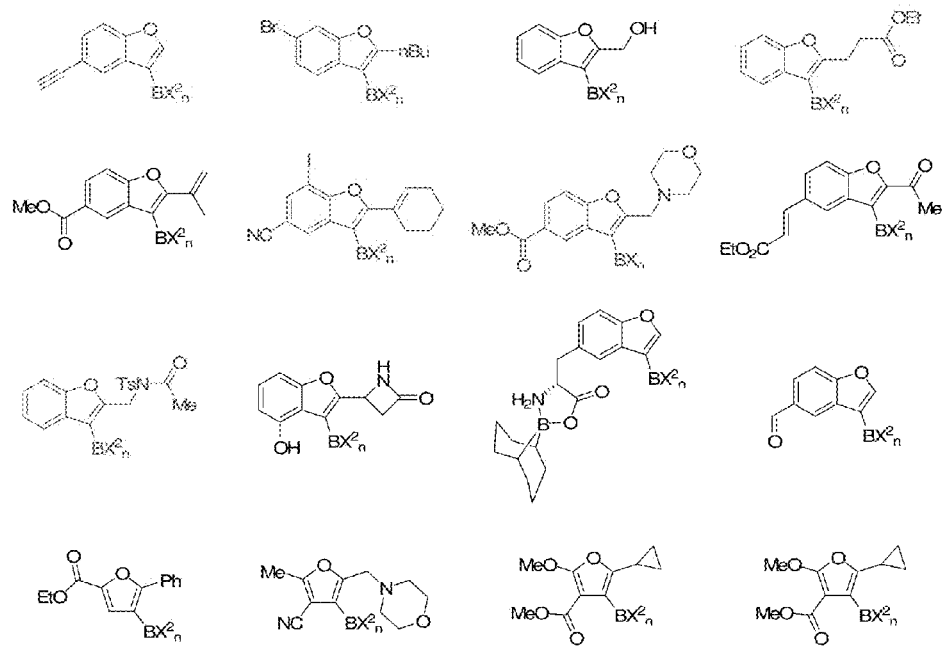
Fig. 1.2
Scheme 1A. Optimized one-pot boric ester formation and alkoxyboration conditions.
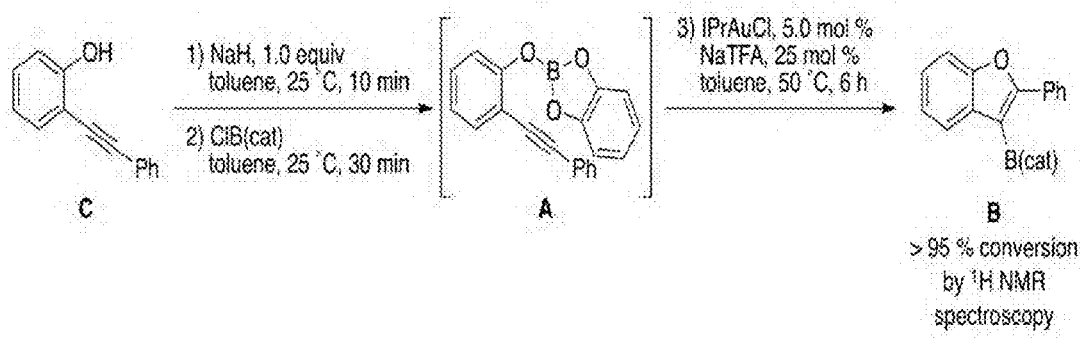
cat = catechol (1,2-dihydroxybenzene).
Fig. 1.3

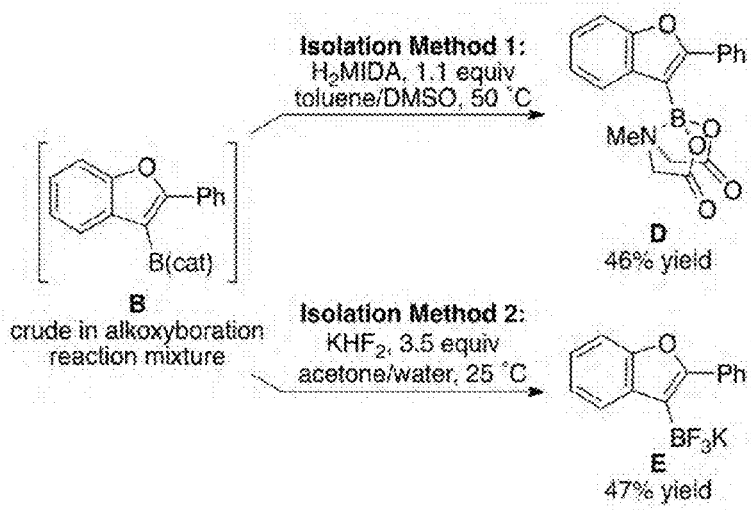
Fig. 1.4
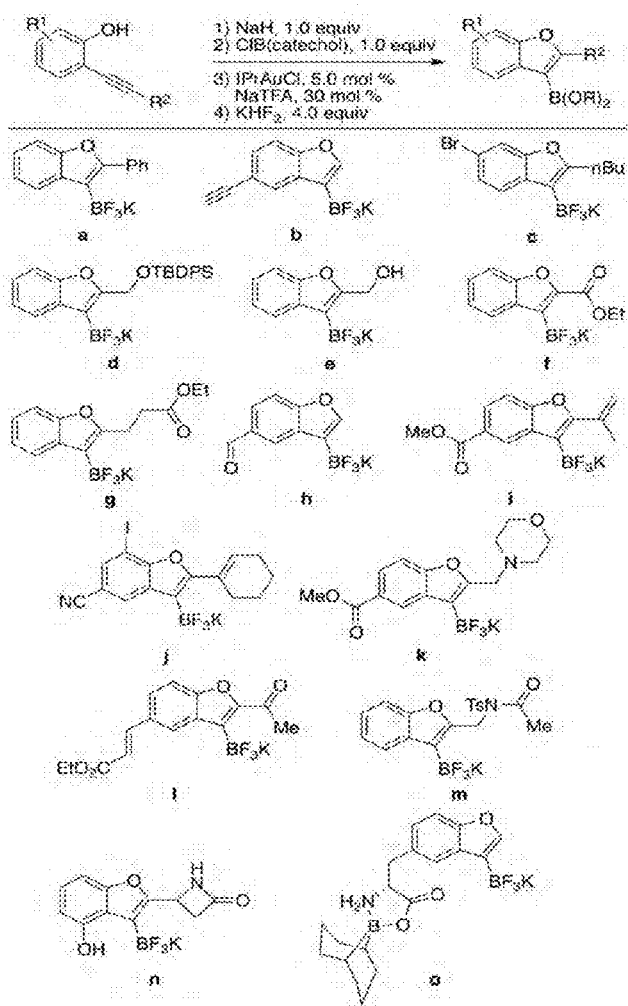
Chart 1. Substrate scope of the one-pot alkoxyboration reaction.
Fig. 1.5
Step 1: toluene, 25 °C, 10 min. Step 2: toluene, 25 °C, 10 min. Step 3: toluene, 50 °C, 6 – 12 h. Step 4: 1:1 toluene:DMSO, 12 h.

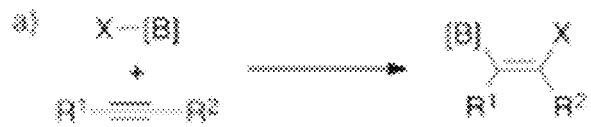
Fig. 2.1A
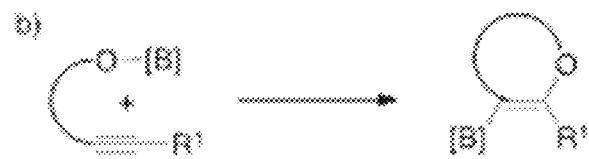
Fig. 2.1B
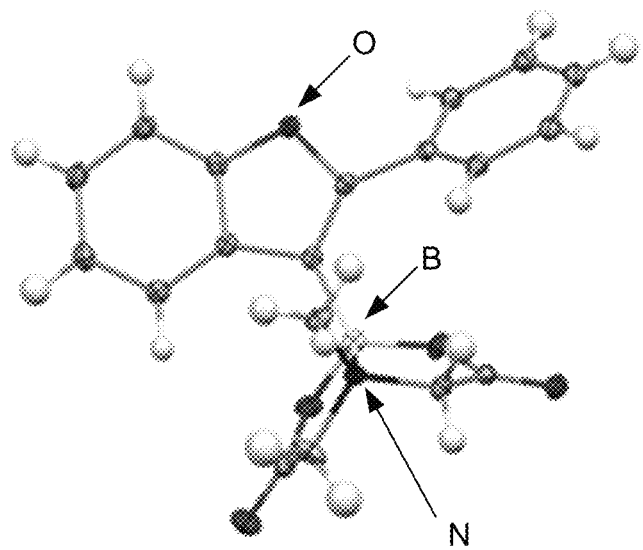
Fig. 2.2

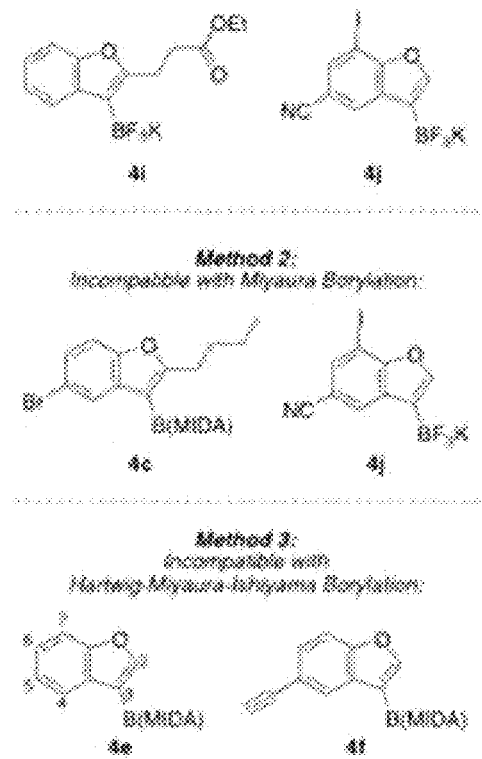
Fig. 2.3
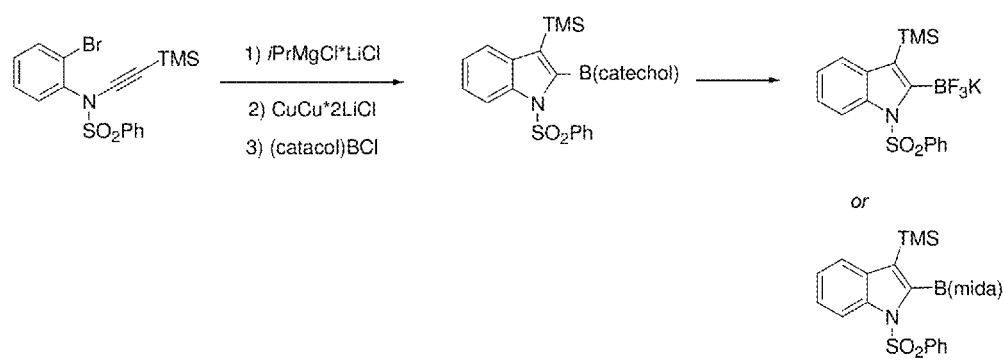
Fig. 3.1

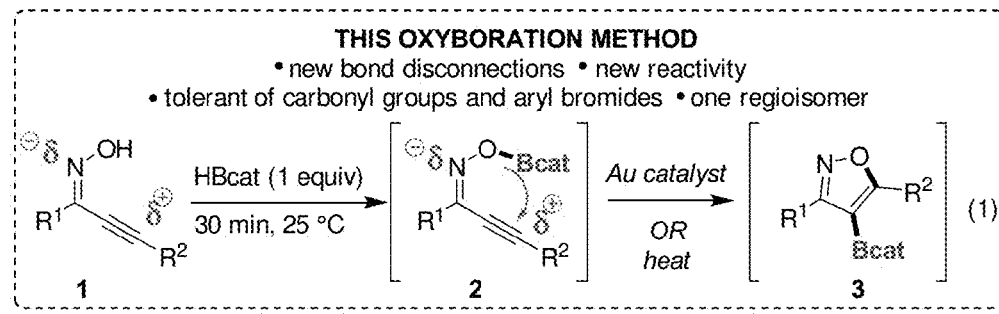
Fig. 4.1
a) Previous work B–E σ bond addition across alkynes: catalyst activates B–E bond
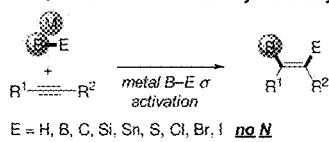
Fig. 5.1A
b) Previous work B–N σ bond addition across alkynes
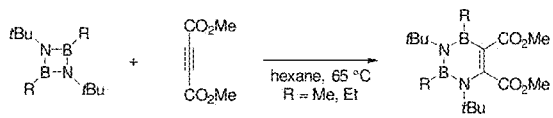
Fig. 5.1B
c) This work B–N σ bond aminoboration of alkynes: catalyst activates C–C π bond
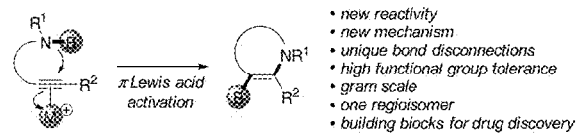
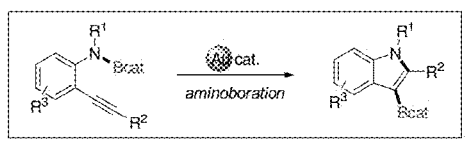
Fig. 5.1C

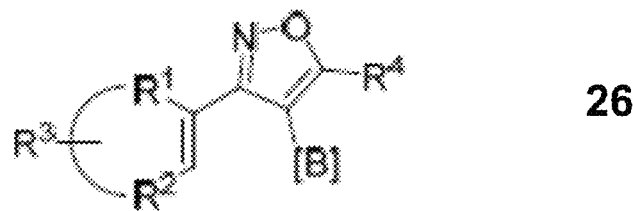
26
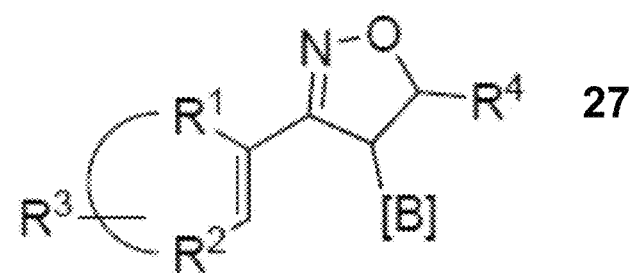
27
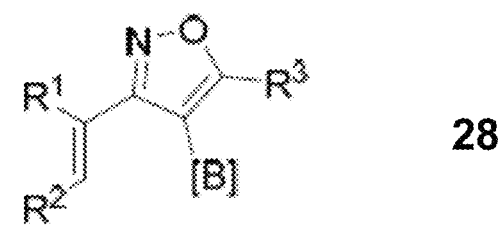
28
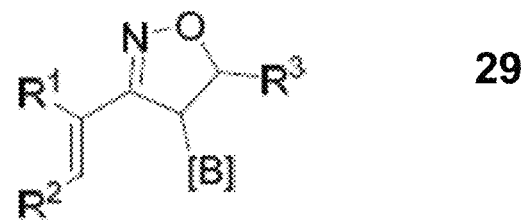
29
Fig. 6.1

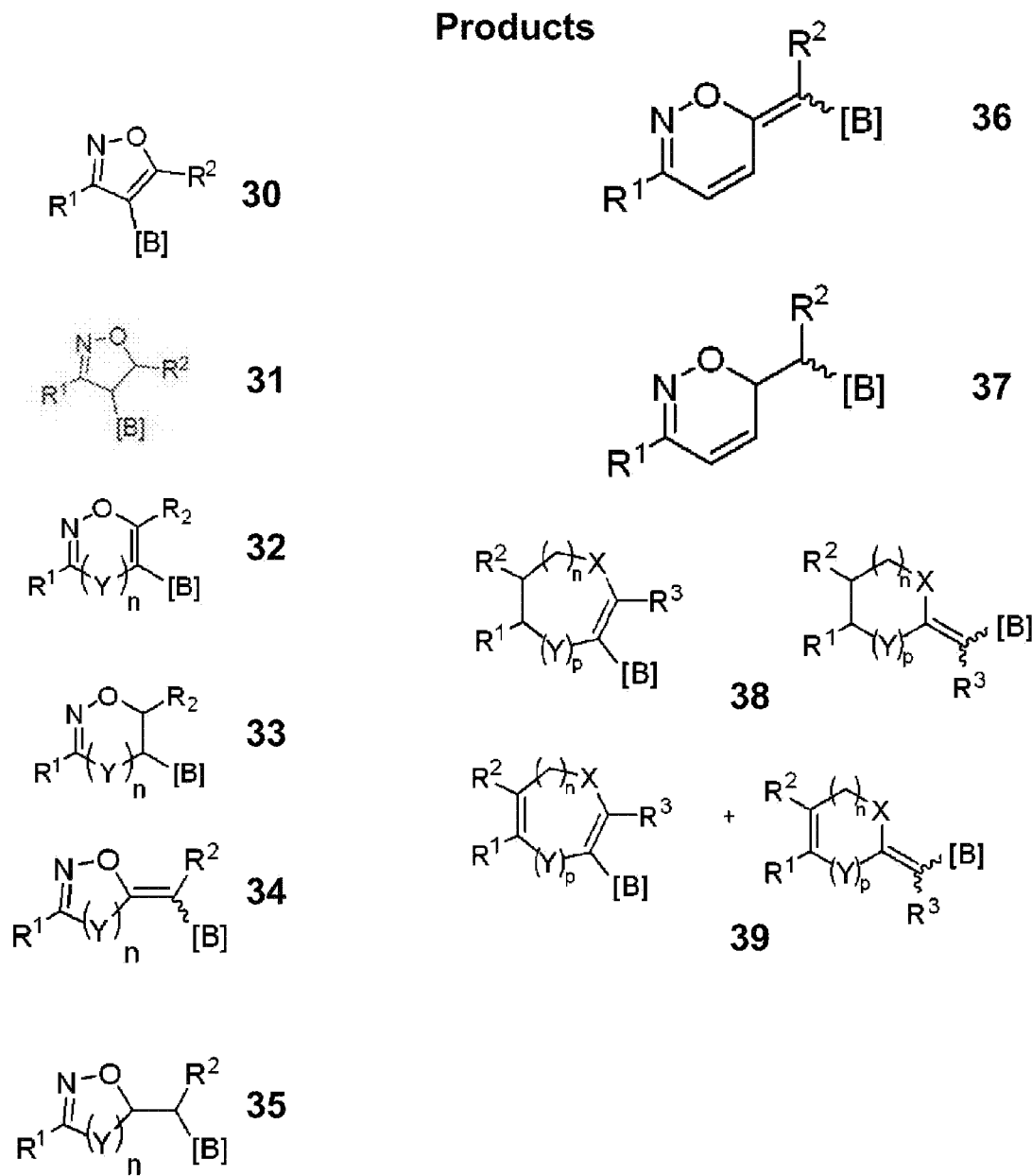
Fig. 6.2

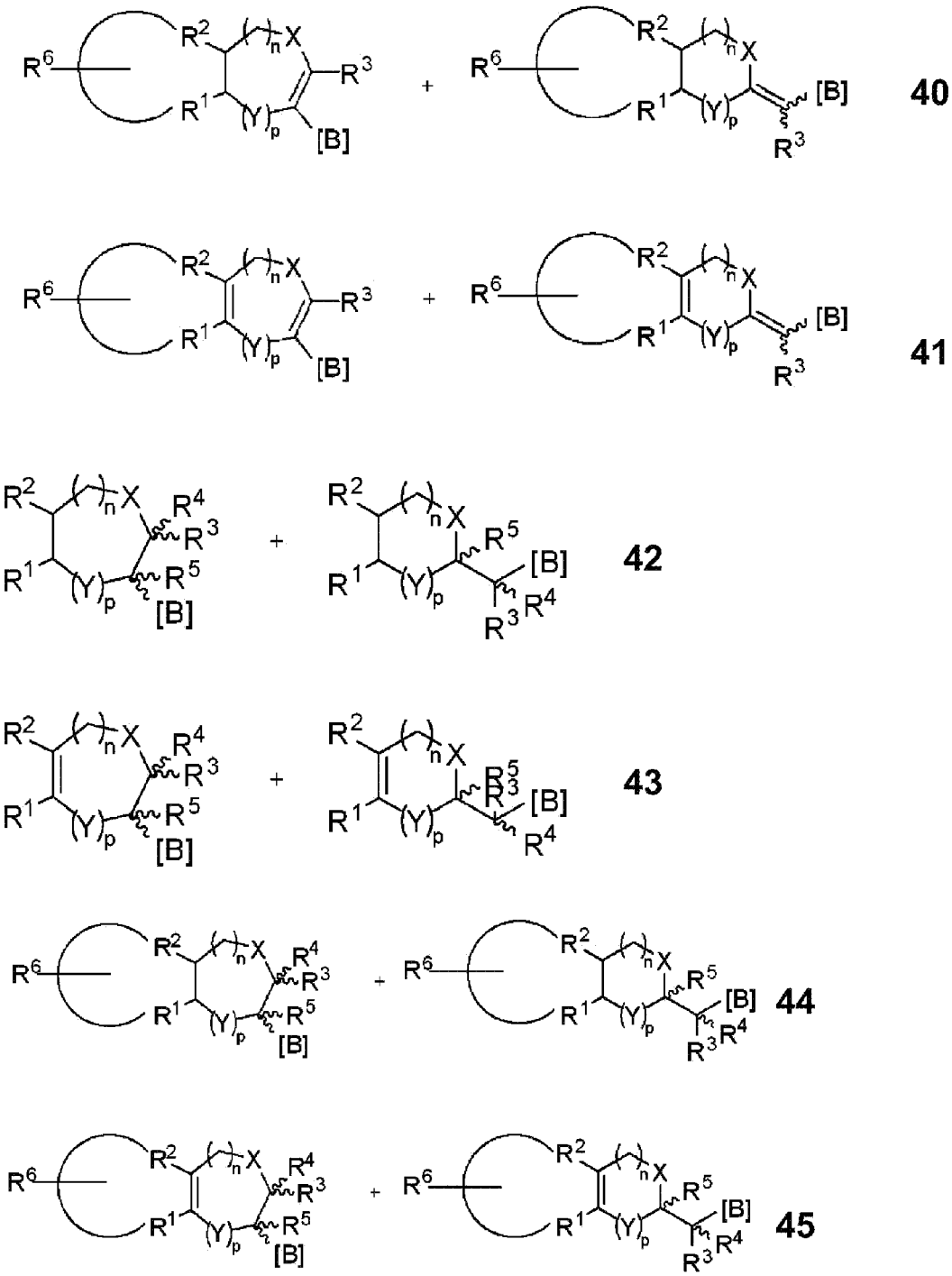
Fig. 6.3

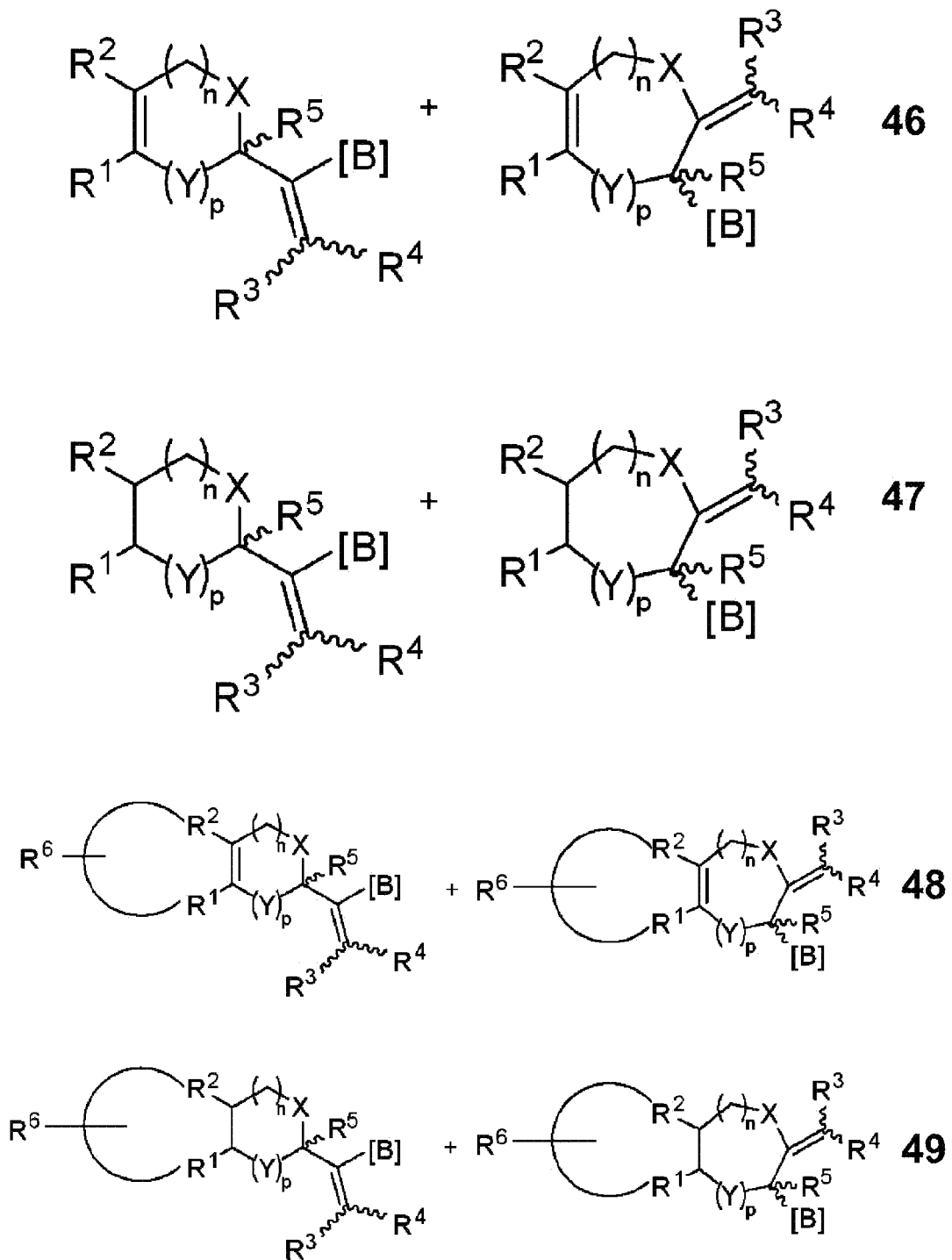
Fig. 6.4

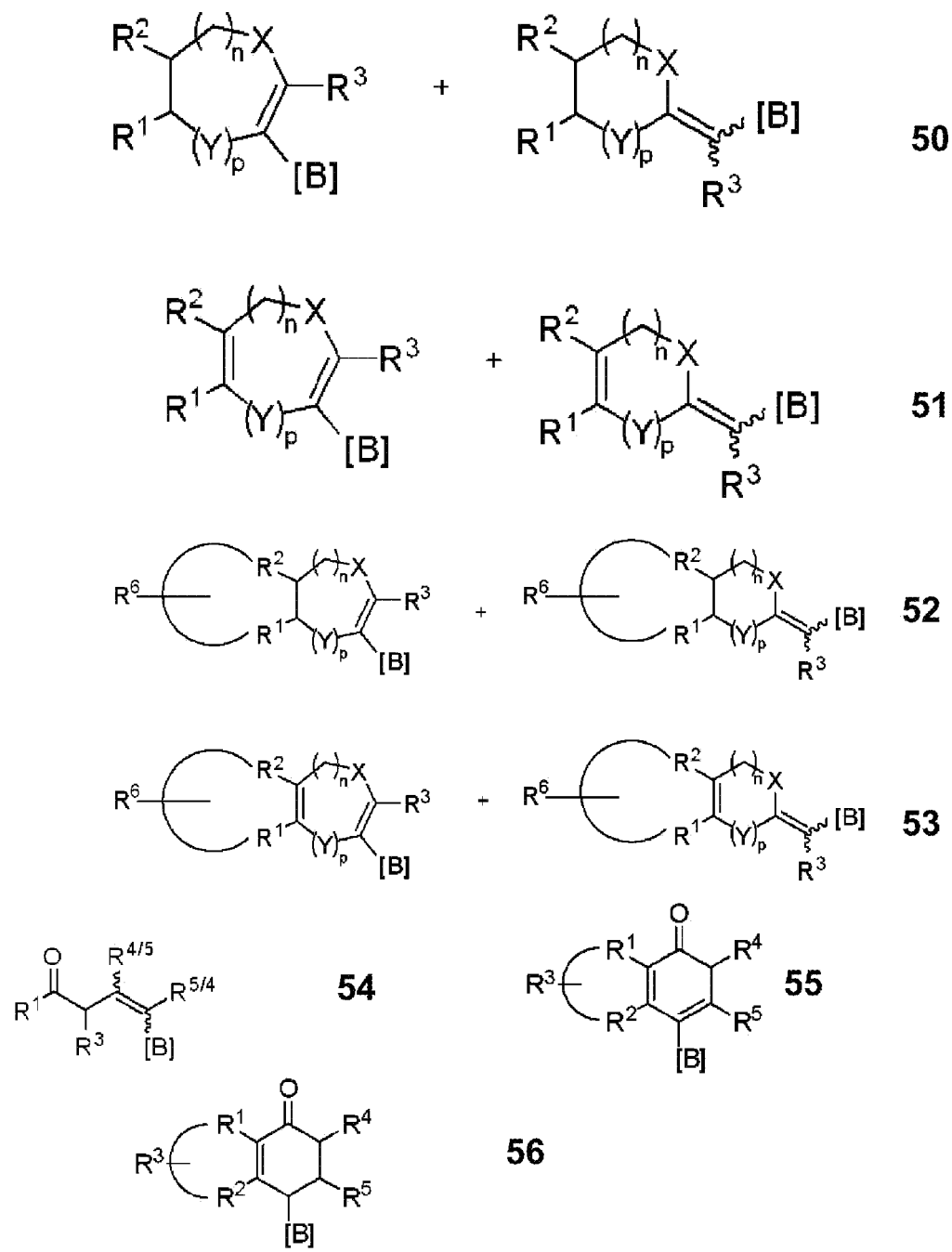
Fig. 6.5

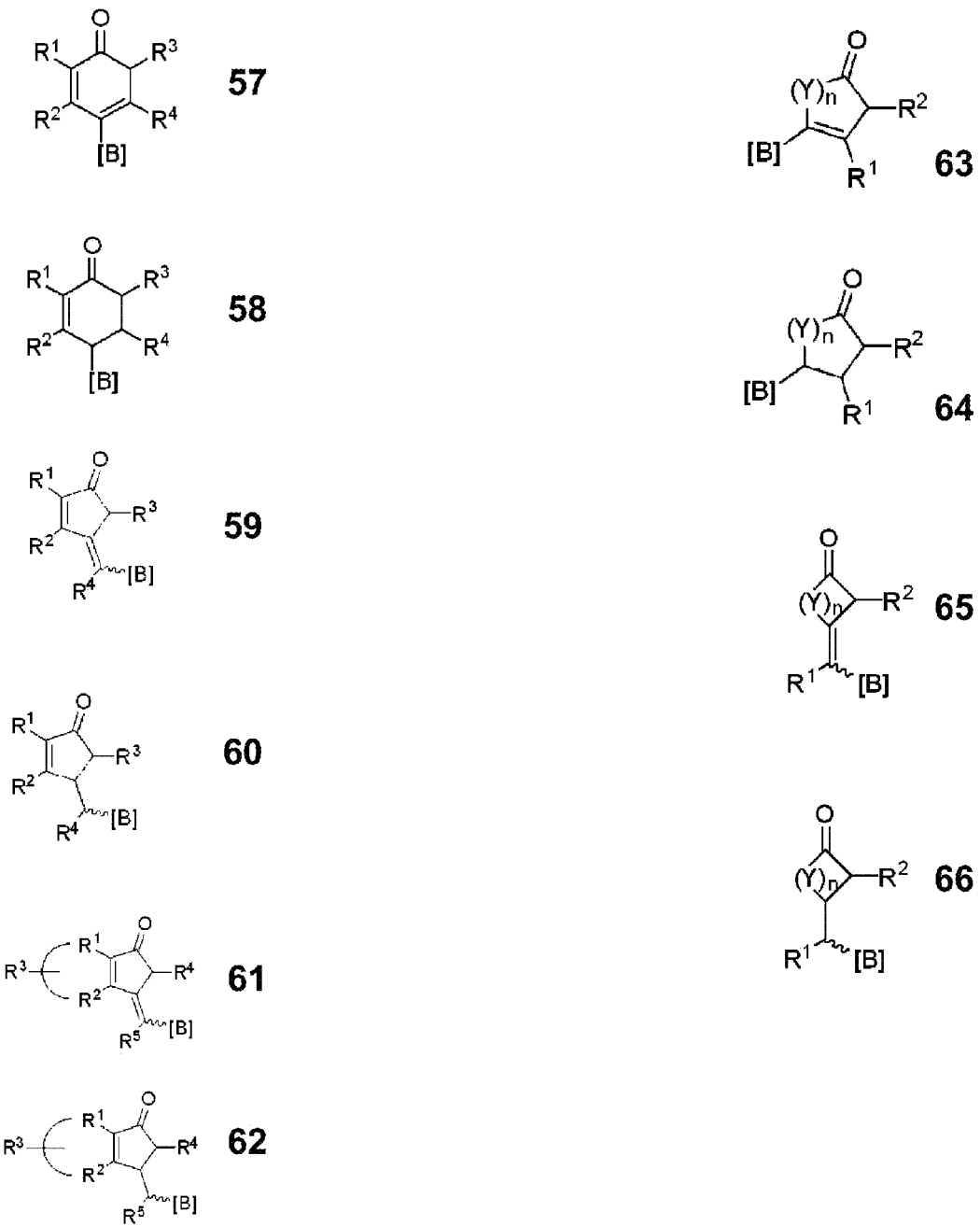
Fig. 6.6

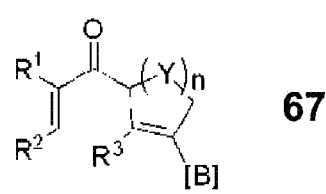 67
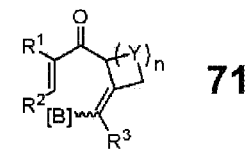 71
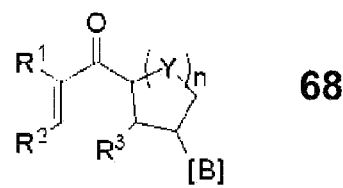 68
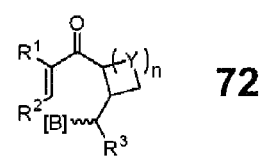 72
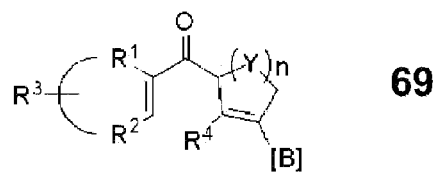 69
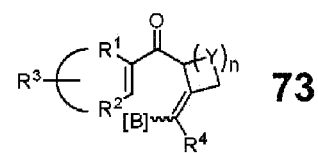 73
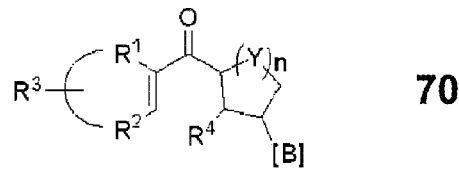 70
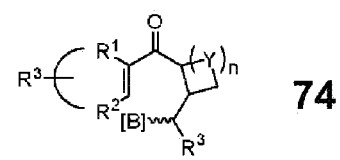 74
Fig. 6.7

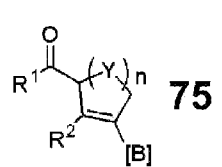 75
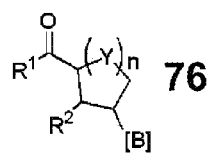 76
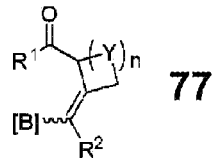 77
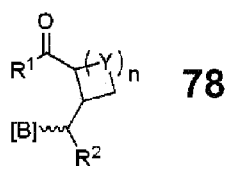 78
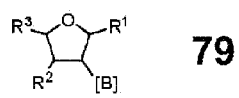 79
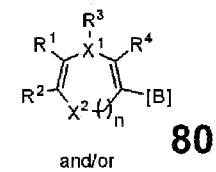 80
and/or
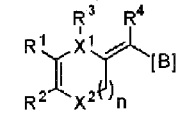
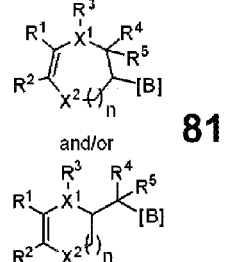 81
and/or
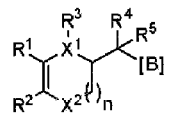
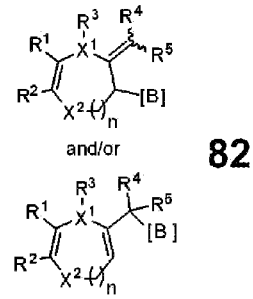 82
and/or
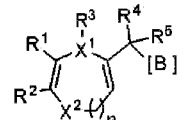
Fig. 6.8

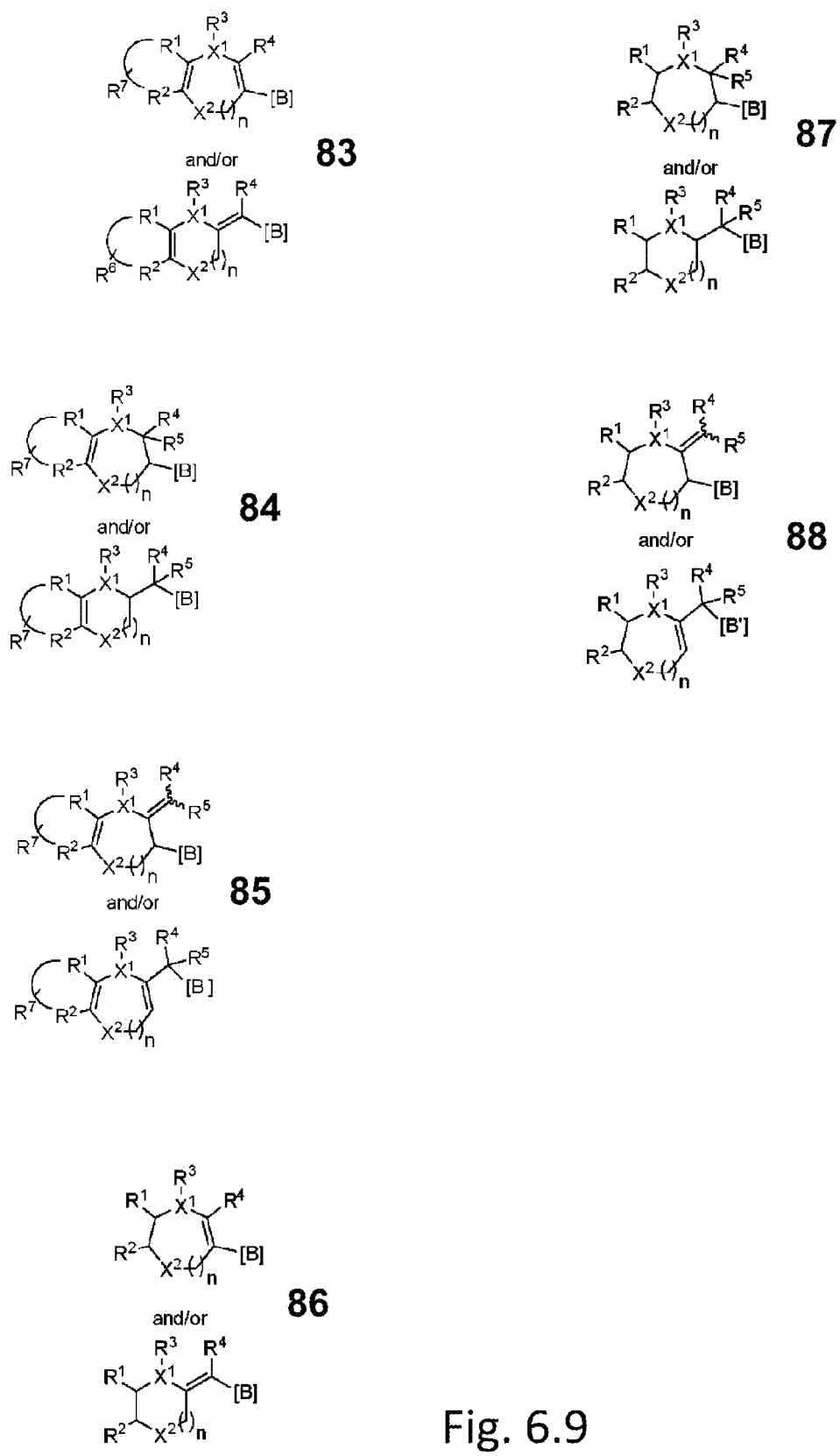
Fig. 6.9

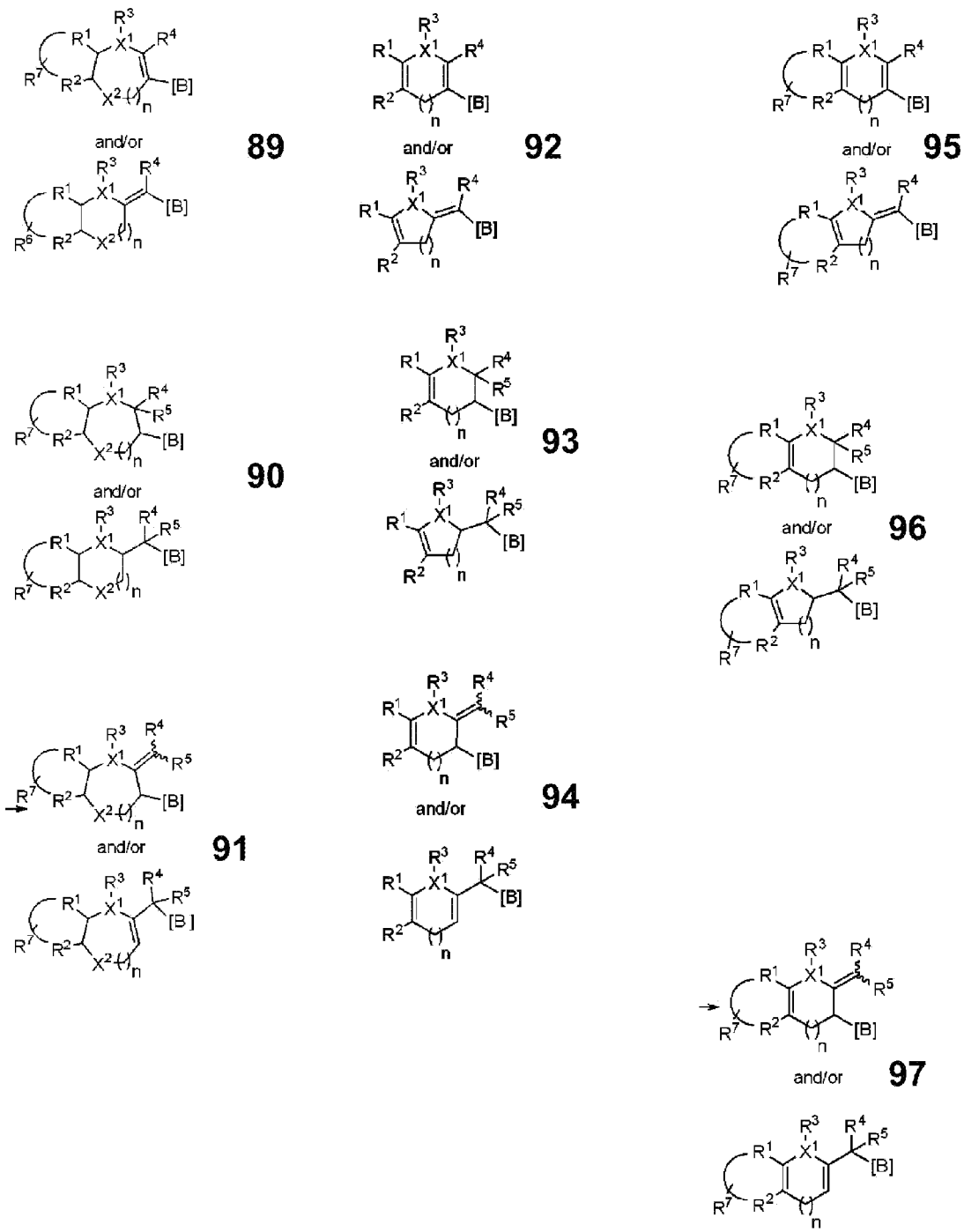
Fig. 6.10

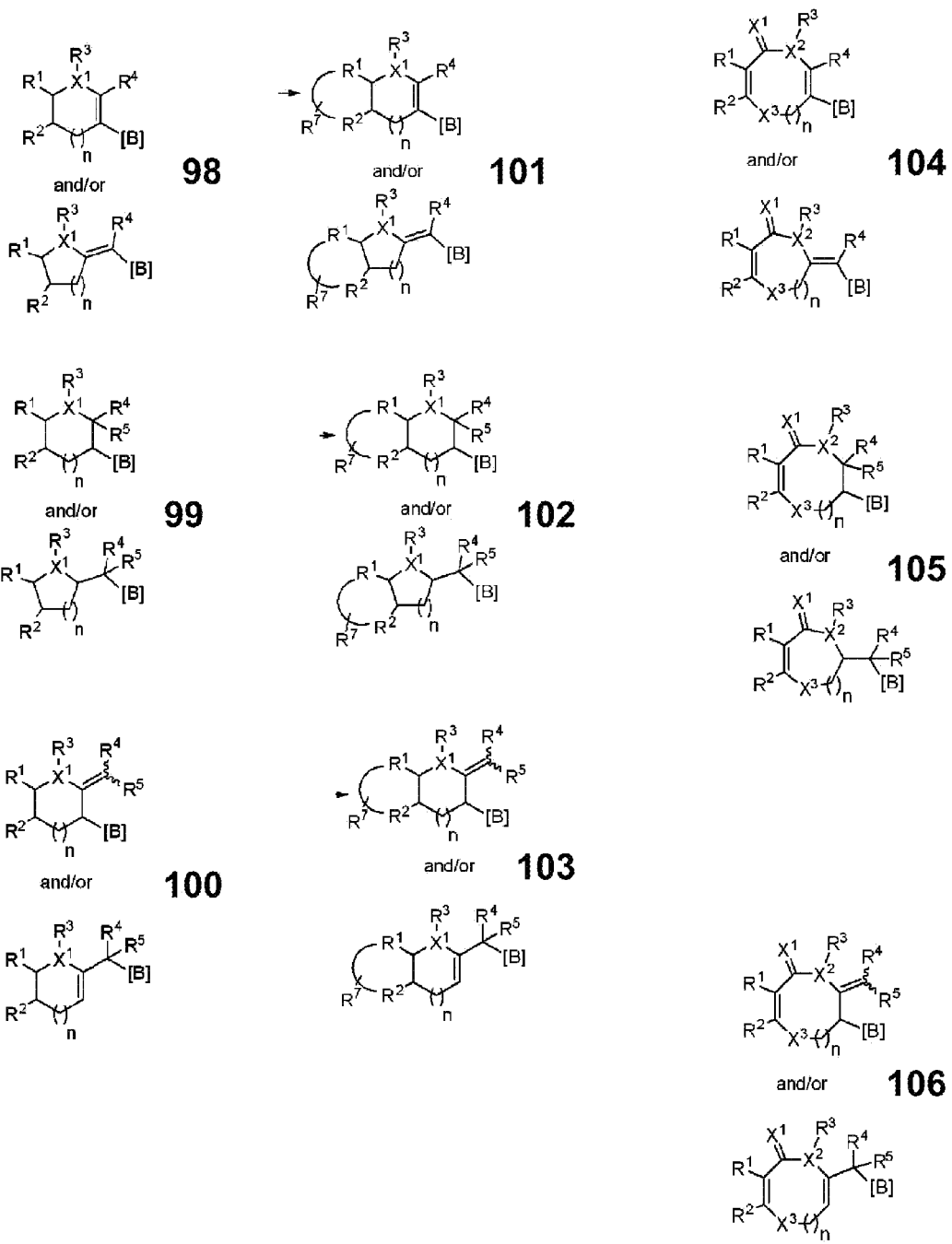
Fig. 6.11

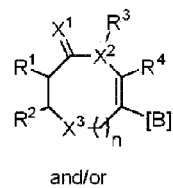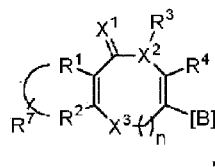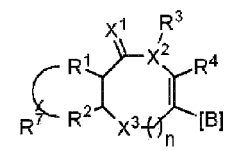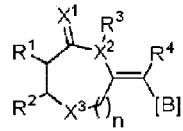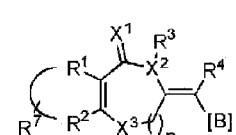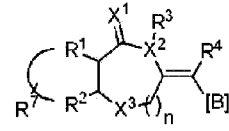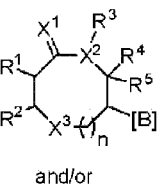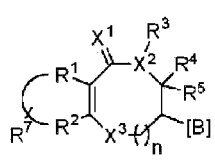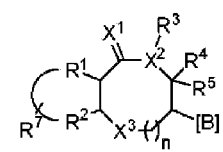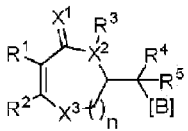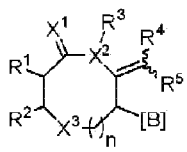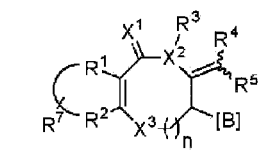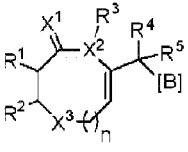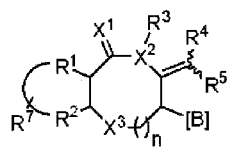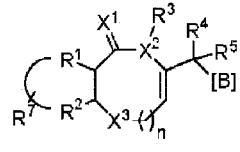
Fig. 6.12

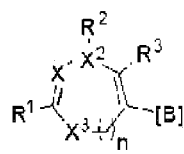 116
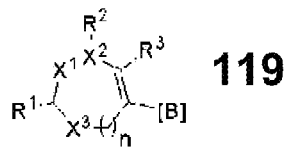 119
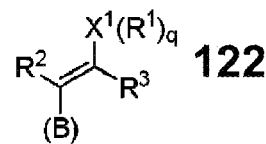 122
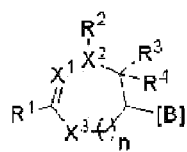 117
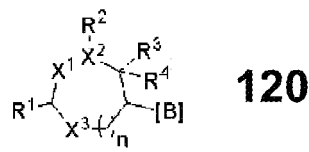 120
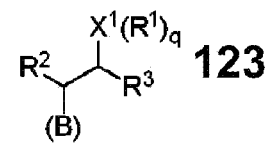 123
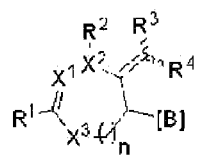
and/or 118
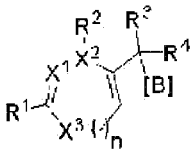
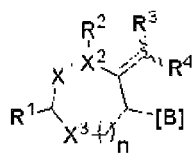
and/or 121
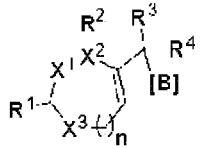
Fig. 6.13

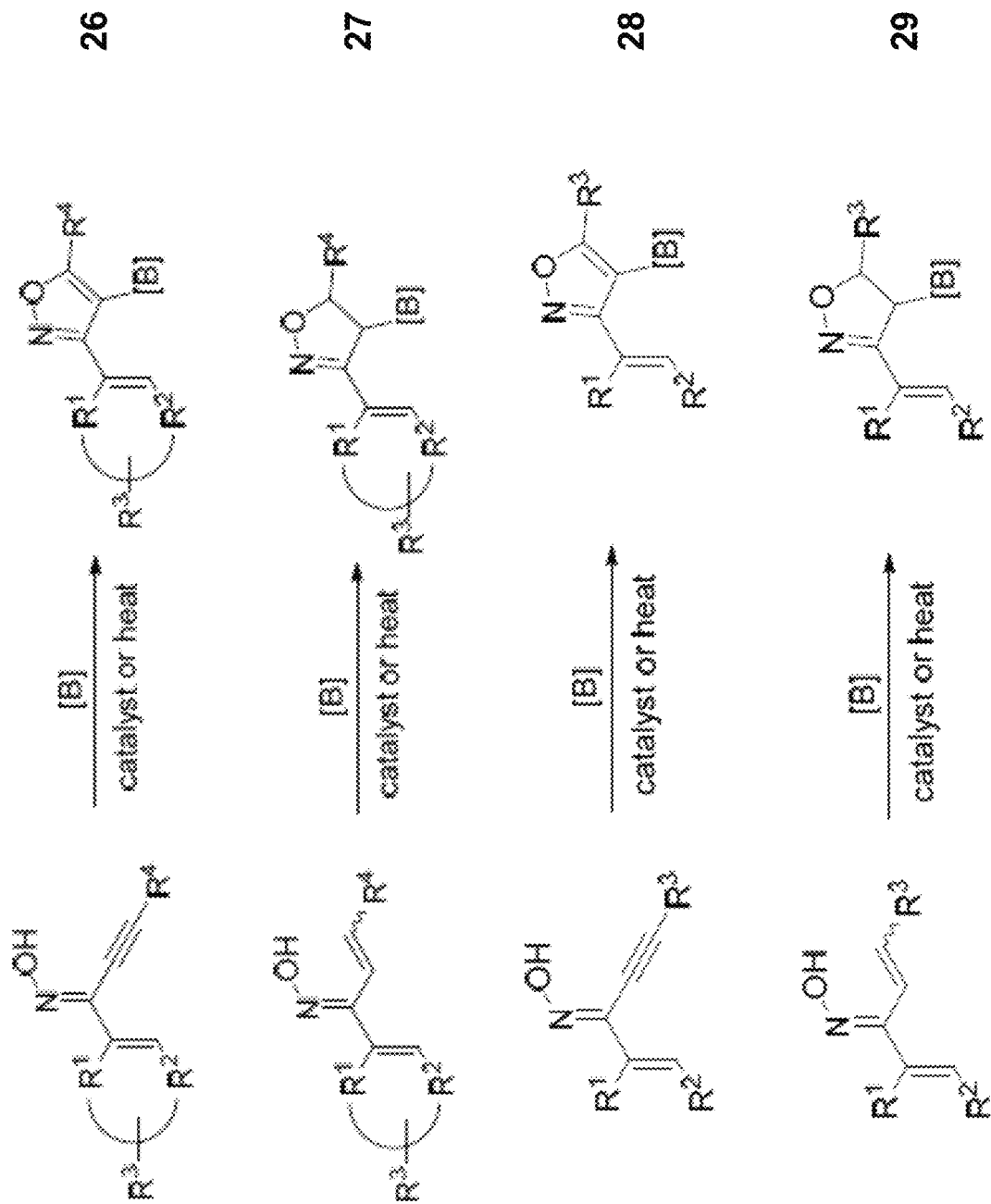
Fig. 6.14

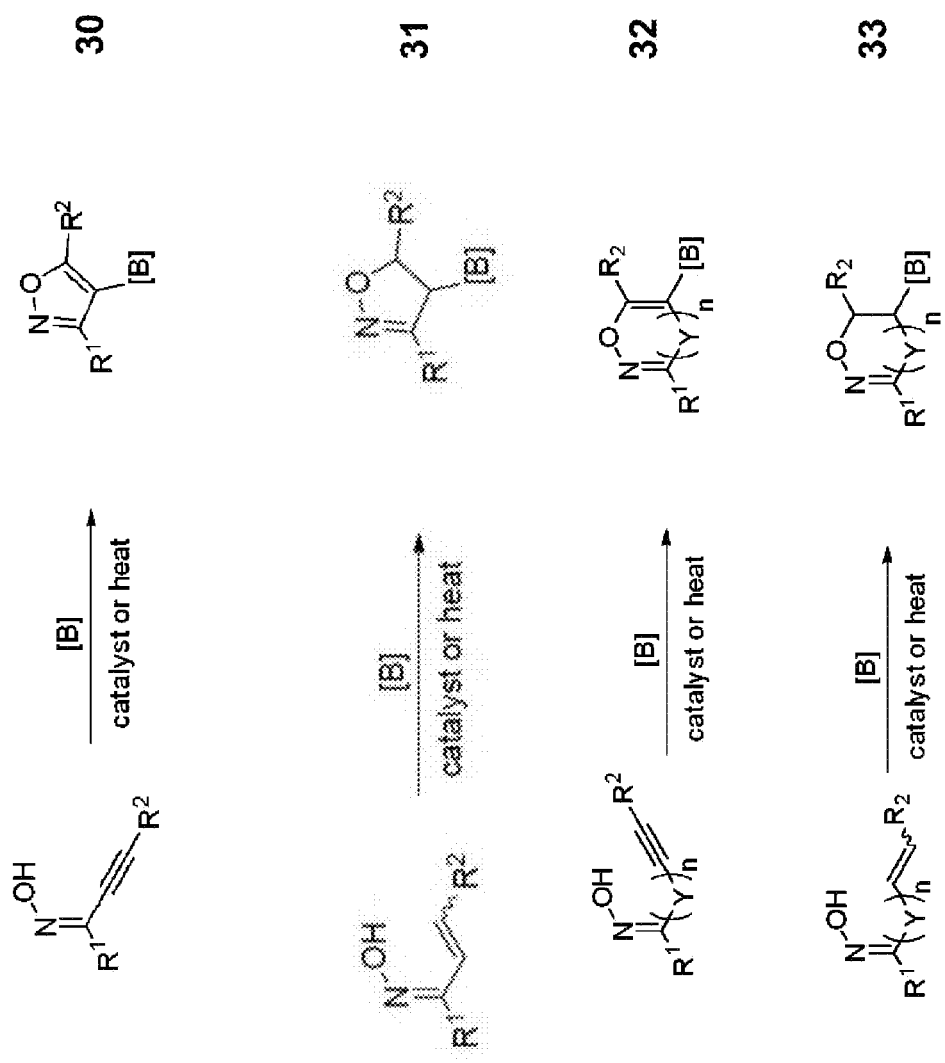
Fig. 6.15

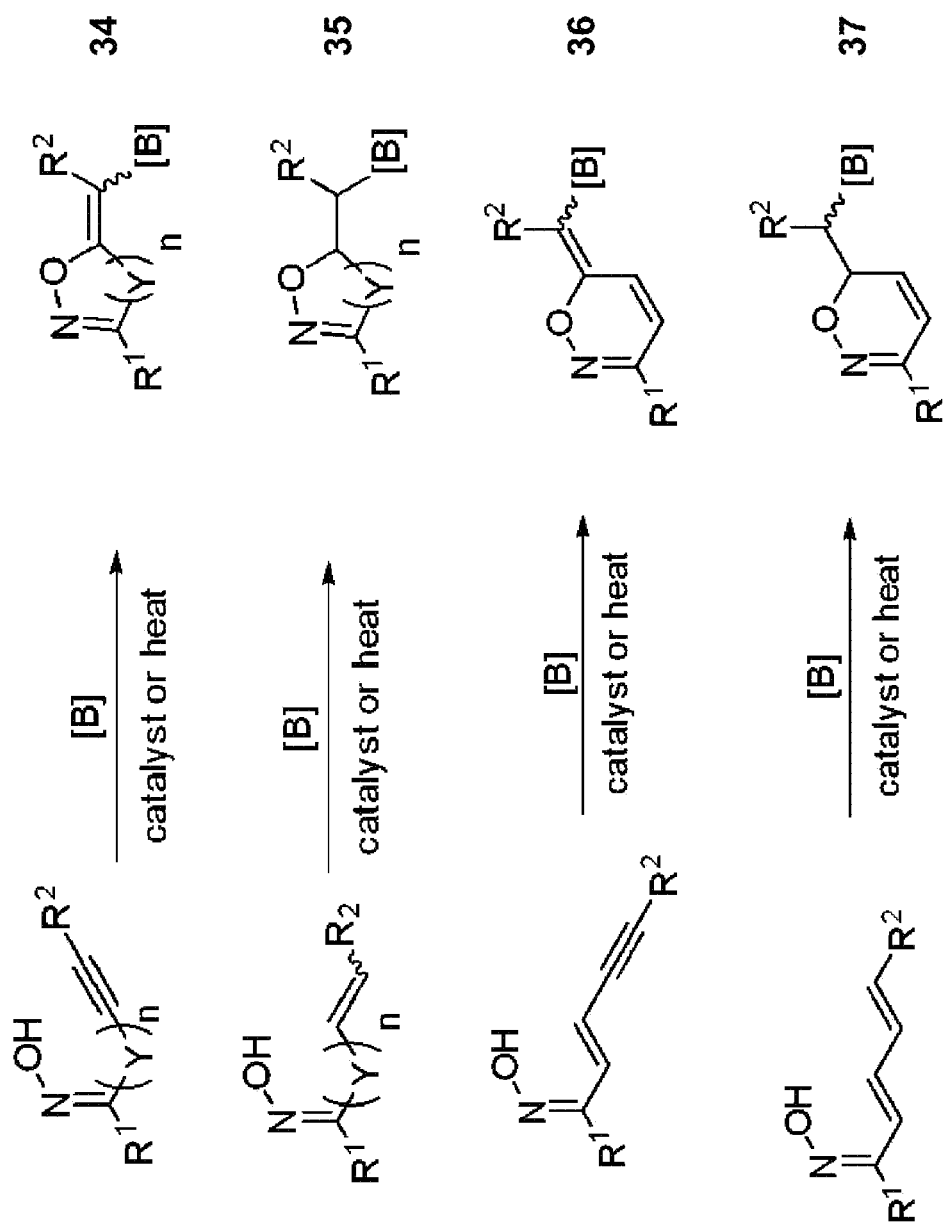
Fig. 6.16

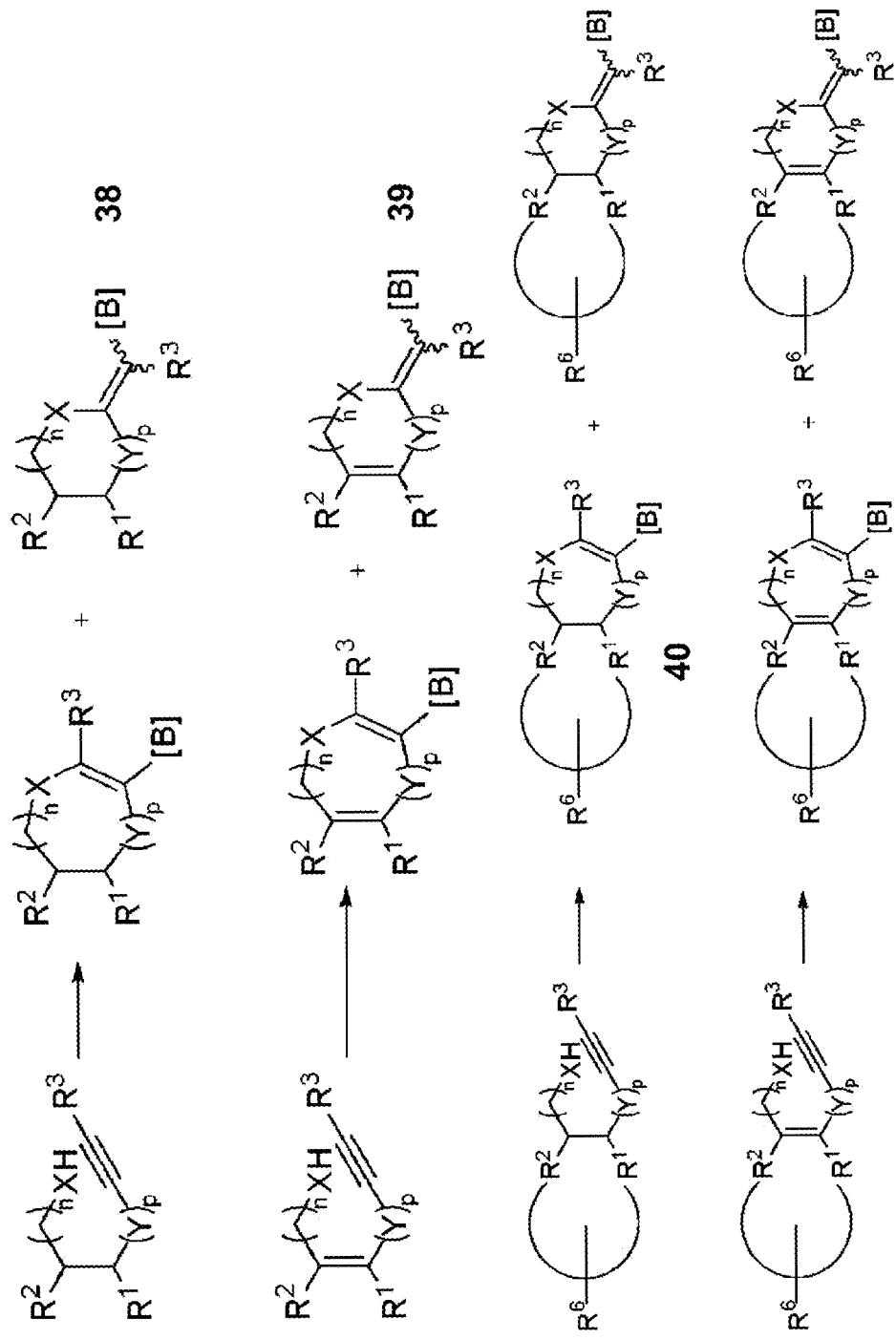
Fig. 6.17

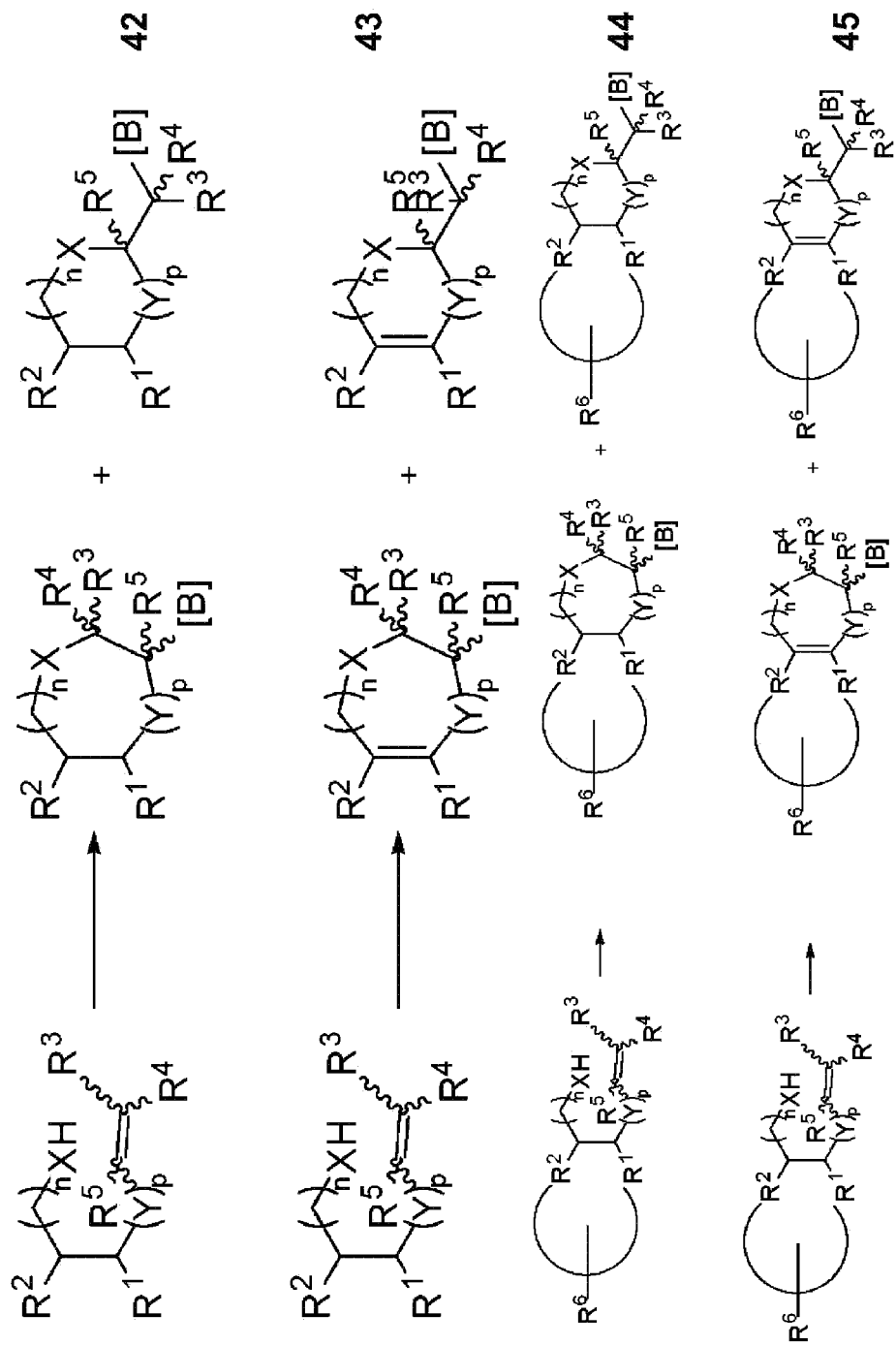
Fig. 6.18

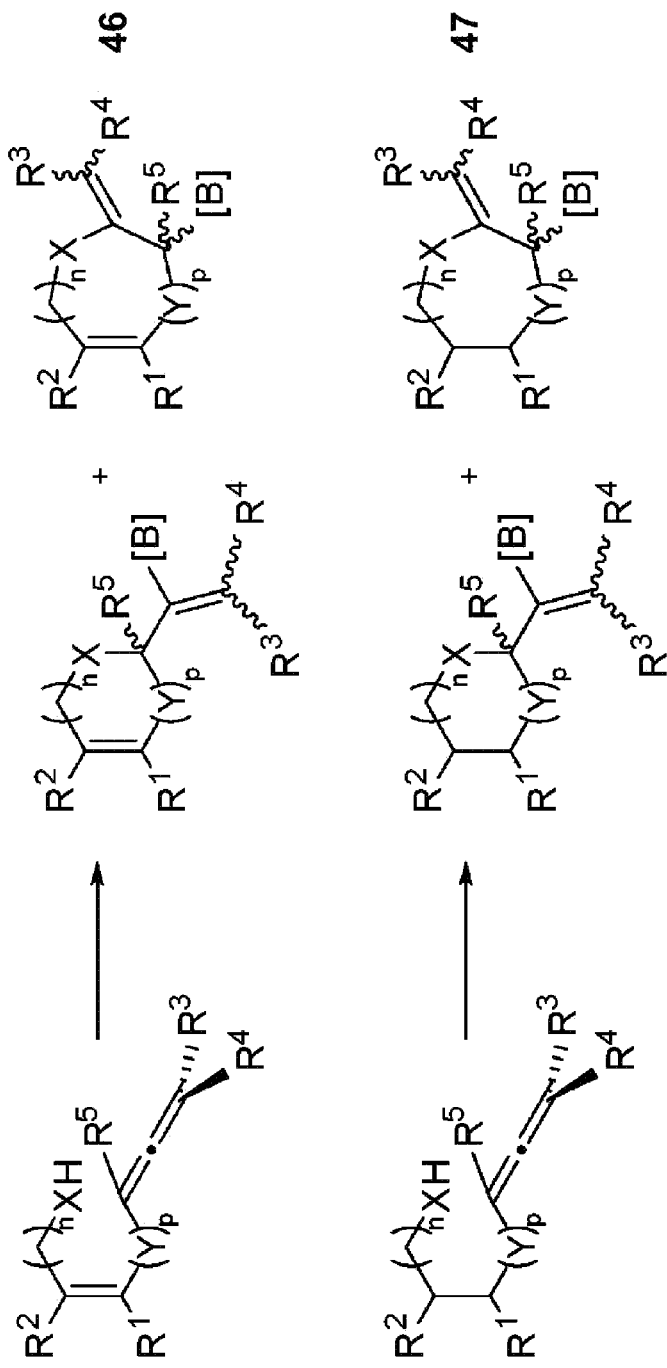
Fig. 6.19

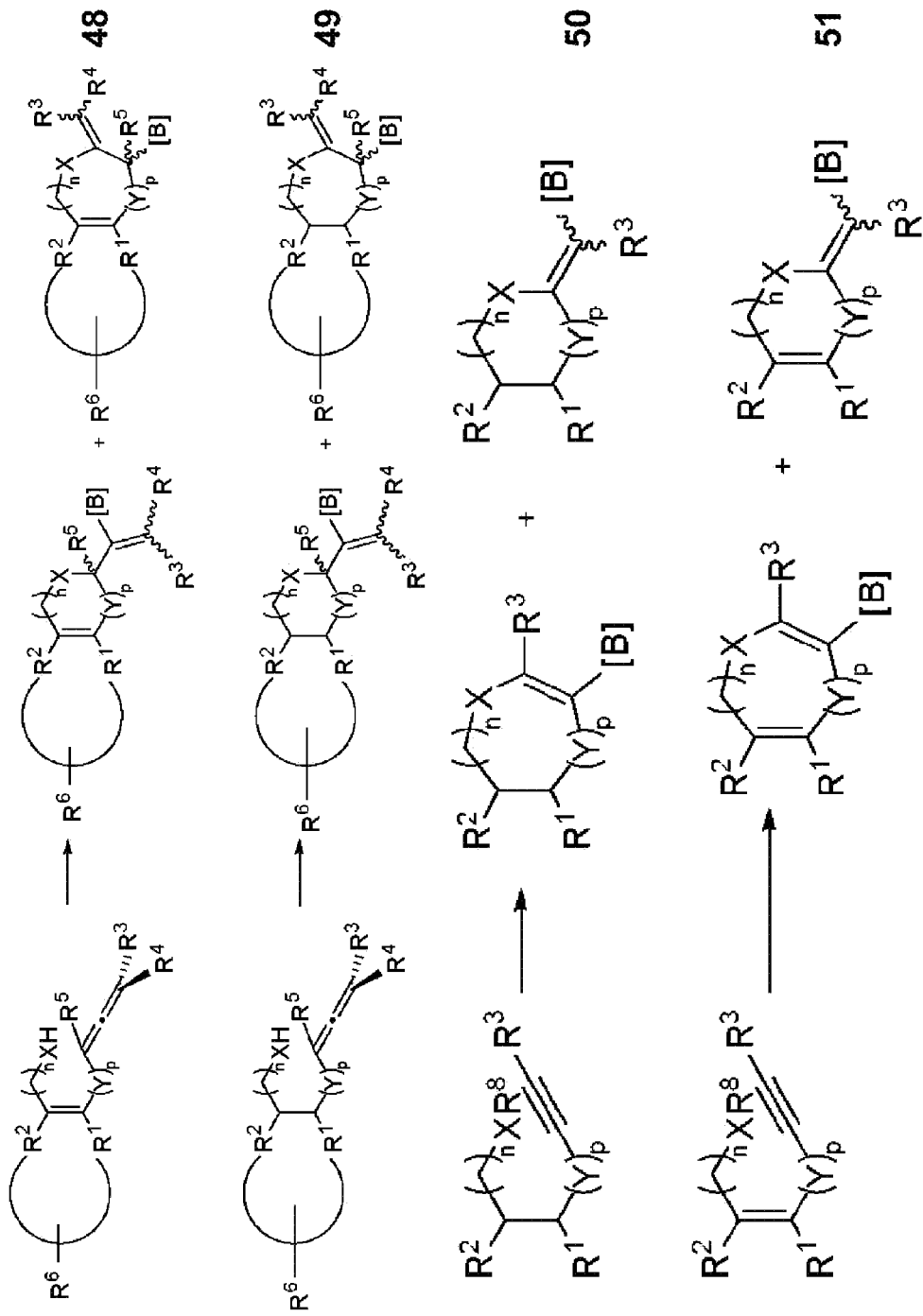
Fig. 6.20

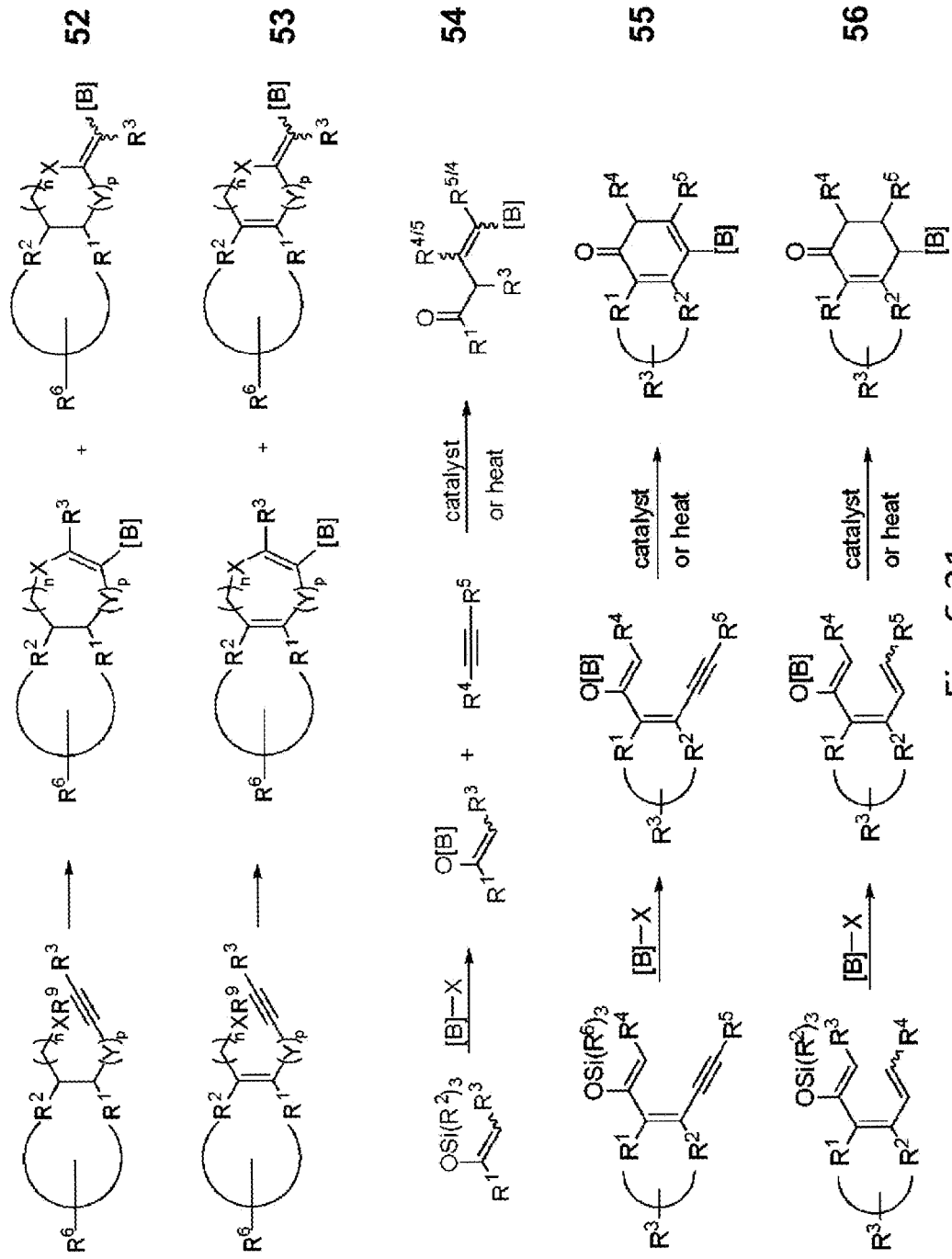
Fig. 6.21

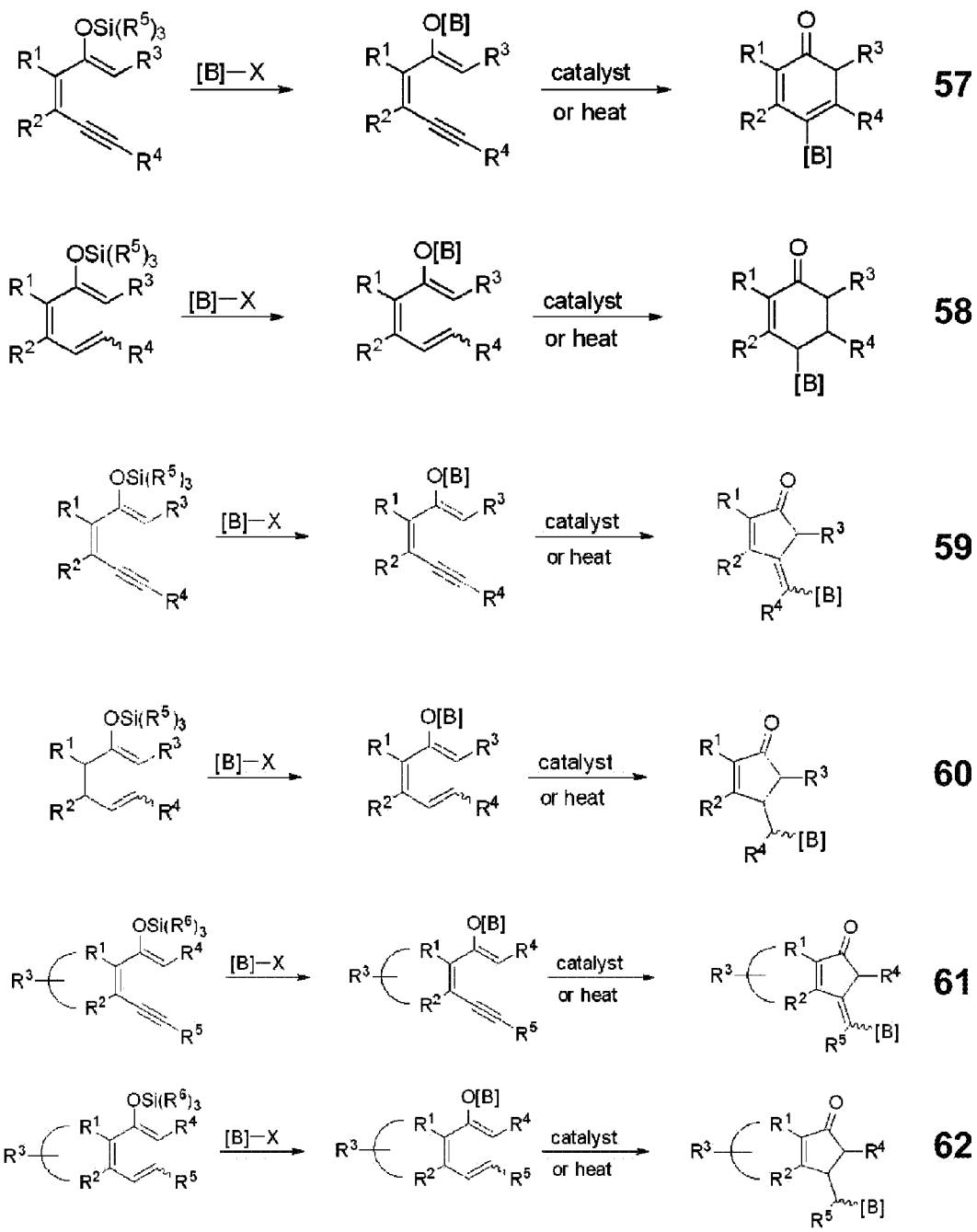
Fig. 6.22

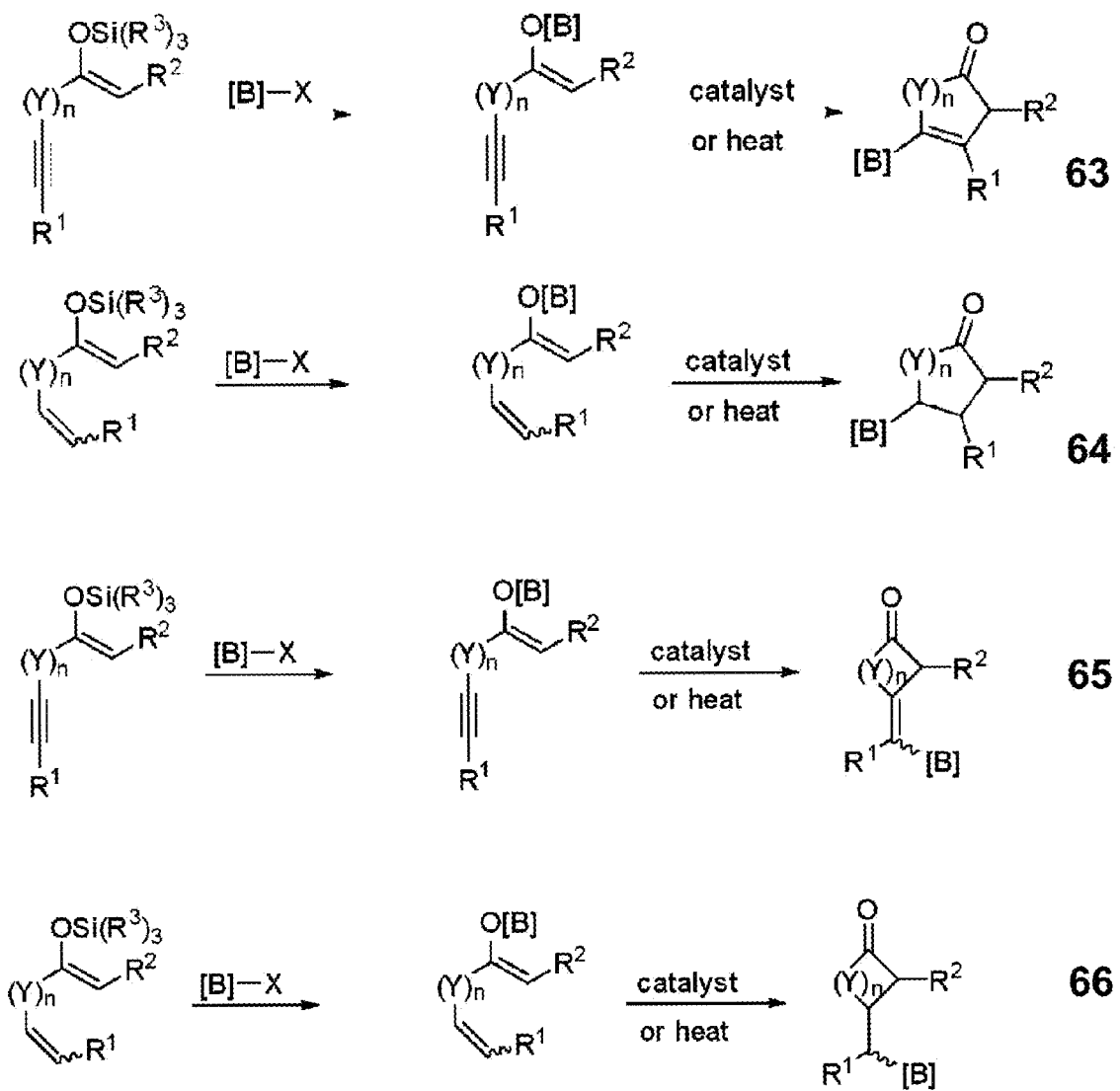
Fig. 6.23

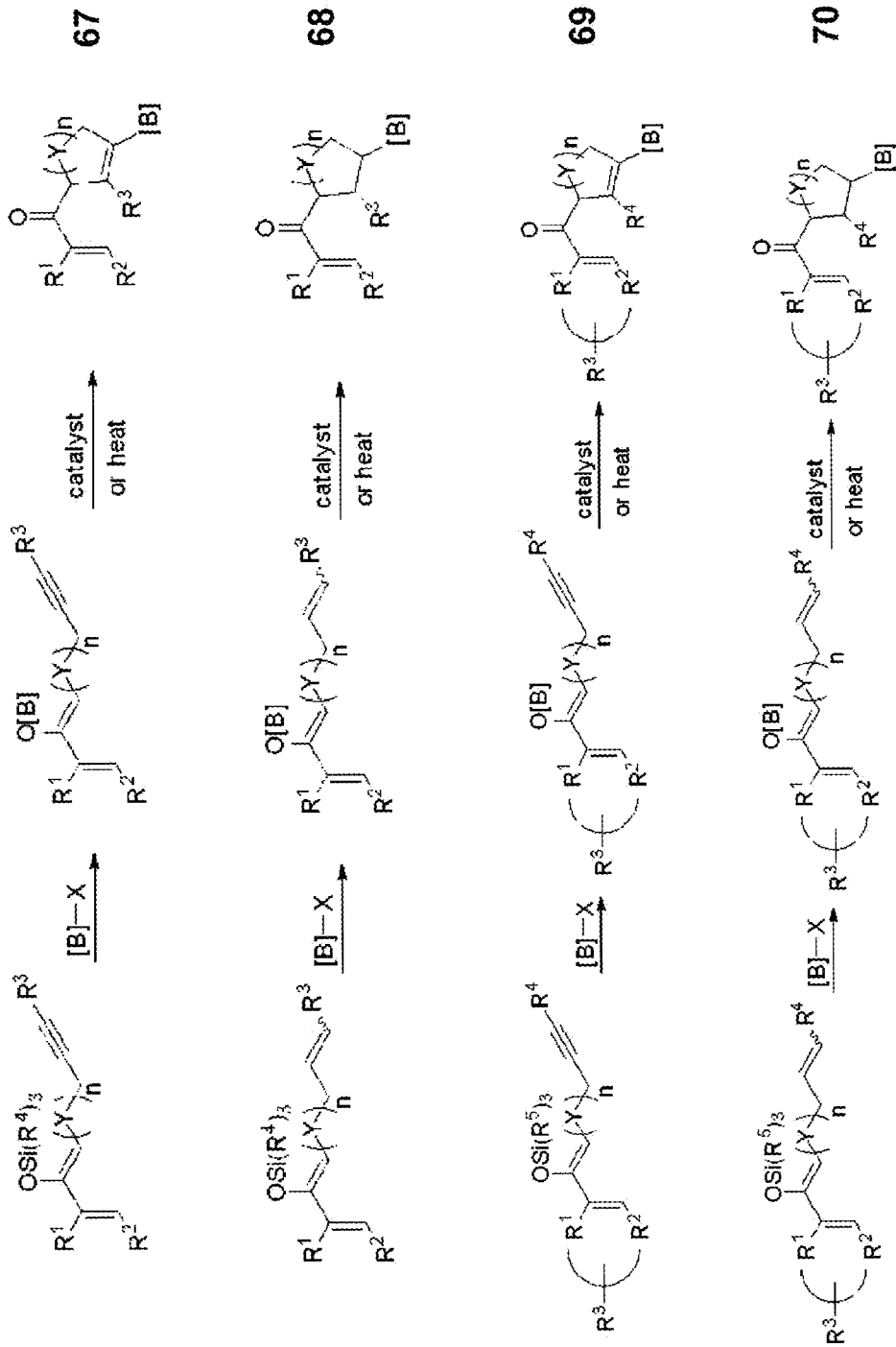
Fig. 6.24

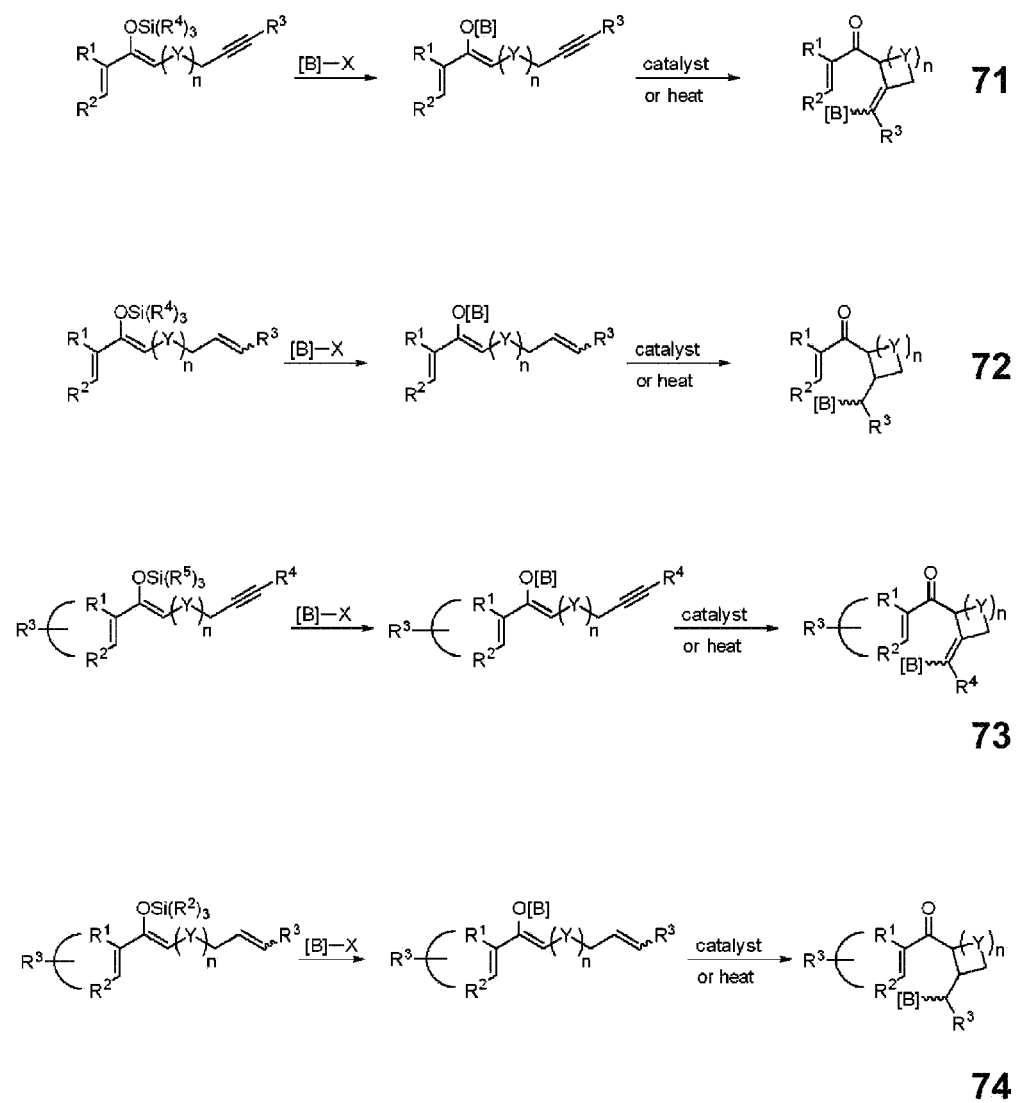
Fig. 6.25

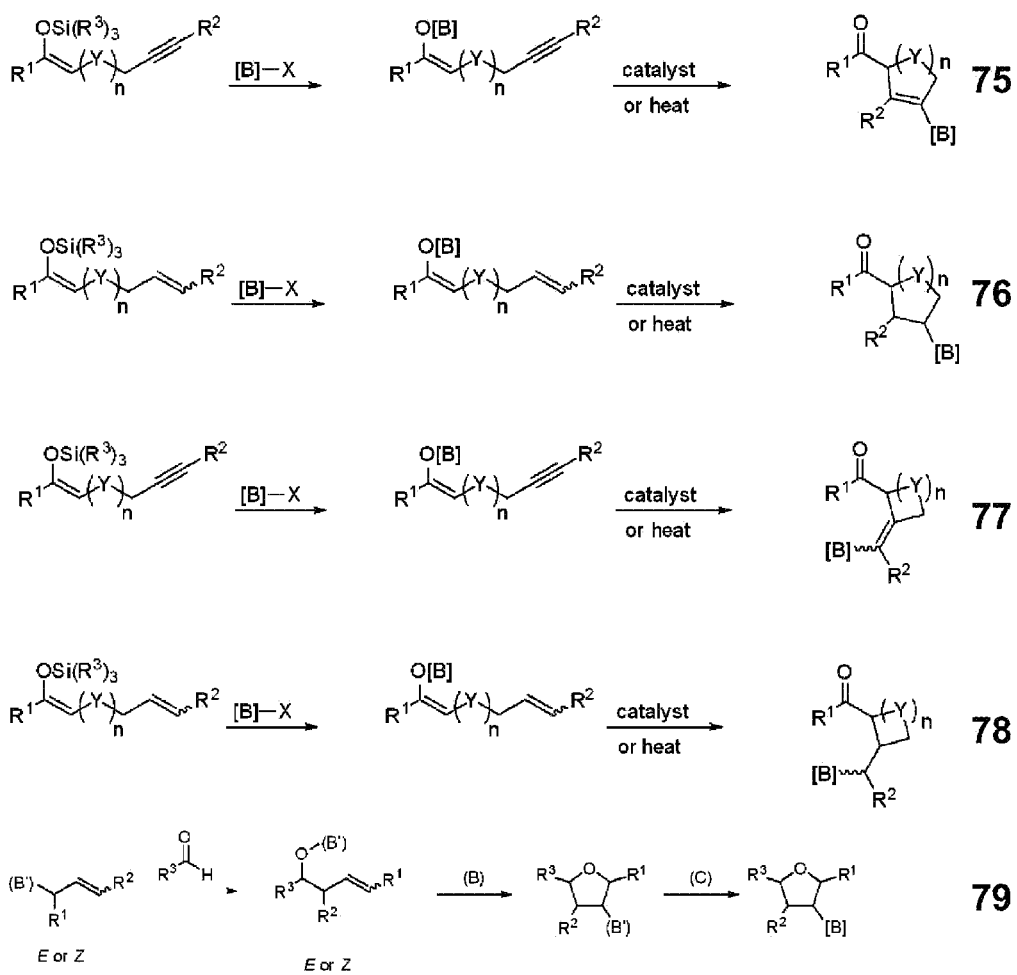
Fig. 6.26

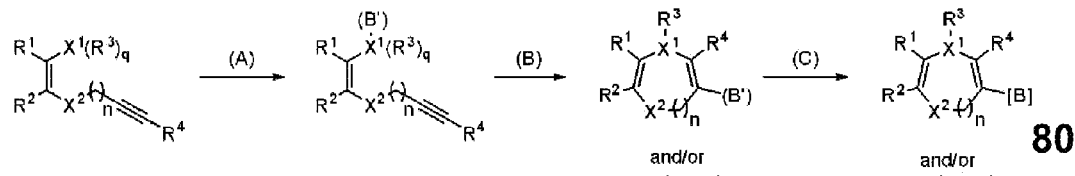
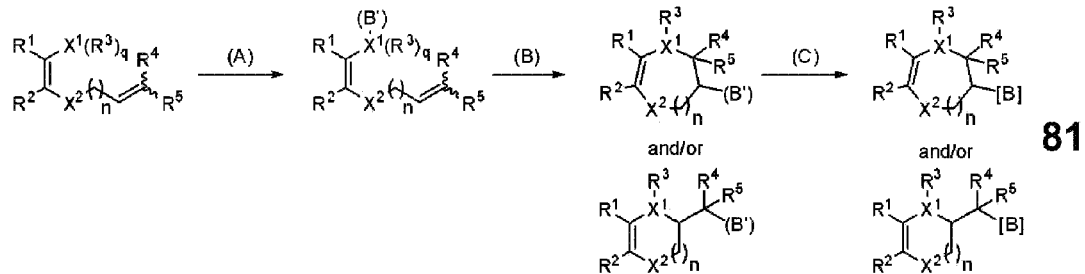
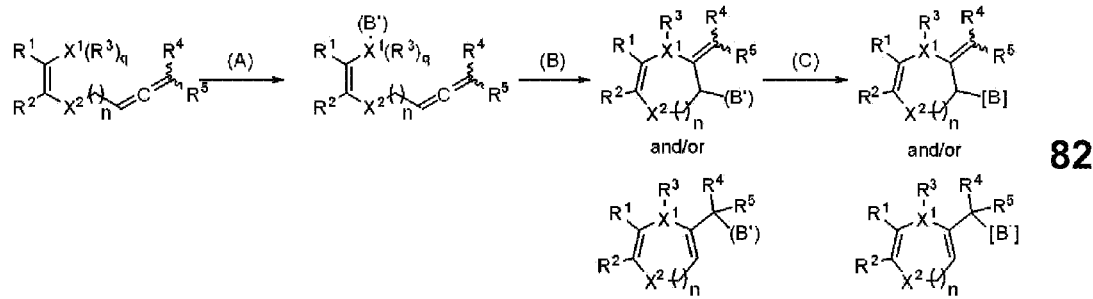
Fig. 6.27

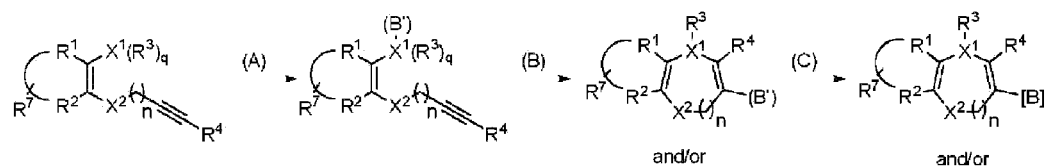
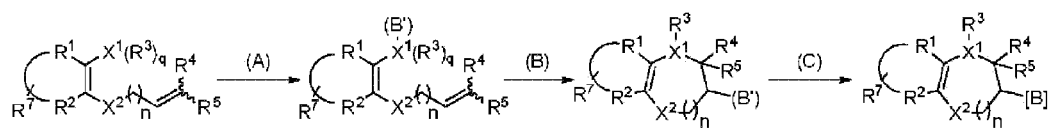
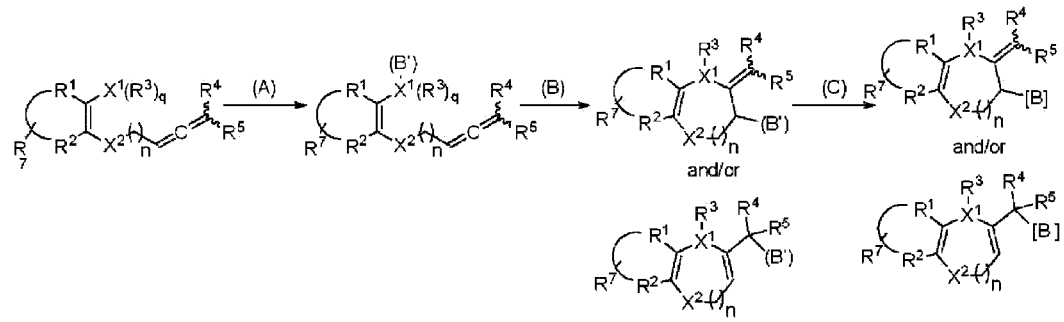
Fig. 6.28

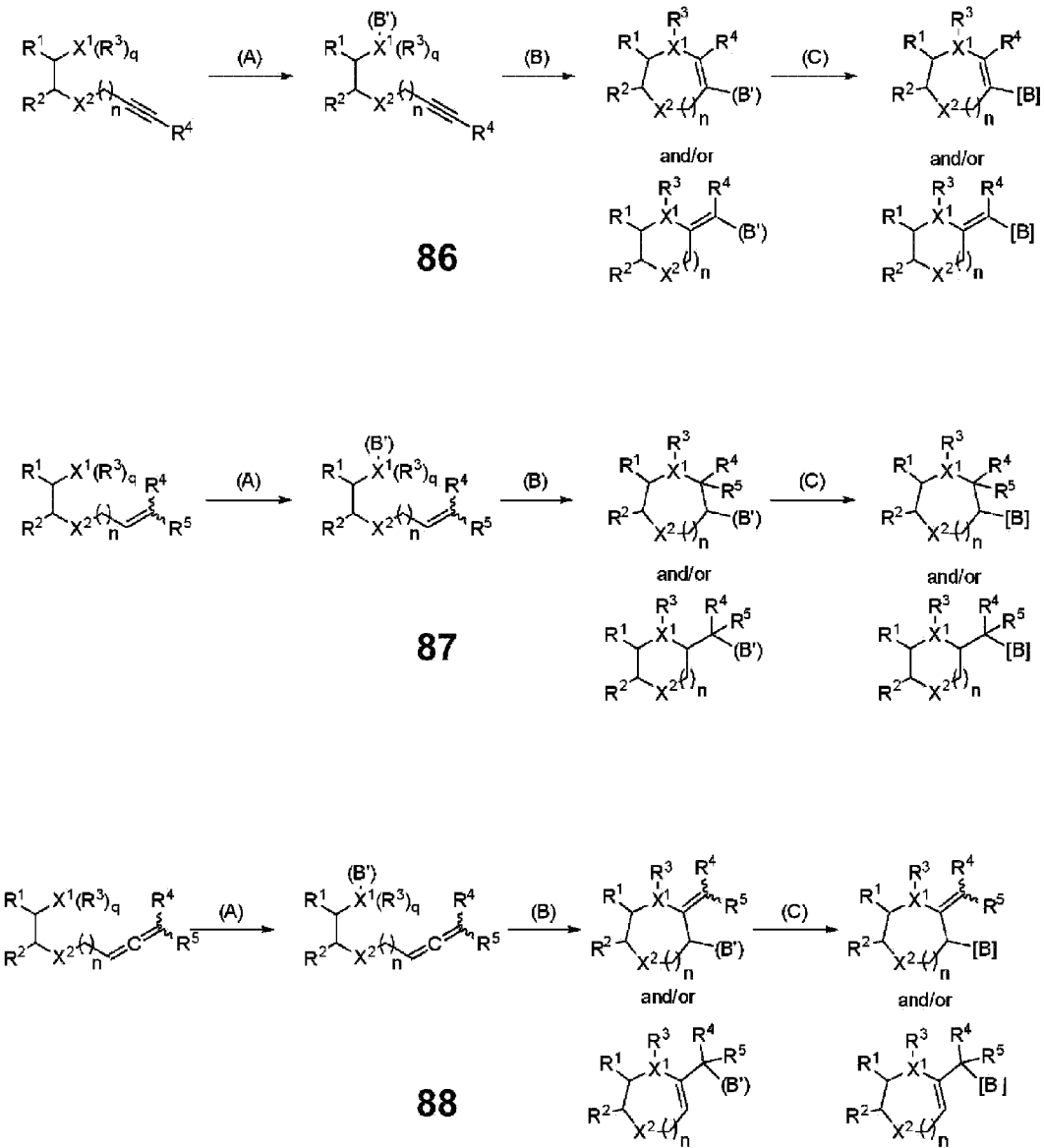
Fig. 6.29

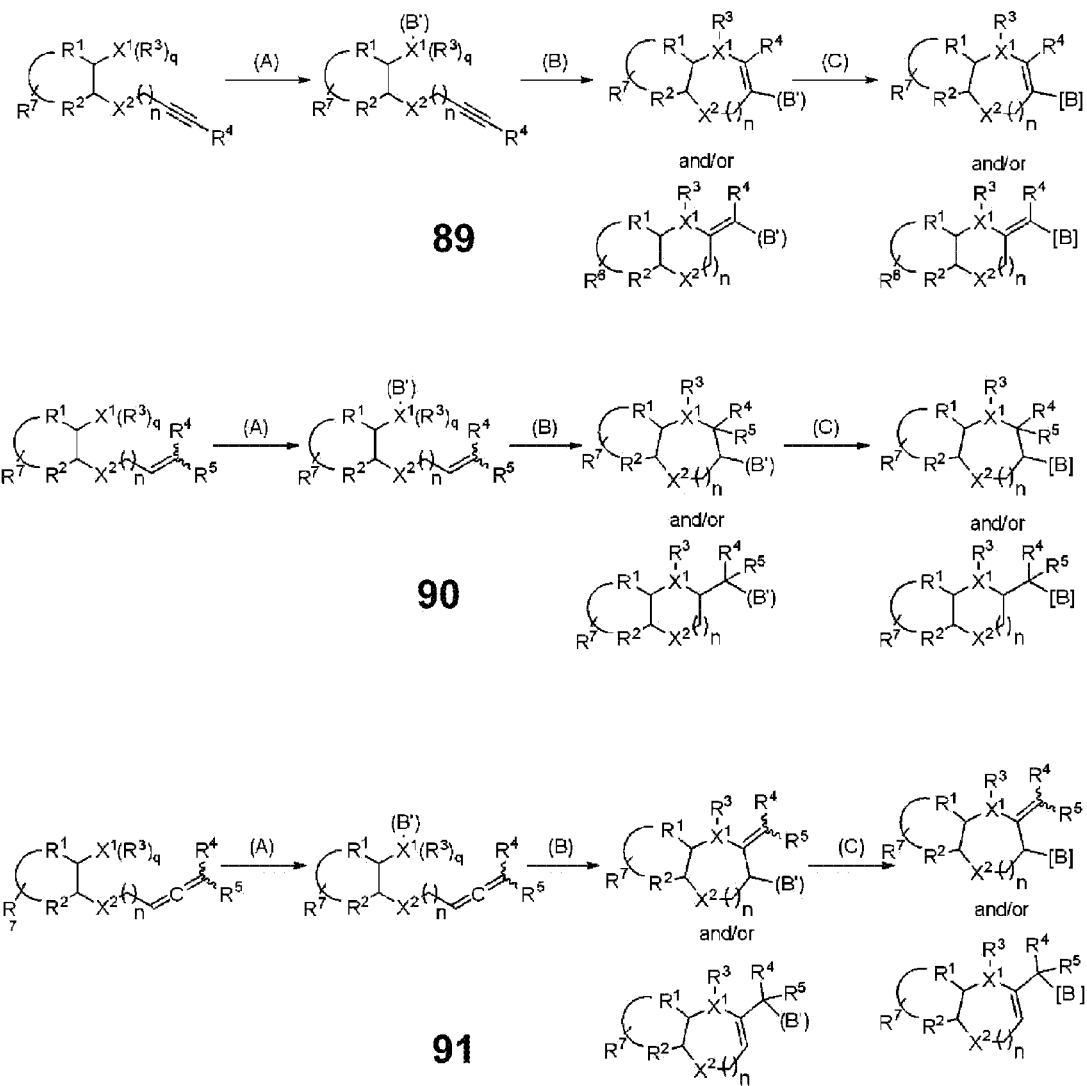
Fig. 6.30

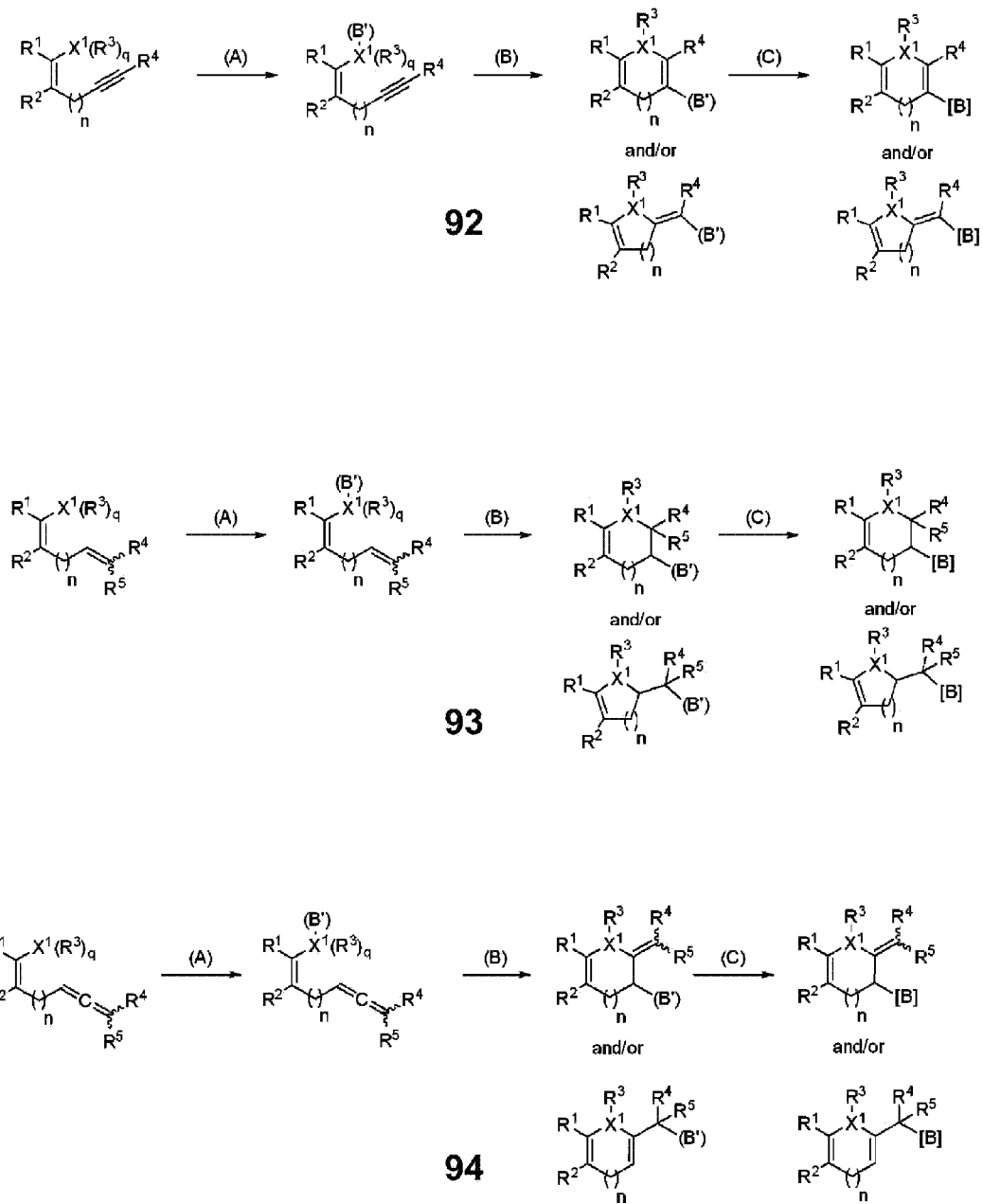
Fig. 6.31

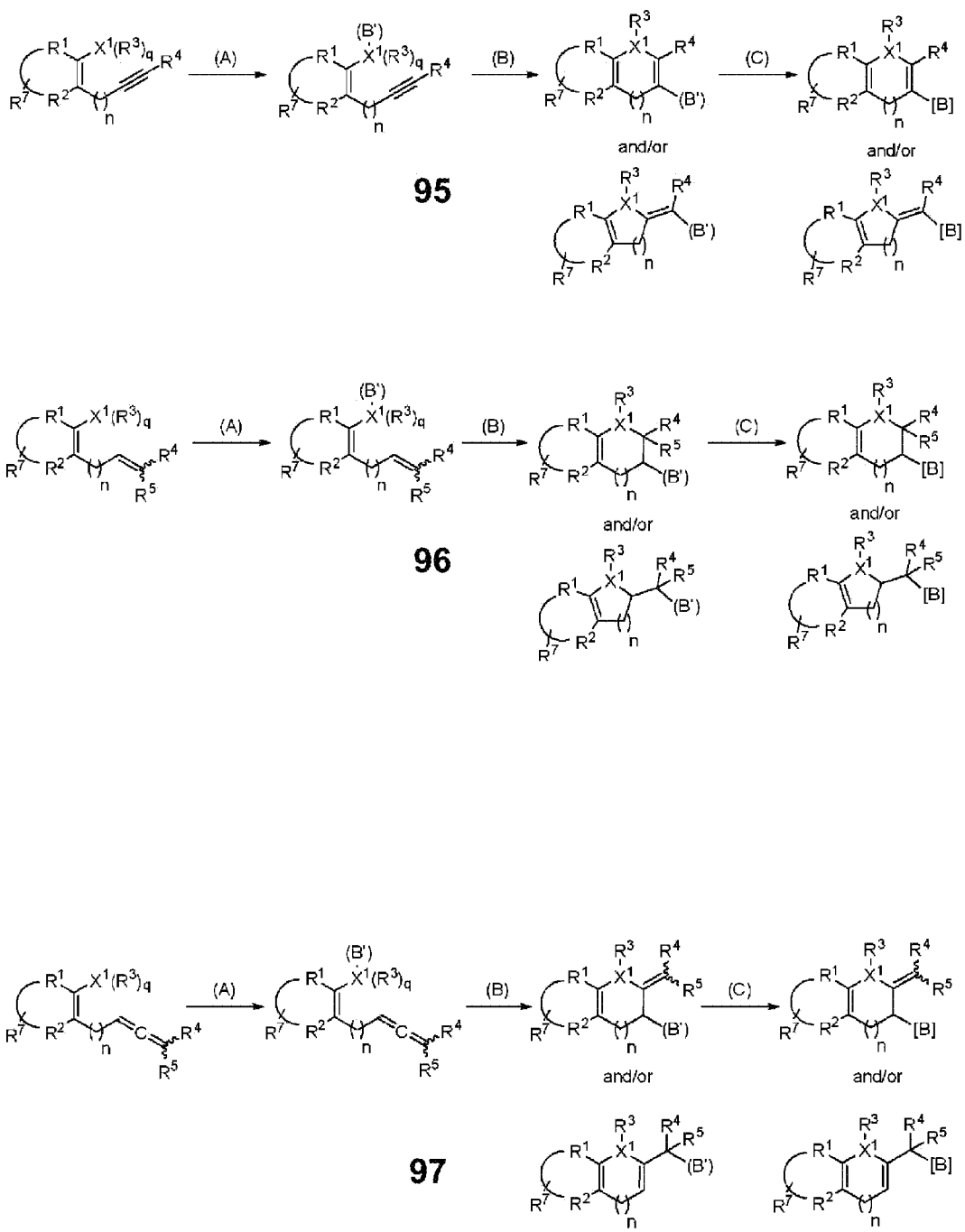
Fig. 6.32

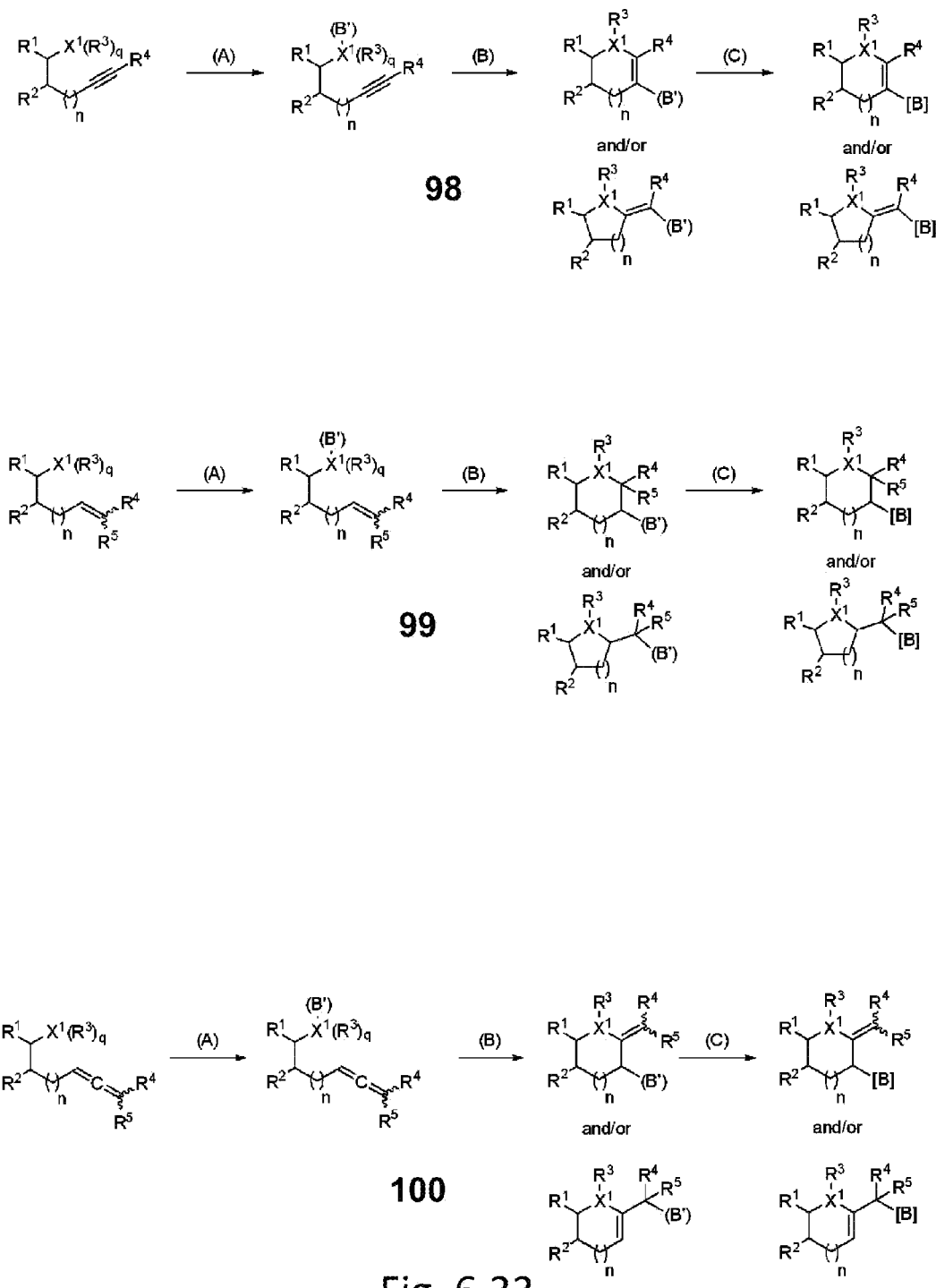
Fig. 6.33

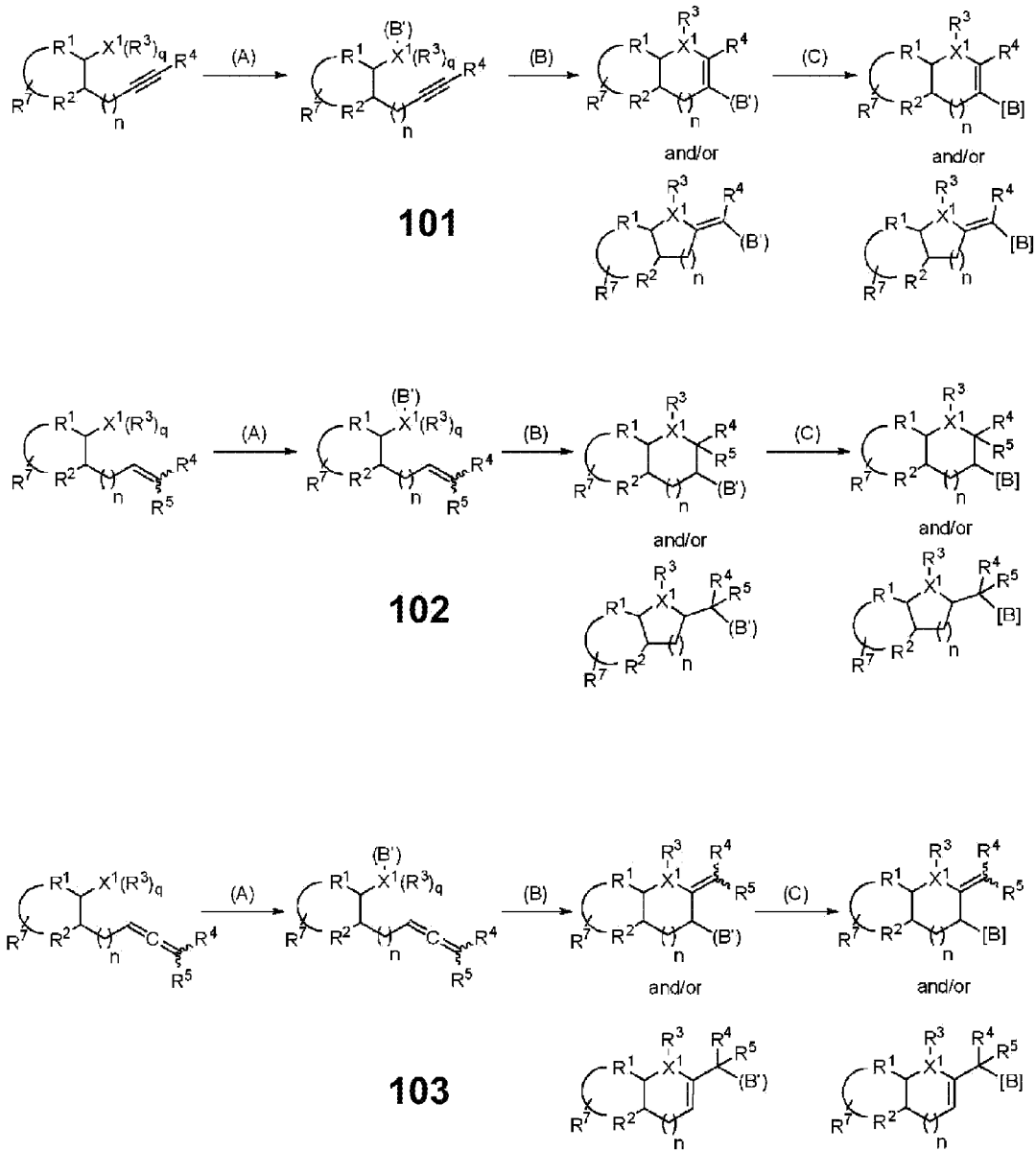
Fig. 6.34

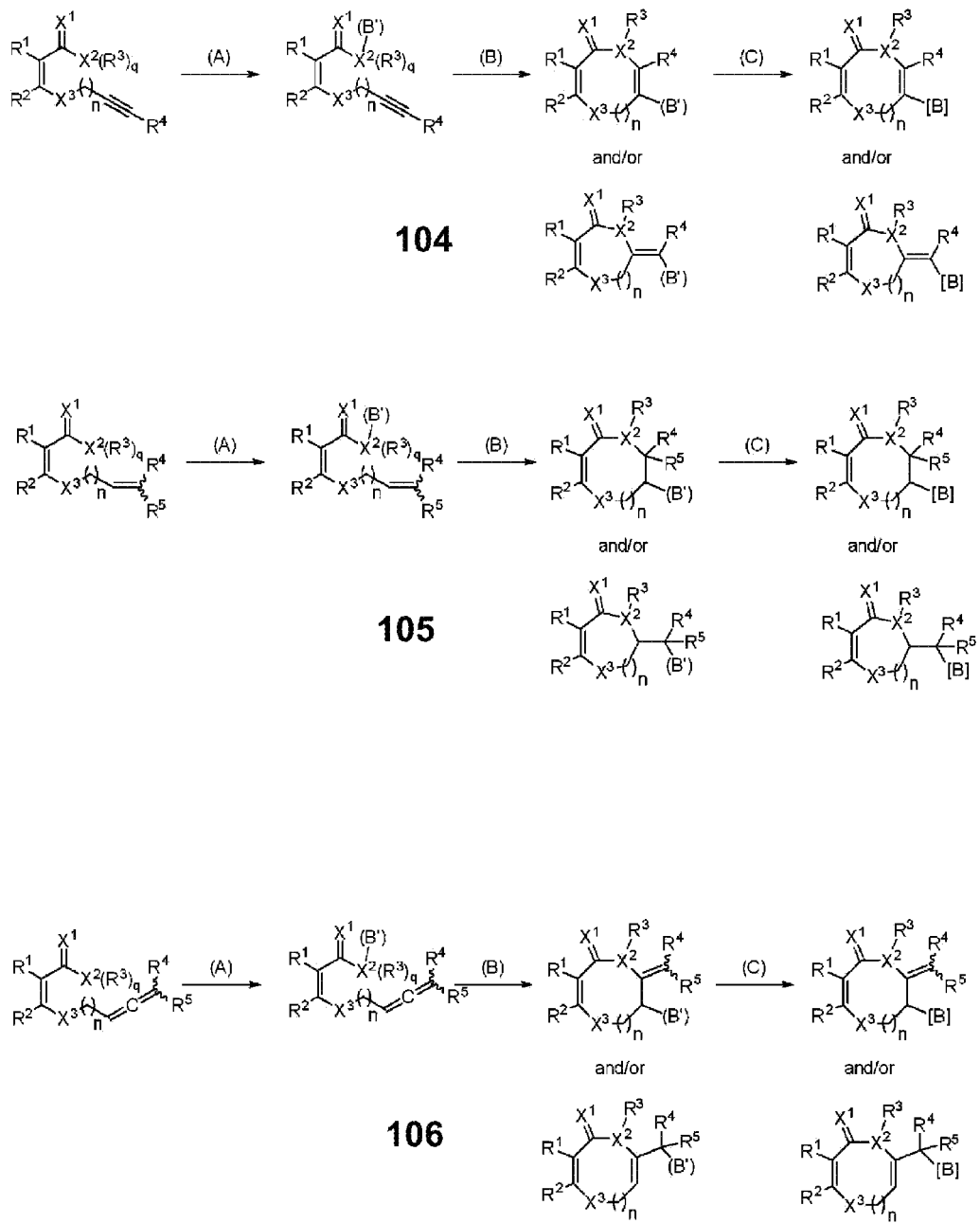
Fig. 6.35

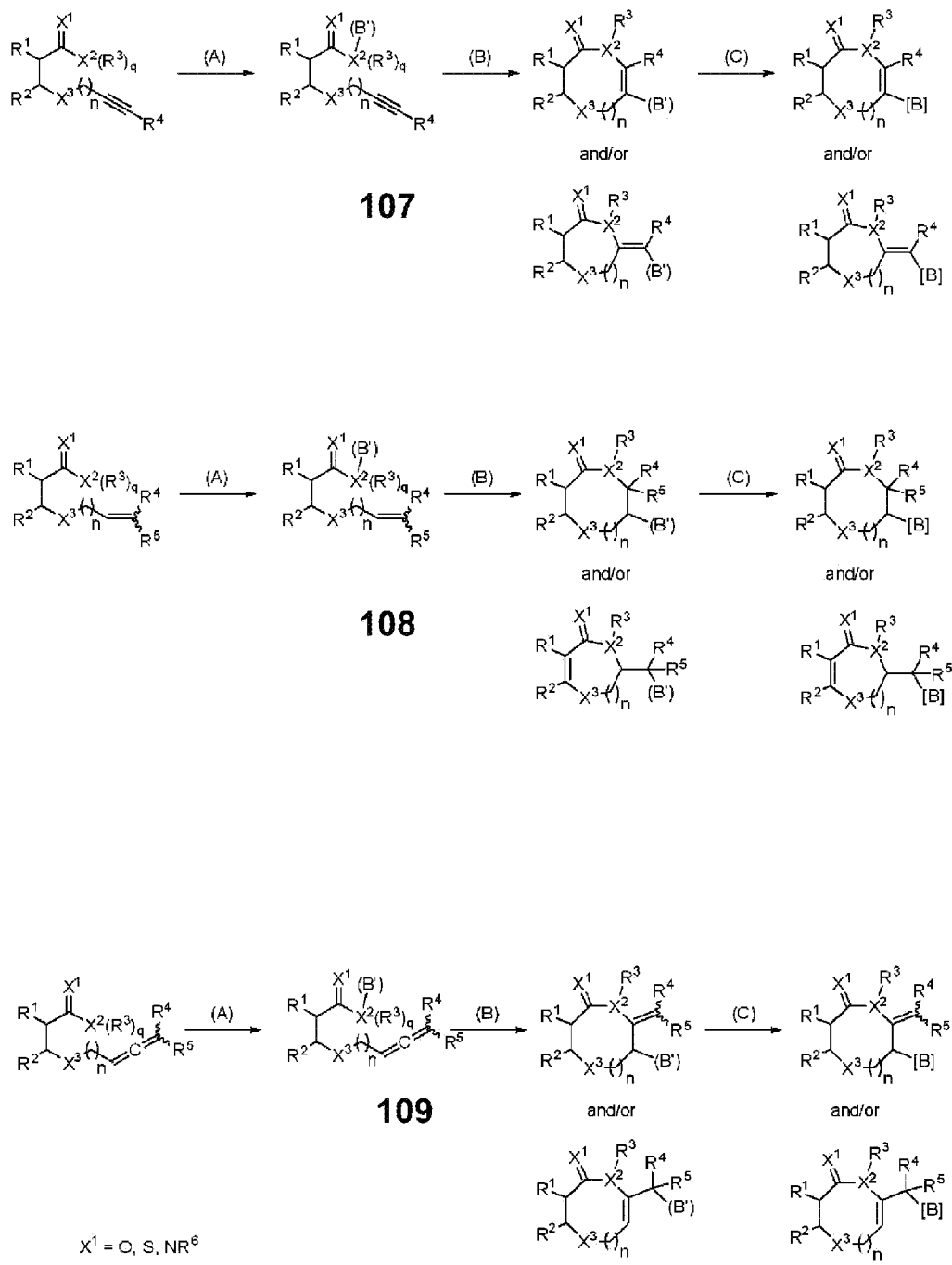
Fig. 6.36

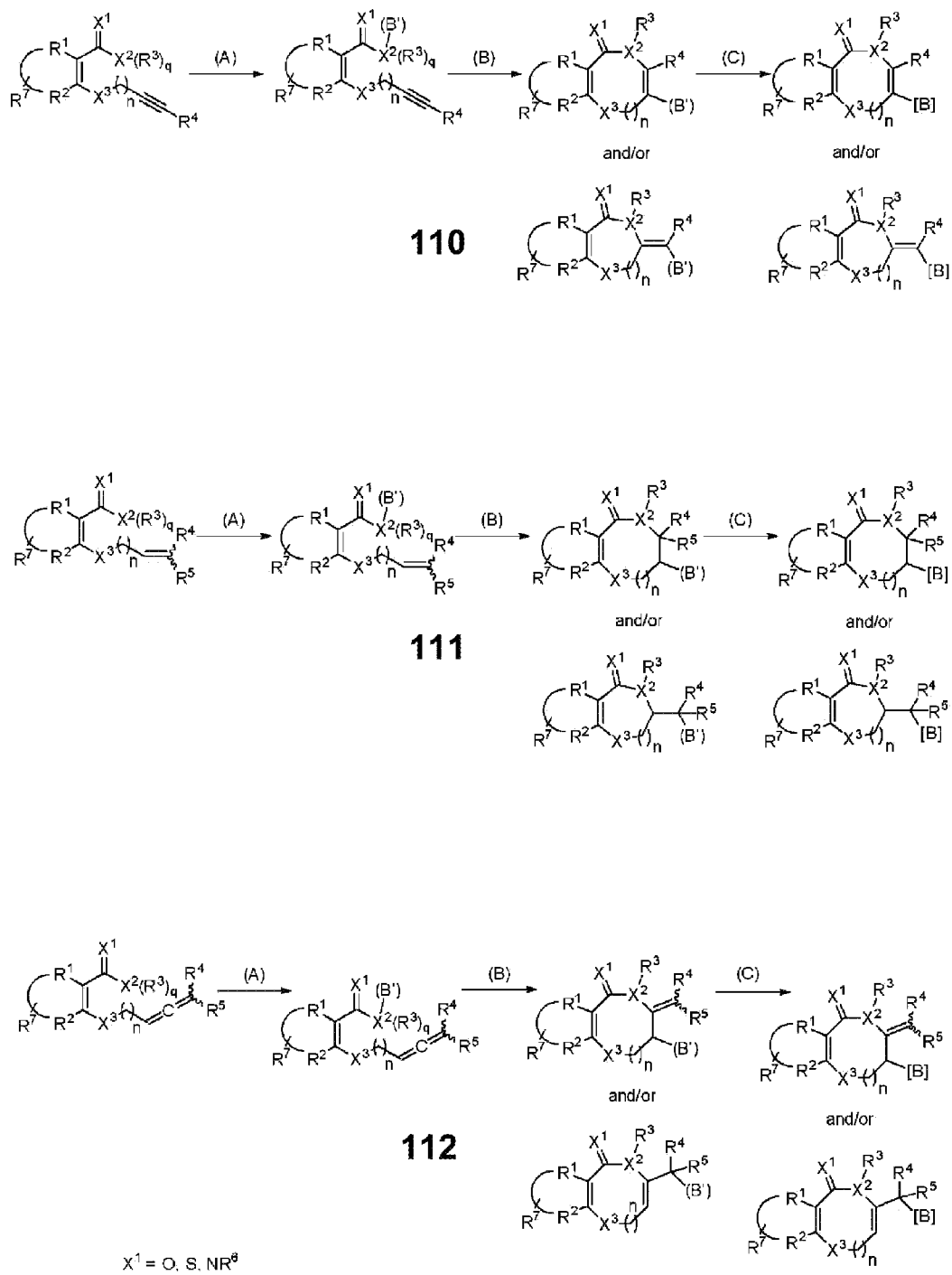
Fig. 6.37

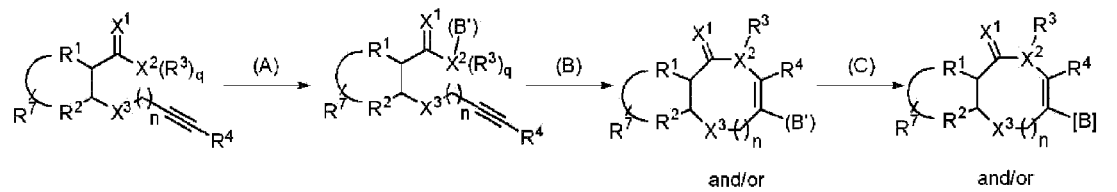
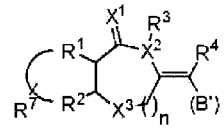 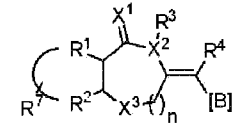
113
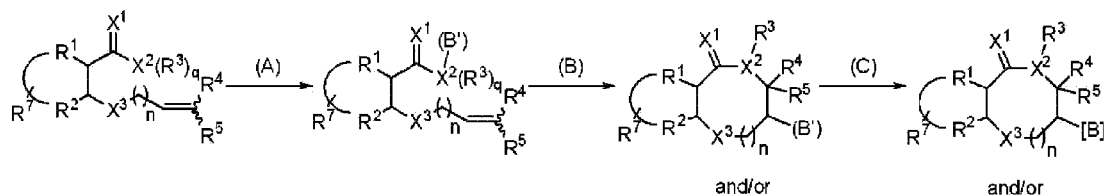
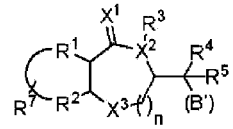 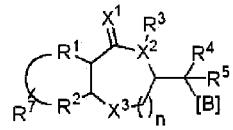
114
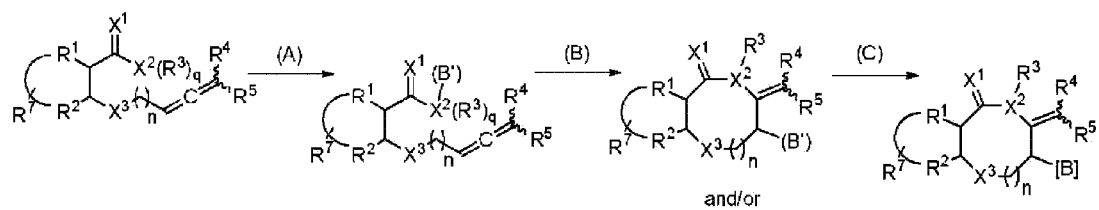
115
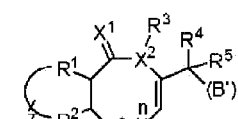 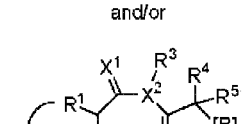
$X^1$ = O, S, $NR^6$
Fig. 6.38

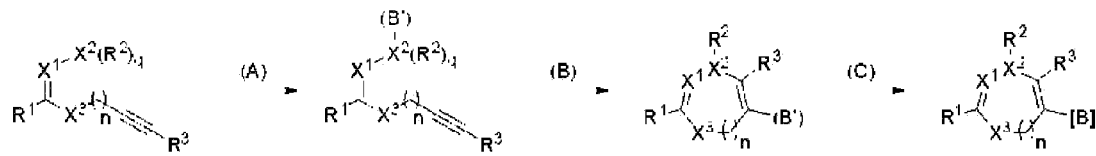
116
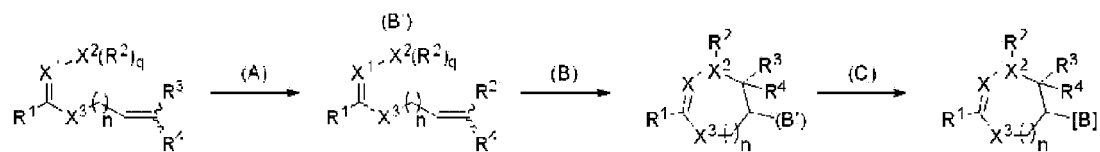
117
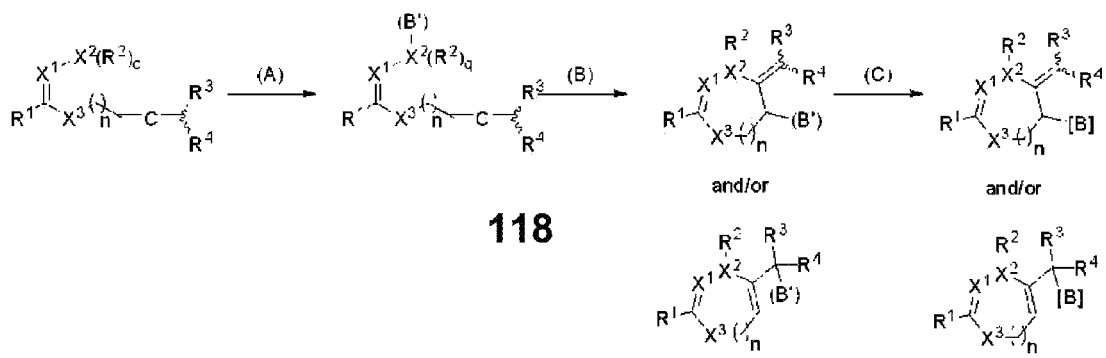
118
Fig. 6.39

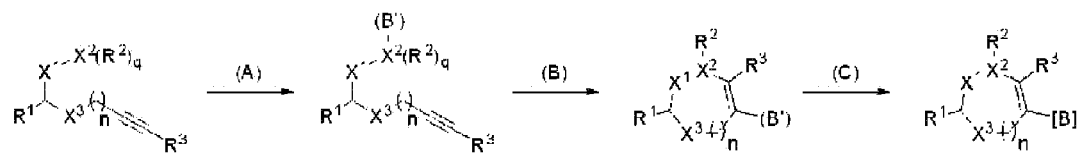
119
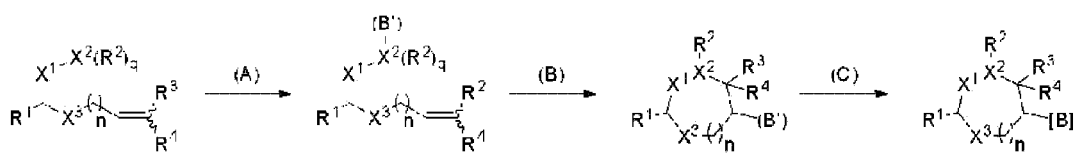
120
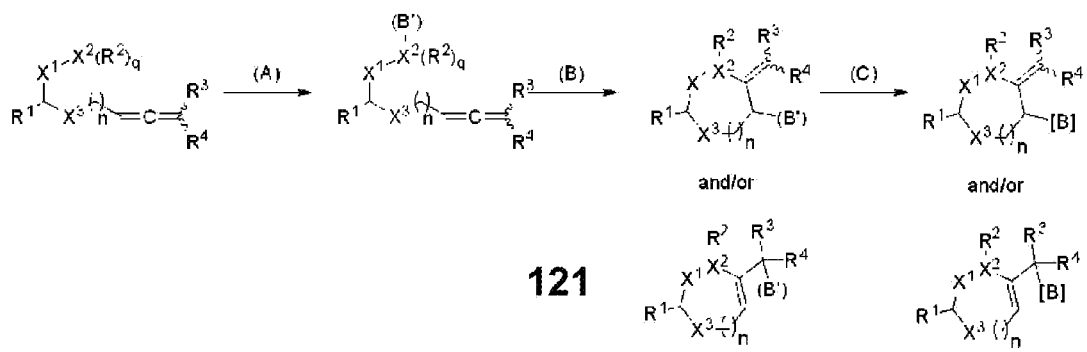
121
Fig. 6.40

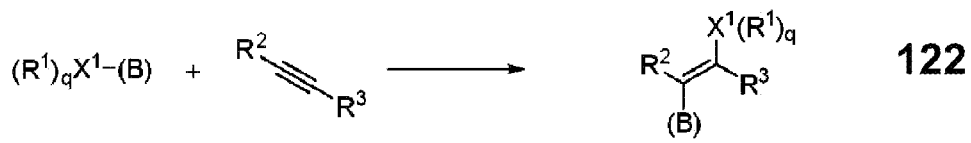
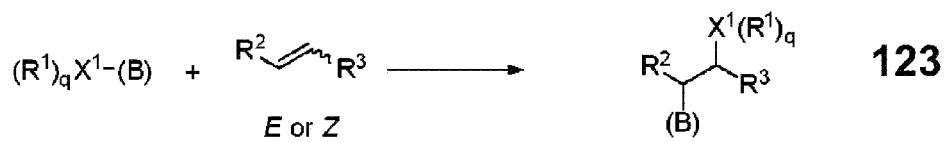
(B) = e.g. 9BBN, Bcat, Bpin
X¹ = O, N
R² and R³ = alkyl, aryl, electron-withdrawing groups e.g. CF₃, esters CO₂Me/Et, heterocycle
Fig. 6.41

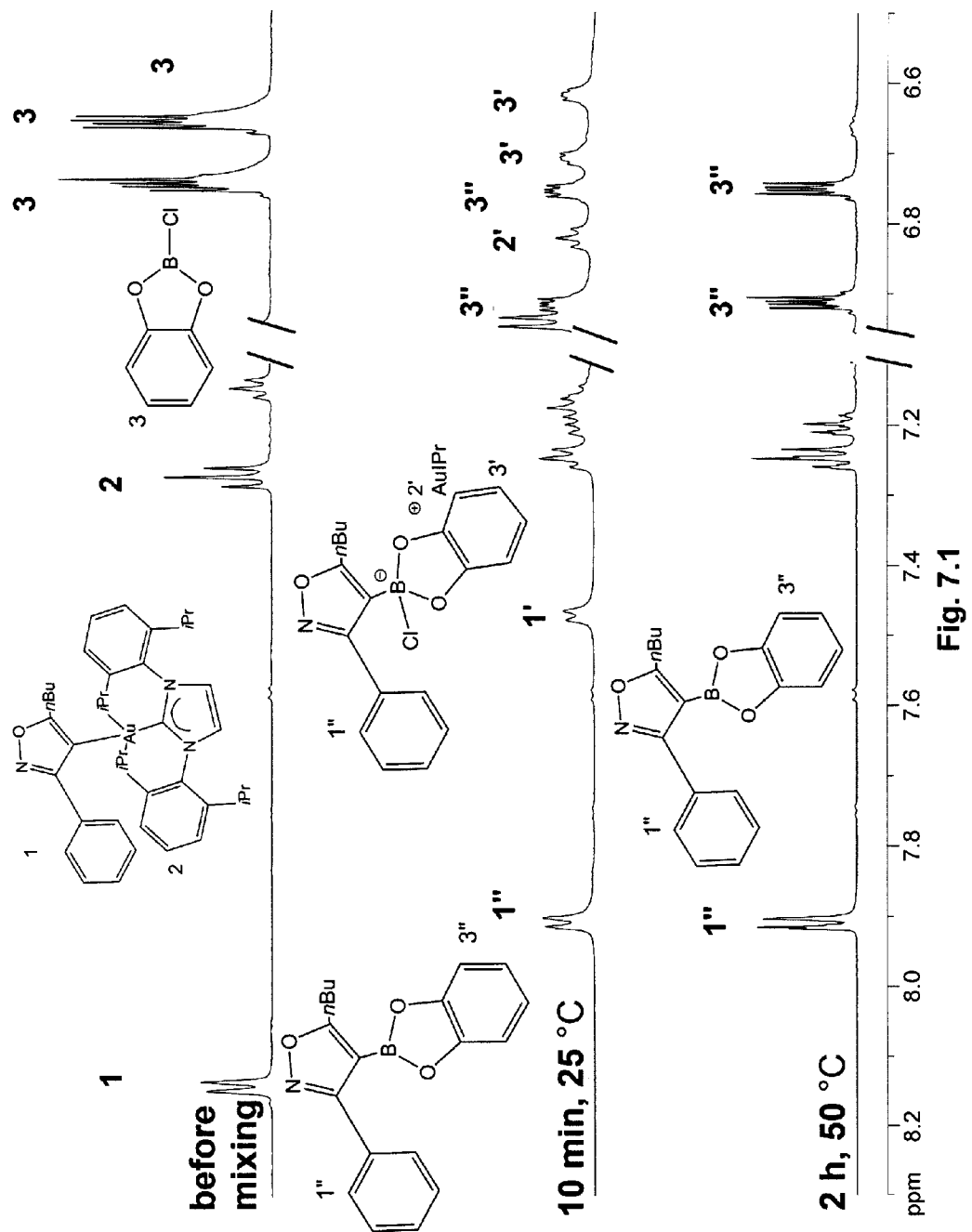
Fig. 7.1

ORGANOBORON COMPOUNDS AND METHODS OF MAKING ORGANOBORON COMPOUNDS

CROSS-REFERENCE TO RELATED APPLICATION

This application is a continuation in part (CIP) of U.S. patent entitled "ORGANOBORON COMPOUNDS AND METHODS OF MAKING ORGANOBORON COMPOUNDS," having Ser. No. 14/303,684, filed on Jun. 13, 2014, which claims priority to U.S. provisional application entitled "BORONIC COMPOUNDS AND METHODS OF MAKING BORONIC COMPOUNDS," having Ser. No. 61/836,391, filed on Jun. 18, 2013, which is entirely incorporated herein by reference. This application also claims priority to U.S. provisional application entitled "BORONIC COMPOUNDS AND METHODS OF MAKING BORONIC COMPOUNDS," having Ser. No. 61/906,040, filed on Nov. 19, 2013, each of which is entirely incorporated herein by reference.

This application also claims priority to U.S. provisional application entitled "BORONIC COMPOUNDS AND METHODS OF MAKING BORONIC COMPOUNDS," having Ser. No. 62/198,410, filed on Jul. 29, 2015, which is entirely incorporated herein by reference.

This application also claims priority to U.S. provisional application entitled "BORONIC COMPOUNDS AND METHODS OF MAKING BORONIC COMPOUNDS," having Ser. No. 62/200,354, filed on Aug. 3, 2015, which is entirely incorporated herein by reference.

FEDERAL SPONSORSHIP

This invention was made with Government support under Contract/Grant No. 1R01GM098512-01, awarded by the National Institutes of Health. The Government has certain rights in this invention.

BACKGROUND

Since the initial report of a hydroboration reaction, the addition of H—B bonds to alkynes has become a widely-used reaction in organic synthesis. The resulting vinyl boranes are versatile intermediates for oxidation, copper-catalyzed conjugate addition, and Suzuki cross-coupling reactions. However, despite the widespread utility of the hydroboration reaction and development of many related X—B bond addition reactions (where X is a non-hydrogen atom), addition by some other types of boron bonds has not been reported.

SUMMARY

Embodiments of the present disclosure provide for methods of making an organoboron compound, organoboron compounds, and the like.

An exemplary embodiment of the present disclosure includes methods, among others, such as those described in the schemes illustrated in FIGS. 1.1A-1.1H and FIGS. 6.14-6.41 and described in the claims.

An exemplary embodiment of the present disclosure includes, among others, a composition, comprising: compounds such as those described in FIGS. 6.1-6.13 as well as the products shown in FIGS. 1.1A-1.1H, and described in the claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1A illustrates Schemes (1) to (3).
FIG. 1.1B illustrates Schemes (4) to (6).
FIG. 1.1C illustrates Schemes (7) to (9).
FIG. 1.1D illustrates Schemes (10) to (12).
FIG. 1.1E illustrates Schemes (13) to (15).
FIG. 1.1F illustrates Schemes (16) to (18).
FIG. 1.1G illustrates Schemes (19) to (22).
FIG. 1.1H illustrates Schemes (23) to (25).
FIG. 1.2 illustrates embodiments of various organoboron compounds made using embodiments of the present disclosure.
FIG. 1.3 illustrates an embodiment of a reaction scheme to form an organoboron compound.
FIG. 1.4 illustrates an embodiment of a reaction scheme to form an organoboron compound.
FIG. 1.5 illustrates embodiments of a reaction scheme to form an organoboron compound and various organoboron compounds.
FIGS. 2.1(*a*) and (*b*) illustrates examples of related B—X bond addition reactivity and an embodiment of a method of the present disclosure.
FIG. 2.2 illustrates a ball and stick figure of an organotrifluoroborate compound.
FIG. 2.3 illustrates an embodiment of various compounds and the corresponding methods.
FIG. 3.1 illustrates an embodiment of a method of making organoboron compounds.
FIG. 4.1 illustrates an oxyboration method of the present disclosure.
FIGS. 5.1A-C illustrate the addition of B-E σ bonds across C—C π bonds.
FIG. 6.1 illustrates the products of Schemes (26) to (29).
FIG. 6.2 illustrates the products of Schemes (30) to (39).
FIG. 6.3 illustrates the products of Schemes (40) to (45).
FIG. 6.4 illustrates the products of Schemes (46) to (49).
FIG. 6.5 illustrates the products of Schemes (50) to (56).
FIG. 6.6 illustrates the products of Schemes (57) to (66).
FIG. 6.7 illustrates the products of Schemes (67) to (74).
FIG. 6.8 illustrates the products of Schemes (75) to (82).
FIG. 6.9 illustrates the products of Schemes (83) to (88).
FIG. 6.10 illustrates the products of Schemes (89) to (97).
FIG. 6.11 illustrates the products of Schemes (98) to (106).
FIG. 6.12 illustrates the products of Schemes (107) to (115).
FIG. 6.13 illustrates the products of Schemes (116) to (121).
FIG. 6.14 illustrates Schemes (26) to (29).
FIG. 6.15 illustrates Schemes (30) to (33).
FIG. 6.16 illustrates Schemes (34) to (37).
FIG. 6.17 illustrates Schemes (38) to (41).
FIG. 6.18 illustrates Schemes (42) to (45).
FIG. 6.19 illustrates Schemes (46) to (47).
FIG. 6.20 illustrates Schemes (48) to (51).
FIG. 6.21 illustrates Schemes (52) to (56).
FIG. 6.22 illustrates Schemes (57) to (62).
FIG. 6.23 illustrates Schemes (63) to (66).
FIG. 6.24 illustrates Schemes (67) to (70).
FIG. 6.25 illustrates Schemes (71) to (74).
FIG. 6.26 illustrates Schemes (75) to (79).
FIG. 6.27 illustrates Schemes (80) to (82).

FIG. 6.28 illustrates Schemes (83) to (85).
FIG. 6.29 illustrates Schemes (86) to (88).
FIG. 6.30 illustrates Schemes (89) to (91).
FIG. 6.31 illustrates Schemes (92) to (94).
FIG. 6.32 illustrates Schemes (95) to (97).
FIG. 6.33 illustrates Schemes (98) to (100).
FIG. 6.34 illustrates Schemes (101) to (103).
FIG. 6.35 illustrates Schemes (104) to (106).
FIG. 6.36 illustrates Schemes (107) to (109).
FIG. 6.37 illustrates Schemes (110) to (112).
FIG. 6.38 illustrates Schemes (113) to (115).
FIG. 6.39 illustrates Schemes (116) to (118).
FIG. 6.40 illustrates Schemes (119) to (121).
FIG. 6.41 illustrates Schemes (122) to (123).
FIG. 7.1 illustrates organogold-to-boron transmetalation via ion pair as shown in Scheme 3, Example 4.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. Different regiochemistry and stereochemistry is also possible, such as products of syn or anti addition could be both possible even if only one is drawn in an embodiment.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom (e.g., a carbon atom) that can be replaced with a selection from the indicated group, provided that the designated atom's normal valence is not exceeded, and that the substitution results in a stable compound. In an embodiment, substituted can refer to substitution of one or more Hs with $CF_3$, CN, $NO_2$, a halogen, an alkyl group (e.g., C1 to C4), an carboxy group (e.g., —C(O)—O—R", where R" can be H or an alkyl group), an amide group (e.g., R"C(O)—N(R")—", where each R" can independently be H or an alkyl group), a thiol group (e.g., —SH), a thioether (e.g., —S—R, where R can be an alkyl group), an alcohol group (e.g., —OH), a carbonyl group (e.g., R"C(O)—, where R" can be H or an alkyl group), an alkoxy group (e.g., —O—R", where R" can be H or an alkyl group), and an amine group (—NR"R", where each R" can independently be H or an alkyl group).

As used herein, "alkyl" or "alkyl group" refers to a linear or branched saturated and unsaturated aliphatic cyclic or acyclic hydrocarbon. Examples of alkyl include, but are not limited to, methyl, ethyl, vinyl, allyl, propyl, butyl, trifluoromethyl, and pentafluoroethyl.

The term "substituted," as in "substituted alkyl", "substituted aryl," "substituted heteroaryl" and the like, in an embodiment can mean that the substituted group may contain in place of one or more hydrogens a group such as alkyl, hydroxy, amino, nitro, halo, trifluoromethyl, cyano, —NH (lower alkyl), —N(lower alkyl)$_2$, lower alkoxy, lower alkylthio, carbonyl, or carboxy, and thus embraces the terms haloalkyl, alkoxy, fluorobenzyl, and the sulfur and phosphorous containing substitutions referred to below, where lower refers to 1 to 6 carbons atoms, for example.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "carbonyl" refers to functional groups such as an amide, ester, ketone, or aldehyde, where each can be substituted or unsubstituted.

The term "carboxy" refers to a subset of carbonyl functional groups such as an amide, carboxylic acid, or ester, where each can be substituted or unsubstituted.

The term "carbocycles" refers to a monocyclic or multicyclic ring system of about 5 to about 14 carbon atoms, preferably of about 6 to about 10 carbon atoms. In an embodiment, carbocycle can refer to an aryl group. Exemplary carbocycles can refer to functional groups such as phenyl and naphthyl. Carbocycles include substituted or unsubstituted carbocycles.

The term "aryl" as used herein, refers to an aromatic monocyclic or multicyclic ring system of about 6 to about 14 carbon atoms, preferably of about 6 to about 10 carbon atoms, substituted or unsubstituted. Exemplary aryl groups include phenyl or naphthyl, or phenyl substituted or naphthyl substituted.

The term "heterocycle" is used herein to denote a ring or fused ring structure of carbon atoms with one or more non-carbon atoms, such as oxygen, nitrogen, and sulfur, in the ring or in one or more of the rings in fused ring structures, substituted or unsubstituted. In an embodiment, heterocycle can refer to a heteroaryl group. Preferred examples are furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, carbazole, thiazole, each of which can be substituted or unsubstituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures, substituted or unsubstituted. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group, substituted or unsubstituted.

The term "fused aryl" refers to a multicyclic ring system as included in the term "aryl," and includes aryl groups and heteroaryl groups that are condensed, substituted or unsubstituted. Examples are naphthyl, anthryl and phenanthryl. The bonds can be attached to any of the rings.

General Discussion

Embodiments of the present disclosure provide for methods of making an organoboron compound, organoboron compounds, and the like. An advantage of an exemplary method (e.g., oxyboration, carboboration, allylboration, amidoboration, thioamidoboration, amidinoboration, alkoxyboration, aminoboration, or thioboration) of the present disclosure is that organoboron compounds can be made that could not be made previously or the synthesis is much more complicated. In addition, exemplary embodiments of the method can be performed in a few steps in a "one-pot" synthesis using temperature or a catalyst to drive the reaction.

FIGS. 1.1A-1.1H and 6.1-6.13 illustrate products formed by reaction schemes (1)-(123). In an exemplary embodiment, a method of the synthesis includes the reactions shown in FIG. 1.1A (Schemes 1-3), FIG. 1.1B (Schemes 4-6), FIG. 1.1C (Schemes 7-9), FIG. 1.1D (Schemes 10-12), FIG. 1.1E (Schemes 13-15), FIG. 1.1F (Schemes 16-18), FIG. 1.1G (Schemes 19-22), FIG. 1.1H (Schemes 23-25), FIG. 6.14 (Schemes 26 to 29), FIG. 6.15 (Schemes 30 to 33), FIG. 6.16 (Schemes 34 to 37), FIG. 6.17 (Schemes 38 to 41), FIG. 6.18 (Schemes 42 to 45), FIG. 6.19 (Schemes 46 to 47), FIG. 6.20 (Schemes 48 to 51), FIG. 6.21 (Schemes 52 to 56), FIG. 6.22 (Schemes 57 to 62), FIG. 6.23 (Schemes 63 to 66), FIG. 6.24 (Schemes 67 to 70), FIG. 6.25 (Schemes 71 to 74), FIG. 6.26 (Schemes 75 to 79), FIG. 6.27 (Schemes 80 to 82), FIG. 6.28 (Schemes 83 to 85), FIG. 6.29 Schemes (86) to (88), FIG. 6.30 (Schemes 89 to 91), FIG. 6.31 (Schemes 92 to 94), FIG. 6.32 (Schemes 95 to 97), FIG. 6.33 (Schemes 98 to 100), FIG. 6.34 (Schemes 101 to 103), FIG. 6.35 (Schemes 104 to 106), FIG. 6.36 (Schemes 107 to 109), FIG. 6.37 (Schemes 110 to 112), FIG. 6.38 (Schemes 113 to 115), FIG. 6.39 (Schemes 116 to 118), FIG. 6.40 (Schemes 119 to 121), FIG. 6.41 (Schemes 122 to 123).

In general, X, $X^1$, $X^2$, $X^3$, Y, [B], (B'), R, $R^1$, $R^2$, $R^3$, $R^4$, $R^5$ $R^6$, $R^7$, and $R^8$ in the reactions scheme and organoboron compounds are described below. In an embodiment, n, y, p, and q can be 0 to 10, 0 to 6, 0 to 3, 1 to 10, 1 to 6, or 1 to 3, or any integer range disclosed therein (e.g., 2 to 8 or 2 to 4).

In an embodiment, [B] can be $BX^2_{(1\ or\ 2)}$, where $X^2$ can independently selected from: catecholate, pinacolate, ethylene glycolate, 1,3-propanediolate, N-methyliminodiacetate, 2,2'-azanediyldiethanolate, fluoride, chloride, bromide, hydrogen, hydroxide, acetate, 9-Borabicyclo[3.3.1]nonane (9-BBN), diisopinocampheyl (Ipc), 1,8-diaminonaphthalene, or similar compounds, each of which can be substituted or unsubstituted. It should be noted that (B') is used to illustrate that one or more groups can be substituted to obtain a more stable product. In this regard, (B') can be the same as [B] or can have a group (X or $X^2$) that is more accommodating to the cyclization reaction, where the group can be substituted to form the product depending upon the stability or other considerations of the product.

In an embodiment, [B] of [B]—X can be $BX^2_{(1\ or\ 2)}$, where $X^2$ can be catecholate, pinacolate, ethylene glycolate, 1,3-propanediolate, N-methyliminodiacetate, 2,2'-azanediyldiethanolate, fluoride, chloride, bromide, hydrogen, hydroxide, acetate, 9-Borabicyclo[3.3.1]nonane (9-BBN), diisopinocampheyl (Ipc), 1,8-diaminonaphthalene, or similar compounds, each of which can be substituted or unsubstituted. In an embodiment, X can be a H, halide, acetoxy (OAc), trifluoroacetate (TFA), tosylate (OTs), mesylate (OMs), or triflate (OTf).

In an embodiment, Y can be $CH_2$, CRH, $CR_2$, NR, O, S, PR or $SiR_2$, where R can be H, a carbonyl functional group (substituted or unsubstituted) (e.g., 1 to 6 carbons), a carboxy functional group (substituted or unsubstituted) (e.g., 2 to 6 carbons), a carbocycle group (substituted or unsubstituted) (e.g., 4 to 8 carbons), a heterocycle (substituted or unsubstituted) (e.g., 4 to 8 carbons), a halide (fluoride, chloride, bromide, iodide), and an alkyl group (substituted or unsubstituted) (e.g., 1 to 6 carbons).

In an embodiment, the carbonyl functional group can be a moiety selected from: a ketone, or an aldehyde, each of which can be substituted or unsubstituted.

In an embodiment, the carboxy functional group can be a moiety selected from: an ester, a carboxylic acid, or an amide, each of which can be substituted or unsubstituted.

In an embodiment, the carbocycle or heterocycle group can be a moiety selected from: phenyl, naphthyl, furan, pyrrole, thiophene, benzofuran, indole, benzothiophene, pyridine, quinoline, isoquinoline, oxazole, benzoxazole, isoxazole, triazole, pyrroline, pyrrolidine, imidazole, imidazoline, pyrazole, pyran, piperidine, dioxane, morpholine, pyrimidine, pyridazine, pyrazine, indolizidine, isoindole, indoline, benzimidazole, or carbazole, thiazole, each of which can be substituted or unsubstituted.

In an embodiment, the alkyl group can be a C1 to C10 hydrocarbon. For example the alkyl group can be: methyl, ethyl, vinyl, allyl, propyl, butyl, trifluoromethyl, or pentafluoroethyl, each of which can be substituted or unsubstituted.

In an embodiment, R can be H, a carbonyl functional group (substituted or unsubstituted) such as a C1 to C6 ketone, a C3 to C6 ketone, a C2 to C6 carboxylic acid, a C3 to C6 ester, a C3 to C6 amide, a C4 to C8 carbocycle group (substituted or unsubstituted), a C4 to C8 heterocycle (substituted or unsubstituted), fluoride, chloride, bromide, iodide, and a C1 to C6 alkyl group (substituted or unsubstituted).

In an embodiment, each of R, $R^1$, $R^2$, $R^3$, $R^4$, $R^5$, $R^6$, $R^7$, or $R^8$ (as well as other none-defined R groups), can independently be selected from: H, a carbonyl functional group (substituted or unsubstituted), a carbocycle group (substituted or unsubstituted), a heterocycle (substituted or unsubstituted), a halide (fluoride, chloride, bromide, iodide), an alkyl group (cyclic or acyclic; substituted or unsubstituted), an alkenyl group (cyclic or acyclic; substituted or unsubstituted), $CF_3$, CN, $NO_2$, an aryl group (substituted or unsubstituted), a heteroaryl group (substituted or unsubstituted), a sulfonyl group, a boryl group, an ether group, a thioether group, a silyl group, an ester group, an amide group, an alkoxy group, a thiol group, an alcohol group, or an amine group. In an embodiment, each of R, $R^1$, $R^2$, $R^3$, $R^4$, $R^5$, $R^6$, $R^7$, or $R^8$ (as well as other yet defined R groups), can independently be selected from: H, a C1 to C6 carbonyl functional group (substituted or unsubstituted), a C4 to C8 carbocycle group (substituted or unsubstituted), a C4 to C8 heterocycle (substituted or unsubstituted), fluoride, chloride, bromide, iodide, a C1 to C8 alkyl group (cyclic or acyclic; substituted or unsubstituted), a C2 to C8 alkenyl group (cyclic or acyclic; substituted or unsubstituted). Any and all individual combinations of moieties of R, $R^1$, $R^2$, $R^3$, $R^4$, $R^5$, $R^6$, $R^7$, and/or $R^8$ are intended to be covered even if not specifically recited (e.g., $R^1$ is a carbonyl functional group, $R^2$ is a hydrogen, $R^3$ is a heterocycle; $R^1$ is a hydrogen, $R^2$ is a carbocycle group, $R^3$ is a heterocycle; $R^1$ is a chloride, $R^2$ is a alkyl group, $R^3$ is a heterocycle; and so on).

In an embodiment, adjacent R groups (e.g., $R^1$, $R^2$, $R^3$, $R^4$, $R^5$, $R^6$, $R^7$, and/or $R^8$, specifically the pair of $R^1$ and $R^2$) together with the carbon atoms they are attached to, can form a cyclic moiety (e.g., C1 to C10, aromatic or non-aromatic (e.g., hetero or nonhetero)). In an embodiment, one or more $R^3$, $R^4$, $R^5$, $R^6$, and $R^7$ moieties, where attached to a cyclic moiety, can be attached to the ring, where if more than one $R^3$, $R^4$, $R^5$, $R^6$, and/or $R^7$ moiety is present, each moiety can be independently selected. In embodiments where only one R group (e.g., $R^6$ and $R^7$) is attached to the ring, that R group represents one or multiple R groups that can be attached to the ring, where each R group is independently selected.

In embodiments having a "curved line" between groups such as R groups (e.g., $R^1$ and $R^2$), the curved line can represent a carbon chain (($CH_2)_q$, where q can be 0 to 10) that can include zero or more heteroatoms (e.g., $(CH_2)_qO$ $(CH_2)_q$ or $(CH_2)_qNH(CH_2)_q$)).

In an embodiment, X can be O, S, or —C(O)O—. —C(O)O— can be present in a ring so that the ring is a heterocyclic ring. In an embodiment X is O. In an embodiment X is S.

In an embodiment, Y can be NR, O, S, $SiR^2$, or $CR^7R^8$. In an embodiment Y is NR. In an embodiment Y is O. In an embodiment Y is S. In an embodiment Y is $SiR^2$. In an embodiment Y is $CR^7R^8$.

In an embodiment, $X^1$ can be O, NR, S, or $CR^1R^2$, where each of R, $R^1$, $R^2$, is independently selected from: H, a carbonyl functional group (e.g. C1 to C6), a carbocycle group (e.g. C4 to C8), a heterocycle (e.g. C4 to C8), a halide, or an alkyl group (e.g. C1 to C6), where, optionally, each can be substituted or unsubstituted.

Any and all individual combinations of moieties of R, $R^1$, $R^2$, $R^3$, $R^4$, $R^5$, $R^6$, $R^7$, $R^8$, Y, [B], (B'), $X^1$, $X^2$, $X^3$, and/or $X^4$, are intended to be covered by the structures provided herein even if the specific combination is not recited. Each and every combination of R, $R^1$, $R^2$, $R^3$, $R^4$, $R^5$, $R^6$, $R^7$, $R^8$, Y, [B], (B'), X, $X^1$, $X^2$, $X^3$, and/or $X^4$ has not been individually provided for sake of clarity.

In an embodiment, the methods of making an organoboron compound can use a catalyst or reagent to produce the organoboron compound products. In an embodiment the catalyst can include a metal catalyst such as a Lewis acid metal catalyst or another reagent or mediator that includes a metal. In general, the catalyst can include a metal (M) such as a transition metal salt (e.g., Cu, Ag, Au, Ni, Pd, Pt, In, Co, Rh, Ir, Ga, and Fe). In an embodiment, the metal can be supported by ligands such as phosphine oxides, aryl phosphines, alkyl phosphines, 1,10-phenanthroline, AsR3, (R)-Binaphane, dialkyl monoaryl phosphines, or N-heterocyclic carbene ligands. The counter anion can include anions such as trifluoroacetate, tosylate, mesylate, bis(trifluoromethylsulfonyl)amide, triflate, perchlorate, tetrafluoroborate, hexafluorophosphate, tetrakis(pentafluorophenyl)borate, acetate, halides, tetrakis(3,5-bis(trifluoromethyl)phenyl)borate.

In an embodiment, the catalyst can be of the form where $L_n$-M-$X_y$, can be selected from P(OAr)$_3$ (e.g.,

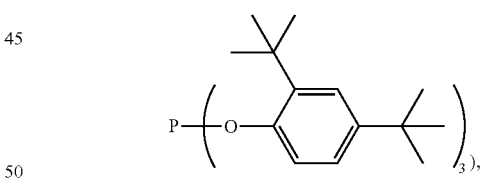

PAr$_3$ (e.g., PPh$_3$), PR$_3$ (e.g., P(tBu)$_3$), PArR$_2$, (e.g.,

PAr$_2$R, and NHC ligands (e.g., IMes, IPr, SIMes, SIPr, 1,10-phenanthroline, AsR3, (R)-Binanphane), M can be selected from Cu, Ag, Au, Ni, Pd, Pt, In, Co, Rh, Ir, Ga, Fe, and the like, and X can be selected from TFA, NTf$_2$, OTf, OTs, OMs, ClO$_4$, BF$_4$, PF$_6$, SbF$_6$, B(C$_6$F$_5$)$_4$, OAc, halides, and

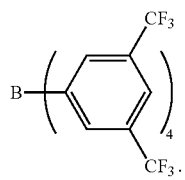

In particular, the catalyst can be of the form LMX, where L can be IPr (NHC ligands), PPh$_3$, P(Ar)$_3$, P(alkyl)$_3$, 1,10-phenanthroline, AsR$_3$, (R)-Binaphane, or include no ligand, M can be selected from Au, Cu, and Ag, and X can be selected from TFA, OTf, OTs, NTf$_2$, OAc, BF$_4$, SbF$_6$, ClO$_4$, F, Cl, Br, I, BArF ([B[3,5-(CF$_3$)$_2$C$_6$H$_3$]$_4$], and B(C$_6$F$_5$)$_4$). In addition, the catalyst can be of the form L$_n$MX$_2$, where n is 0, 1, or 2, L can be selected from IPr (NHC ligands), PPh$_3$, P(Ar)$_3$, P(alkyl)$_3$, 1,10-phenanthroline, AsR$_3$, (R)-Binaphane, M can be selected from Cu, Pd, Fe, Ni, and Pt, and X can be selected from TFA, OTf, OTs, NTf$_2$, OAc, BF$_4$, SbF$_6$, ClO$_4$, F, Cl, Br, I, BArF ([B[3,5-(CF$_3$)$_2$C$_6$H$_3$]$_4$], or B(C$_6$F$_5$)$_4^-$). Furthermore, the catalyst can be L$_n$MX$_3$, where n can be 1 or 3, L can be selected from IPr (NHC ligands), PPh$_3$, P(Ar)$_3$, P(alkyl)$_3$, 1,10-phenanthroline, AsR$_3$, and (R)-Binaphane, M can be selected from Au, Fe, Ag, In, Ga, and Sn, and X can be selected from TFA, OTf, OTs, NTf$_2$, OAc, BF$_4$, SbF$_6$, ClO$_4$, F, Cl, Br, I, BArF ([B[3,5-(CF$_3$)$_2$C$_6$H$_3$]$_4$], B(C$_6$F$_5$)$_4$), EtAlCl$_2$, and B(C$_6$F$_5$)$_3$. In an embodiment, the catalyst can include IPrAuTFA, IPrAuOTs, IPrAuOH, IPrAuCl, IPrAuCl/NaTFA, CuOTf, CuI, CuTFA, IPrCuCl, IPrAuCl/AgOTf, IPrCuCl/AgTFA, IPrAuCl/AgOTs, IPrAuCl/AgTFA, IPrAuOTf, PEPPSI-IPr/AgOTf, PdCl$_2$(PPh$_3$)$_2$/AgOTf, PPh$_3$AuTFA, PPh$_3$AuCl/NaTFA, or CuCN*2LiCl, as well Na salts of each of these where Ag is replaced with Na.

In general, reaction schemes (1)-(123) to produce the organoboron compounds of the present disclosure can be formed using the following general guidelines. The following general reaction parameters can be used to perform reaction schemes (1)-(123) to form the products of the present disclosure. In an exemplary embodiment, the reactant(s) (e.g., such as those in schemes (1) to (123)) can be first reacted with a base, such as NaH, KH, CaH$_2$, sodium dimsyl, sodium pentadieneide, diethyl zinc, or n-butyl-lithium or a transmetallation partner such as iPrMgCl in an appropriate solvent, such as toluene, benzene, hexane, dichloroethane, dichloromethane, tetrahydrofuran, cyclopentyl methyl ether, tert-butyl methyl ether, diethyl ether, or triethylamine at a temperature in the range of about −78° C. to 50° C. for less than 1 minute to about 30 minutes.

Next, the mixture can be reacted with a salt of BX$^2_{(1\ or\ 2)}$ at about room temperature for about 10 to 60 minutes. Then the mixture can be, optionally, reacted with a Lewis acid metal catalyst or stoichiometric reagent at a temperature of about 25° C. to 110° C. for about 1 to 24 hours. In some instances, a promoter, such as the sodium, potassium, lithium, and silver salts of trifluoroacetic acid, p-toluenesulfonic acid, triflic acid, bis(trifluoromethane)sulfonimide, hexafluoroantimonic acid, hexafluorophosphoric acid, or tetrafluoroboric acid, may also be used. Alternatively to using a catalyst, the mixture can be heated to a temperature of about 75 to 130° C. to initiate the reaction for about 15 to 48 hours.

Optionally, for some substrates the mixture can be reacted with a compound of BX$^2_{(1\ or\ 2)}$ at about 25° C. to 110° C. for about 1 to 24 hours in the presence of a Lewis acid metal catalyst or stoichiometric reagent. In an embodiment, the substrates could be selected from the above lists containing esters (COOR like COOCH$_3$ or thioethers SR, SCH$_3$). In some instances, a promoter, such as the sodium, potassium, lithium, and silver salts of trifluoroacetic acid, p-toluenesulfonic acid, triflic acid, bis(trifluoromethane)sulfonimide, hexafluoroantimonic acid, hexafluorophosphoric acid, or tetrafluoroboric acid, may also be used. Alternatively to using a catalyst, the mixture can be heated to a temperature of about 50 to 130° C. to initiate the reaction for about 15 to 540 hours.

Optionally, the cyclic organoboron compound (e.g., such as those with (B')) can be reacted with a diol, such as pinacol, or with acidic or basic or neutral water, or with a diacid such as N-methyliminodiacetic acid, or with an ionic salt, such as potassium bifluoride, and an amine such as trimethylamine in an appropriate solvent, such as toluene, benzene, dichloroethane, dichloromethane, tetrahydrofuran, cyclopentyl methyl ether, diethyl ether, trimethylamine, or triethylamine at a temperature of about 25° C. to 110° C. for 30 to 180 minutes to form a final cyclic organoboron compound.

The order of the steps and the order of the addition of additives, promoters, catalysts, and stoichiometric reagents can be adjusted or changed so long as the products are still produced. In an embodiment, the conversion can be greater than about 90% or greater than about 95%.

In an embodiment, the amount of Lewis acid metal catalyst used can be about 1 mol % to about 25 mol % or about 2.5 mol % to about 10 mol %. The amount of a stoichiometric Lewis acid metal reagent can be about 30 mol % to about 100 mol %. The concentrations of the components can be adjusted accordingly depending upon the reactants, products, temperature, pH, reaction time, and the like. Examples 1-4 and schemes (1)-(123) illustrates an exemplary method and compounds formed using an embodiment of the method.

FIGS. 1.1A-1.1H and 6.1-6.13 illustrate embodiments of various organoboron compounds that can be made using reaction schemes (1)-(123). X, X$^1$, X$^2$, X$^3$, Y, [B], (B'), R, R$^1$, R$^2$, R$^3$, R$^4$, R$^5$ R$^6$, R$^7$, and R$^8$ as well as n, y, p, and q are defined above. Now having described the reactions and products in general, additional detail will be described below.

Schemes (1) to (3) illustrate the formation of the organoboron products where the starting compound includes C=O, C=N, or C=S and the C—C multiple bond is an alkyne.

Schemes (4) to (6) illustrate the formation of the organoboron products where the starting compound includes an alcohol, amine, or a thiol and the C—C multiple bond is an alkyne.

Schemes (7) to (9) illustrate the formation of the organoboron products where the starting compound includes C=O, C=N, or C=S and the C—C multiple bond is an alkene.

Schemes (10) to (12) illustrate the formation of the organoboron products where the starting compound includes an alcohol, amine, or a thiol and the C—C multiple bond is an alkene.

Schemes (13) to (15) illustrate the formation of the organoboron products where the starting compound includes C=O, C=N, or C=S and the C—C multiple bond is an allene.

Schemes (16) to (18) illustrate the formation of the organoboron products where the starting compound includes an alcohol, amine, or a thiol and the C—C multiple bond is an allene.

Schemes (19) to (22) illustrate the formation of the organoboron products through an intermolecular reaction where the starting compound includes an alcohol, amine, or a thiol and the C—C multiple bond is an alkyne, alkene, or allene.

Schemes (23) to (25) illustrate the formation of the organoboron products through an intermolecular reaction where the starting compound includes $X^4$ (a halide or pseudohalide), $X^3$ (any non-hydrogen atom), and the C—C multiple bond is an alkyne or alkene.

Schemes (26) to (37) illustrate the formation of the organoboron products through an oxyboration reaction. $R^1$, $R^2$, $R^3$, $R^4$, [B], Y, and n are defined above. The reaction can be initiated using a catalyst, such as those described herein or temperature (e.g., about 110 to 130° C.) without the use of a catalyst.

The following reaction provides mechanistic illustration of the reaction that may occur in schemes (26) to (37).

Activated Substrates: With and Without Catalysts

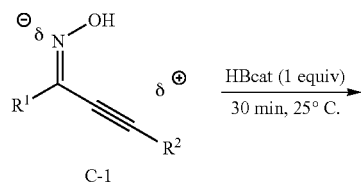

C-1

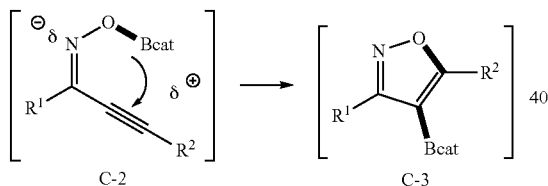

C-2　　　　　C-3

Illustrative examples products that can be produced using schemes (26) to (37) include:

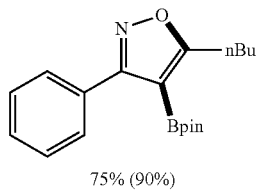

4a

75% (90%)

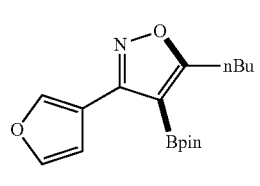

4b

71% (85%)

-continued

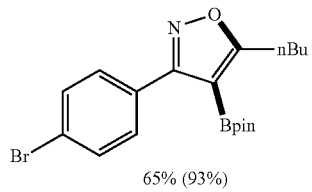

4c

65% (93%)

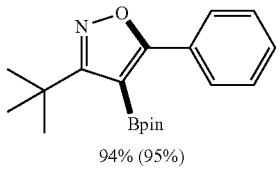

4d

94% (95%)

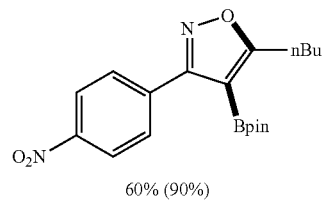

4e

60% (90%)

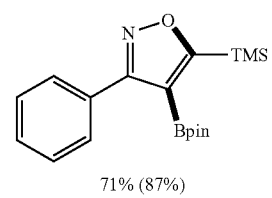

4f

71% (87%)

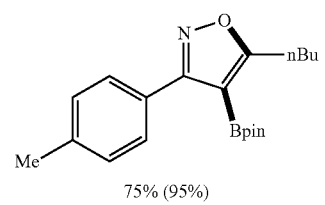

4g

75% (95%)

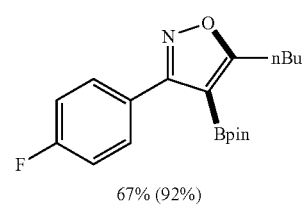

4h

67% (92%)

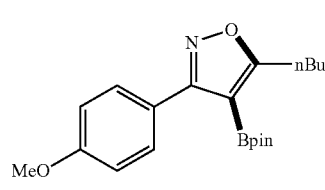

4i

74% (92%)

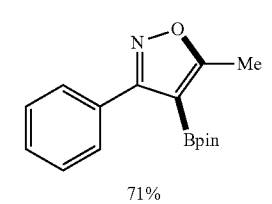

4j

71%

-continued

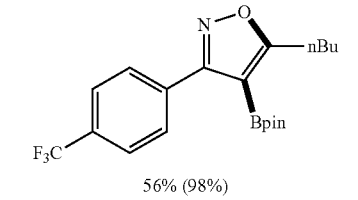

4j

56% (98%)

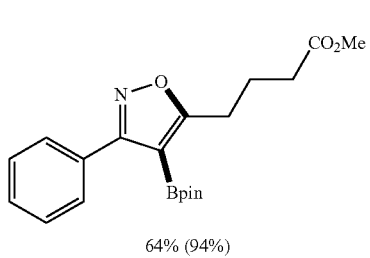

4k

64% (94%)

Schemes (38) to (41) illustrate the formation of the organoboron products through an oxy/thioboration reaction across alkynes. $R^1$, $R^2$, $R^3$, $R^6$, $R^7$, $R^8$, [B], X, Y, p, and n are defined above. The reaction can be initiated using a catalyst, such as those described herein or temperature (e.g., about 110 to 130° C.) without the use of a catalyst.

The following reaction provides an illustration of the reaction that may occur in schemes (38) to (41) as well as products.

Sample Reaction Sequence

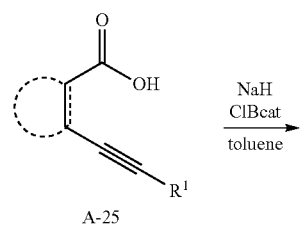

A-25

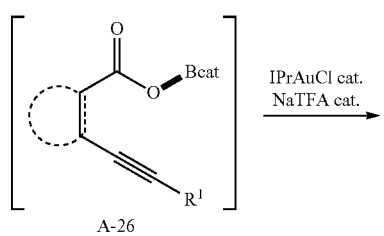

A-26

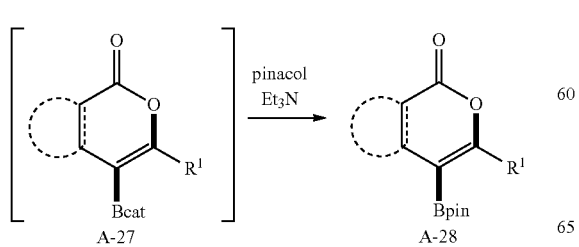

A-27    A-28

-continued

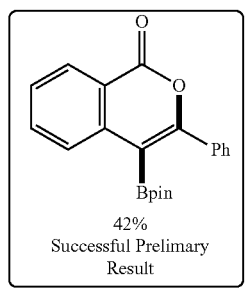

A-28a

42% Successful Prelimary Result

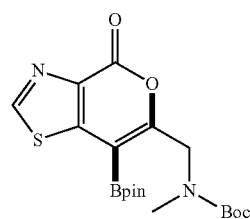

A-28b

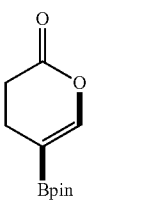

A-28c

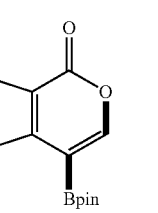

A-28d

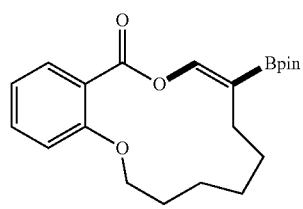

A-28e

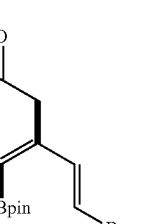

A-28f

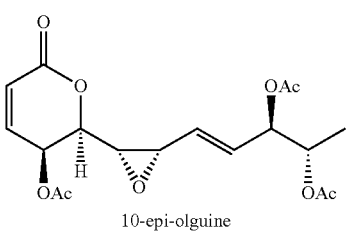

A-29

10-epi-olguine

Second Reaction Sequence

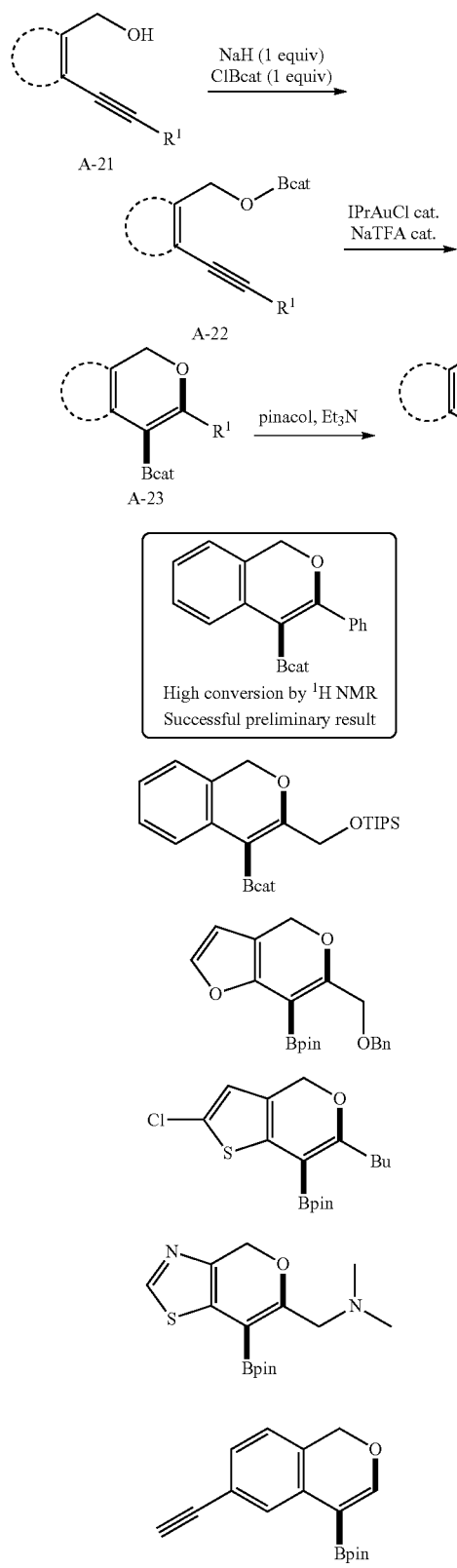

High conversion by ¹H NMR
Successful preliminary result

A-23a

A-24a

A-24b

A-24c

A-24d

A-24de

Schemes (42) to (45) illustrate the formation of the organoboron products through an oxy/thioboration reaction across alkenes. $R^1$, $R^2$, $R^3$, $R^4$, $R^5$, $R^6$, $R^7$, $R^8$, [B], X, Y, p, and n are defined above. The reaction can be initiated using a catalyst, such as those described herein or temperature (e.g., about 110 to 130° C.) without the use of a catalyst.

Schemes (46) to (49) illustrate the formation of the organoboron products through an oxy/thioboration reaction across allenes. $R^1$, $R^2$, $R^3$, $R^4$, $R^5$, $R^6$, $R^7$, $R^8$, [B], X, Y, p, and n are defined above. The reaction can be initiated using a catalyst, such as those described herein or temperature (e.g., about 110 to 130° C.) without the use of a catalyst.

The following reaction provides an illustration of the reaction that may occur in schemes (46) to (49) as well as products.

Sample Reaction Sequence

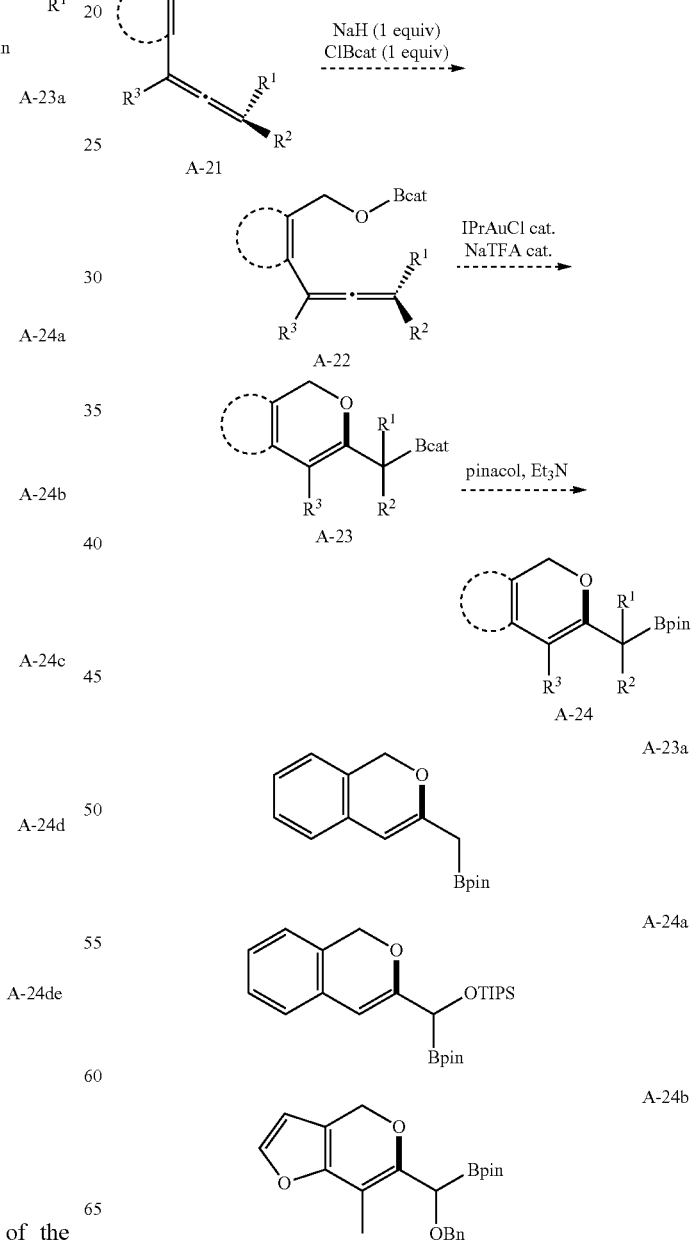

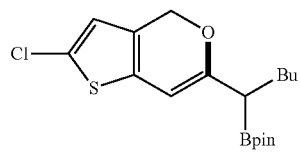
A-24c

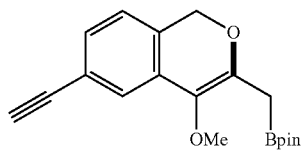
A-24e

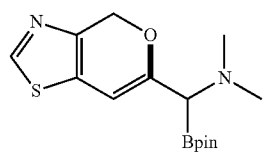
A-24d

Schemes (50) to (53) illustrate the formation of the organoboron products through formal borylation across alkynes. $R^1$, $R^2$, $R^3$, $R^4$, $R^5$, $R^6$, $R^7$, $R^8$, [B], X, Y, p, and n are defined above. The reaction can be initiated using a catalyst, such as those described herein or temperature (e.g., about 45° C. to 130° C.) without the use of a catalyst.

The following reaction provides an illustration of the reaction that may occur in schemes (50) to (53) as well as products.

Sample Reaction Sequence

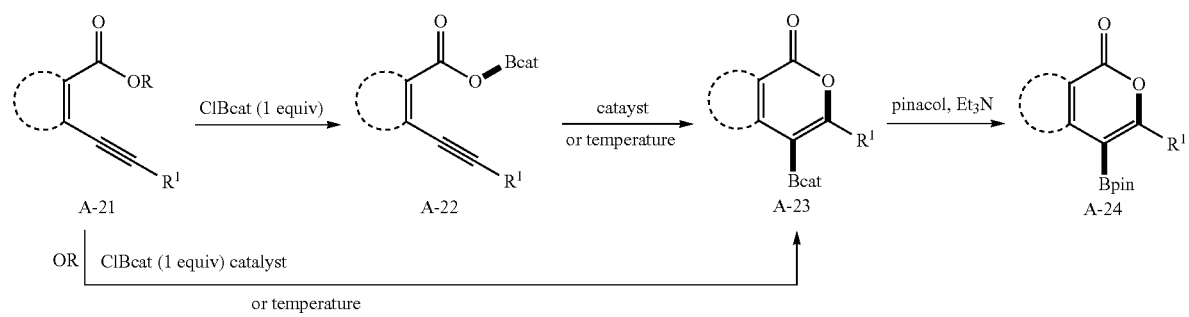

A-23a

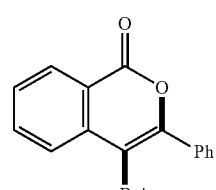

75% isolated yield
successful result

A-24a

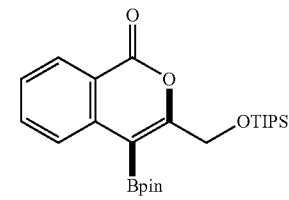

A-24b

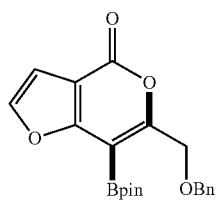

A-24c

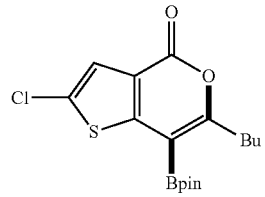

A-24d

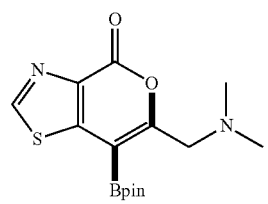

A-24e

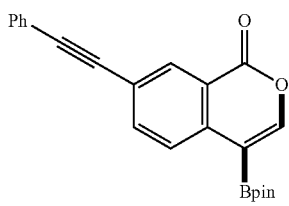

66% isolated yield
successful result

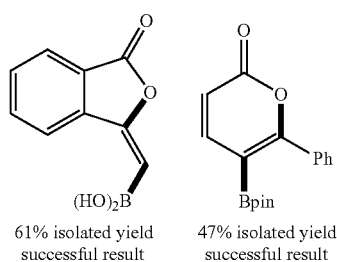

61% isolated yield
successful result

47% isolated yield
successful result

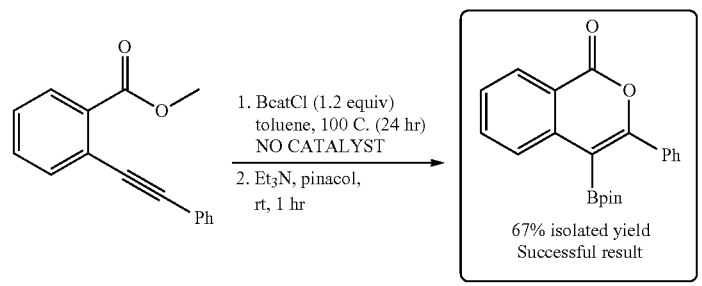

67% isolated yield
Successful result

Scheme (54) illustrates the formation of the organoboron products through intermolecular carboboration via boron enolates. $R^1$, $R^2$, $R^3$, $R^4$, $R^5$, and [B]—X are defined above. The reaction can be initiated using a catalyst, such as those described herein or temperature (e.g., about 110 to 130° C.) without the use of a catalyst.

The following reaction provides an illustration of the reaction that may occur in scheme (54) as well as products.

Ex:

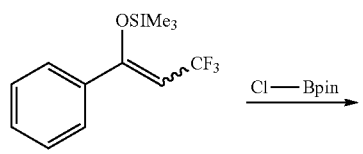

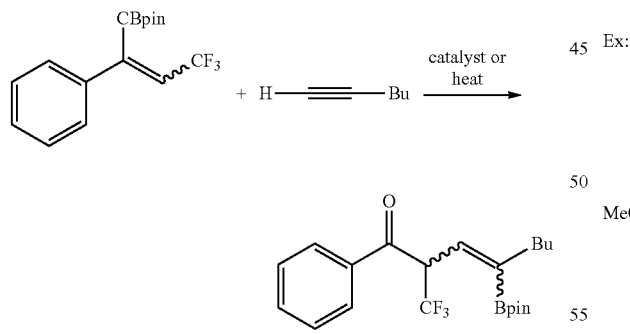

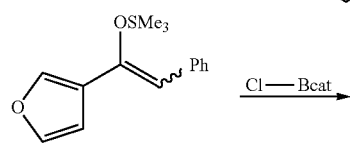

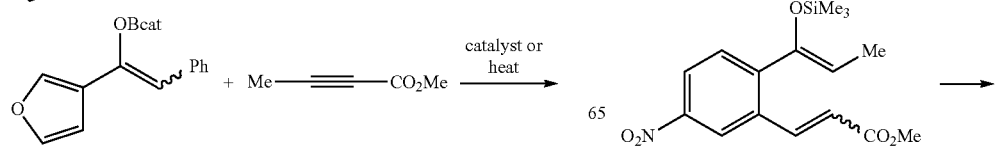

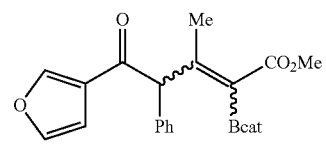

Schemes (55) to (78) illustrate the formation of the organoboron products through intermolecular carboboration via boron enolates. $R^1$, $R^2$, $R^3$, $R^4$, $R^5$, and [B]—X are defined above. The reaction can be initiated using a catalyst, such as those described herein or temperature (e.g., about 110 to 130° C.) without the use of a catalyst.

The following reactions provide an illustration of the reaction that may occur in schemes (55) to (78) as well as products.

Ex:

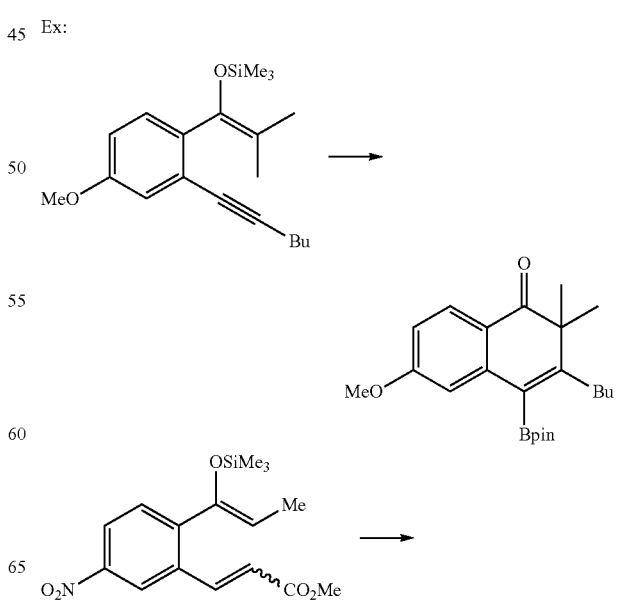

Ex
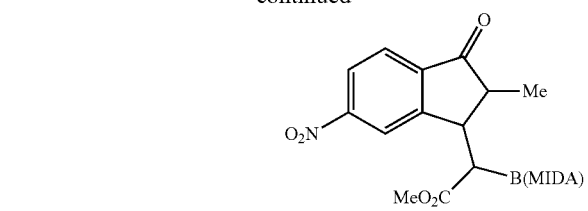

Ex
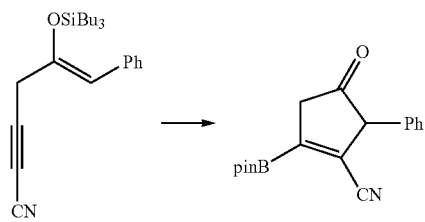

Ex
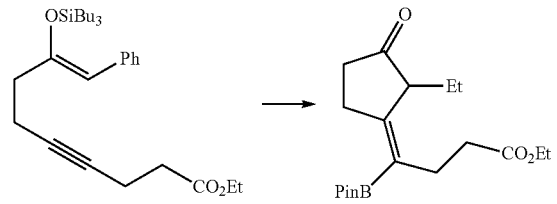

Ex
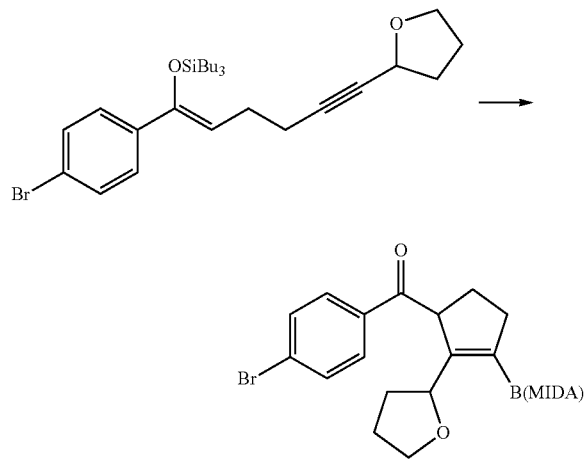

Ex
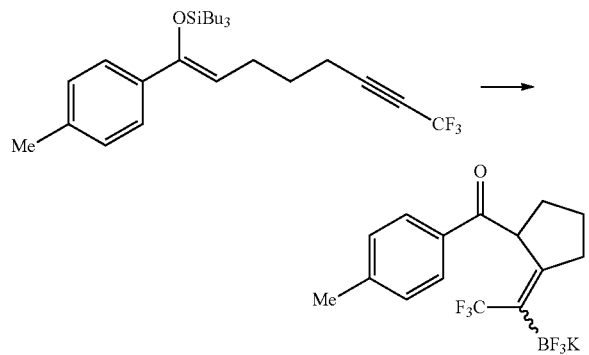

Ex
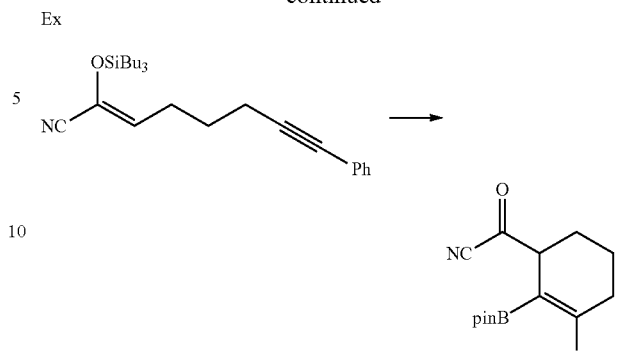

Ex
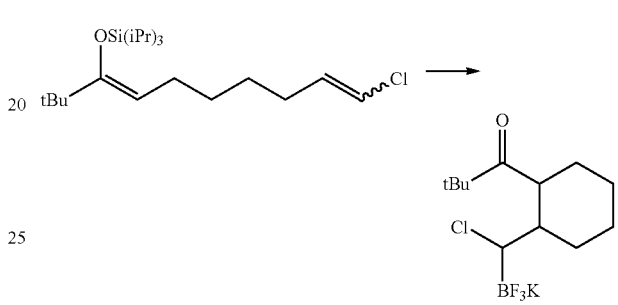

Scheme (79) illustrates the formation of the organoboron products through a tandem allylboration/oxyboration reaction. $R^1$, $R^2$, $R^3$, (B'), and [B] are defined above. The reaction can be initiated using a catalyst, such as those described herein or temperature (e.g., about 110 to 130° C.) without the use of a catalyst.

The following reactions provide an illustration of products that may result for a reaction as shown in scheme (79).

examples

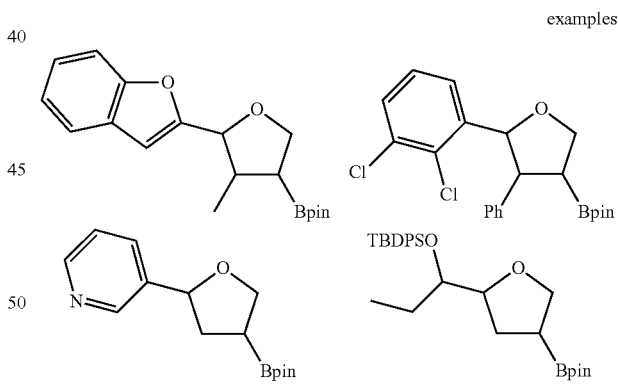

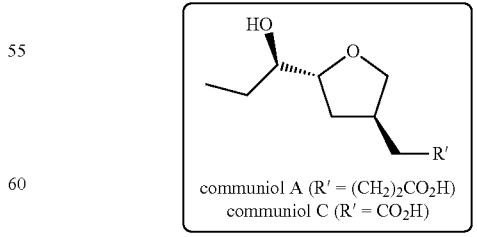

communiol A (R' = (CH$_2$)$_2$CO$_2$H)
communiol C (R' = CO$_2$H)

Schemes (80) to (103) illustrate the formation of the organoboron products through an aminoboration reaction. $R^1$, $R^2$, $R^3$, $R^4$, $R^5$, $R^6$, $R^7$, $R^8$, [B], X1, X2, q, and n are defined above. The reaction can be initiated using a catalyst, such as those described herein or temperature (e.g., about 110 to 130° C.) without the use of a catalyst.

The following reactions provide an illustration of products that may result for a reaction according to schemes (80) to (103) as well as products.

Successful Borylated Indole Examples (X$^1$=N, X$^2$=none, n=0)

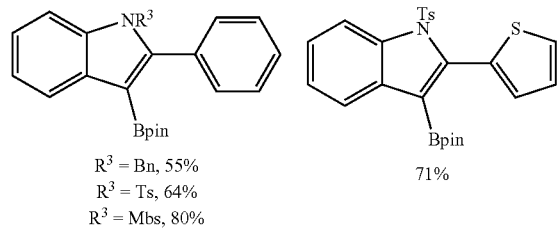

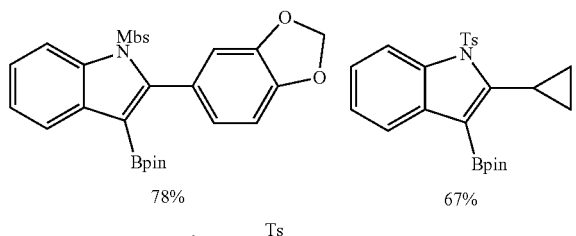

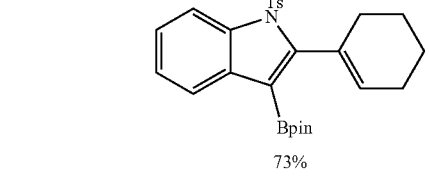

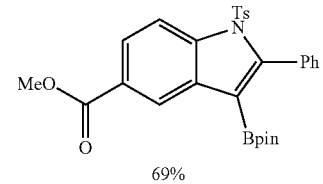

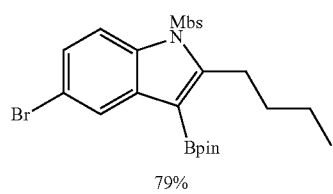

Protecting-Group-Free Borylated Indole Examples (X$^1$ = N, X$^2$ = none, R$^3$ = Bcat, n = 0)

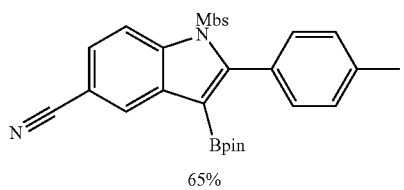

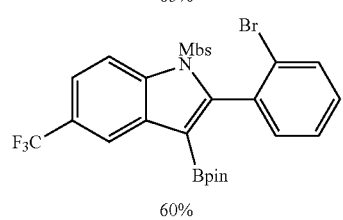

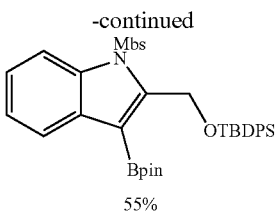

Borylated Dihydropyrrole Examples (X$^1$ = N, X$^2$ = none, R$^1$ & R$^2$ = H, n = 0)

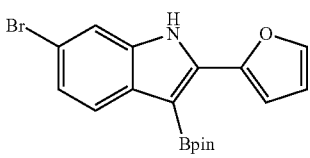

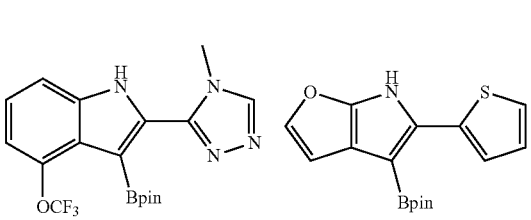

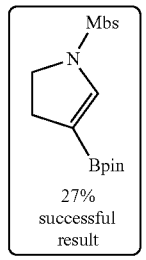

Borylated 1,4-Dihydroquinoline Examples (X$^1$ = N, X$^2$ = none, n = 1)

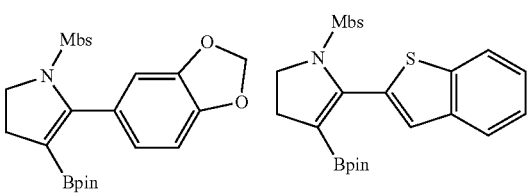

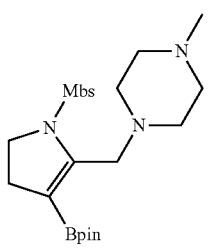

Chiral Borylated Tetrahydroquinoline Possibility

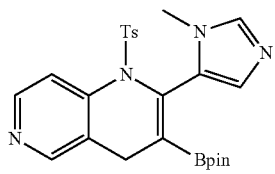

-continued

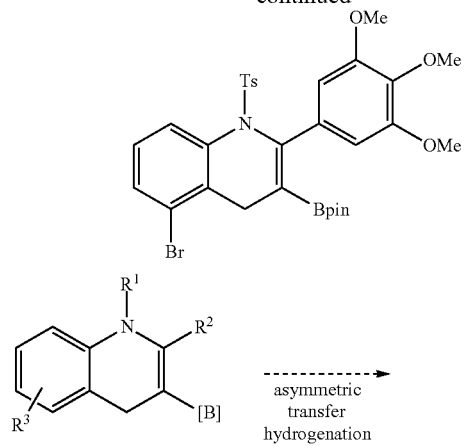

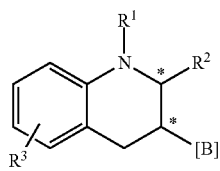

Schemes (104) to (123) illustrate the formation of the organoboron products through amidoboration/thioamidoboration/amidinoboration reactions. $R^1$, $R^2$, $R^3$, $R^4$, $R^5$, $R^6$, $R^7$, $R^8$, [B], X1, X2, q, and n are defined above. The reaction can be initiated using a catalyst, such as those described herein or temperature (e.g., about 110 to 130° C.) without the use of a catalyst.

The following reactions provide an illustration of reactions and products that may result for a reaction according to schemes (104) to (123) as well as products.

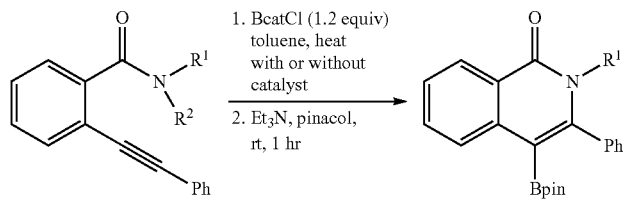

$R^1$ and $R^2$ can be H or alkyl

Borylated Pyridone and Isoquinolinone Examples ($X^1$ = O, $X^2$ = N, $X^3$ = none, n = 0)

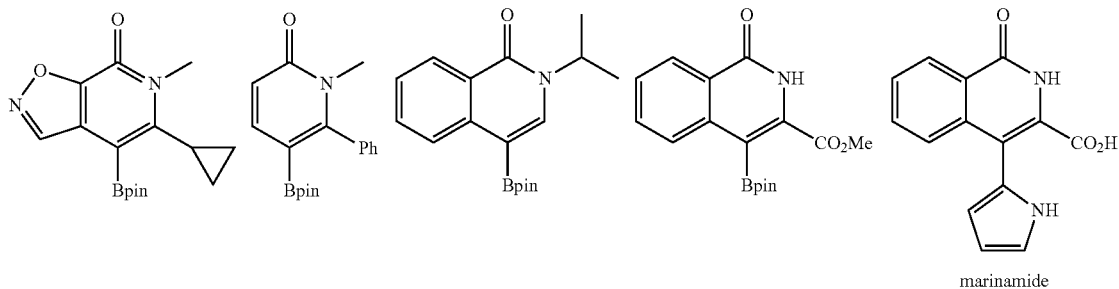

marinamide

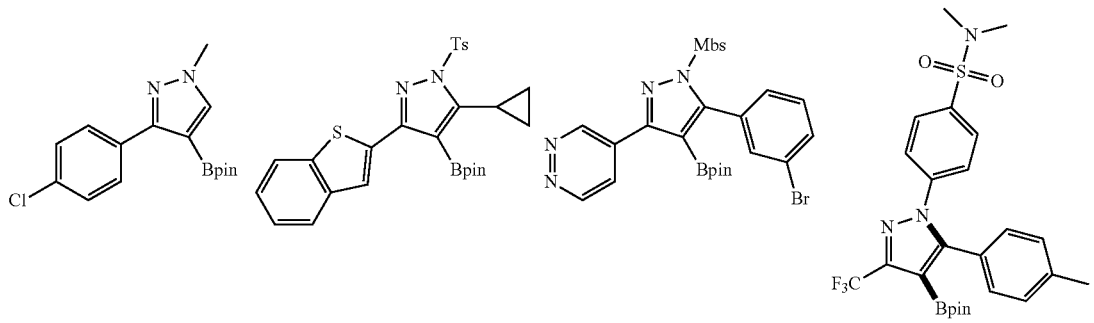

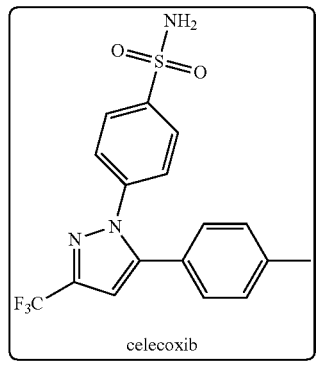

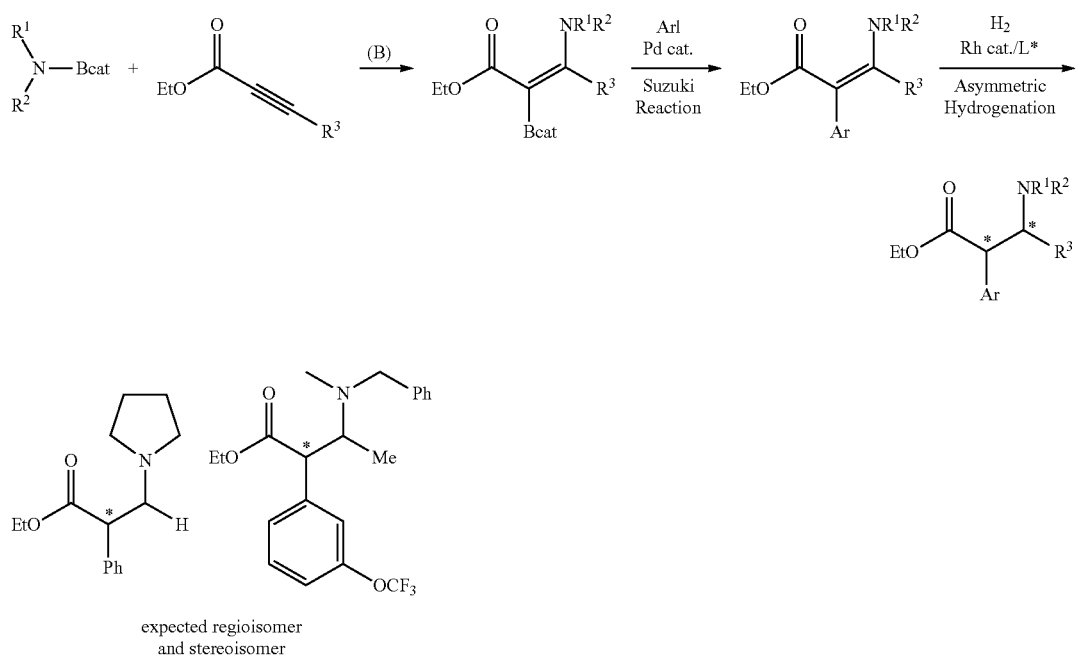

expected regioisomer
and stereoisomer

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

A method for the intramolecular anti addition of boron-oxygen bonds across alkynes is disclosed. This alkoxyboration reaction is conducted as a one-pot sequence starting from 2-alkynylphenols and generates 3-benzofuranyl boronic esters inaccessible using other borylation methods. The products are isolated as the corresponding trifluoroborate salts or MIDA boronate for synthetic ease.

Discussion:

We have developed an alkoxyboration reaction of alkynes to simultaneously install new C—O and C—B bonds from the easily generated B—O bonds of boric esters (such as A). This new reactivity is compatible with a wide variety of functional groups sensitive to other borylation methods and provides access to new bench-stable organotrifluoroborate or MIDA boronate coupling partners.

We envisioned that an intramolecular anti-alkoxyboration reaction could be promoted by a Lewis acidic metal catalyst. A variety of metal catalysts were examined for competence in converting boric ester A into boronic ester B (Table 1, Example 1). In the absence of catalyst, no conversion of boric ester n was observed (entry 1). The N-heterocyclic carbene gold complexes IPrAuOH and IPrAuCl (entries 2 and 3) gave unreacted boric ester A. However, IPrAuCl with a variety of silver salt activators afforded the desired alkoxyboration catalyst in high conversion (entries 4-6). Identical reactivity was observed with authentic IPrAuOTf, eliminating the possibility of a "silver effect" (entry 7). Interestingly, other commonly used late transition metal complexes were found to be ineffective as alkoxyboration catalysts (entries 8-10).

TABLE 1

Example 1. Optimization of alkoxyboration metal catalyst.

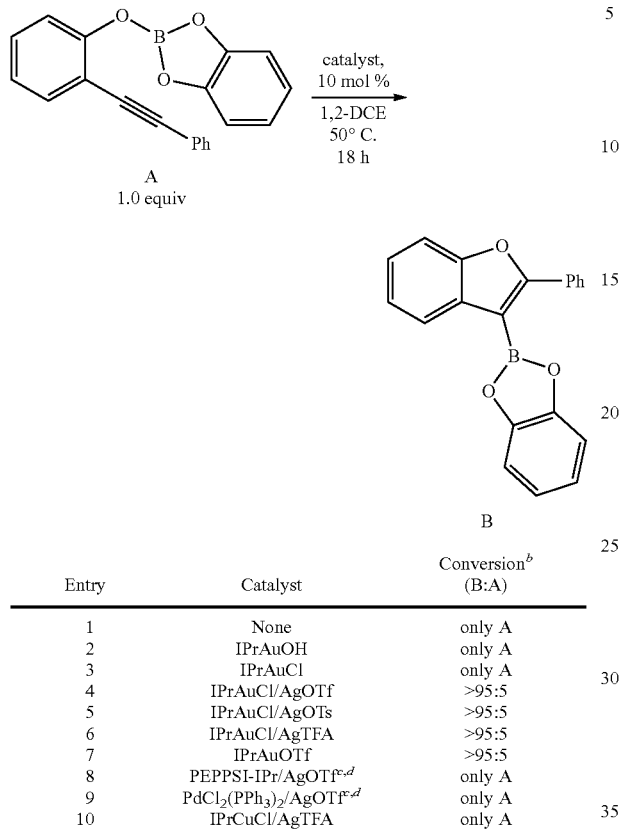

| Entry | Catalyst | Conversion[b] (B:A) |
|---|---|---|
| 1 | None | only A |
| 2 | IPrAuOH | only A |
| 3 | IPrAuCl | only A |
| 4 | IPrAuCl/AgOTf | >95:5 |
| 5 | IPrAuCl/AgOTs | >95:5 |
| 6 | IPrAuCl/AgTFA | >95:5 |
| 7 | IPrAuOTf | >95:5 |
| 8 | PEPPSI-IPr/AgOTf[c,d] | only A |
| 9 | PdCl$_2$(PPh$_3$)$_2$/AgOTf[c,d] | only A |
| 10 | IPrCuCl/AgTFA | only A |

IPr = 1,3-bis(2,6-diisopropylphenyl)-1,3-dihydro-2H-imidazol-2-ylidene
[a]Conditions: 0.10 M A in 1,2-dichloroethane.
[b]Determined by $^1$H and $^{11}$B NMR spectroscopy.
[c]Using 20. mol % AgOTf.
[d]Reaction time, 6 h.

Further optimization of the reaction conditions resulted in a one-pot procedure starting from 2-alkynyl phenols (Scheme 1A, Example 1 as shown in FIG. 1.3). Following deprotonation of substrate C by NaH, the boric ester moiety was installed by electrophilic trapping using B-chlorocatecholborane, a commercially available reagent used in the deprotection of MOM-protected alcohols. Heating intermediate A in the presence of catalytic IPrAuCl/NaTFA afforded the desired alkoxyboration product B in high conversion. In this one-pot procedure, NaTFA was used as an activator instead of the silver salts shown in Table 1 due to its tolerance of the equivalent of NaCl present after installation of the boric ester in step 2.

Isolation of alkoxyboration product B proved to be challenging. The electron-rich nature of the 3-benzofuranyl system renders the C—B bond sensitive to protonolysis by atmospheric moisture. We therefore sought to isolate alkoxyboration product B as the corresponding MIDA boronate or trifluoroborate salt, both of which are air-stable indefinitely. Treatment of a microscale alkoxyboration reaction mixture with N-methyliminodiacetic acid (H$_2$MIDA) allowed for isolation of the desired product in 46% yield (Scheme 1B, Example 1 as shown in FIG. 1.4) with the protodeboronated product as the mass balance. Alternatively, treatment of the alkoxyboration reaction mixture with KHF$_2$ afforded the benzofuranyl trifluoroborate salt in 47% yield. For synthetic ease and optimal yields, we therefore opted to isolate the catechol boronic ester alkoxyboration products as the corresponding triflouroborate salts.

With optimized reaction and isolation conditions in hand, we set out to explore the substrate scope of this alkoxyboration reaction (FIG. 1.5).

Simple aryl and alkyl substitution at the benzofuran 2-position is tolerated with high yield (a). The reaction is regioselective when using a diethynylphenol to afford alkyne-substituted benzofuran (b). Unlike traditional metalation/electrophilic trapping methods of generating boronic esters, the alkoxyboration reaction is compatible with a variety of reactive functional groups, such as aryl halides (c, j), silyl ethers (d), free alcohols (e, n), amides (m, n), esters (f, g, i, k, and l), nitriles (j), protected amino acids (o), and aldehydes (h), and is expected to be compatible with ketones (l). The high degree of functionality available in the alkoxyboration products provides many functional group handles for subsequent transformations.

Example 2

Despite nearly 70 years of research into the addition of B—X σ bonds to C—C multiple bonds, a method for B—O bond activation has not yet been reported. Such a transformation could allow for the synthesis of versatile oxygen-containing organoboron reagents for organic synthesis. We herein report the realization of an alkoxyboration reaction, adding B—O σ bonds to alkynes. O-Heterocyclic boronic acid derivatives can be produced using this transformation, which is mild and exhibits broad functional group compatibility.

Discussion:

Boronic acids and their derivatives are versatile reagents in modern organic synthesis, and the hydroboration reaction is a well-established method for generating these building blocks through the addition of B—H bonds across C—C multiple bonds (1). First described by Hurd in 1948 (2) and later developed in detail by Brown (3), this reaction has inspired many catalyzed variants (4, 5). Recently, several compelling examples of related B—X bond addition reactivity have been reported for X=C (6, 7), Si (8, 9), Sn (10), and S (11) (FIG. 2.1.*a*). These transformations generally proceed through the oxidative addition of a catalytic transition metal such Ni(0), Pd(0), or Pt(0) into the B—X σ bond.

Despite this progress, the corresponding activation of B—O bonds and addition to C—C multiple bonds—alkyoxyboration—has remained elusive for 65 years (12,13). This striking dearth of B—O bond activation reactivity may be due to the high strength of the B—O bond (14), rendering it unreactive towards oxidative addition and thus preventing the successful application of Ni, Pd, or Pt catalysis (6-11). Given that ethers are found in many diverse classes of natural products (15) and in nearly 25% of the top-grossing pharmaceuticals in the United States for 2012 (16), the development of an alkoxyboration reaction could allow for the preparation of oxygen-containing building blocks useful in drug discovery and materials science (16,17).

Herein we report the realization of an alkoxyboration reaction of alkynes, through which new O-heterocyclic organoboronate coupling partners are available for downstream functionalization. The high functional-group tolerance of this reaction enables downstream divergent synthesis of functionalized benzofurans—the ability to accesses multiple benzofurans from one bench stable precursor. In contrast, current methods for synthesizing benzofurans often rely on harsh conditions that limit compatibility with functional groups desirable for divergent synthesis (18).

We envisioned that the desired alkoxyboration reactivity could be promoted through an activation pathway employing a bifunctional Lewis acidic/Lewis basic catalyst, which could simultaneously activate both the alkyne and the B—O σ bond partners. We anticipated that this unique strategy could allow for the anti addition of B—O bonds across alkynes by circumventing the previous problematic strategy of oxidative cleavage of the B—O bond.

Our optimized one-pot procedure begins with 2-alkynyl phenols (1), which are converted into the requisite boric ester intermediate 2 using the readily available reagent B-chlorocatecholborane (Scheme 2A, Example 2, FIG. 1.5). Treatment of this intermediate with the commercially available Lewis acidic gold(I) precatalyst IPrAuCl and NaTFA affords alkoxyboration product 3 in good to excellent conversion. Interestingly, our examination of alternative π-Lewis acidic transition metal catalysts revealed no other active catalysts aside from Au(I) (19). For synthetic ease, the catechol boronic ester alkoxyboration product 3 was converted into either the organotrifluoroborate (20) or N-methyliminodiacetic acid (MIDA) boronate (21) derivative, 4, both of which are air stable indefinitely.

Organotrifluoroborate 4a is readily isolated in high yield using a chromatography-free purification, making this derivatization method particularly amenable to applying the alkoxyboration reaction on preparative scale (FIG. 2.2). The corresponding MIDA derivative (4b) provides an option for purification by silica gel chromatography, but this comes at the cost of slightly diminished yield. Single-crystal X-ray diffraction analysis of 4b allowed for the unambiguous identification of the alkoxyboration product.

The alkoxyboration reaction is tolerant of a variety of functional groups suitable for downstream reactivity. Aryl bromide 4c, silyl-protected alcohol 4d, terminal alkyne 4f, amide 4g, esters 4h and 4i, and the functionally-dense iodonitrile 4j are compatible with the reaction conditions. Many of these alkoxyboration reactions proceed smoothly at 50° C., although the reactions generating 4d, 4g, 4h, and 4j required heating to 90° C. in order to affect full conversion. We attribute the relatively slow formation of 4d to the high steric encumbrance from the silyl ether at the 2-position of the benzofuran. The cyclization of substrates containing Lewis basic nitrogen atoms (forming 4g, 4h, and 4j) was likely retarded by reversible N—B coordination that was observed by $^{11}$B nuclear magnetic resonance (NMR) spectroscopy.

Notably, many of these products contain functional groups incompatible with commonly employed methods of benzofuran synthesis (18), including via other borylation techniques (FIG. 2.3). In one frequently used borylation technique, an aryl lithium intermediate is trapped by a boron electrophile (Method 1); thus electrophiles such as carbonyl or nitrile groups and enolizable protons are not generally tolerated due to the highly nucleophilic and basic nature of the requisite organolithium intermediate (22). Aryl halides may also suffer from undesired lithium/halogen exchange. The Miyaura borylation is a more mild alternative that is compatible with electrophilic functional groups (Method 2), but aryl halides are not tolerated because this reaction is catalyzed by Pd(0), which also activates aryl halide bonds (23). Finally, the Ir-catalyzed C—H activation/borylation reaction is an effective means of accessing aryl boronic acid derivatives through C—H activation (Method 3), but this reaction is regioselective for either 2- or 7-borylation; 3-borylated benzofurans such as those available through the alkoxyboration reaction cannot be synthesized regioselectively through C—H activation/borylation (24).

We set out to demonstrate the utility in divergent synthesis of the alkoxyboration products enabled through this synthesis in subsequent functionalization steps. Rh-catalyzed conjugate addition of 4a into methyl vinyl ketone using the method developed by Batey (25) provides β-benzofuranyl ketone 6 in moderate yield (eq 1). Organotrifluoroborate 4i was subjected to Suzuki-Miyaura coupling conditions described by Molander and Biolatto (26) to afford the cross-coupled product 3-arylated benzofuran 8 with concomitant methanolysis of the ethyl ester (eq 2). These two transformations suggest the potential for broad applicability of these functionalized alkoxyboration products in a variety of C—C bond-forming reactions.

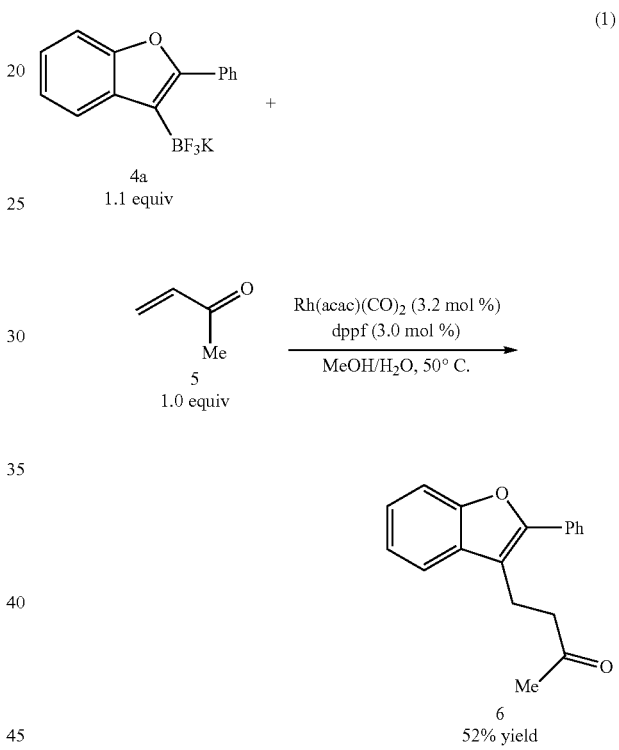

(1)

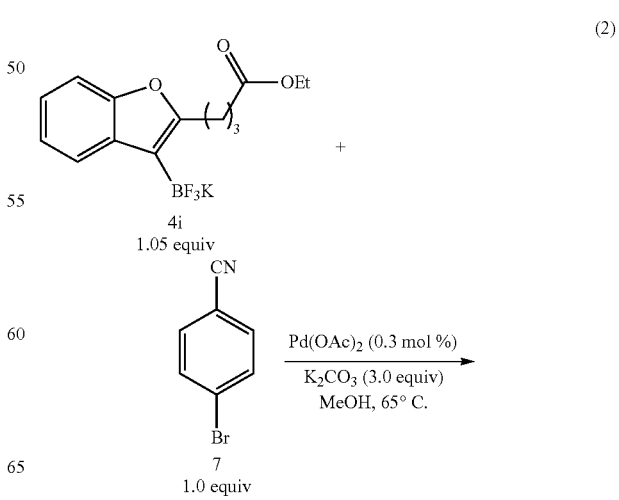

(2)

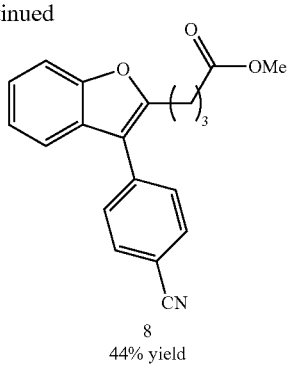

8
44% yield

We next explored the scalability of the alkoxyboration reaction and tolerance of lower catalyst loading. Bromide-containing phenol 1c was successfully converted to more than 1 g of MIDA boronate 4c on a 5.1 mmol scale with 2.0% gold catalyst (eq 3). Full conversion of starting material was affected even with a lower Au catalyst loading. This convenient scalability demonstrates that quantities of O-heterocyclic boronic acid derivatives sufficient for multistep synthesis may be prepared using the alkoxyboration method.

(3)

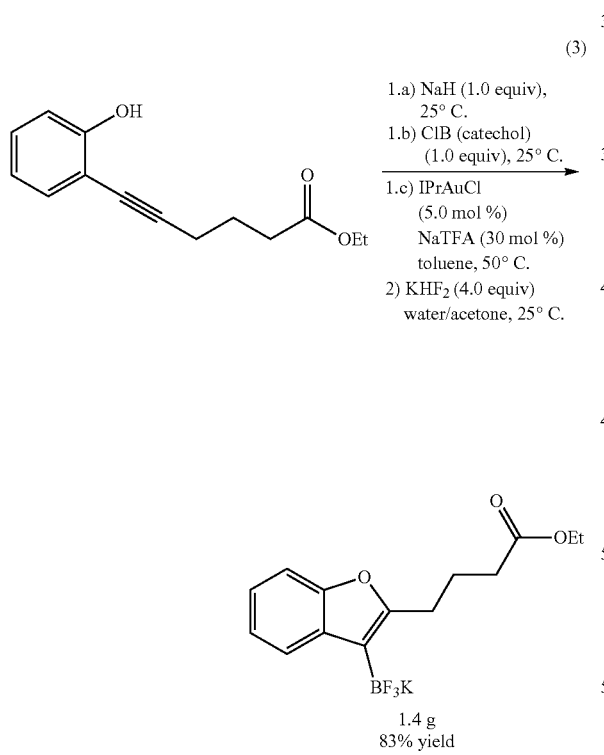

Having demonstrated the utility of this transformation in generating members of the benzofuran class of O-heteroaryl boronic acid derivatives, we explored its application to the synthesis of a non-aromatic oxygen-containing heterocycle (eq 4). Simple and commercially available homopropargyl alcohol 9 was subjected to standard alkoxyboration reaction conditions to prepare the dihydrofuran product 10. This substrate demonstrates the potential for great generality in the alkoxyboration reaction: The reaction features low labor "setup cost" by employing simple starting materials to generate highly value-added O-heterocyclic organoboronate compounds in one synthetic step, and the cyclization proceeds without requiring the gain of product aromaticity or the need for a fused ring system that enforces a conformational bias towards cyclization.

(4)

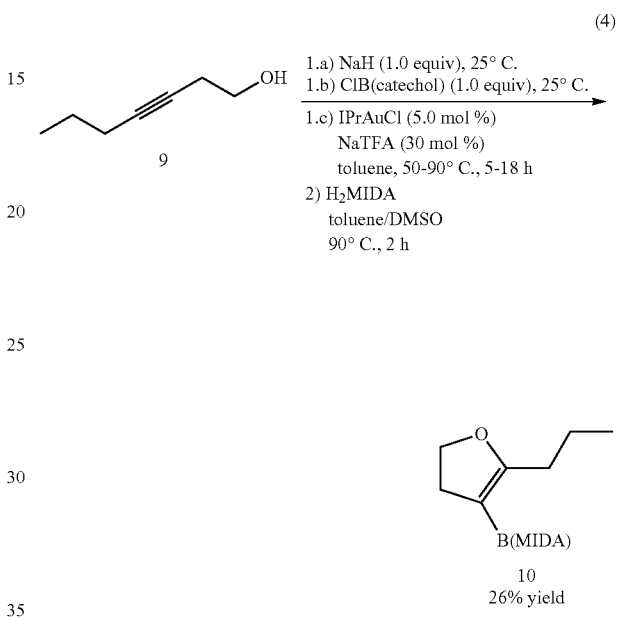

10
26% yield

In accordance with our strategy for bifunctional Lewis acidic/Lewis basic substrate activation, we propose the catalytic cycle shown in Scheme 2B, Example 2. The bifunctional catalyst IPrAuTFA can be generated in situ from IPrAuCl and NaTFA. Reaction of the Lewis basic trifluoroacetate moiety with electrophilic boric ester 2a gives nucleophilic boronate 12. The resulting Lewis acidic Au(I) cation may then bind to the alkyne (13), increasing its electrophilicity. Nucleophilic attack on the alkyne-Au π complex by the phenol B—O bond would provide neutral intermediates: boron electrophile 14 and organogold nucleophile 15, which could recombine to regenerate 11 with concomitant formation of the observed alkoxyboration product 3a. Thus, the IPrAu$^+$ moiety of the catalyst activates the alkyne for nucleophilic attack, and the TFA counterion allows for reversible tuning at boron from electrophilic to nucleophilic. This reaction manifold is fundamentally unique from the metal-catalyzed addition of B—C, B—Si, B—Sn, and B—S addition reactions, which often proceed through oxidative addition of a low-valent metal catalyst into the B—X bond. We believe that the new activation strategy employed in the alkoxyboration reaction could be extended to other types of B—X bonds in order to provide additional reactivity complementary to preexisting methods.

Scheme 2B, Example 2. Mechanistic hypothesis featuring the bifunctional Lewis acidic/Lewis basic catalyst IPrAuTFA.

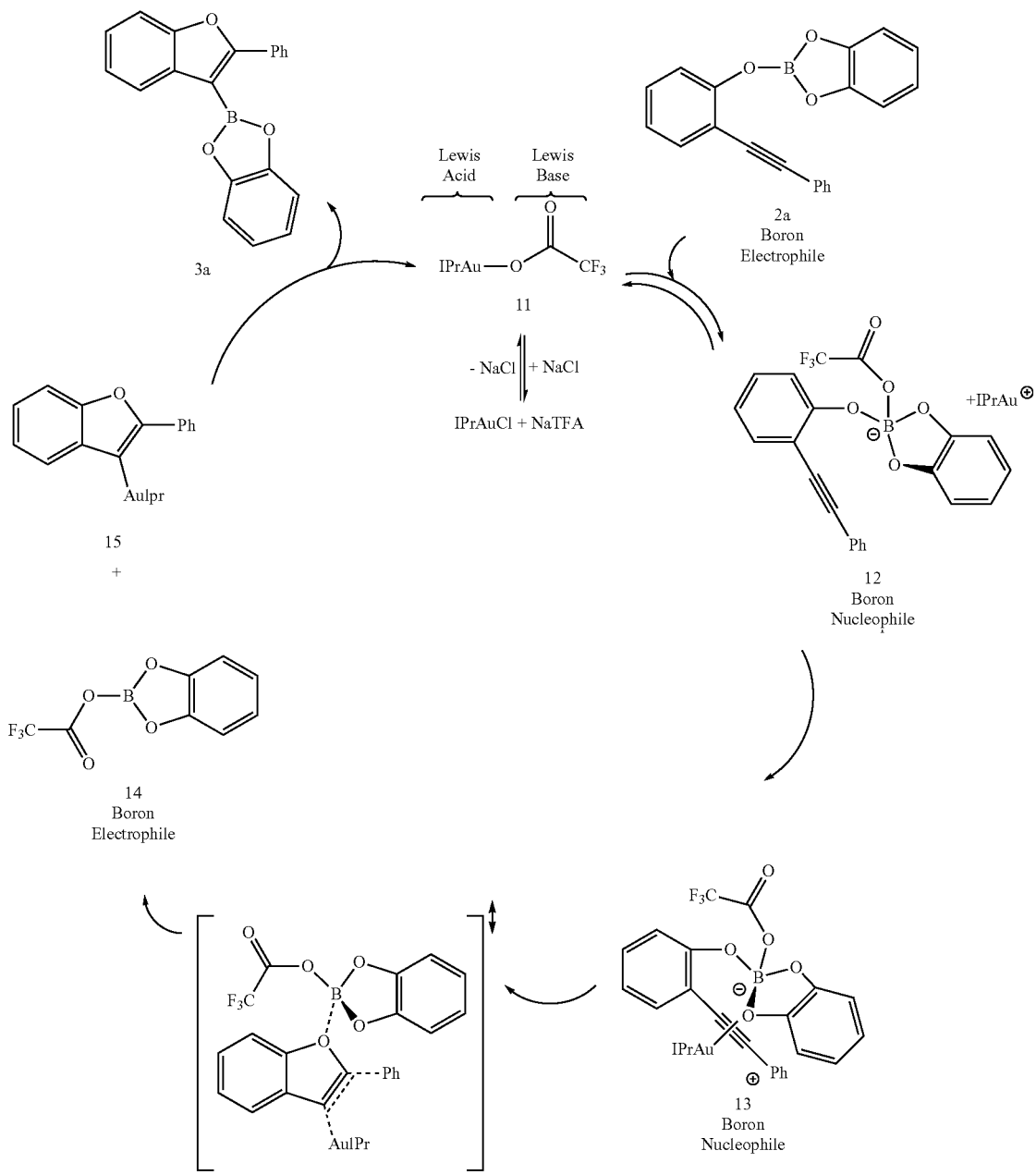

This alkoxyboration reaction proceeds through an unprecedented B—O bond activation. This fundamentally new activation is showcased in a mild, scalable technique for the preparation of O-heterocyclic boronic acid derivatives and downstream functionalized benzofurans. The reaction provides a simple new bond disconnection for constructing these motifs with different regioselectivity and broader functional group compatibility than existing methods. This compatibility yields highly functionalized bench-stable cross-coupling and Michael addition partners for divergent synthesis that are not directly accessible using alternative methods.

REFERENCES

1. D. G. Hall, *Boronic Acids: Preparation and Applications in Organic Synthesis, Medicine, and Materials* (Wiley-VCH, Weinheim, Germany, 2011).
2. D. T. Hurd, *J. Am. Chem. Soc.* 70, 2053-2055 (1948).
3. H. C. Brown, *Tetrahedron* 12, 117-138 (1961).
4. D. Männig, H. Nöth, *Angew. Chem. Int. Ed. Engl.* 24 878-879 (1985).
5. A.-M. Carrol, T. P. O'Sullivan, P. J. Guiry, *Adv. Synth. Catal.* 347, 609-631, (2005).
6. M. Suginome, A. Yamamoto, M. Murakami, *J. Am. Chem. Soc.* 125, 6358-6359 (2003).
7. M. Suginome, M. Shirakura, A. Yamamoto, *J. Am Chem. Soc.* 128, 14438-14439 (2009).

8. M. Suginome, H. Nakamura, Y. Ito, *Chem. Commun.* 2777-2778 (1996).
9. M. Suginome, H. Nakamura, Y. Ito, *Angew. Chem. Int. Ed. Engl.* 36, 2516-2518 (1997).
10. S. Onozawa, Y. Hatanaka, T. Sakakura, S. Shimada, M. Tanaka, *Organometallics* 15, 5450-5452 (1996).
11. T. Ishiyama, K. Nishijima, N. Miyaura, A. Suzuki, *J. Am. Chem. Soc.* 115, 7219-7225 (1993).
12. C—N bonds, see: R. H. Cragg, M. F. Lappert, B. P. Tilley, *J. Chem. Soc.* 2108-2115 (1964).
13. N. Matsumi, Y. Chujo, *Macromolecules* 31, 3802-3806 (1998).
14. R. T. Sanderson, *Polar Covalence* (Academic Press, Waltham, Mass., United States, 1983).
15. P. Domínguez de María, R. W. van Gemert, A. J. J. Straathof, U. Hanefeld, *Nat. Prod. Rep.* 27, 370-392 (2010).
16. Drugs.com, *U.S. Pharmaceutical Sales* —2012 (http://www.drugs.com/stats/top100/2012/sales).
17. S. Anderson, P. N. Taylor, G. L. B. Verschoor, *Chem. Eur. J.* 10, 518-527 (2004).
18. J. A. Joule, K. Mills, *Heterocyclic Chemistry*, $5^{th}$ Ed. (Chichester, United Kingdom, 2010).
19. Materials, methods, and X-ray diffraction details are available as supplementary materials on *Science* Online.
20. G. A. Molander, N. Ellis, *Acc. Chem. Res.* 40, 275-286 (2007).
21. E. P. Gillis, M. D. Burke, *J. Am. Chem. Soc.* 130, 14084-14085 (2008).
22. A. Nagaki, Y. Moriwaki, J. Yoshida, *Chem. Commun.* 48, 11211-11213 (2012).
23. T. Ishiyama, M. Murata, N. Miyaura, *J. Org. Chem.* 60, 7508-7510 (1995).
24. I. A. I. Mkhalid, J. H. Barnard, T. B. Marder, J. M. Murphy, J. F. Hartwig, *Chem. Rev.* 110, 890-931 (2010).
25. R. A. Batey, A. N. Thadani, D. V. Smil, *Org. Lett.* 1, 1683-1686 (1999).
26. G. A. Molander, B. Biolatto, *J. Org. Chem.* 68, 4302-4314 (2003).
27. S. Akoka, L. Barantin, M. Trierweiler, *Anal. Chem*, 71 2554-2557 (1999).

Example 3

FIG. 3.1 illustrates an embodiment of forming a boronic compound. The aryl bromide starting material is converted to the corresponding Grignard reagent through a magnesium/halogen exchange reaction. Treatment with a stoichiometric copper reagent, such as CuCN.2LiCl, promotes anti addition across the tethered alkyne to form a 2-metallated indole. Trapping of this organocopper nucleophile with an electrophilic boron reagent or other boron transmetalation reagent such as B-chlorocatecholborane, B-chloropinacolborane, or B-trifluoroacetocatecholborane is expected to provide the 2-borylated indole shown (product shown for trapping with B-chlorocatecholborane), which could be converted to the corresponding organotrifluoroborate or MIDA boronate derivative. Thus, this method provides selective borylation at the 2 position of the new heterocyclic ring in a manner complementary to the 3-selective borylations shown in FIGS. 1.1A-2.3.

Example 4

In this Example an oxyboration reaction with activated substrates that employs B—O a bond additions to C—C π bonds to form borylated isoxazoles, which are potential building blocks for drug discovery. While this reaction can be effectively catalyzed by gold, it is the first example of uncatalyzed oxyboration of C—C π bonds by B—O σ bonds—and only the second example that is catalyzed. This oxyboration reaction is tolerant of groups incompatible with alternative lithiation/borylation and palladium-catalyzed C—H activation/borylation technologies for the synthesis of borylated isoxazoles. Mechanistic experiments, including a stoichiometric organogold-to-boron transmetalation reaction, identify a two-step transmetalation process with breakdown of a tetracoordinate borate/cationic gold ion pair as the rate-determining step in this transmetalation reaction and plausibly in the overall catalytic oxyboration reaction. The complimentary bond disconnections and functional-group tolerance enabled by this method are highlighted in the synthesis of valdecoxib, a COX-2 inhibitor, and its ester-containing analog. The scalability of the reaction is demonstrated by a gram-scale uncatalyzed oxyboration reaction.

Isoxazoles[1] exhibit a wide variety of biological activities, including analgesic,[2] antibiotic,[3] antidepressants,[4] and anticancer[5] activities. Consequently, borylated isoxazoles are valuable bench-stable building blocks for drug discovery.[6-9] Oxyboration reactions that proceed through the addition of B—O σ bonds to C—C π bonds would be an attractive route to these and other building blocks by transforming easily formed B—O σ bonds into more difficult to form B—C σ bonds. Yet the addition of B—O σ bonds to C—C multiple bonds had remained elusive for 65 years[10,11] until our first report last year.[12,13] We herein develop catalyzed and uncatalyzed oxyboration routes to borylated isoxazoles. This is the first report of uncatalyzed oxyboration of C—C π bonds with B—O σ bonds. The functional group tolerance of these methods provides access to borylated building blocks containing carbonyl, heterocyclic, and aryl bromide functional groups that are incompatible with alternative metalation routes for their production, and this oxyboration method produces exclusively the 4-borylated regioisomer. These examples establish the generality of oxyboration strategies[12,13] to generate borylated heterocycles for drug discovery.

Specifically, compounds of this type may currently be accessed through the [3+2] cycloaddition reaction of nitrile oxides and alkynylboronates as shown in Scheme 1. However, this method can produce two regioisomers and the alkynylboronate synthesis involves a lithiation step.[14] Alternatively, the Pd(0)-catalyzed Miyaura borylation[15] and lithiation/electrophilic borylation[16] have been used for the synthesis of borylated heterocycles, but, as with lithiation/cycloaddition, aryl bromides and electrophilic functional groups are reactive under these conditions.

Inspired by previous reports from Perumal[17] and Che and Wong,[18] who demonstrated analogous Au-catalyzed rearrangements of oximes to form 4-protonated isoxazoles without boron (i.e., cyclizing substrates 1 with no boron rather than borylated substrates 2), we considered that analogous routes to borylated Scheme 1. Comparision of Previous Methods and New Oxyboration Method for the Synthesis of 4-Borylated Isoxazoles

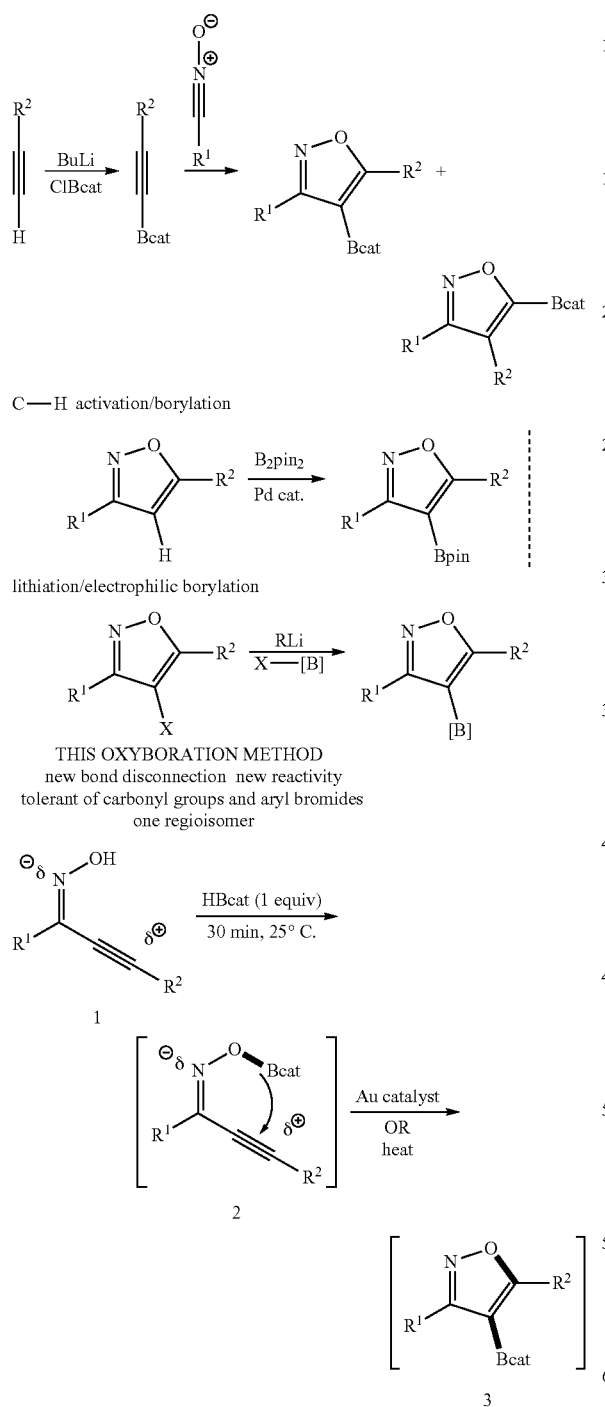

isoxazoles may be assessable through oxyboration. We hypothesized that this gold-catalyzed oxyboration reaction could proceed through carbophilic Lewis acid activation of the C—C π bond, a mechanistically distinct route to B-El- ement addition reactions.[12,13] The oxyboration reaction developed here is an operationally simple one-pot procedure from oximes and requires no isolation of reaction intermediates (Scheme 1).

Alkynyloximes (1) were prepared for oxyboration via O-borylation with commercially available catecholborane (catBH) with concomitant evolution of $H_2$, producing boric ester intermediates 2. Without isolation, treatment of these synthetic intermediates in the same pot with catalytic IPrAu-TFA initiated oxyboration to afford 4-borylated isoxazoles 3 in good to excellent $^1$H NMR yields (Table 1). These boronic esters were converted to pinacol (pin) boronic esters 4, which are isolable by silica gel chromatography and are bench-stable building blocks for a variety of downstream reactions.[6,19]

The reaction was developed through initial studies with substrate 1a. Conversion of 1a to boric ester intermediate 2a and subsequent treatment with 2.5 mol % IPrAuTFA for 6 h at 50° C. afforded oxyboration product 3a in 90% $^1$H NMR spectroscopy yield, calculated from an external mesitylene standard. A control reaction under identical conditions (6 h, 50° C.) in the absence of catalyst yielded 3a in <1% $^1$H NMR spectroscopy yield. Interestingly, oxyboration of 1a could be carried out under catalyst-free conditions, albeit with higher temperatures and longer reaction times. Specifically, heating 1a to 110° C. for 17 h afforded 3a in 58% $^1$H NMR spectroscopy yield, with the remaining of the mass balance accounted for by competing formation of the 4-H (unsubstituted) isoxazole. Similarly, cyclization of 1c under catalyst-free conditions of 110° C. for 17 h produced 3c in 89% $^1$H NMR yield. We hypothesize that the Michael-acceptor/polar character of the starting materials enables this catalyst-free oxyboration through lowering the barrier of cyclization (eq 1); alternatively, the nucleophilic nitrogen lone pair[29] of the hydroxylimine may coordinate and activate the boron Identification of this class of activated substrates thus provides access to catalyst-free reactivity that was not possible previously within our earlier reported oxyboration substrates.[12]

TABLE 1

Example 4. Initial Reaction Development With and Without Catalyst.

| | $R^1/R^2$ | IPrAuTFA 6 h, 50° C. | Uncat. 6 h, 50° C. | Uncat. 17 h, 110° C. |
|---|---|---|---|---|
| 1a | Ph/Bu | 90% | <1% | 58% |
| 1c | 4-BrPh/Bu | 93% | 4% | 89% |
| 1f | Ph/TMS | 87% | <1% | <1% |

In contrast to the reactivity exhibited by 1a and 1f, when silylated 1f was used as the substrate for catalyst-free oxyboration, only B—O σ bond formation was observed (boric ester 2f), and no cyclized products were formed even after an extended time of heating at 110° C. This lack of reactivity possibly derives from the steric hinderance and the electron-donating ability of the trimethylsilyl group[21] adjacent to the alkyne carbon, which may alter the polarization of the alkyne, rendering it less susceptible toward nucleophilic attack in the key carbon-oxygen bond-forming/cyclization step (proposed mechanism, Scheme 1). Due to its reduced temperatures, shorter reaction times, and action with the silylated substrate, the metal-catalyzed route was selected for further optimization and isolation.

This oxyboration method provided a new set of bond disconnections to access previously unreported isoxazole pinacol boronic esters 4a-4k (except 4f[14]) as shown in Table 1. The numbers in parentheses denote the $^1$H NMR spectroscopy yield of catechol boronic ester 3 relative to an external standard. The numbers outside the parentheses on the first row denote the isolated yield of bench-stable pinacol boronic ester 4.[22] The numbers outside the parentheses on the second row correspond to the reaction time of the uncatalyzed oxyboration when run at 110° C. After completion of the catalytic reaction, PPh$_3$ was employed to quench the active catalyst IPrAuTFA by trapping it as the catalytically inactive [IPrAuPPh$_3$]$^+$.[23] A control reaction with catalytic NaTFA in place of IPrAuTFA exhibited no conversion of starting material 2a to product after 6 h at 50° C., confirming a key role for the carbophilic Lewis acid.

We herein compare the catalyzed reaction yields with those obtained through the uncatalyzed method for each substrate. With the exception of silylated 1f, all substrates showed uncatalyzed reactivity at longer reaction times, which ranged typically from 20 h to 65 h. Bulky substituents such as t-butyl and trimethylsilyl, however, only produced very low $^1$H NMR spectroscopy yield (24% for 3d and <1% for 3f), with the starting materials remaining. Thus they required catalysis for synthetically useful product formation. The electron poor p-CF$_3$ substrate and furyl substrate, required a rather lengthy 18-21 d to reach full conversion at 110° C. In many cases, the cost benefit of obtaining the product under catalyst-free conditions may be desired in exchange for elevated temperatures and marginally longer reaction times, most notably with 4c, 4e, 4h, 4i, 4k, reactions which achieved similar $^1$H NMR yields to the catalyzed reactions in 20-65 h.

Interestingly, substrates that exhibited slow conversions under the catalyzed conditions for apparent electronic reasons (rather than steric reasons) such as 1i and 1k were the faster converting substrates under the uncatalyzed conditions; it may be that the electronics that favor u Lewis acid catalysis though gold-alkyne binding disfavor cyclization in the absence of a catalyst. This orthogonality in electronic and steric substrate reactivity highlights the complementarity provided by the catalyzed and uncatalyzed methods.

Both the metal-catalyzed oxyboration reaction and the uncatalyzed oxyboration reaction are tolerant of functional groups that would be sensitive to alternative methods for the borylation of heterocycles. For example, aryl bromide 1c smoothly undergoes oxyboration to produce borylated isoxazole 3c (93% $^1$H NMR yield, 65% isolated yield of 4c with a catalyst; 91% $^1$H NMR yield without a catalyst). This substrate would be sensitive to a lithiation/borylation sequence[16,24] due to competitive lithium/halogen exchange,[25] and to an alternative palladium-catalyzed borylation[15] due to competitive oxidative addition of the aryl-bromide bond. The nitro group in 1e and the ester group in 1k are similarly tolerated, producing oxyboration product 3e in 90% $^1$H NMR yield (60% isolated yield of 4e) and 3k in 94% $^1$H NMR yield (64% isolated yield of 4k) under catalysis, whereas these groups are intolerant of alternative lithiation techniques.[16] Furan-substituted 4b demonstrates the complementary bond disconnections enabled by oxyboration to avoid competitive ortho-borylation of the furan ring[26] which would compete under alternative lithiation/borylation strategies (85% $^1$H NMR yield of 3b; 71% isolated yield of 4b).

In addition, heteroaryl (4b), aliphatic group (4d), electron-poor aryl (4e, 4j and 4k), silyl (4f), and electron-rich aryl (4g and 4i) were all compatible with the reaction conditions. Some substrates required higher reaction temperature and/or longer reaction time to achieve full conversion under catalytic conditions, while no reaction was observed when the same conditions were applied in the absence of an Au catalyst. Oxyboration products 3d and 3f required 110° C. for 4 h and 90° C. for 24 h, respectively, which may be caused by the steric hinderance of the t-butyl and the silyl groups. Electron-rich aryl 3i and heteroaryl 3b required heating at 60° C. for 24 h and 50° C. for 24 h, respectively, which may be attributed to the electron-donating ability of these substituents to reduce the electrophilicity of boron.

A plausible catalytic cycle for the π Lewis acid catalyzed oxyboration reaction is shown in Scheme 2A that highlights the proposed activation of the C—C π bond by the carbophilic Lewis Table 2, Example 4. Reaction Substrate Scope. Substrates Shown in Blue Are Incompatible with Alternative Routes. All Substrates Give Exclusively 4-Borylated Regioisomer.

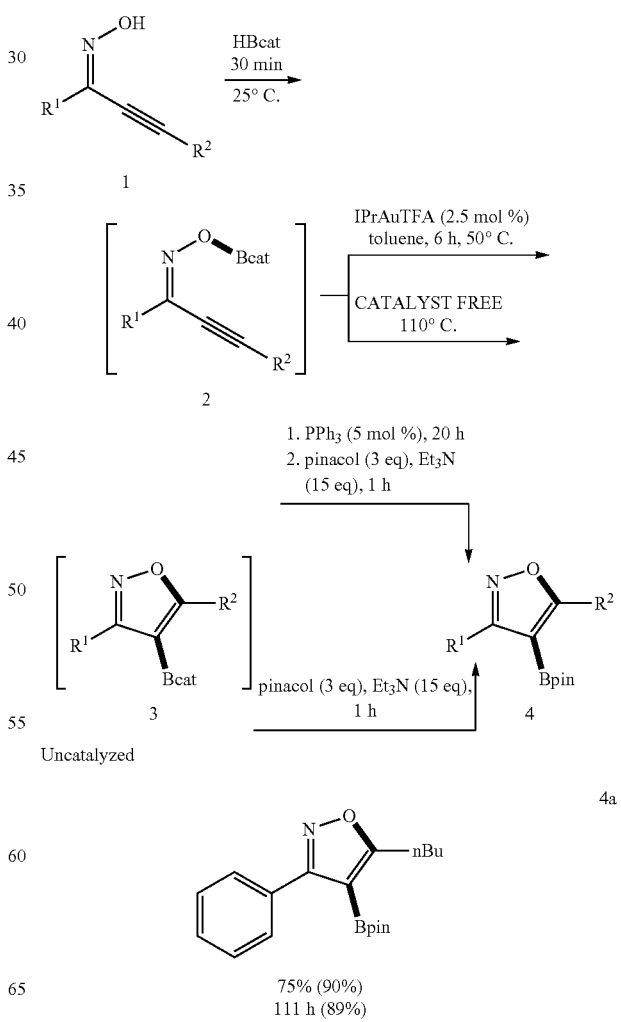

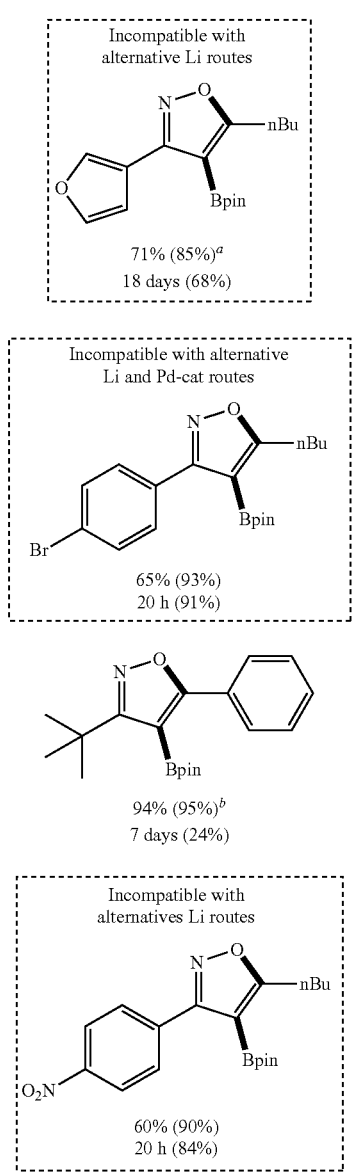
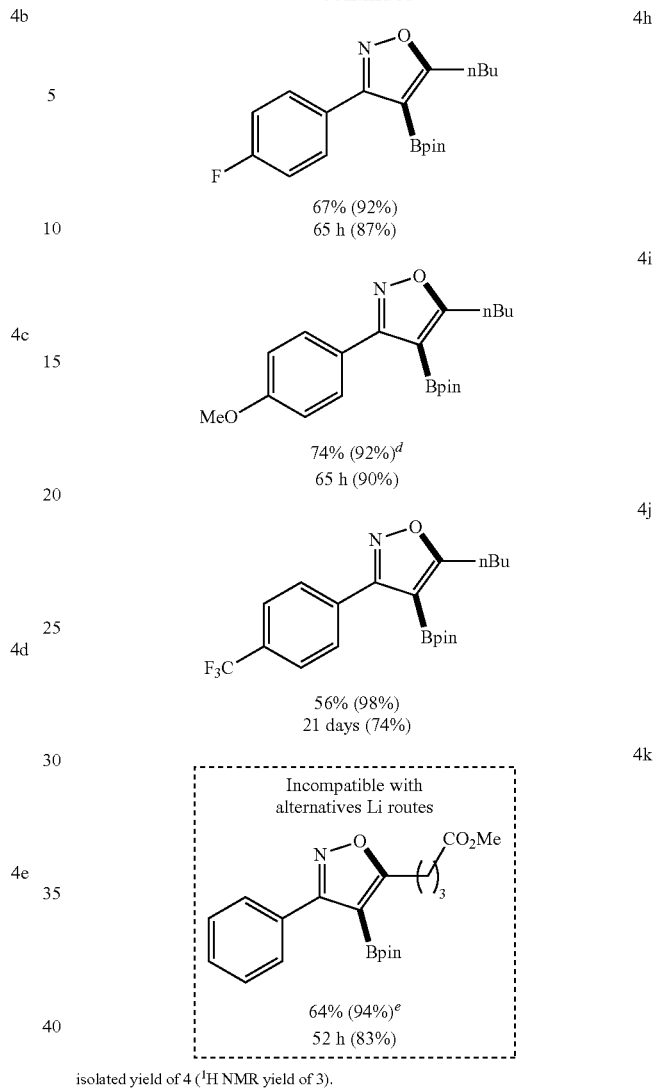

isolated yield of 4 ($^1$H NMR yield of 3).
Uncatalyzed: Reaction time ($^1$H NMR yield of 3)
[a]50° C., 24 h. [b]110° C., 4 h, [c]90° C., 24 h. [d]60° C., 24 h. [e]50° C., 8 h.

acid catalyst[27,29] that provides a mechanistically distinct route for B—X σ bond addition, and possible concurrent activation of the B—O σ bond by coordination of trifluoroacetate ion in intermediate 6. Subsequent addition of the nucleophilic B—O σ bond to the resulting Au-alkyne π complex of intermediate 6 in a concerted manner forms the carbon-oxygen bond of the isoxazole core and generates a new carbon-gold σ-bond as shown in intermediate 7.

Alternatively, the π Lewis acid catalyzed cyclization steps can occur in a different order, in which the nucleophilic oxygen of the boric ester 8 attacks the activated alkyne to generate an oxonium ion 9 in the first step, and then the outersphere trifluoroacetate ion removes the Bcat group in the second step to produce 7 and 10 (eq 1). This pathway is supported by similar mechanisms in gold-catalyzed and -mediated cyclizations, such as has been detected by $^1$H NMR spectroscopy in stoichiometric studies,[29] proposed as intermediates in the fluorination of oxime ethers to generate 4-fluoroisoxazoles,[39] and detected as likely catalytic intermediates in gold and palladium cooperatively catalyzed cyclization/cross-coupling reactions.[23,31]

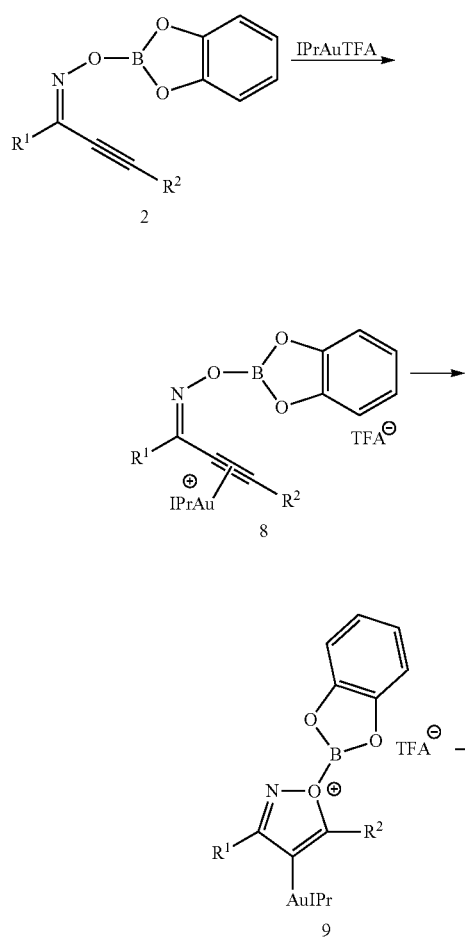

In the next step of the proposed mechanism, the carbon-gold bond in 7 is nucleophilic at carbon[13,32,33] and is primed for transmetalation with electrophilic boron intermediate 10. The mechanism of the reaction between 7 and 10 to form ion pair 11 may involve an electrophilic aromatic substitution, with rearomatization and loss of the AuIPr cation. The accessibility of this transmetalation step is not well-established; to our knowledge, our report last year is the first of transmetalation from organogold to boron.[12,13,34] The reverse reaction from organoboron to gold is better studied,[35-38] as is the general ability of organogold compounds to transmetalate with other metals and metalloids.[31,39-43]

The proposed mechanism for the uncatalyzed oxyboration reaction is shown in Scheme 2B. A nucleophile (Nu) could coordinate to boron in 2, activating the B—O σ bond as shown in 13. This tetracoordinate boron species 13 then undergo cyclization with 14 to form boronate 3 and regenerate the nucleophile. The nature of the nucleophile is currently unknown but it may be another molecule of 2, potentially coordinating to boron through the nucleophilic lone pair on the nitrogen.[20]

Mechanistic Studies. Optimization of the counterion in the catalyst IPrAuX produced yield data consistent with the assignment of an active role for the X⁻ rather than simply a spectator required for charge balance. Specifically, the catalyst IPrAuOTs, with the less coordinating tosylate counterion is often employed in other reported Au(I) catalyzed reactions,[44,45] a result attributed to its weakly coordinated tosylate and thus highly Lewis acidic Au⁺ cation equivalent. Yet in oxyboration, this tosylate catalyst produced product 3a in lower yield than did IPrAuTFA, despite the fact that trifluoroacetate anion is more strongly coordinating and should therefore produce a weaker and less active gold catalyst[44,45] (¹H NMR spectroscopy yield at t=6 h for IPrAuOTs (34%; IPrAuTFA 90%). This result is somewhat surprising in light of the other reported applications of weakly coordinating anions in homogeneous Au(I) catalysis;[44,45] and is consistent with the hypothesis that the anion could be assisting the reaction by coordinating to boron to activate the B—O σ bond in borate 5 Scheme 2, Example 4. Proposed Mechanisms for Catalyzed and Uncatalyzed Oxyboration

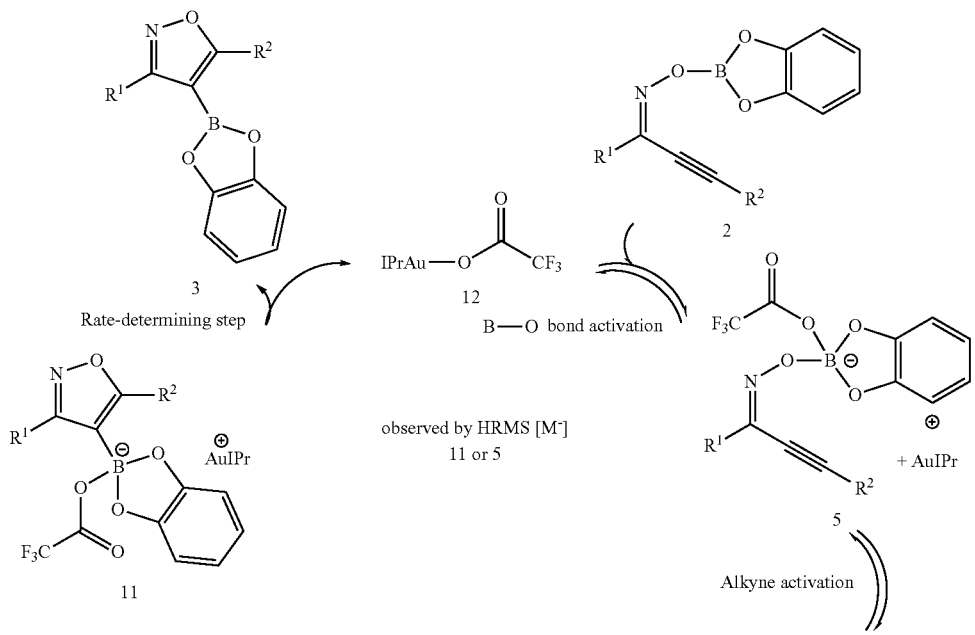

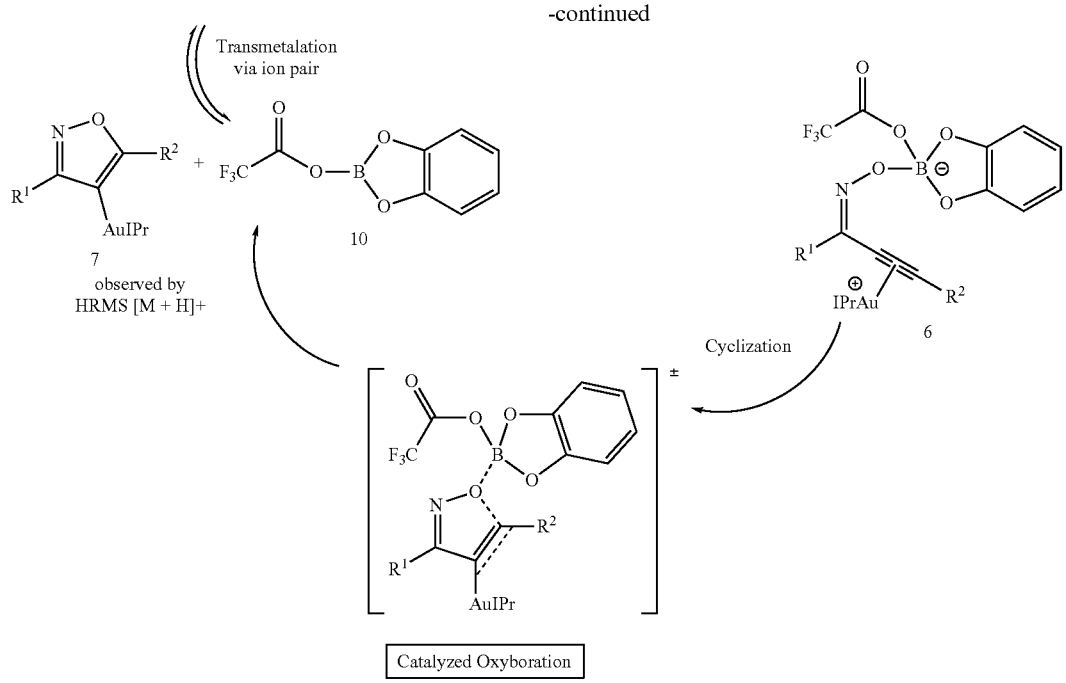

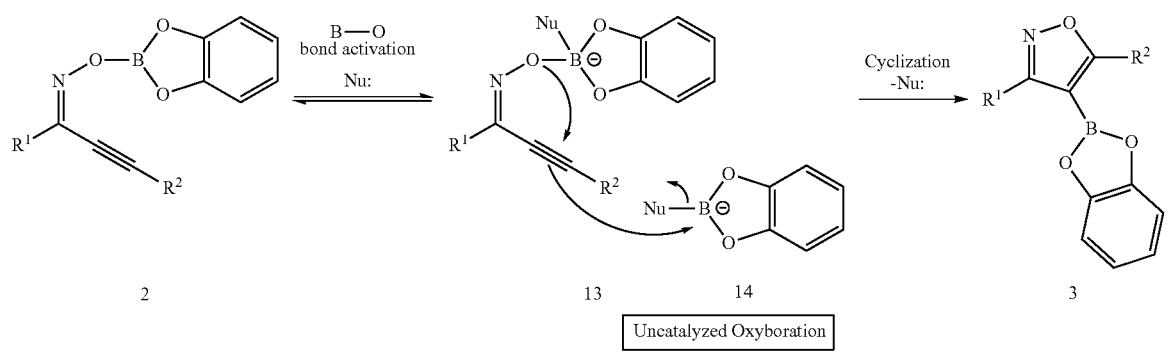

and/or by assisting transmetalation in 10 or 11.[12] The catalyst IPrAuTFA proved an optimal balance of counterion coordinating ability. The complex IPrAuOAc, with the more strongly coordinating acetate ion[45] did not lead to any detectable product formation.

In order to probe the viability of the proposed intermolecular organogold-to-boron transmetalation reaction in our system, the proposed neutral organogold intermediate 7a was generated by independent synthesis[30] (Scheme 3, see FIG. 7.1). In our hands, an attempted in situ synthesis of TFA-Bcat (proposed intermediate 10), adapted from the previously reported synthesis of TfO-Bcat,[46] yielded multiple products. We therefore examined the stoichiometric transmetalation reaction between organogold 7a and readily available B-chlorocatecholborane 15 as a substitute (Scheme 3, see FIG. 7.1). This reaction produced the anticipated transmetalation product, catechol boronic ester 3a, in 96% $^1$H NMR yield, supporting the plausibility of this intermolecular organogold-to-boron transmetalation step in our proposed mechanism. A white precipitate formed gradually during this reaction, which was presumably coproduct IPrAuCl 17, and which accounted for the initially detected substoichiometric integration (at t=10 min) and eventual disappearance (at t=2 h) of the $^1$H NMR spectroscopy signals corresponding to 17 in solution.

Interestingly, $^1$H NMR spectroscopic analysis of the reaction at t=10 min, prior to completion, characterized the mechanism of this transmetalation reaction as a two-step process wherein an initial fast transfer of the organic group from gold to boron to make an ion pair is followed by rate-determining breakdown of the ion pair to generate the final neutral products. In Scheme 2, 1, 1', 1" are the same proton in the starting material, intermediate, and final product respectively. Specifically, $^1$H and $^{11}$B NMR spectroscopy analysis indicated that the consumption of both starting materials was complete at the first data point, t=10 min, to generate ion pair 16. The ratio of 17 to final neutral organoboron product 3a at this time point was 1:1.5 ($^{11}$B NMR signal at 17.6 ppm for 16 and 31.0 ppm for 3a). This ion pair then decomposed to yield 3a in 96% final $^1$H NMR spectroscopy yield relative to external standard.

Scheme 3, Example 4. Organogold-to-Boron Transmetalation via Ion Pair

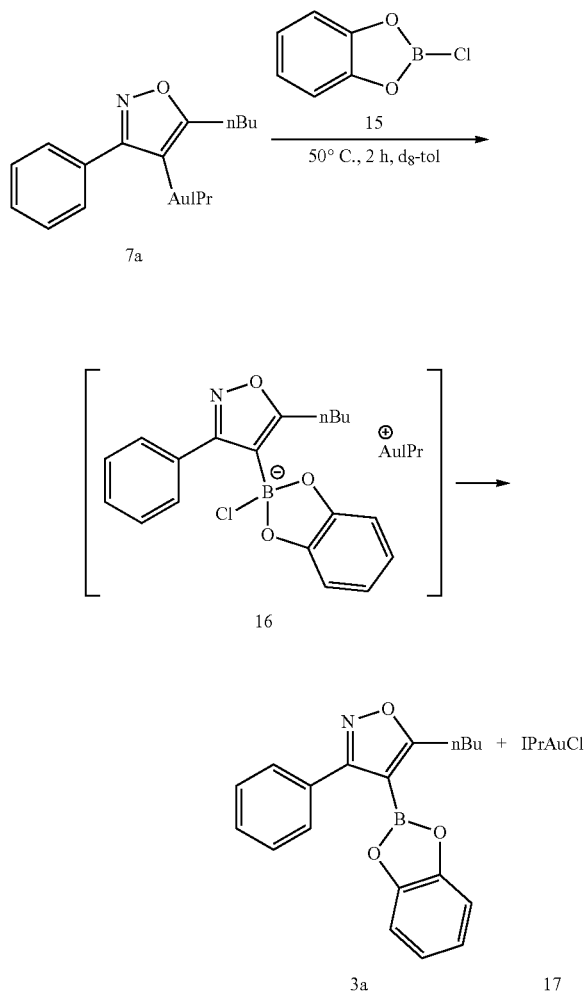

This two-step transmetalation reaction from organogold-to-boron establishes catalytic relevance to the previous observation of tetracoordinate boronate species in mixtures of organogold and boron compounds in model systems with simple substrates.[13]

HRMS analysis of the catalytic oxyboration reaction mixture prior to completion of the reaction at t=30 min identified two complexes consistent with the mechanistic proposal in Scheme 1: neutral organogold complex 7c (m/z [M]⁺=864.2803) and a second mass m/z [M]⁻=510.0458. Due to the identical m/z of anionic complexes 11c and 5c, the mass could correspond to either species or both. The detection of neutral organogold complex 7c, however, suggests the possibility of a catalyst resting state involving the equilibrium between ion pair 11 with 7 and 10 (favoring 11, as seen in the stoichiometric NMR studies, with small concentrations of 7 and 10) followed by breakdown of 11 to yield 3 and regenerate catalyst 12; although its detection alone is not sufficient to establish the catalytic relevance of 7c. These studies suggest that the rate of the overall catalytic cycle may be similarly dictated by the breakdown of the tetracoordinate boronate intermediate in the transmetalation reaction, which may serve as the rate-determining step.

The detection of TFA-coordinated boron complexes by HRMS is further consistent with an active role for the counterion in the oxyboration reaction rather than simply serving as a spectator to balance the charge on gold(I), as previously suggested by the catalyst optimization studies.

In order to further probe the intermolecularity of the proposed reaction through the intermediacy of 7 and 10, a double-label crossover experiment was conducted. Specifically, 2.5 mol % IPrAuTFA was added to 0.5 equiv of 2a and 0.5 equiv of 18 in a single reaction vessel (eq 2). Non-crossover products 3a plus 20 and crossover products 21 plus 3c were observed by $^1$H and $^{11}$B NMR spectroscopy. However, a control experiment revealed that the starting boric esters 2a and 18 underwent rapid ligand redistribution at ambient temperature even in the absence of catalyst, forming all four possible boric ester starting materials (2a, 2c, 18, 19). Exchange of the catechol groups in the starting materials was observed as line broadening in the $^1$H NMR spectra of the mixture generated by combination of 2a and 18. This exchange on the $^1$H NMR spectroscopy timescale at ambient temperature therefore was significantly more rapid than both the catalyzed and uncatalyzed oxyboration reactions and therefore precluded the employment of a double-label crossover experiment in the evaluation of the intermolecularity of the oxyboration mechanism.

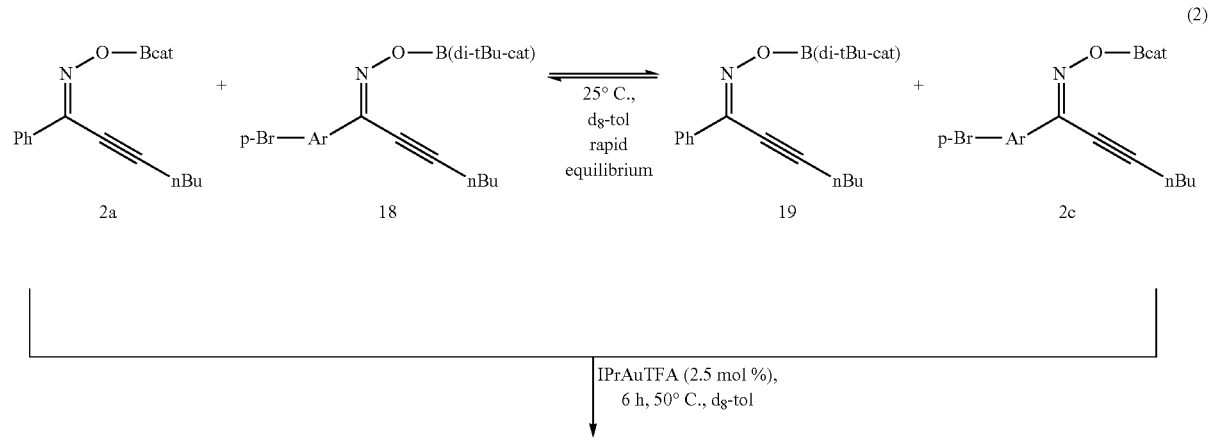

(2)

51 52

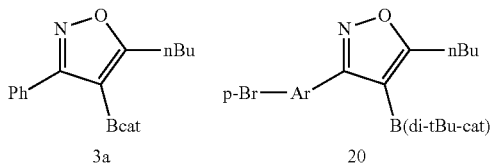

-continued

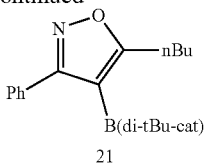

Synthetic Utility. The utility of the oxyboration reaction to generate building blocks for pharmaceutical targets was showcased through the synthesis of valdecoxib, a non-steroidal anti-inflammatory drug (NSAID)[47] and its analog. Our synthetic route is shown in Scheme 4. Under standard catalytic conditions, bench-stable pinacol boronate building blocks 23 and 4k were generated from oximes 22 and 1k in 71% and 64% isolated yields, respectively. Suzuki cross coupling of these borylated isoxazoles with p-bromobenzene sulfonamide 24 afforded valdecoxib 25 and valdecoxib ester analog 26 in 62% and 74% isolated yields, respectively. This synthesis provides the key substituted organoboron building block 23 in higher isolated yield, compared to the competing methodology with [3+2] cycloaddition of nitrile oxides and alkylboronates, which formed the same organoboron 23 in only 54% isolated yield in a route employed in a previously reported synthesis of valdecoxib.[14]

Additionally, the application of oxyboration to the synthesis of ester-containing valdecoxib analog 26 showcases the utility of the functional group tolerance of this oxyboration method. Previously reported syntheses of valdecoxib from academic[14,16] and industrial[47] laboratories involve lithiation steps that are not compatible with ester functional groups. These applications demonstrate the versatility and efficiency of the oxyboration reaction for the construction of pharmaceutical targets.

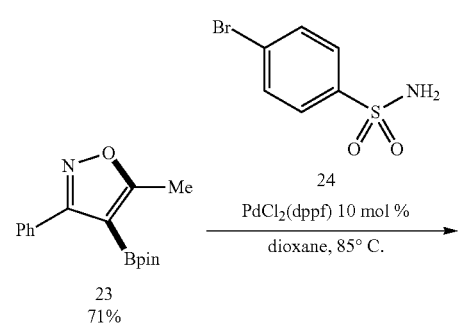

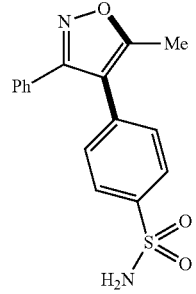

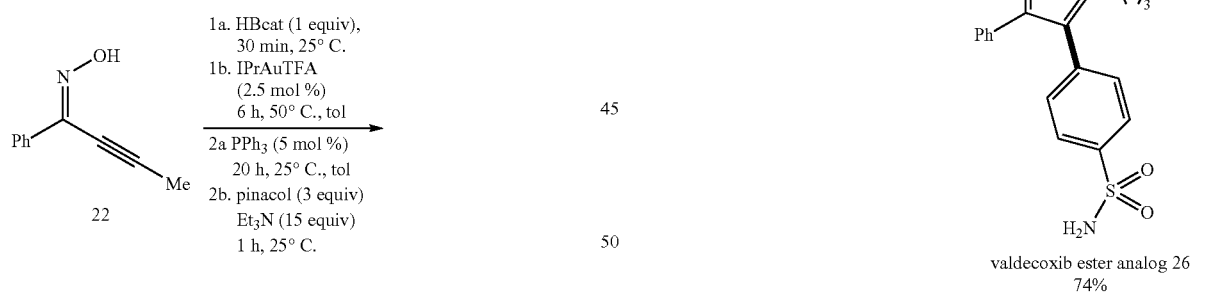

Access to a cost-effective uncatalyzed version of the reaction is particularly desirable on scale, wherein the cost of the catalyst may become a significant consideration that outweighs time considerations. The uncatalyzed oxyboration reaction scales well. Compound 1a was successfully converted to 1.7 g of pinacol boronate 4a on an 8 mmol scale under catalyst free conditions (eq 3). This convenient scalability demonstrates that quantities of these heterocyclic boronic acid building blocks that are sufficient for multistep downstream synthesis may be prepared by this oxyboration method.

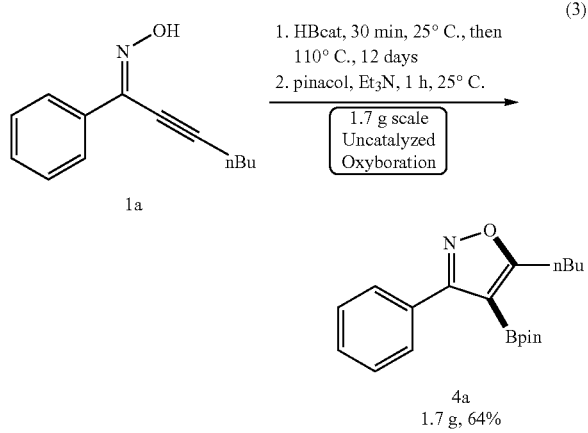

(3)

In conclusion, we have developed a method for preparing 4-borylated isoxazoles via oxyboration. This reaction proceeds with catalytic gold(I), or for many substrates without an added catalyst in the first reported uncatalyzed oxyboration reaction of C—C multiple bonds with B—O σ bonds. The reaction conditions are sufficiently mild to form functionalized borylated isoxazoles in good yields and in exclusively one regioisomer. The utility and functional group compatibility of this methodology was highlighted in the synthesis of valdecoxib and a valdecoxib ester analog. Probable reaction intermediates detected by mass spectrometry and by a stoichiometric transmetalation experiment between the organogold intermediate and the boron electrophile, are consistent with a catalyzed mechanism in which the carbophilic Lewis acid catalyst activates the C—C π bond towards B—O σ bond, a new strategy in B-Element addition reactions.[12]

REFERENCES, EXAMPLE 4

(1) Pinho, e M.; Teresa, M. V. D. *Curr. Org. Chem.* 2005, 9, 925-958.
(2) Daidone, G.; Raffa, D.; Maggio, B.; Plescia, F.; Cutuli, V. M. C.; Mangano, N. G.; Caruso, A. *Arch. Pharm.* 1999, 332, 50-54.
(3) Cali, P.; Nrum, L.; Mukhija, S.; Hjelmencrantz, A. *Bioorg. Med. Chem. Lett.* 2004, 14, 5997-6000.
(4) Liu, J.; Yu, L.-F.; Eaton, J. B.; Caldarone, B.; Cavino, K.; Ruiz, C.; Terry, M.; Fedolak, A.; Wang, D.; Ghavami, A.; Lowe, D. A.; Brunner, D.; Lukas, R. J.; Kozikowski, A. P. *J. Med. Chem.* 2011, 54, 7280-7288.
(5) Kumbhare, R. M.; Kosurkar, U. B.; Janaki Ramaiah, M.; Dadmal, T. L.; Pushpavalli, S. N.; Pal-Bhadra, M. *Bioorg. Med. Chem. Lett.* 2012, 22, 5424-5427.
(6) Burke, M. D.; Berger, E. M.; Schreiber, S. L. *J. Am. Chem. Soc.* 2004, 126, 14095-14104.
(7) Gutiérrez, M.; Matus, M. F.; Poblete, T.; Amigo, J.; Vallejos, G.; Astudillo, L. *J. Pharm. Pharmacol.* 2013, 65, 1796-1804.
(8) Vitale, P.; Tacconelli, S.; Perrone, M. G.; Malerba, P.; Simone, L.; Scilimati, A.; Lavecchia, A.; Dovizio, M.; Marcantoni, E.; Bruno, A.; Patrignani, P. *J. Med. Chem.* 2013, 56, 4277-4299.
(9) Tzanetou, E.; Liekens, S.; Kasiotis, K. M.; Melagraki, G.; Afantitis, A.; Fokialakis, N.; Haroutounian, S. A. *Eur. J. Med. Chem.* 2014, 81, 139-149.
(10) Cragg, R. H.; Lappert, M. F.; Tilley, B. P. *J. Chem. Soc.* 1964, 2108-2115.
(11) Matsumi, N.; Chujo, Y. *Macromolecules* 1998, 31, 3802-3806.
(12) (a) Hirner, J. J.; Faizi, D. J.; Blum, S. A. *J. Am. Chem. Soc.* 2014, 136, 4740-4745. (b) Chong, E.; Blum, S. A. *J. Am. Chem. Soc.* 2015, 137, 10144-10147.
(13) Hirner, J. J.; Blum, S. A. *Tetrahedron* 2015, 71, 4445-4449.
(14) Moore, J. E.; Davies, M. W.; Goodenough, K. M.; Wybrow, R. A. J.; York, M.; Johnson, C. N.; Harrity, J. P. A. *Tetrahedron* 2005, 61, 6707-6714.
(15) Tang, W.; Keshipeddy, S.; Zhang, Y.; Wei, X.; Savoie, J.; Patel, N. D.; Yee, N. K.; Senanayake, C. H. *Org. Lett.* 2011, 13, 1366-1369.
(16) Velcicky, J.; Soicke, A.; Steiner, R.; Schmalz, H.-G. *J. Am. Chem. Soc.* 2011, 133, 6948-6951.
(17) Praveen, C.; Kalyanasundaram, A.; Perumal, P. T. *Synlett.* 2010, 5, 777-781.
(18) Kung, K. K-Y., Lo, V. K-Y.; Ko, H-M.; Li, G-L.; Chan, P-Y.; Leung, K-C.; Zhou, Z.; Wang, M-Z.; Che, C-M.; Wong, M-K. *Adv. Synth. Catal.* 2013, 10, 2055-2070.
(19) Mlynarski, S. N.; Karns, A. S.; Morken, J. P. *J. Am. Chem. Soc.* 2012, 134, 16449-16451.
(20) Fina, N. J.; Edwards, J. O. *Int. J. Chem. Kinet.* 1973, 5, 1-26.
(21) Gassman, P. G.; Deck, P. A.; Winter, C. H.; Dobbs, D. A.; Cao, D. H. *Organometallics* 1992, 11, 959-960.
(22) Del Grosso, A.; Singleton, P. J.; Muryn, C. A.; Ingleson, M. J. *Angew. Chem. Int. Ed.* 2011, 50, 2102-2106.
(23) Shi, Y.; Roth, K. E.; Ramgren, S. D.; Blum, S. A. *J. Am. Chem. Soc.* 2009, 131, 18022-18023.
(24) Scott, H. K.; Aggarwal, V. K. *Chem.-Eur. J.* 2011, 17, 13124-13132.
(25) Bailey, W. F.; Patricia, J. J. *J. Organomet. Chem.* 1988, 352, 1-46.
(26) Yeung, K-S. *Top. Heterocycl. Chem.* 2012, 29, 47-76.
(27) Gimeno, A.; Cuenca, A. B.; Suarez-Pantiga, S.; Ramirez de Arellano, C.; Medio-Simon, M.; Asensio, G. *Chem.-Eur. J.* 2014, 20, 683-688.
(28) Tang, Y.; Li, J.; Zhu, Y.; Li, Y.; Yu, B. *J. Am. Chem. Soc.* 2013, 135, 18396-18405.
(29) Liu, L.-P; Xu, B.; Mashuta, M. S.; Hammond, G. B. *J. Am. Chem. Soc.* 2008, 130, 17642-17643.
(30) Jeong, Y.; Kim, B-I.; Lee, J. K.; Ryu, J-S. *J. Org. Chem.* 2014, 79, 6444-6455.
(31) Hirner, J. J.; Shi, Y.; Blum, S. A. *Acc. Chem. Res.* 2011, 44, 603-613.
(32) Roth, K. E.; Blum, S. A. *Organometallics* 2010, 29, 1712-1716.
(33) Hasmi, A. S. K.; Toste, F. D. *Modern Gold Catalyzed Synthesis*, 1st ed.; Wiley-VCH: Weinheim, Germany, 2012.
(34) Hansmann, M. M.; Rominger, F.; Boone, M. P.; Stephan, D. W.; Hashmi, A. S. K. *Organometallics* 2014, 33, 4461-4470.
(35) Sladek, A.; Hofreiter, S.; Paul, M.; Schmidbaur, H. *J. Organomet. Chem.* 1995, 501, 47-51.
(36) Forward, J. M.; Fackler, J. P., Jr.; Staples, R. J. *Organometallics* 1995, 14, 4194-4198.
(37) Partyka, D. V.; Zeller, M.; Hunter, A. D.; Gray, T. G. *Angew. Chem. Int. Ed.* 2006, 45, 8188-8191.
(38) Partyka, D. V.; Zeller, M.; Hunter, A. D.; Gray, T. G. *Inorg. Chem.* 2012, 51, 8394-8401.
(39) Al-Amin, M.; Johnson, J. S.; Blum, S. A. *Organometallics* 2014, 33, 5448-5456.
(40) Al-Amin, M. Roth, K. E.; Blum, S. A. *ACS Catal.* 2014, 4, 622-629.

(41) Hirner, J. J.; Roth, K. E.; Shi, Y.; Blum, S. A. *Organometallics* 2012, 31, 6843-6850.

(42) Roth, K. E.; Blum, S. A. *Organometallics* 2011, 30, 4811-4813.

(43) Hirner, J. J.; Blum, S. A. *Organometallics* 2011, 30, 1299-1302.

(44) Ciancaleoni, G.; Belpassi, L.; Zuccaccia, D.; Tarantelli, F.; Belanzoni, P. *ACS Catal.* 2015, 5, 803-814.

(45) Jia, M.; Bandini, M. *ACS Catal.* 2015, 5, 1638-1652.

(46) Del Grosso, A.; Pritchard, R. G.; Muryn, C. A.; Ingleson, M. J. *Organometallics* 2010, 29, 241-249.

(47) Talley, J. J.; Brown, D. L.; Carter, J. S.; Graneto, M. J.; Koboldt, C. M.; Masferrer, J. L.; Perkins, W. E.; Rogers, R. S.; Shaffer, A. F.; Zhang, Y. Y.; Zweifel, B. S.; Seibert, K. *J. Med. Chem.* 2010, 43, 775-777.

Supporting Information for Example 4

I. General Methods

All reagents were used as received from commercial sources unless otherwise noted. Tetrahydrofuran, acetonitrile and triethylamine were dried by passing through an alumina column under argon pressure on a push still solvent system. Toluene-d8 was dried over CaH2, degassed using three freeze-pump-thaw cycles, and vacuum transferred before use. Dioxane was degassed by sparging with nitrogen gas for 1 h. Manipulations were performed in a glovebox under nitrogen atmosphere unless otherwise noted. Analytical thin layer chromatography (TLC) was performed using Merck F250 plates and visualized under UV irradiation at 254 nm, or using a basic aqueous solution of potassium permanganate. Flash chromatography was conducted using a Teledyne Isco Combiflash® Rf 200 Automatic Flash Chromatography System, and Teledyne Isco Redisep® 35-70 μm silica gel. All proton and carbon nuclear magnetic resonance (1H and 13C NMR) spectra were recorded on a Bruker DRX-400 spectrometer, Bruker DRX-500 spectrometer outfitted with a cryoprobe, or a Bruker AVANCE-600 spectrometer. Boron nuclear magnetic resonance (11B NMR) spectra were recorded on a Bruker AVANCE-600 spectrometer. Fluorine nuclear magnetic resonance (19F NMR) spectra were recorded on a Bruker DRX-400 spectrometer. All coupling constants were measured in Hertz (Hz). Chemical shifts were reported in ppm and referenced to residual protonated solvent peak ($\delta H$=7.26 ppm for CDCl3, $\delta H$=2.08 ppm for d8-toluene, $\delta H$=2.05 ppm for d6-acetone in 1H NMR spectroscopy experiments; $\delta C$=77.16 ppm for CDCl3, $\delta C$=20.43 ppm for d8-toluene, $\delta C$=29.84 ppm for d6-acetone in 13C NMR spectroscopy experiments). 11B and 19F NMR spectroscopy experiments were referenced to the absolute frequency of 0 ppm in the 1H dimension according to the Xi scale. High-resolution mass spectrometry data were obtained at the University of California, Irvine.

II. Synthetic Procedures

A. Preparation of Alkynyl Ketone SI-2(a-i). General Procedure

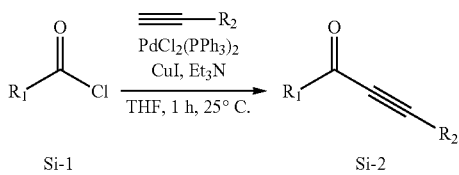

Ketones were prepared according to a literature procedure.1 Using standard Schlenk line, to a flame-dried round bottom flask equipped with stir bar under N2 atmosphere was added acid chloride SI-1 (10.0 mmol, 1.00 equiv), PdCl2(PPh3)2 (140 mg, 0.20 mmol, 2.0 mol %), CuI (76 mg, 0.40 mmol, 4.0 mol %), Et3N (1.39 mL, 10.0 mmol, 1.00 equiv), and alkyne (1.0 equiv) in dry THF (50 mL) at 25° C. The resulting reaction mixture was stirred at room temperature for 1 h. The reaction was quenched with DI water (30 mL). The aqueous layer was extracted with EtOAc (3×30 mL). The combined organic layers were washed with brine (30 mL), dried over MgSO4, filtered, and concentrated in vacuo. The resulting crude solid was purified by silica gel flash column chromatography using an elution gradient from 100% hexanes to 10% EtOAc in hexanes. Product-containing fractions were combined and concentrated in vacuo to afford SI-2.

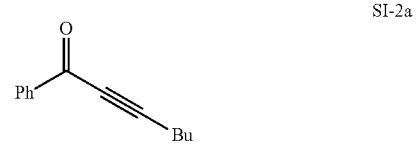

1-phenylhept-2-yn-1-one (SI-2a) was obtained as yellow oil (1.60 g, 86% isolated yield). TLC (20% EtOAc/hexanes): Rf=0.50, visualized by UV absorbance. 1H NMR (CDCl3, 500 MHz): δ 8.15-8.13 (m, 2H), 7.61-7.58 (m, 1H), 7.49-7.46 (m, 2H), 2.51 (t, J=7.0 Hz, 2H), 1.67 (quintet, J=7.5 Hz, 2H), 1.52 (sextet, J=7.5 Hz, 2H), 0.97 (t, J=7.5 Hz, 3H). This spectrum is in agreement with previously reported spectral data.[2]

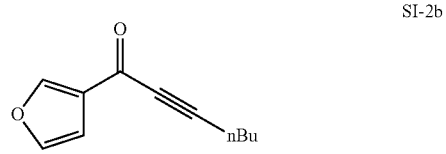

1-(3-furyl)hept-2-yn-1-one (SI-2b) was obtained as brown oil (1.53 g, 87% isolated yield). TLC (20% EtOAc/hexanes): Rf=0.47, visualized by UV absorbance. 1H NMR (CDCl3, 500 MHz): δ 8.11 (s, 1H), 7.42 (s, 1H), 6.81 (s, 1H), 2.44 (t, J=7.0 Hz, 2H), 1.63 (quintet, J=7.0 Hz, 2H), 1.49 (sextet, J=7.5 Hz, 2H), 0.95 (t, J=7.5 Hz, 3H). This spectrum is in agreement with previously reported spectral data.[3]

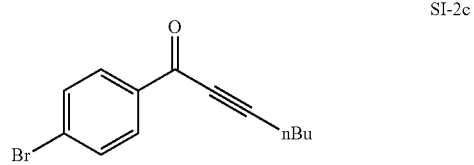

1-(4-Bromophenyl)hept-2-yn-1-one (SI-2c) was obtained as dark brown oil (2.31 g, 87% isolated yield). TLC (20% EtOAc/hexanes): Rf=0.55, visualized by UV absorbance. 1H NMR (CDCl3, 500 MHz): δ 7.98 (d, J=8.5 Hz, 2H), 7.62 (d, J=8.0 Hz, 2H), 2.50 (t, J=7.0 Hz, 2H), 1.66 (quintet, J=7.5 Hz, 2H), 1.50 (sextet, J=7.5 Hz, 2H), 0.96 (t, J=7.5 Hz, 3H). This spectrum is in agreement with previously reported spectral data.[4]

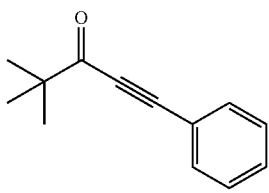

SI-2d

1-Phenyl-4,4-dimethyl-pent-1-yn-3-one (SI-2d) was obtained as yellow oil (1.35 g, 74% isolated yield). TLC (20% EtOAc/hexanes): $R_f$=0.61, visualized by UV absorbance. $^1$H NMR (CDCl$_3$, 500 MHz): δ 7.59-7.37 (m, 5H), 1.28 (s, 9H). This spectrum is in agreement with previously reported spectral data.[5]

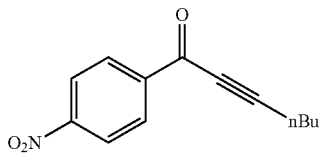

SI-2e 1-(4-Nitrophenyl)hept-2-yn-1-one (SI-2e) was obtained as reddish orange oil (1.76 g, 76% isolated yield). TLC (20% EtOAc/hexanes): $R_f$=0.47, visualized by UV absorbance. $^1$H NMR (CDCl$_3$, 600 MHz): δ 8.33-8.28 (m, 4H), 2.55 (t, J=7.2 Hz, 2H), 1.69 (quintet, J=7.2 Hz, 2H), 1.51 (sextet, J=7.2 Hz, 2H), 0.98 (t, J=7.2 Hz, 3H). This spectrum is in agreement with previously reported spectral data.[6]

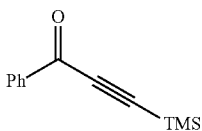

SI-2f 1-phenyl-3-trimethylsilyl-prop-2-yn-1-one (SI-2f) was obtained as pale yellow oil (1.62 g, 80% isolated yield). TLC (20% EtOAc/hexanes): $R_f$=0.67, visualized by UV absorbance. $^1$H NMR (CDCl$_3$, 500 MHz): δ 8.15 (d, J=7.0 Hz, 2H), 7.62 (t, J=7.0 Hz, 1H), 7.49 (t, J=7.0 Hz, 2H), 0.32 (s, 9H). This spectrum is in agreement with previously reported spectral data.[7]

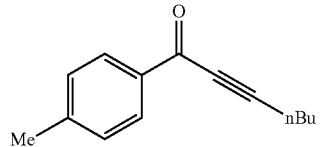

SI-2g 1-(4-Methylphenyl)hept-2-yn-1-one (SI-2g) was obtained as yellow oil (1.70 g, 85% isolated yield). TLC (20% EtOAc/hexanes): $R_f$=0.52, visualized by UV absorbance. $^1$H NMR (CDCl$_3$, 500 MHz): δ 8.03 (d, J=8.5 Hz, 2H), 7.27 (d, J=9.0 Hz, 2H), 2.50 (t, J=7.0 Hz, 2H), 2.43 (s, 3H), 1.66 (quintet, J=7.5 Hz, 2H), 1.50 (sextet, J=7.5 Hz, 2H), 0.96 (t, J=7.5 Hz, 3H). This spectrum is in agreement with previously reported spectral data.[6]

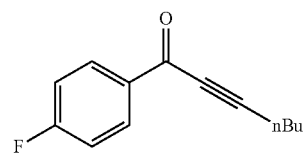

SI-2h 1-(4-Fluorophenyl)hept-2-yn-1-one (SI-2h) was obtained as yellow oil (1.51 g, 74% isolated yield). TLC (20% EtOAc/hexanes): $R_f$=0.57, visualized by UV absorbance. $^1$H NMR (CDCl$_3$, 500 MHz): δ 8.17-8.14 (m, 2H), 7.15 (t, J=8.5 Hz, 2H), 2.51 (t, J=7.0 Hz, 2H), 1.67 (quintet, J=7.5 Hz, 2H), 1.52 (sextet, J=7.5 Hz, 2H), 0.97 (t, J=7.5 Hz, 3H). This spectrum is in agreement with previously reported spectral data.[8]

SI-2i 1-(4-Methoxyphenyl)hept-2-yn-1-one (SI-2i) was obtained as yellow oil (1.74 g, 81% isolated yield). TLC (20% EtOAc/hexanes): $R_f$=0.38, visualized by UV absorbance. $^1$H NMR (CDCl$_3$, 600 MHz): δ 8.10 (d, J=9.0 Hz, 2H), 6.94 (d, J=8.4 Hz, 2H), 3.88 (s, 3H), 2.49 (t, J=7.2 Hz, 2H), 1.66 (quintet, J=7.2 Hz, 2H), 1.50 (sext, J=7.8 Hz, 2H), 0.96 (t, J=7.2 Hz, 3H). This spectrum is in agreement with previously reported spectral data.[6]

SI-2j 1-(4-Trifluoromethylphenyl)hept-2-yn-1-one (SI-2j) was obtained as dark yellow oil (2.19 g, 87% isolated yield). TLC (20% EtOAc/hexanes): $R_f$=0.48, visualized by UV absorbance. $^1$H NMR (CDCl$_3$, 500 MHz): δ 8.24 (d, J=8.0 Hz, 2H), 7.75 (d, J=8.0 Hz, 2H), 2.53 (t, J=7.0 Hz, 2H), 1.68 (quintet, J=7.0 Hz, 2H), 1.51 (sext, J=7.5 Hz, 2H), 0.97 (t, J=7.5 Hz, 3H). This spectrum is in agreement with previously reported spectral data.[4]

SI-2k

Methyl 7-oxo-7-phenyl-hept-5-yn-1-oate (SI-2k) was obtained as dark yellow solid (1.95 g, 85% isolated yield). TLC (20% EtOAc/hexanes): $R_f$=0.22, visualized by UV absorbance. $^1$H NMR (CDCl$_3$, 500 MHz): δ 8.12 (d, J=8.0

Hz, 2H), 7.61 (t, J=7.5 Hz, 1H), 7.48 (t, J=7.5 Hz, 2H), 3.70 (s, 3H), 2.60 (t, J=7.0 Hz, 2H), 2.53 (t, J=7.0 Hz, 2H), 2.01 (quintet, J=7.0 Hz, 2H). $^{13}$C NMR (CDCl$_3$, 125 MHz): δ 178.2, 173.3, 136.9, 134.1, 129.7, 128.7, 95.1, 80.3, 51.9, 32.8, 23.2, 18.8. HRMS (ESI+) m/z calcd for C$_{14}$H$_{14}$O$_3$ ([M+Na]$^+$) 253.0841. found 253.0832.

B. Preparation of Alkynyl Oxime 1a-k. General Procedure

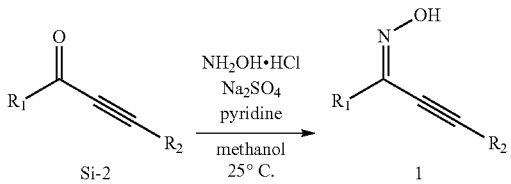

Oximes were prepared according to a literature procedure.[9] Open to air, a 50 mL round bottom flask was charged with H$_2$NOH·HCl (2.2 equiv), Na$_2$SO$_4$ (3.0 equiv), and a stir bar. The solids were suspended in MeOH (20 mL). Pyridine (4.0 equiv) and then ketone SI-2 (1.0 equiv) were added. The reaction was allowed to stir at room temperature until the starting material was consumed completely, as shown by TLC after 5 h. The reaction was quenched with DI water (25 mL) and extracted with EtOAc (3×25 mL). The combined organic layers were washed with brine (25 mL), dried over MgSO$_4$, filtered, and concentrated in vacuo. The crude was purified by silica gel flash column chromatography using a stepwise gradient from 5% to 10% EtOAc in hexanes. Product-containing fractions were combined and concentrated in vacuo to afford 1.

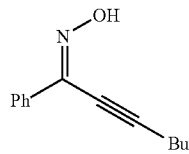

1a (Z)-1-phenylhept-2-yn-1-one oxime (1a) was obtained as light yellow solid (38 mg, 22% isolated yield). TLC (20% EtOAc/hexanes): R$_f$=0.30, visualized by UV absorbance. $^1$H NMR (d$_8$-toluene, 500 MHz): δ 9.12 (s, 1H), 7.98 (d, J=7.5 Hz, 2H), 7.12-7.05 (m, 3H), 2.16 (t, J=7.0 Hz, 2H), 1.37-1.23 (m, 4H), 0.75 (t, J=7.5 Hz, 3H). This spectrum is in agreement with previously reported spectral data.[3]

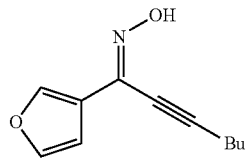

1b (Z)-1-(3-furyl)hept-2-yn-1-one oxime (1b) was obtained as yellow solid (115 mg, 6.9% isolated yield).). TLC (20% EtOAc/hexanes): R$_f$=0.27, visualized by UV absorbance. $^1$H NMR (CDCl$_3$, 500 MHz): δ 7.85 (s, 1H), 7.74 (s, 1H), 7.39 (s, 1H), 6.69 (s, 1H), 2.52 (t, J=7.0 Hz, 2H), 1.65 (quintet, J=7.0 Hz, 2H), 1.50 (sextet, J=7.5 Hz, 2H), 0.96 (t, J=7.0 Hz, 3H). $^{13}$C NMR (CDCl$_3$, 125 MHz): δ 143.9, 143.3, 136.0, 122.4, 107.5, 102.9, 70.2, 30.4, 22.2, 19.4, 13.7. HRMS (ESI+) m/z calcd for C$_{11}$H$_{13}$NO$_2$ ([M+Na]$^+$) 214.0844. found 214.0849.

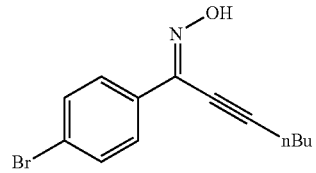

1c (Z)-1-(4-Bromophenyl)hept-2-yn-1-one oxime (1c) was obtained as brown solid (0.234 g, 9.6% isolated yield). TLC (20% EtOAc/hexanes): R$_f$=0.26, visualized by UV absorbance. $^1$H NMR (CDCl$_3$, 500 MHz): δ 8.34 (s, 1H), 7.69 (d, J=8.6 Hz, 2H), 7.51 (d, J=8.6 Hz, 2H), 2.58 (t, J=7.1 Hz, 2H), 1.67 (quintet, J=7.1 Hz, 2H), 1.51 (sextet, J=7.5 Hz, 2H), 0.96 (t, J=7.4 Hz, 3H). $^{13}$C NMR (CDCl$_3$, 125 MHz): δ 141.6, 132.7, 131.7, 128.2, 124.3, 106.2, 70.2, 30.4, 22.2, 19.6, 13.7. HRMS (ESI+) m/z calcd for C$_{13}$H$_{14}$BrNO ([M+Na]$^+$) 302.0157. found 302.0148.

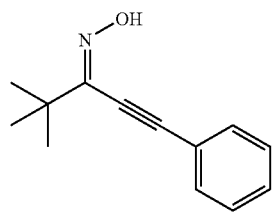

1d (Z)-1-Phenyl-4,4-dimethylpent-1-yn-3-one oxime (1d) was obtained as white solid (0.863 g, 58% isolated yield). TLC (20% EtOAc/hexanes): R$_f$=0.38, visualized by UV absorbance. $^1$H NMR (d$_8$-toluene, 600 MHz): δ 9.58 (s, 1H), 7.37-7.36 (m, 2H), 6.97-6.90 (m, 3H), 1.23 (s, 9H). This spectrum is in agreement with previously reported spectral data.[3]

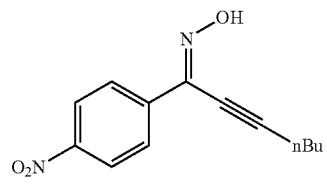

1e (Z)-1-(4-Nitrophenyl)hept-2-yn-1-one oxime (1e) was obtained as dark yellow solid (0.112 g, 6.0% isolated yield). TLC (20% EtOAc/hexanes): R$_f$=0.26, visualized by UV absorbance. $^1$H NMR (CDCl$_3$, 600 MHz): δ 8.20 (s, 1H), 8.14-8.13 (m, 2H), 7.91-7.89 (m, 2H), 2.50 (t, J=7.2 Hz, 2H), 1.59 (quintet, J=7.3 Hz, 2H), 1.42 (sextet, J=7.5 Hz 2H), 0.88 (t, J=7.4 Hz, 3H). $^{13}$C NMR (CDCl$_3$, 150 MHz): δ 148.6, 140.8, 139.7, 127.4, 123.8, 107.2, 69.9, 30.3, 22.2, 19.6, 13.7. HRMS (ESI-) m/z calcd for C$_{13}$H$_{14}$N$_2$O$_3$ ([M-H]$^-$) 245.0926. found 245.0929.

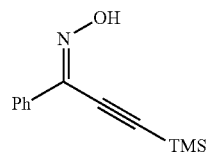

1f (Z)-1-phenyl-3-trimethylsilyl-prop-2-yn-1-one oxime (1f) was obtained as white solid (0.885 g, 51% isolated yield). TLC (20% EtOAc/hexanes): $R_f$=0.41, visualized by UV absorbance. $^1$H NMR (CDCl$_3$, 500 MHz): δ 8.11 (s, 1H), 7.83-7.81 (m, 2H), 7.40-7.39 (m, 3H), 0.33 (s, 9H). $^{13}$C NMR (CDCl$_3$, 125 MHz): δ 142.1, 133.1, 130.1, 128.6, 126.6, 110.4, 92.7, −0.19. HRMS (ESI+) m/z calcd for C$_{12}$H$_{15}$NOSi ([M+Na]$^+$) 240.0821. found 240.0815.

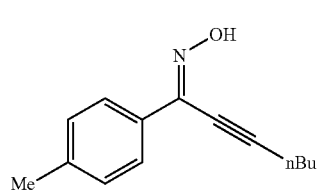

1g (Z)-1-(4-Methylphenyl)hept-2-yn-1-one oxime (1g) was obtained as light yellow solid (0.347 g, 19% isolated yield). TLC (20% EtOAc/hexanes): $R_f$=0.34, visualized by UV absorbance. $^1$H NMR (CDCl$_3$, 500 MHz): δ 8.49 (s, 1H), 7.71 (d, J=8.2 Hz, 2H), 7.19 (d, J=8.2 Hz, 2H), 2.58 (t, J=7.1 Hz, 2H), 2.37 (s, 3H), 1.68 (quintet, J=7.3 Hz, 2H), 1.52 (sextet, J=7.5 Hz, 2H), 0.97 (t, J=7.3 Hz, 3H). $^{13}$C NMR (CDCl$_3$, 125 MHz): δ 142.4, 140.1, 131.0, 129.5, 126.6, 105.5, 70.7, 30.5, 22.2, 21.5, 19.6, 13.7. HRMS (ESI+) m/z calcd for C$_{14}$H$_{17}$NO ([M+Na]$^+$) 238.1208. found 238.1200.

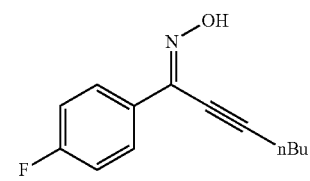

1h (Z)-1-(4-Fluorophenyl)hept-2-yn-1-one oxime (1h) was obtained as yellow oil (0.178 g, 11% isolated yield). TLC (20% EtOAc/hexanes): $R_f$=0.29, visualized by UV absorbance. $^1$H NMR (CDCl$_3$, 400 MHz): δ 8.02 (s, 1H), 7.83-7.80 (m, 2H), 7.07 (t, J=8.4 Hz, 2H), 2.58 (t, J=7.2 Hz, 2H), 1.68 (quintet, J=7.2 Hz, 2H), 1.53 (sextet, J=7.6 Hz, 2H), 0.97 (t, J=7.6 Hz, 3H). $^{13}$C NMR (CDCl$_3$, 125 MHz): δ 164.9, 162.9, 141.5, 129.85, 129.82, 128.57, 128.50, 115.65, 115.48, 106.0, 70.3, 30.4, 22.2, 19.6, 13.7. $^{19}$F NMR (CDCl$_3$, 376 MHz): δ −111.2. HRMS (ESI+) m/z calcd for C$_{13}$H$_{14}$FNO ([M+Na]$^+$) 242.0957. found 242.0957.

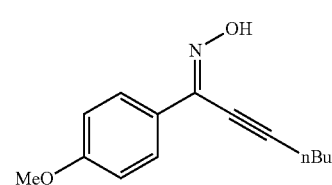

1i (Z)-1-(4-Methoxyphenyl)hept-2-yn-1-one oxime (1i) was obtained as yellow solid (0.318 g, 17% isolated yield). TLC (20% EtOAc/hexanes): $R_f$=0.19, visualized by UV absorbance. $^1$H NMR (CDCl$_3$, 600 MHz): δ 8.15 (s, 1H), 7.77-7.76 (m, 2H), 6.91-6.89 (m, 2H), 3.84 (s, 3H), 2.57 (t, J=7.1 Hz, 2H), 1.67 (quintet, J=7.2 Hz, 2H), 1.51 (sextet, J=7.6 Hz, 2H), 0.97 (t, J=7.4 Hz, 3H). $^{13}$C NMR (CDCl$_3$, 125 MHz): δ 161.1, 142.1, 128.1, 126.4, 113.9, 105.4, 70.6, 55.5, 30.5, 22.2, 19.6, 13.7. HRMS (ESI+) m/z calcd for C$_{14}$H$_{17}$NO$_2$ ([M+Na]$^+$) 254.1157. found 254.1158.

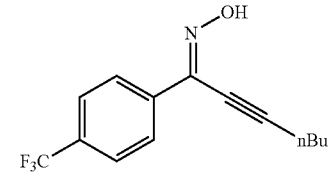

1j (Z)-1-(4-Trifluoromethylphenyl)hept-2-yn-1-one oxime (1j) was obtained as light brown solid (0.262 g, 11% isolated yield). TLC (20% EtOAc/hexanes): $R_f$=0.32, visualized by UV absorbance. $^1$H NMR (CDCl$_3$, 500 MHz): δ 8.26 (s, 1H), 7.94 (d, J=8.0 Hz, 2H), 7.64 (d, J=8.0 Hz, 2H), 2.59 (t, J=7.5 Hz, 2H), 1.68 (quintet, J=7.0 Hz, 2H), 1.52 (sextet, J=7.5 Hz, 2H), 0.97 (t, J=7.5 Hz, 3H). $^{13}$C NMR (CDCl$_3$, 125 MHz): δ 141.1, 137.0, 131.7, 131.5, 126.9, 125.5 (q, J=15 Hz), 123.0, 106.6, 70.0, 30, 4, 22.2, 19.6, 13.7. $^{19}$F NMR (CDCl$_3$, 376 MHz): δ −62.8. HRMS (ESI+) m/z calcd for C$_{14}$H$_{14}$F$_3$NO ([M+Na]$^+$) 292.0925. found 292.0920.

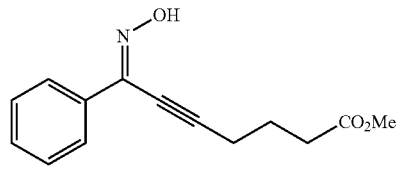

1k

Methyl 7-hydroxyimino-7-phenylhept-5-yn-1-oate (1k) was obtained as light yellow solid (0.175 g, 8.4% isolated yield). TLC (20% EtOAc/hexanes): $R_f$=0.21, visualized by UV absorbance. $^1$H NMR (CDCl$_3$, 500 MHz): δ 8.51 (s, 1H), 7.82-7.80 (m, 2H), 7.39-7.38 (m, 3H), 3.69 (s, 3H), 2.66 (t, J=7.0 Hz, 2H), 2.56 (t, J=7.5 Hz, 2H), 2.02 (quintet, J=7.0 Hz, 2H). $^{13}$C NMR (CDCl$_3$, 125 MHz): δ 173.5, 133.5, 130.0, 129.0 128.6, 126.6, 103.9, 85.6, 51.9, 32.9, 23.6, 19.3. HRMS (ESI+) m/z calcd for C$_{14}$H$_{15}$NO$_3$ ([M+Na]$^+$) 268.0950. found 268.0951.

C. Preparation of IPrAuTFA Catalyst

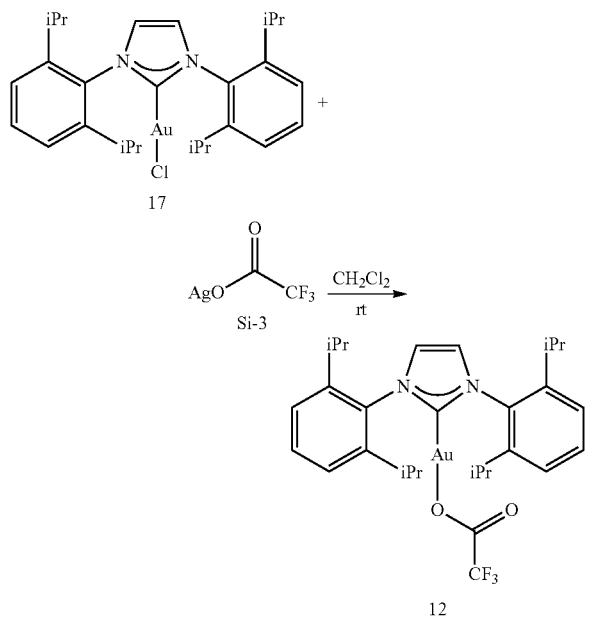

No precautions were taken to exclude air or water. The reaction was conducted in a fume hood with the light turned off. A solution of IPrAuCl 17 (124 mg, 200. μmol, 1.00 equiv) in DCM (2.0 mL) was added to a dram vial containing AgTFA SI-3 (48.6 mg, 220. μmol, 1.10 equiv) and a stirbar. A white precipitation was observed. The vial was capped and wrapped with aluminum foil to protect the reaction mixture from light. The reaction was stirred vigorously at 25° C. for 7 h. The resulting suspension was then filtered through a Celite plug (ca. 0.5 mL). The Celite was rinsed with additional DCM (3×0.5 mL), and the resulting solution was concentrated in vacuo to a a white solid. The solid was crushed to a fine powder, from which volatiles were removed at 25° C. and ca. 10 mTorr for 18 h to afford IPrAuTFA 12 as a white powder (135 mg, 97% isolated yield). $^1$H NMR (CDCl$_3$, 500 MHz): δ 7.53 (t, J=7.8 Hz, 2H), 7.31 (d, J=7.8 Hz, 4H), 7.21 (s, 2H), 2.53 (sept, J=7.0 Hz, 4H), 1.35 (d, J=7.0 Hz, 12H), 1.23 (d, J=7.0 Hz, 12H). $^{19}$F NMR (CDCl$_3$, 376 MHz): δ −74.1 (s). This spectrum is in agreement with previously reported spectral data.[10]

D. Optimization of Oxyboration Reaction Conditions

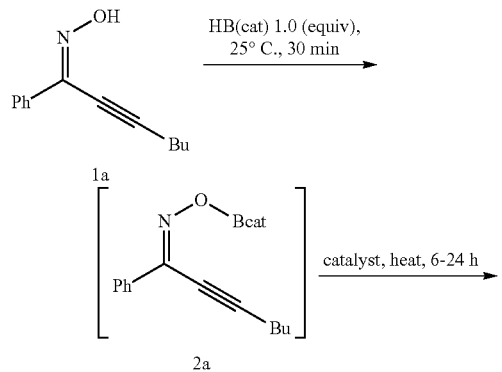

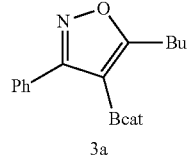

Boric ester 2a. The reaction was performed inside N$_2$-filled glovebox. A 4-dram vial was charged with a solution of 1a (20.1 mg, 0.100 mmol, 1.00 equiv) in d$_8$-toluene (0.30 mL). To this solution was added catecholborane (10.7 μL, 0.100 mmol, 1.00 equiv) at 25° C. The reaction mixture was stirred for 30 min during which the evolution of H$_2$ gas was observed, to afford 2a, which was used directly in the screen of reaction conditions without further purification.

$^1$H NMR (d$_8$-toluene, 600 MHz): δ 8.10-8.09 (m, 2H), 7.12-7.10 (m, 3H), 6.91-6.90 (m, 2H), 6.72 (dd, J=5.3, 3.4 Hz, 2H), 2.12 (t, J=6.8 Hz, 2H), 1.35-1.28 (m, 4H), 0.79 (t, J=7.1 Hz, 3H).

$^{11}$B NMR (d$_8$-toluene, 600 MHz): δ 25.4 (s).

Boronic ester 3a. Catalyst was dissolved in d$_8$-toluene (0.2 mL) and added to the dram vial containing 2a. After mixing thoroughly, the reaction mixture was transferred to a J. Young NMR tube, which was capped and removed from the glovebox. The tube was heated in a preheated oil bath at the temperature listed in Table SI-1. After heating for the indicated time, the progress of the reaction was monitored by $^1$H and $^{11}$B NMR spectroscopy.

$^1$H NMR (d$_8$-toluene, 600 MHz): δ 7.92-7.90 (m, 2H), 7.26-7.19 (m, 3H), 6.92-6.90 (m, 2H), 3.26 (s, 3H), 6.76-6.74 (m, 2H), 2.97 (t, J=7.6 Hz, 2H), 1.64 (quintet, J=7.5 Hz, 2H), 1.28 (sextet, J=7.4 Hz, 2H), 0.84 (t, J=7.2 Hz, 3H).

$^{11}$B NMR (d$_8$-toluene, 600 MHz): δ 31.2 (s).

TABLE SI-1

Example 4. Optimization of oxyboration reaction conditions by $^1$H NMR spectroscopy

| Entry | Catalyst | Temperature (° C.) | Cat. loading (% mol) | Reaction time (h) | $^1$H NMR yield$^a$ 3a (%) |
|---|---|---|---|---|---|
| 1 | IPrAuTFA | 25 | 10 | 22 | 89 |
| 2 | IPrAuTFA | 50 | 10 | 2 | 92 |
| 3 | IPrAuTFA | 50 | 5.0 | 2 | 90 |
| 4 | IPrAuTFA | 50 | 2.5 | 6 | 90 |
| 5 | IPrAuTFA | 50 | 1.0 | 23 | 85 |
| 6 | IPrAuCl | 50 | 2.5 | 6 | 0 |
| 7 | IPrAuOTs | 50 | 2.5 | 6 | 34 |
| 8 | AuCl | 50 | 2.5 | 6 | 0 |
| 9 | AuCl$_3$ | 50 | 2.5 | 6 | 0 |
| 10 | IPrOAc | 50 | 2.5 | 6 | 0 |
| 11 | NaTFA | 50 | 10 | 18 | 0 |

$^a$Determined by ERECTIC using mesitylene as external standard

E. General Procedure NMR Conversions Using ERECTIC

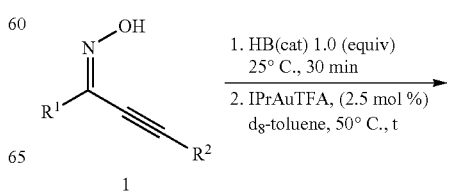

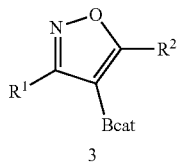

In a N$_2$-filled glovebox, an alkynyloxime (0.10 mmol, 1.0 equiv) was dissolved in 0.3 mL d$_8$-toluene in a 4-dram vial equipped with stir bar. Catecholborane (10.7 μL, 0.100 mmol, 1.00 equiv) was added via gastight syringe to the solution above. The resulting solution was allowed to stir at room temperature for 0.5 h. The catalyst IPrAuTFA (1.8 mg, 0.0025 mmol, 2.5 mol %) was dissolved in 0.2 mL d$_8$-toluene and transferred via syringe to the solution above. This mixture was then transferred into a J. Young NMR tube, which was sealed and removed from the glove box. Reaction progress was monitored by $^1$H NMR spectroscopy (600 MHz, d$_8$-toluene) of 3 using the ERECTIC method relative to external mesitylene standard (252 mmol/L in d$_8$-toluene). This general procedure was used for R$_1$=Ph, R$_2$=nBu (3a, 90%, 6 h, 50° C.); R$_1$=3-furyl, R$_2$=nBu (3b, 85%, 24 h, 50° C.); R$_1$=4-BrPh, R$_2$=nBu (3c, 93%, 6 h, 50° C.); R$_1$=t-Bu, R$_2$=Ph (3d, 95%, 4 h, 110° C.); R$_1$=4-NO$_2$Ph, R$_2$=nBu (3e, 90%, 6 h, 50° C.); R$_1$=Ph, R$_2$=TMS (3f, 87%, 24 h, 90° C.); R$_1$=4-MePh, R$_2$=nBu (3g, 95%, 6 h, 50° C.); R$_1$=4-FPh, R$_2$=nBu (3h, 92%, 6 h, 50° C.); R$_1$=4-MeOPh, R$_2$=nBu (3i, 92%, 24 h, 60° C.); R$_1$=4-CF$_3$Ph, R$_2$=nBu (3j, 98%, 6 h, 50° C.); R$_1$=Ph, R$_2$=(CH$_2$)$_3$CO$_2$Me (3k, 94%, 8 h, 50° C.).

F. Synthesis of Pinacol Boronates 4: General Procedure

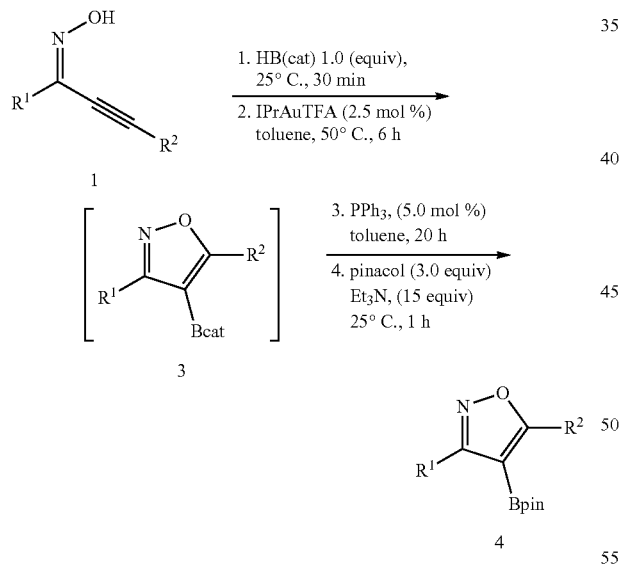

In a N$_2$-filled glovebox, oxime 1 (0.50 mmol, 1.0 equiv) was dissolved in 1.5 mL toluene in a 20-dram vial equipped with stir bar. Catecholborane (53.5 μL, 0.500 mmol, 1.00 equiv) was added via gastight syringe to the solution above. The resulting solution was allowed to stir at room temperature for 0.5 h. The catalyst IPrAuTFA (8.8 mg, 0.012 mmol, 2.5 mol %) was dissolved in 1.0 mL toluene and transferred via syringe to the solution above in a capped vial and the resulting suspension was stirred in a pre-heated copper shot heating bath at appropriate temperature and time. The reaction mixture was then cooled to room temperature and a solution of PPh$_3$ (6.6 mg, 0.025 mmol, 5.0 mol %) in toluene (3.0 mL) was added. The resulting suspension was stirred for 20 h at room temperature in order to quench IPrAuTFA before proceeding.

Pinacol (177 mg, 1.50 mmol, 3.00 equiv) was dissolved in anhydrous Et$_3$N (1.04 mL, 7.50 mmol, 15.0 equiv). The resulting solution was added to the quenched reaction mixture, and the resulting suspension was stirred at 25° C. for 1 h. The reaction mixture was then removed from the glovebox. Volatiles were removed in vacuo. The resulting light brown oil was purified by silica gel chromatography using an elution gradient from 100% hexanes to 100% CH$_2$Cl$_2$. Solvents were removed in vacuo to afford the desired pinacol boronate 4. All of the pinacol boronates 4a-4k are missing one carbon signal in the $^{13}$C NMR spectroscopy data. This carbon atom is assigned to the carbon in the newly formed C—B σ bond. This is expected due to the quadrupolar relaxation of B.[11]

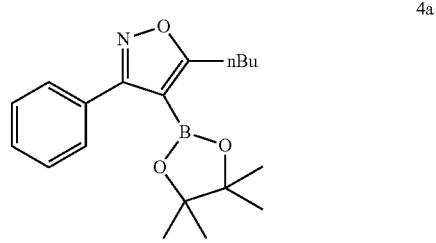

Pinacol boronate (4a) was obtained as clear oil at 50° C. after 6 h (0.123 g, 75% isolated yield). TLC (40% CH$_2$Cl$_2$/hexanes): R$_f$=0.10, visualized by UV absorbance. $^1$H NMR (CDCl$_3$, 600 MHz): δ 7.82-7.80 (m, 2H), 7.41-7.40 (m, 3H), 3.00 (t, J=7.8 Hz, 2H), 1.73 (quintet, J=7.8 Hz, 2H), 1.40 (sextet, J=7.8 Hz, 2H), 1.30 (s, 12H), 0.95 (t, J=7.2 Hz, 3H). $^{13}$C NMR (CDCl$_3$, 125 MHz): δ 182.8, 166.1, 130.3, 129.4, 129.1, 128.1, 83.7, 30.7, 27.0, 24.9, 22.4, 13.8. $^{11}$B NMR (CDCl$_3$, 192 MHz): δ 29.9 (s). HRMS (ESI+) m/z calcd for C$_{19}$H$_{26}$BNO$_3$ ([M+Na]$^+$) 350.1907. found 350.1903.

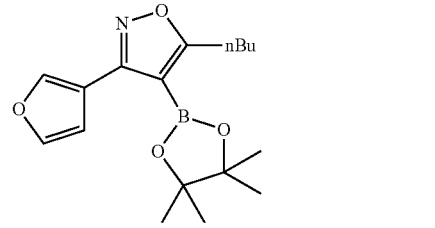

Pinacol boronate (4b) was obtained as clear oil at 50° C. after 24 h (0.113 g, 71% isolated yield). TLC (40% CH$_2$Cl$_2$/hexanes): R$_f$=0.09, visualized by UV absorbance. $^1$H NMR (CDCl$_3$, 500 MHz): δ 8.43 (s, 1H), 7.45-7.44 (m, 1H), 6.96 (s, 1H), 3.00 (t, J=7.5 Hz, 2H), 1.69 (quintet, J=7.5 Hz, 2H), 1.37 (sextet, J=7.5 Hz, 2H), 1.34 (s, 12H), 0.93 (t, J=7.5 Hz, 3H). $^{13}$C NMR (CDCl$_3$, 125 MHz): δ 183.6, 158.5, 144.3, 142.9, 116.3, 109.7, 83.8, 30.6, 26.8, 25.0, 22.3, 13.8. $^{11}$B NMR (CDCl$_3$, 192 MHz): δ 29.6 (s). HRMS (ESI+) m/z calcd for C$_{17}$H$_{24}$BNO$_4$ ([M+Na]$^+$) 340.1699. found 340.1691.

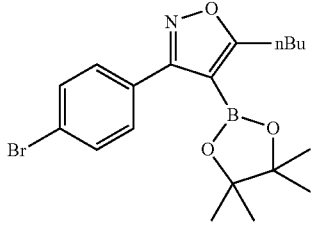

4c

Pinacol boronate (4c) was obtained as yellow solid at 50° C. after 6 h (0.131 g, 65% isolated yield). TLC (40% CH$_2$Cl$_2$/hexanes): R$_f$=0.09, visualized by UV absorbance. $^1$H NMR (CDCl$_3$, 500 MHz): δ 7.71 (d, J=8.5 Hz, 2H), 7.53 (d, J=8.5 Hz, 2H), 3.00 (t, J=7.5 Hz, 2H), 1.71 (quintet, J=7.5 Hz, 2H), 1.41 (sextet, J=7.0 Hz, 2H), 1.30 (s, 12H), 0.95 (t, J=7.0 Hz, 3H). $^{13}$C NMR (CDCl$_3$, 125 MHz): δ 183.3, 165.2, 131.3, 130.7, 129.3, 123.8, 83.8, 30.6, 27.0, 24.9, 22.3, 13.8. $^{11}$B NMR (CDCl$_3$, 192 MHz): δ 29.7 (s). HRMS (ESI+) m/z calcd for C$_{19}$H$_{25}$BBrNO$_3$ ([M+H]$^+$) 408.1175. found 408.1163.

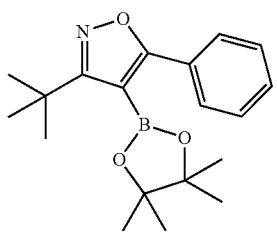

4d

Pinacol boronate (4d) was obtained as white solid at 110° C. after 4 h (0.154 g, 94% isolated yield). TLC (40% CH$_2$Cl$_2$/hexanes): R$_f$=0.11, visualized by UV absorbance. $^1$H NMR (CDCl$_3$, 600 MHz): δ 7.78-7.76 (m, 2H), 7.42-7.41 (m, 3H), 1.44 (s, 9H), 1.34 (s, 12H). $^{13}$C NMR (CDCl$_3$, 125 MHz): δ 175.4, 174.7, 130.1, 129.1, 128.3, 125.8, 84.3, 33.4, 29.5, 25.1. $^{11}$B NMR (CDCl$_3$, 192 MHz): δ 30.5 (s). HRMS (ESI+) m/z calcd for C$_{19}$H$_{26}$BNO$_3$ ([M+H]$^+$) 328.2088. found 328.2091.

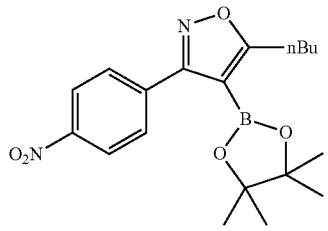

4e

Pinacol boronate (4e) was obtained as light yellow solid at 50° C. after 6 h (0.112 g, 60% isolated yield). TLC (40% CH$_2$Cl$_2$/hexanes): R$_f$=0.10, visualized by UV absorbance. $^1$H NMR (CDCl$_3$, 500 MHz): δ 8.27 (d, J=9.0 Hz, 2H), 8.03 (d, J=8.5 Hz, 2H), 3.04 (t, J=7.5 Hz, 2H), 1.73 (quintet, J=7.0 Hz, 2H), 1.40 (sextet, J=7.0 Hz, 2H), 1.31 (s, 12H), 0.96 (t, J=7.5 Hz, 3H). $^{13}$C NMR (CDCl$_3$, 125 MHz): δ 184.0, 164.4, 148.5, 136.8, 130.1, 123.3, 84.0, 30.6, 27.0, 24.9, 22.3, 13.8. $^{11}$B NMR (CDCl$_3$, 192 MHz): δ 29.5 (s). HRMS (ESI+) m/z calcd for C$_{19}$H$_{25}$BN$_2$O$_5$ ([M+Na]$^+$) 395.1758. found 395.1760.

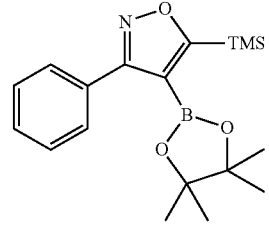

4f

Pinacol boronate (4f) was obtained as white solid at 90° C. after 24 h (0.122 g, 71% isolated yield). TLC (40% CH$_2$Cl$_2$/hexanes): R$_f$=0.15, visualized by UV absorbance. $^1$H NMR (CDCl$_3$, 500 MHz): δ 7.78-7.76 (m, 2H), 7.41-7.40 (m, 3H), 1.30 (s, 12H), 0.43 (s, 9H). This spectrum is in agreement with previously reported spectral data.[12]

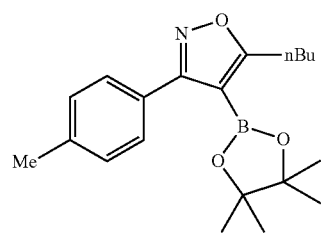

4g

Pinacol boronate (4g) was obtained as light yellow solid at 50° C. after 6 h (0.128 g, 75% isolated yield). TLC (40% CH$_2$Cl$_2$/hexanes): R$_f$=0.14, visualized by UV absorbance. $^1$H NMR (CDCl$_3$, 500 MHz): δ 7.71 (d, J=8.0 Hz, 2H), 7.21 (d, J=8.0 Hz, 2H), 2.99 (t, J=7.5 Hz, 2H), 2.39 (s, 3H), 1.72 (quintet, J=7.5 Hz, 2H), 1.39 (sextet, J=7.5 Hz, 2H), 1.30 (s, 12H), 0.95 (t, J=7.5 Hz, 3H). $^{13}$C NMR (CDCl$_3$, 125 MHz): δ 182.7, 166.0, 139.3, 128.92, 128.87, 127.4, 83.7, 30.7, 27.0, 24.9, 22.4, 21.5, 13.8. $^{11}$B NMR (CDCl$_3$, 192 MHz): δ 29.9 (s). HRMS (ESI+) m/z calcd for C$_{20}$H$_{28}$BNO$_3$ ([M+H]$^+$) 342.2244. found 342.2241.

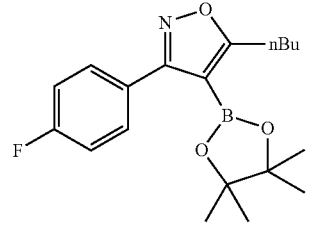

4h

Pinacol boronate (4h) was obtained as clear oil at 50° C. after 6 h (0.115 g, 67% isolated yield). TLC (40% CH$_2$Cl$_2$/hexanes): R$_f$=0.11, visualized by UV absorbance. $^1$H NMR (CDCl$_3$, 500 MHz): δ 7.83-7.80 (m, 2H), 7.09 (t, J=8.7 Hz, 2H), 3.00 (t, J=7.5 Hz, 2H), 1.72 (quintet, J=7.4 Hz, 2H), 1.40 (sextet, J=7.5 Hz, 2H), 1.30 (s, 12H), 0.95 (t, J=7.3 Hz, 3H). $^{13}$C NMR (CDCl$_3$, 125 MHz): δ 183.2, 165.3, 164.7, 162.7, 131.0, 126.4, 115.1, 83.8, 30.6, 27.0, 24.9, 22.4, 13.8. $^{11}$B NMR (CDCl$_3$, 192 MHz): δ 29.8 (s). $^{19}$F NMR (CDCl$_3$, 376 MHz): δ −112.3. HRMS (ESI+) m/z calcd for C$_{19}$H$_{25}$BFNO$_3$ ([M+Na]$^+$) 368.1813. found 368.1802.

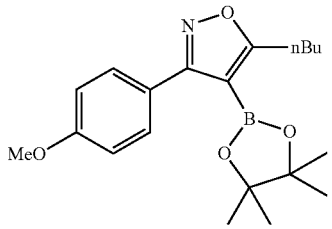

Pinacol boronate (4i) was obtained as off white solid at 60° C. after 24 h (0.132 g, 74% isolated yield). TLC (40% CH$_2$Cl$_2$/hexanes): R$_f$=0.23, visualized by UV absorbance. $^1$H NMR (CDCl$_3$, 600 MHz): δ 7.79 (d, J=8.8 Hz, 2H), 6.92 (d, J=8.8 Hz, 2H), 3.83 (s, 3H), 2.99 (t, J=7.5 Hz, 2H), 1.72 (quintet, J=7.6 Hz, 2H), 1.39 (sextet, J=7.4 Hz, 2H), 1.30 (s, 12H), 0.95 (t, J=7.3 Hz, 3H). $^{13}$C NMR (CDCl$_3$, 125 MHz): δ 182.8, 165.7, 160.6, 130.4, 122.8, 113.5, 83.7, 55.4, 30.7, 27.0, 24.9, 22.4, 13.8. $^{11}$B NMR (CDCl$_3$, 192 MHz): δ 29.8 (s). HRMS (ESI+) m/z calcd for C$_{20}$H$_{28}$BNO$_4$ ([M+Na]$^+$) 380.2013. found 380.2002.

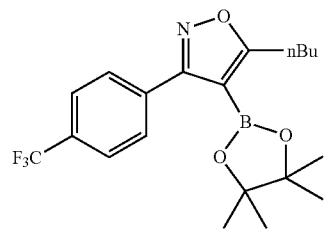

Pinacol boronate (4j) was obtained as off white solid at 50° C. after 6 h (0.110 g, 56% isolated yield). TLC (40% CH$_2$Cl$_2$/hexanes): R$_f$=0.15, visualized by UV absorbance. $^1$H NMR (CDCl$_3$, 600 MHz): δ 7.96 (d, J=8.4 Hz, 2H), 7.66 (d, J=8.4 Hz, 2H), 3.03 (t, J=7.8 Hz, 2H), 1.73 (quintet, J=7.2 Hz, 2H), 1.41 (sextet, J=7.8 Hz, 2H), 1.30 (s, 12H), 0.96 (t, J=7.8 Hz, 3H). $^{13}$C NMR (CDCl$_3$, 125 MHz): δ 183.6, 165.1, 133.9, 131.4, 131.2, 129.5, 125.1 (q, J=15.5 Hz), 123.2, 83.9, 30.6, 27.0, 24.9, 22.4, 13.8. $^{11}$B NMR (CDCl$_3$, 192 MHz): δ 29.7 (s). $^{19}$F NMR (CDCl$_3$, 376 MHz): δ -62.7. HRMS (ESI+) m/z calcd for C$_{20}$H$_{25}$BF$_3$NO$_3$ ([M+H]$^+$) 396.1962. found 396.1970.

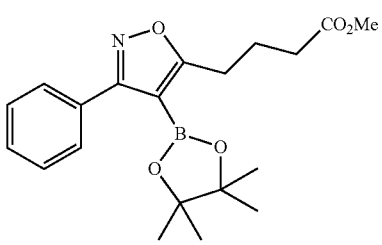

Pinacol boronate (4k) was obtained as clear oil at 50° C. after 8 h (0.119 g, 64% isolated yield). TLC (100% CH$_2$Cl$_2$): R$_f$=0.28, visualized by UV absorbance. $^1$H NMR (CDCl$_3$, 600 MHz): δ 7.81-7.80 (m, 2H), 7.42-7.38 (m, 3H), 3.67 (s, 3H), 3.07 (t, J=7.8 Hz, 2H), 2.40 (t, J=7.8 Hz, 2H), 2.09 (quintet, J=7.2 Hz, 2H), 1.30 (s, 12H). $^{13}$C NMR (CDCl$_3$, 125 MHz): δ 181.4, 173.5, 16.2, 130.0, 129.5, 129.1, 128.1, 83.9, 51.7, 33.3, 26.6, 24.9, 23.6. $^{11}$B NMR (CDCl$_3$, 192 MHz): δ 29.7 (s). HRMS (ESI+) m/z calcd for C$_{20}$H$_{28}$BNO$_5$ ([M+H]$^+$) 372.1986. found 372.1983.

G. Uncatalyzed Oxyboration

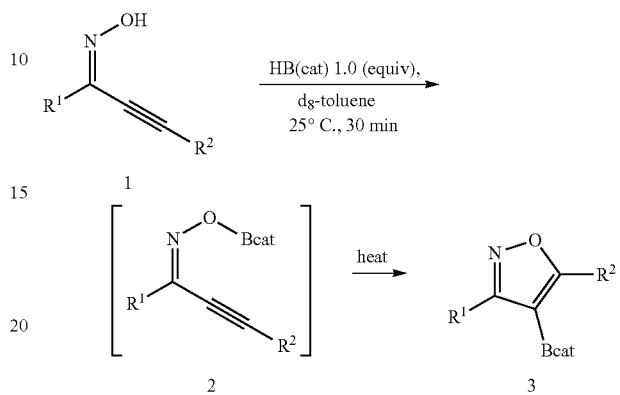

In a N$_2$-filled glovebox, oxime 1 (0.10 mmol, 1.0 equiv) was dissolved in 0.5 mL d$_8$-toluene in a 4-dram vial equipped with stir bar. Catecholborane (10.7 μL, 0.100 mmol, 1.00 equiv) was added via gastight syringe to the solution above. The resulting solution was allowed to stir at room temperature for 0.5 h. The reaction mixture was transferred via syringe to a J. Young NMR tube, removed from the glovebox, and heated in a preheated oil bath at 110° C. until full consumption of starting materials was achieved, after which the $^1$H NMR yields were recorded. The $^1$H NMR yields were determined by the ERECTIC method using mesitylene as the external standard.

TABLE SI-2

| | | Example 4. Uncatalyzed Oxyboration | |
|---|---|---|---|
| | R$^1$/R$^2$ | Uncatalyzed $^1$H NMR yield | Time |
| 3a | Ph/Bu | 89% | 111 h |
| 3b | 3-Furyl/Bu | 68% | 18 days |
| 3c | 4-BrPh/Bu | 91% | 20 h |
| 3d | t-Bu/Ph | 24% | 7 days |
| 3e | 4-NO$_2$Ph/Bu | 84% | 20 h |
| 3f | Ph/TMS | 0% | 48 h |
| 3g | 4-MePh/Bu | 78% | 15 days |
| 3h | 4-FPh/Bu | 87% | 65 h |
| 3i | 4-MeO/Bu | 90% | 65 h |
| 3j | 4-CF$_3$Ph/Bu | 74% | 21 days |
| 3k | Ph/(CH$_2$)$_3$CO$_2$Me | 83% | 52 h |

H. General Procedure for HRMS Detection of Reaction Intermediates

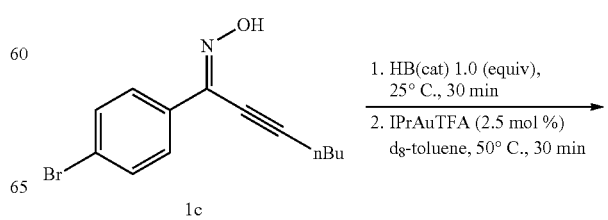

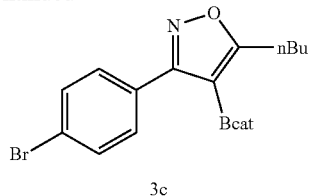

3c

In a N$_2$-filled glovebox, alkynyloxime 1c (28.0 mg, 0.100 mmol, 1.00 equiv) was dissolved in 0.3 mL d$_8$-toluene in a 4-dram vial equipped with stir bar. Catecholborane (10.7 μL, 0.100 mmol, 1.00 equiv) was added via gastight syringe to the solution above. The resulting solution was allowed to stir at room temperature for 0.5 h. The catalyst IPrAuTFA (1.8 mg, 0.0025 mmol, 2.5 mol %) was dissolved in 0.2 mL toluene and transferred via syringe to the solution above. The vial was capped and the resulting suspension was stirred in a pre-heated 50° C. copper shot heating bath for 30 min. An aliquot of the reaction mixture was withdrawn into a Hamilton 1700 Series Gastight Syringes N Termination (250 μL, N, Gauge: 22 s, 2 in., Point style: 3), the tip was placed in a septum as a cap before removing from the glovebox. The sample-containing syringe was quickly carried to the HRMS instrument and injected using ESI technique in positive and negative modes. Due to the extremely high air and moisture sensitivity of the reaction components, no mass calibration was done.

I. Synthesis of Organogold Intermediate 7a

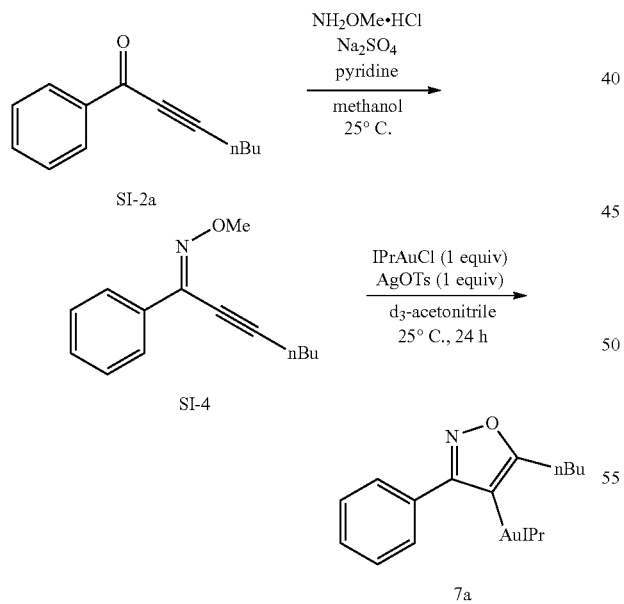

(Z)-1-phenylhept-2-yn-1-one oxime ether (SI-4) was prepared according to a literature procedure.[13] In N$_2$-filled glovebox, a 50 mL round bottom flask was charged with H$_2$NOMe·HCl (418 mg, 10.0 mmol, 2.00 equiv), Na$_2$SO$_4$ (1.42 g, 10.0 mmol, 2.00 equiv), and a stir bar. The solids were suspended in MeOH (15 mL). Pyridine (1.50 mL, 18.5 mmol, 3.70 equiv) and then ketone SI-2a (0.93 g, 5.0 mmol, 1.0 equiv) were added. The reaction was allowed to stir at 25° C. for 19 h. The reaction was quenched with 30 mL DI water and extracted with EtOAc (3×30 mL). The combined organic layers were washed with brine (30 mL), dried over MgSO$_4$, filtered, and concentrated in vacuo. The crude was purified by silica gel flash column chromatography using a stepwise gradient from 5% to 10% EtOAc in hexanes. Product-containing fractions were combined and concentrated in vacuo to afford SI-4 as light yellow oil (0.53 g, 49% isolated yield). TLC (40% CH$_2$Cl$_2$/hexanes): R$_f$=0.43, visualized by UV absorbance. $^1$H NMR (CDCl$_3$, 500 MHz) δ: 7.84-7.82 (m, 2H), 7.37-7.36 (m, 3H), 4.08 (s, 3H), 2.55 (t, J=7.5 Hz, 2H), 1.66 (quintet, J=7.5 Hz, 2H), 1.50 (sextet, J=7.5 Hz, 2H), 0.96 (t, J=7.5 Hz, 3H). This spectrum is in agreement with previously reported spectral data.[14] Organogold intermediate (7a) was prepared according to a lit procedure.[13] In a N$_2$-filled glovebox, alkynyloxime ether SI-4 (43.0 mg, 0.20 mmol, 1.00 equiv) was dissolved in 1.0 mL anhydrous CH$_3$CN in a 4-dram vial equipped with stir bar. The resulting solution was transferred into a vial containing IPrAuCl (124 mg, 0.200 mmol, 1.00 equiv) and AgOTs (55.8 mg, 0.200 mmol, 1.00 equiv), allowed to stir at 25° C. for 24 h. The resulting suspension was filtered, washed with anhydrous CH$_3$CN (3×1 ml). The precipitate was dissolved in anhydrous CH$_2$Cl$_2$, filtered, and the filtrates were combined. The solvents were removed in vacuo to afford the crude product as a white solid. The crude product was recrystallized with CH$_3$CN at −35° C. for two days. The purified product was filtered to afford a white solid (89.8 mg, 57% isolated yield). $^1$H NMR (d$_8$-toluene, 600 MHz): δ 8.14 (d, J=7.9 Hz, 2H), 7.28 (t, J=7.8 Hz, 2H), 7.15 (t, J=7.4 Hz, 1H), 7.06 (d, J=7.8 Hz, 4H), 7.00 (t, J=7.7 Hz, 2H), 6.44 (s, 2H), 2.60 (quintet, J=6.9 Hz, 4H), 2.40 (t, J=7.4 Hz, 2H), 1.43 (quintet, J=7.6 Hz, 2H), 1.29 (d, J=6.9 Hz, 12H), 1.19 (sextet, J=7.6 Hz, 2H), 1.06 (d, J=6.9 Hz, 12H), 0.86 (t, J=7.3 Hz, 3H). $^{13}$C NMR (d$_8$-toluene, 150 MHz): δ 197.1, 178.0, 169.4, 146.0, 135.4, 135.1, 130.7, 129.6, 128.1, 127.1, 124.3, 122.9, 32.2, 29.5, 29.1, 24.6, 23.9, 22.8.

J. Organogold-to-Boron Transmetalation Stoichiometric Study

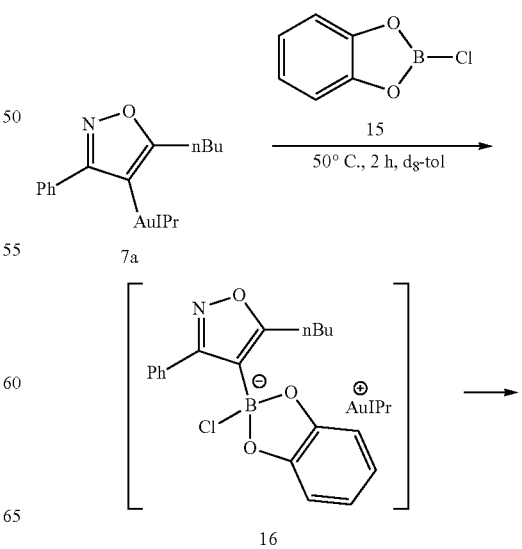

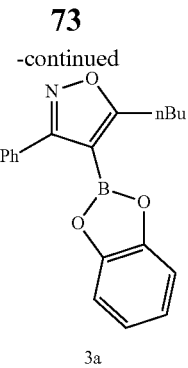

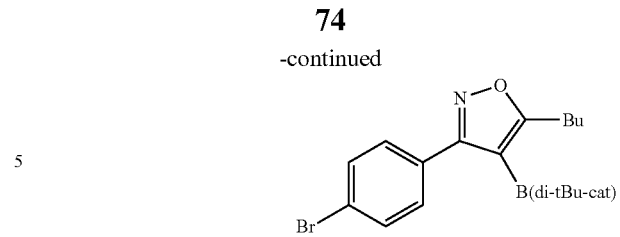

In a $N_2$-filled glovebox, B-chlorocatecholborane 15 (3.1 mg, 0.020 mmol, 1.0 equiv) was dissolved in $d_8$-toluene (0.4 mL). The resulting solution was transferred via pipette to a 4-dram vial containing organogold complex 7a (15.7 mg, 0.0200 mmol, 1.00 equiv). The resulting mixture was transferred via pipette to a J. Young NMR tube, which was capped and removed from the glovebox. An off-white precipitate started to form very early in the reaction mixture. $^1$H and $^{11}$B NMR spectra were acquired at t=10 min. Then the sample was heated in a preheated oil bath at 50° C. The progress of the reaction was monitored by $^1$H and $^{11}$B NMR spectroscopy. After 2 h, the reaction was complete and boronic ester 3a was afforded in 96% NMR yield, determined by ERECTIC method with mesitylene as the external standard. For comparison and to facilitate analysis, the $^1$H NMR stacked plot image in Scheme 3 was made by combining the independent $^1$H NMR spectra of the organogold complex 7a and B-chlorocatecholborane in two separate NMR spectroscopy samples (before mixing) into the top most line in the image. The spectrum to the left of the break is from complex 7a and to the right of the break is from B-chlorocatecholborane. The ppm scale for the x-axis was identical for all four spectra included in this stack plot.

K. Crossover Experiment 3,5-di-t-butylcatechol boric ester 18. In a $N_2$-filled glovebox, alkynyloxime 1c (28.0 mg, 0.100 mmol, 1.00 equiv) was dissolved in 0.3 mL $d_8$-toluene in a 4-dram vial equipped with stir bar. 3,5-Di-t-butylcatecholborane (23.2 mg, 0.100 mmol, 1.00 equiv) was added via gastight syringe to the solution above. The resulting solution was allowed to stir at room temperature for 0.5 h.

$^1$H NMR ($d_8$-toluene, 600 MHz): δ 7.78 (bs, 2H), 7.15 (d, J=8.4 Hz, 2H), 7.08-7.07 (m, 2H), 2.10 (t, J=6.6 Hz, 2H), 1.44 (s, 9H), 1.33-1.28 (m, 4H), 1.23 (s, 9H), 0.80 (t, J=7.0 Hz, 3H).

$^{11}$B NMR ($d_8$-toluene, 600 MHz): δ 25.5 (s).

3,5-di-t-butylcatechol boronic ester 20. In order to acquire an authentic $^1$H NMR spectrum of one of the expected products in the crossover experiment, IPrAuTFA (1.8 mg, 0.0025 mmol, 2.5 mol %) was dissolved in 0.2 mL $d_8$-toluene and transferred via syringe to the dram vial containing 18. After mixing thoroughly, the reaction mixture was transferred to a J. Young NMR tube, which was capped and removed from the glovebox, and heated in a preheated oil bath at 50° C. The progress of the reaction was monitored by $^1$H and $^{11}$B NMR spectroscopy. After 6 h, 55.6% conversion was observed.

$^1$H NMR ($d_8$-toluene, 600 MHz): δ 7.64 (d, J=6.6 Hz, 2H), 7.36 (d, J=6.6 Hz, 2H), 7.13-7.12 (m, 2H), 3.02 (t, J=7.7 Hz, 2H), 1.68 (quintet, J=7.7 Hz, 2H), 1.46 (s, 9H), 1.32-1.30 (m, 2H), 1.25 (s, 9H), 0.86 (t, J=7.4 Hz, 3H).

$^{11}$B NMR ($d_8$-toluene, 600 MHz): δ 30.2 (s).

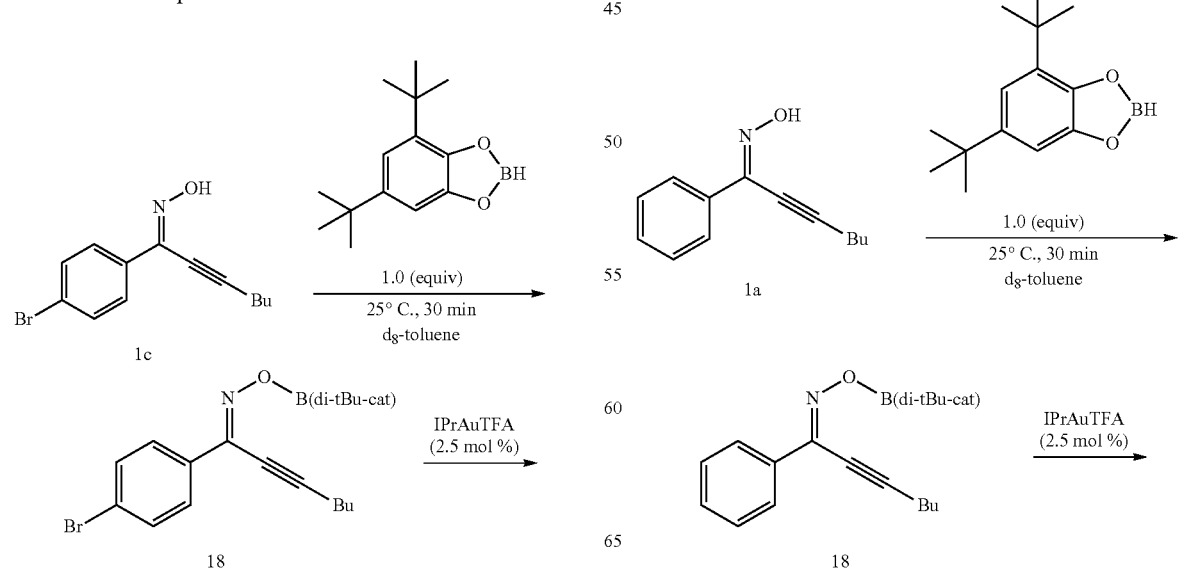

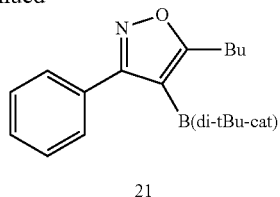

21

3,5-di-t-butylcatechol boric ester 19. In a N$_2$-filled glovebox, alkynyloxime 1a (20.1 mg, 0.100 mmol, 1.00 equiv) was dissolved in 0.3 mL d$_8$-toluene in a 4-dram vial equipped with stir bar. 3,5-Di-t-butylcatecholborane (23.2 mg, 0.100 mmol, 1.00 equiv) was added via gastight syringe to the solution above. The resulting solution was allowed to stir at room temperature for 0.5 h.

$^1$H NMR (d$_8$-toluene, 600 MHz): δ 8.10 (bs, 1H), 7.13-7.10 (m, 3H), 7.08-7.06 (m, 2H), 2.12 (t, J=6.7 Hz, 2H), 1.44 (s, 9H), 1.35-1.29 (m, 4H), 1.23 (s, 9H), 0.79 (t, J=7.1 Hz, 3H).

$^{11}$B NMR (d$_8$-toluene, 600 MHz): δ 25.5 (s).

3,5-di-t-butylcatechol boronic ester 21. In order to acquire an authentic $^1$H NMR spectrum of one of the expected products in the crossover experiment, IPrAuTFA (1.8 mg, 0.0025 mmol, 2.5 mol %) was dissolved in 0.2 mL d$_8$-toluene and transferred via syringe to the dram vial containing 19. After mixing thoroughly, the reaction mixture was transferred to a J. Young NMR tube, which was capped and removed from the glovebox, and heated in a preheated oil bath at 50° C. The progress of the reaction was monitored by $^1$H and $^{11}$B NMR spectroscopy. After 6 h, 37.8% conversion was observed.

$^1$H NMR (d$_8$-toluene, 600 MHz): δ 7.94 (d, J=7.6 Hz, 2H), 7.26-7.25 (m, 2H), 7.13-7.12 (m, 2H), 3.03 (t, J=7.8 Hz, 2H), 1.69 (quintet, J=7.6 Hz, 2H), 1.38 (s, 9H), 1.37-1.35 (m, 2H), 1.23 (s, 9H), 0.85 (t, J=7.4 Hz, 3H).

$^{11}$B NMR (d$_8$-toluene, 600 MHz): δ 30.3 (s).

the reaction was monitored by $^1$H and $^{11}$B NMR spectroscopy. The NMR spectroscopy data indicated the presence of all four products (non-crossover products 3a and 20, and crossover products 21 and 3c). Establishing That the Crossover Products Formed through Preequilibrium. In a N$_2$-filled glovebox, boric ester 2a (0.050 mmol, 1.0 equiv) and 11 (0.050 mmol, 1.0 equiv) were synthesized in two separate 4-dram vials according to the procedures described above in d$_8$-toluene (0.2 mL each). All two solutions were mixed thoroughly and transferred to a J. Young NMR tube, removed from the glovebox. The progress of the reaction was monitored by $^1$H and $^{11}$B NMR spectroscopy. $^1$H NMR spectroscopy indicated a rapid interconversion between 2a and 18 to form a mixture of four boric esters 2a, 18, 19, and 2c in a 1:1:1:1 ratio, approximately.

L. Synthesis of Valdecoxib and Valdecoxib Ester Analog

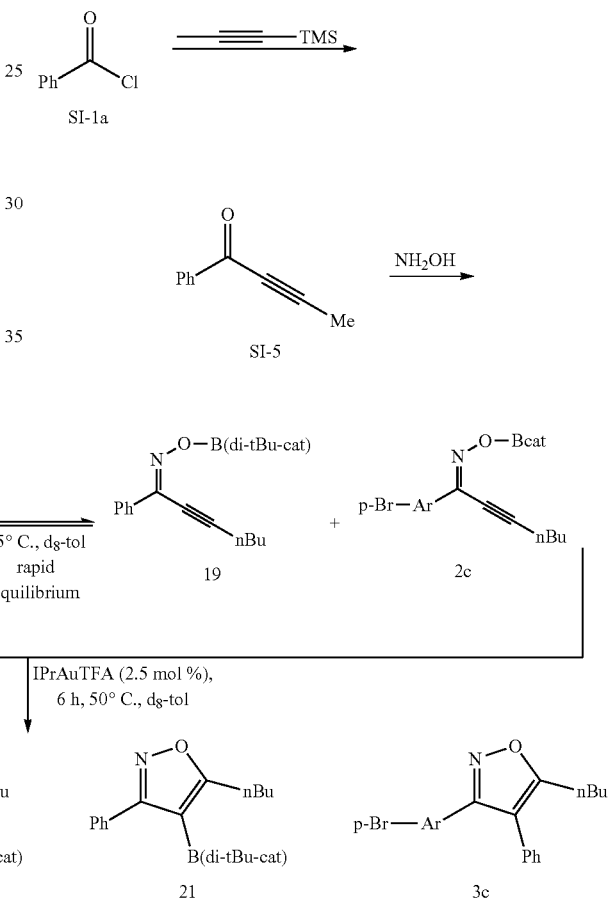

Crossover Experiment. In a N$_2$-filled glovebox, boric ester 2a (0.050 mmol, 1.0 equiv) and 18 (0.050 mmol, 1.0 equiv) were synthesized in two separate 4-dram vials according to the procedures described above in d$_8$-toluene (0.2 mL each). The catalyst IPrAuTFA (1.8 mg, 0.0025 mmol, 2.5 mol %) was dissolved in 0.1 mL d$_8$-toluene in a separate 4-dram vial. All three solutions were mixed thoroughly and transferred to a J. Young NMR tube, removed from the glovebox, and heated in a preheated oil bath at 50° C. The progress of -continued

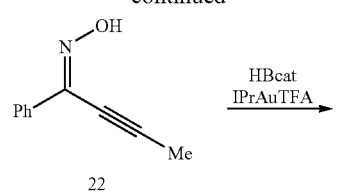

22

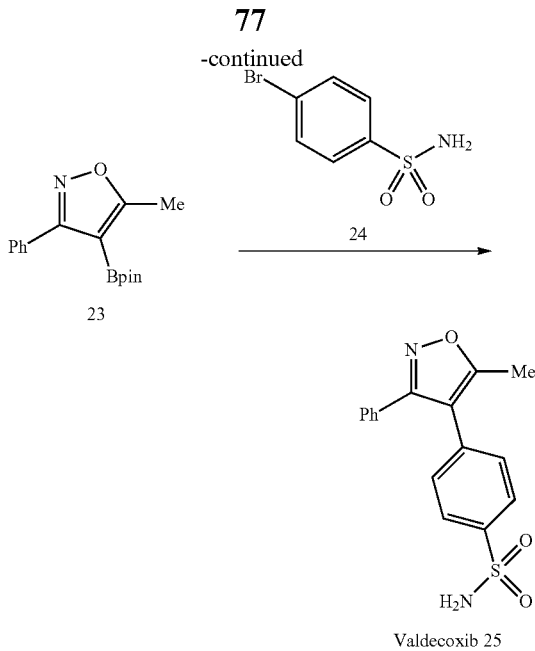

1-phenylbut-2-yn-1-one (SI-5) was prepared according to a literature procedure.[15] To a flame-dried 100 mL round bottom flask equipped with stir bar under $N_2$ atmosphere was added $FeCl_3$ (162 mg, 1.00 mmol, 0.10 equiv). The flask was evacuated and purged with $N_2$ in three cycles. The reaction flask was cooled to 0° C. in an ice-water bath. Acid chloride SI-1a (1.16 mL, 10.0 mmol, 1.00 equiv), trimethylsilylpropyne (2.22 mL, 15.0 mmol, 1.50 equiv), and $CH_3NO_2$ (20.0 mL) were added to the reaction flask at 0° C. under $N_2$ atmosphere. The reaction mixture was stirred at 0° C. for 6 h. The reaction mixture was then allowed to warm to 25° C. The suspension was filtered through a Celite plug (ca. 0.5 mL), and rinsed with dichloromethane (3×5 mL). The crude reaction mixture was concentrated in vacuo, purified by silica gel flash column chromatography (5% EtOAc in hexanes) to afford SI-5 as a yellow oil (0.867 g, 60% isolated yield). TLC (20% EtOAc/hexanes): $R_f$=0.42, visualized by UV absorbance. $^1H$ NMR ($CDCl_3$, 500 MHz) δ: 8.14 (d, J=7.5 Hz, 2H), 7.60 (t, J=7.5 Hz, 1H), 7.48 (t, J=8.0 Hz, 2H), 2.16 (s, 3H). This spectrum is in agreement with previously reported spectral data.[15] (Z)-1-phenylbut-2-yn-1-one oxime (22) was prepared according to a literature procedure.[9] A 50 mL round bottom flask was charged with $H_2NOH \cdot HCl$ (2.2 equiv), $Na_2SO_4$ (3.0 equiv), and a stir bar. The solids were suspended in MeOH (10 mL). Pyridine (4.0 equiv) and then ketone SI-5 (1.0 equiv) were added. The reaction was stirred at room temperature until the starting material was consumed completely, as shown by TLC. The reaction was quenched with 15 mL DI water and extracted with EtOAc (3×15 mL). The combined organic layers were washed with brine (15 mL), dried over $MgSO_4$, filtered, and concentrated in vacuo. The crude was purified by silica gel flash column chromatography using a stepwise gradient from 5% to 10% EtOAc in hexanes. Product-containing fractions were combined and concentrated in vacuo to afford 22 as a yellow solid (111 mg, 12% isolated yield). TLC (20% EtOAc/hexanes): $R_f$=0.19, visualized by UV absorbance. $^1H$ NMR ($d_8$-toluene, 500 MHz): δ 9.03 (s, 1H), 7.95-7.93 (m, 2H), 7.11-7.06 (m, 3H), 1.61 (s, 3H). $^{13}C$ NMR ($d_8$-toluene, 125 MHz): δ 142.1, 134.4, 129.7, 128.6, 126.9, 100.5, 71.0, 4.1. HRMS (ESI+) m/z calcd for $C_{10}H_9NO$ ([M+Na]+) 182.0582. found 182.0579. Pinacol boronate (23). In a $N_2$-filled glovebox, alkynyloxime 22 (31.8 mg, 0.200 mmol, 1.00 equiv) was dissolved in 0.6 mL toluene in a 4-dram vial equipped with stir bar. Catecholborane (21.4 μL, 0.200 mmol, 1.00 equiv) was added via gastight syringe to the solution above. The resulting solution was allowed to stir at room temperature for 0.5 h. The catalyst IPrAuTFA (3.5 mg, 0.0050 mmol, 2.5 mol %) was dissolved in 0.4 mL toluene and transferred via syringe to the solution above in a capped vial and the resulting suspension was stirred in a pre-heated 50° C. copper shot heating bath for 6 h. The reaction mixture was then cooled to room temperature and a solution of $PPh_3$ (2.6 mg, 0.010 mmol, 5.0 mol %) in toluene (1.2 mL) was added. The resulting suspension was stirred for 20 h at room temperature in order to quench IPrAuTFA before proceeding.

Pinacol (70.8 mg, 0.600 mmol, 3.00 equiv) was dissolved in anhydrous $Et_3N$ (0.42 mL, 3.0 mmol, 15.0 equiv). The resulting solution was added to the quenched reaction mixture, and the resulting suspension was stirred at 25° C. for 1 h. The reaction mixture was then removed from the glovebox. Volatiles were removed in vacuo. The resulting light brown oil was purified by silica gel chromatography using an elution gradient from 100% hexanes to 100% $CH_2Cl_2$. Solvents were removed in vacuo to afford the desired pinacol boronate 23 as white solid (40.5 mg, 71% isolated yield). TLC (40% $CH_2Cl_2$/hexanes): $R_f$=0.08, visualized by UV absorbance. $^1H$ NMR ($CDCl_3$, 600 MHz): δ 7.83-7.81 (m, 2H), 7.43-7.39 (m, 3H), 2.61 (s, 3H), 1.30 (s, 12H). This spectrum is in agreement with previously reported spectral data.[12]

Valdecoxib (25) was prepared according to a literature procedure, but with using building block 14 from our method.[123] To a flame-dried 10 mL round bottom flask equipped with stir bar under $N_2$ atmosphere was added pinacol boronate 23 (54.4 mg, 0.191 mmol, 1.00 equiv), $PdCl_2(dppf) \cdot DCM$ (15.5 mg, 0.0190 mmol, 0.100 equiv), $K_3PO_4$ (122 mg, 0.574 mmol, 3.00 equiv), sulfonamide 24 (90.2 mg, 0.382 mmol, 2.00 equiv), and degassed dioxane (1.2 mL). The reaction mixture was stirred at 85° C. for 21 h. The reaction mixture was allowed to cool to 25° C., quenched by DI water (10 mL). The aqueous layer was extracted with dichloromethane (3×20 mL). The combined organic layer was washed with brine (20 mL), dried over $MgSO_4$, filtered, and concentrated in vacuo. The crude was purified by silica gel flash column chromatography using an elution gradient from 30% to 40% EtOAc in hexanes to afford 25 as a light yellow solid (37.4 mg, 62% isolated yield). TLC (40% EtOAc/hexanes): $R_f$=0.14, visualized by UV absorbance. $^1H$ NMR ($CD_3OD$, 600 MHz) δ: 7.91 (d, J=8.4 Hz, 2H), 7.44-7.35 (m, 7H), 4.84 (s, 2H), 2.49 (s, 3H). This spectrum is in agreement with previously reported spectral data.[12]

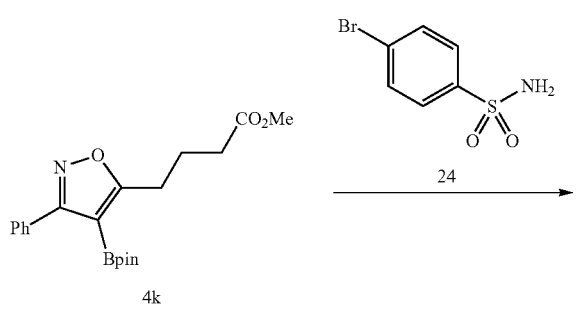

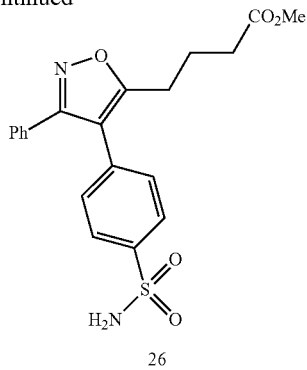

26

Valdecoxib ester analog (26) was prepared according to a literature procedure,[12] using building block 4k from our method. To a flame-dried 10 mL round bottom flask equipped with stir bar under $N_2$ atmosphere was added pinacol boronate 4k (59.0 mg, 0.159 mmol, 1.00 equiv), $PdCl_2(dppf) \cdot DCM$ (13.0 mg, 0.0159 mmol, 0.100 equiv), $K_3PO_4$ (101 mg, 0.477 mmol, 3.00 equiv), sulfonamide 24 (75.0 mg, 0.318 mmol, 2.00 equiv), and degassed dioxane (1.20 mL). The reaction mixture was stirred at 90° C. for 46 h. The reaction mixture was allowed to cool to 25° C., quenched by DI water (10 mL). The aqueous layer was extracted with dichloromethane (3×20 mL). The combined organic layer was washed with brine (20 mL), dried over $MgSO_4$, filtered, and concentrated in vacuo. The crude was purified by silica gel flash column chromatography using an elution gradient from 30% to 40% EtOAc in hexanes to afford 26 as a white solid (47.1 mg, 74% isolated yield). TLC (40% EtOAc/hexanes): $R_f$=0.14, visualized by UV absorbance. $^1H$ NMR ($d_6$-acetone, 500 MHz) δ: 7.93-7.91 (m, 2H), 7.45-7.36 (m, 7H), 6.70 (bs, 1H), 3.81 (bs, 1H), 3.57 (s, 3H), 2.94-2.91 (m, 4H), 2.40 (t, J=7.0 Hz, 2H). $^{13}C$ NMR ($d_6$-acetone, 125 MHz): δ 173.3, 170.8, 161.6, 144.3, 134.8, 131.2, 130.3, 129.8, 129.4, 129.1, 127.2, 115.5, 51.6, 33.2, 25.4, 23.5. HRMS (ESI+) m/z calcd for $C_{20}H_{20}N_2O_3S$ ([M+Na]$^+$) 423.0991. found 423.0987.

L. Gram-Scale Preparation of 4a

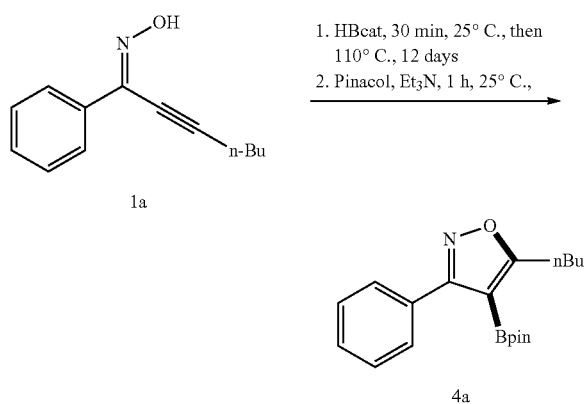

The gram-scale uncatalyzed oxyboration reaction was conducted in a $N_2$-filled glovebox. A flame-dried 100-mL round bottom flask with a stirbar was charged with oxime 1a (1.63 g, 8.10 mmol, 1.00 equiv). Anhydrous toluene (15.0 mL) was added. To the resulting rapidly stirring suspension was added catecholborane (0.867 mL, 8.10 mmol, 1.00 equiv) via gastight syringe, and allowed to stir at room temperature for 30 min. The round bottom flask was heated in a preheated copper shot heating bath at 110° C. until full consumption of starting materials was achieved (12 days). Pinacol (2.87 g, 24.3 mmol, 3.00 equiv) was dissolved in anhydrous $Et_3N$ (3.37 mL, 24.3 mmol, 3.00 equiv). The resulting solution was added to the quenched reaction mixture, and the resulting suspension was stirred at 25° C. for 2 h. The reaction mixture was then removed from the glovebox. Volatiles were removed in vacuo. The resulting light brown oil was purified by silica gel chromatography using an elution gradient from 100% hexanes to 100% $CH_2Cl_2$. Solvents were removed in vacuo to afford the desired pinacol boronate 4a as a light yellow oil (1.70 g, 64% isolated yield). Spectral data were identical to those previously obtained for this compound.

REFERENCES

1. Karpov, A. S.; Müller, T. J. J. Org. Lett. 2003, 5, 3451-3454.
2. Trost, B. M.; Schmidt, T. J. Am. Chem. Soc. 1988, 110, 2301-2303.
3. Eagon, S.; DeLieto, C.; McDonald, W. J.; Haddenham, D.; Saavedra, J.; Kim, J.; Singaram, B. J. Org. Chem. 2010, 75, 7717-7725.
4. Natte, K.; Chen, J.; Neumann, H.; Beller, M.; Wu, X-F. Org. Biomol. Chem. 2014, 12, 5590-5593.
5. Alonso, D. A.; Najera, C.; Pacheco, M. C. J. Org. Chem. 2004, 69, 1615-1619.
6. Huang, B.; Yin, L.; Cai, M. New J. Chem. 2013, 37, 3137-3144.
7. Arnold, D. M.; Laporte, M. G.; Anderson, S. M.; Wipf, P. Tetrahedron 2013, 69, 7719-7731.
8. Roy, S.; Davydova, M. P.; Pal, R.; Gilmore, K.; Tolstikov, G. A.; Vasilevsky, S. F.; Alabugin, I. V. J. Org. Chem. 2011, 76, 7482-7490.
9. Kung, K. K-Y.; Lo, V. K-Y.; Ko, H-M.; Li, G-L.; Chan, P-Y.; Leung, K-C.; Zhou, Z.; Wang, M-Z.; Che, C-M.; Wong, M-K. Adv. Synth. Catal. 2013, 355, 2055-2070.
10. Biasiolo, L.; Trinchillo, M.; Belanzoni, P.; Belpassi, L.; Busico, V.; Ciancaleoni, G.; D'Amora, A.; Macchioni, A.; Tarantelli, F.; Zuccaccia, D. Chem.—Eur. J. 2014, 20, 14594-14598.
11. Akitt. J. W. J. Magn. Reson. 1970, 3, 411-414.
12. Moore, J. E.; Davies, M. W.; Goodenough, K. M.; Wybrow, R. A. J.; York, M.; Johnson, C. N.; Harrity, J. P. A. Tetrahedron 2005, 61, 6707-6714.
13. Jeong, Y.; Kim, B-I.; Lee, J. K.; Ryu, J-S. J. Org. Chem. 2014, 79, 6444-6455.
14. Waldo, J. P.; Larock, R. C. J. Org. Chem. 2007, 72, 9643-9647.
15. Gandeepan, P.; Parthasarathy, K.; Su, T-H.; Cheng, C—H. Adv. Synth. Catal. 2012, 354, 457-458.

Example 5

This communication demonstrates the first catalytic aminoboration of C—C π bonds by B—N σ bonds and its application to the synthesis of 3-borylated indoles. The regiochemistry and broad functional group compatibility of this addition reaction enable substitution patterns that are incompatible with major competing technologies. This aminoboration reaction effects the formation of C—B and C—N bonds in a single step from aminoboronic esters, which are simple starting materials available on the gram scale. This reaction generates synthetically valuable N-heterocyclic organoboron compounds as potential building blocks for drug discovery. The working mechanistic hypothesis involves a bifunctional Lewis acid/base catalysis strategy involving the combination of a carbophilic gold cation and a trifluoroacetate anion that activate the C—C π bond and the B—N π bond simultaneously Discussion:

Boron-element additions to unsaturated compounds have played a pivotal role in organic synthesis since the discovery of hydroboration by Hurd and Brown.[2] These transformations provide a route to synthetically valuable organoboron compounds that are widely used as versatile reagents in carbon-carbon and carbon-heteroatom bond forming reactions, such as the Suzuki-Miyaura reaction[3] and Chan-Lam cross-coupling[4]. Thus, transition metal-catalyzed 1,2-addition of boron-element bonds (B-E, where E=H,[5-8] B,[8-10] C,[11-13] Si [8,14,15] Sn,[8,16] S,[17] Cl,[18] Br,[19] I[19]) to C—C multiple bonds have received significant attention (FIG. 5.1A). In most of these methods, the B-E single bonds are activated via oxidative addition to a low-valent late transition metal center (e.g., Rh, Ni, Pd, Pt) or via a-bond metathesis with a late-metal catalyst (e.g., Cu[20]) prior to insertion across alkynes. Given that amines are present in 85% of all pharmaceutical compounds, it is striking that the corresponding addition chemistry with B—N bonds has not been developed for synthetic applications; possibly because the relatively high strength of the B—N σ bond prevented application of existing mechanistic strategies. We herein realize this aminoboration reaction by employing a different mechanistic strategy: activation of the C—C π bond—the other partner in the reaction—with a carbophilic Lewis acid (FIG. 5.1C). This reaction employs starting materials containing B—N σ bonds that are readily available on the gram scale from their corresponding amines and commercially available B-chlorocatecholborane. It generates 3-borylated indoles via unique bond disconnections as potential building blocks for drug discovery, and it is orthogonal to major competing technologies as it tolerates aryl halides, nitriles, and esters.

The resistance of B—N σ bonds to react with unactivated C—C π bonds is not surprising given that aminoboranes ($R_2B$—$NR_2$) are known to have isostructural and isoelectronic relationship to alkenes due to the u-interaction between nitrogen's lone pair and boron's empty p orbital.[21,22] Resultantly, prior work on aminoboration was limited to the addition of B—N bonds to polarized C-heteroatom π bonds that included isocyanate,[23-25] isothiocyanate,[23] and carbodiimide.[26] Such an approach is less synthetically useful, however, as the resulting B-heteroatom bond formed in those transformations are usually hydrolyzed and the boryl component lost at the end of the reaction.[23-26] To our knowledge, the only reported example of aminoboration of a C—C multiple bond with a B—N σ bond is the [4+2] cycloaddition of a strained diazadiboretidine with dimethylacetylenedicarboxylate, which leads to a heterocycle of limited synthetic utility for downstream functionalization (FIG. 5.1B).[27] More recently, a formal aminoboration of alkenes was reported using a Cu-catalyzed borylation with bis(pinacolato)diboron (pinB-Bpin) followed by an electrophilic amination using O-benzoyl-N,N-dialkylhydroxylamine ($R_2$N-OBz).[28-32] Furthermore, despite a recent development on the addition chemistry involving the analogous B—P bond,[33] the catalytic aminoboration of alkynes with the B—N bond was unknown prior to this work.

Indoles are privileged scaffolds found in numerous biologically active molecules and employed in medicinal chemistry,[34-37] including recent therapeutic leads.[38] Thus, the construction of indole ring system was targeted (initial development, Table 1), which would give access to 3-borylated indoles as potential building blocks for drug discovery. During initial reaction identification, the requisite B—N bond of aminoboronic ester 2 was formed from the reaction of 2-alkynylaniline 1 and commercially available catecholborane in $d_8$-toluene with heating and the release of $H_2$. The formation of this B—N bond was monitored and confirmed by $^{11}$B NMR spectroscopy, at δ ~26 ppm[39] with concurrent disappearance of the signal from catecholborane at δ 28.7 ppm.

TABLE 1

Example 5. Initial Development of Aminoboration

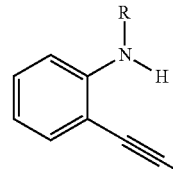

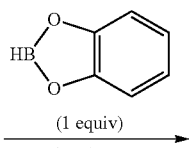

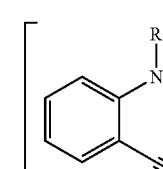

| entry | substrate | R | conditions | yield (%)[a] 3 |
|---|---|---|---|---|
| 1 | 1a | H | 50° C., 15.5 h | 0[b] |
| 2 | 1b | CH$_2$Ph | 80° C., 5 h | n.r.[c] |
| 3 | 1b | CH$_2$Ph | 110° C., 17 h | 55 |
| 4 | 1c | Ts | 50° C., 4 h | n.r.[c] |
| 5 | 1c | Ts | 80° C., 20 h | 64[d] |
| 6 | 1d | Mbs | 80° C., 20 h | 66 |

[a]Isolated yield of the Bpin product.
[b]Only 2-phenyl-1H-indole was obtained in 69% yield.
[c]No reaction observed as monitored by $^1$H NMR spectroscopy.
[d]Average of two runs.

When the aminoboronic ester 2a (Table 1, entry 1), derived from primary aniline 1a, was treated with IPrAuTFA catalyse[40] and heated at 50° C., the desired 3-borylated indole 3 was not obtained. Instead, only 2-phenyl-1H-indole was isolated in 69% yield, suggesting that protodeborylation occurs in the presence of an N—H bond. To circumvent this problem, secondary anilines 1 b-1d (entries 2-6) were examined for aminoboration. Gratifyingly, the use of N-benzyl substituent provided the first aminoboration reactivity in 55% yield (entry 3), but high temperatures of 110° C. were required. Examination of N-sulfonyl substituents, tosyl (entry 4 and 5) and 4-methoxybenzenesulfonyl (Mbs, entry 6), showed that the reaction can be accomplished at the lower temperature of 80° C. The moderate yields obtained under the conditions of initial reaction development are attributed to the degradation of catecholborane (HBcat) into $B_2cat_3$ via catechol ligand redistribution,[41] observed by a signal at δ 23.1 ppm in the $^{11}B$ spectrum, as well as unreacted 1 remaining from the first aminolysis step with HBcat.

Switching to aminolysis of commercially available B-chlorocatecholborane (ClBcat) by 2-alkynlaniline 1 provided a solution for easily assembling the requisite B—N bond at room temperature within an hour using triethylamine as a base to trap the released HCl byproduct (eq 1).[42,43] In situ formed 2 does not undergo cyclization in the absence of the IPrAuTFA catalyst; for example, substrate 2d remains unreacted with the B—N bond intact when heated to 110° C. in $d_8$-toluene for 20 h in the absence of a catalyst.

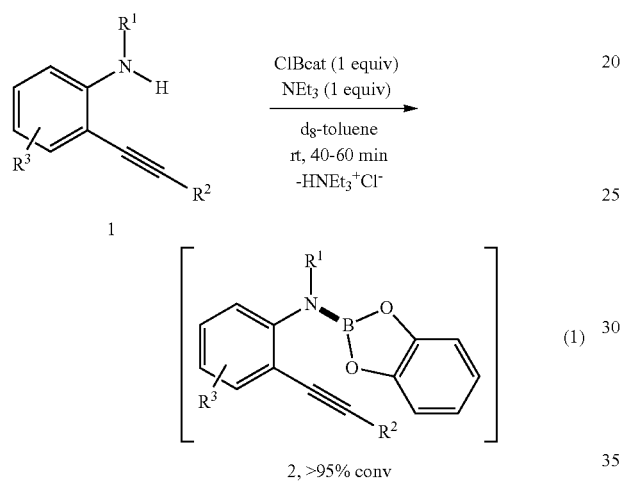

Our aminoboration strategy allows access to 3-borylated indoles with complementary regiochemistry and with functional groups that are incompatible with conventional routes or recent synthetic efforts (Chart 1). Alternative iridium-catalyzed C—H activation routes are regioselective for borylation at the 2-[44] or 7-positions[45,46] of indoles. Traditional metal-halogen exchange/borylation strategy[47] of aryl halides with magnesium or o-lithiation/borylation[48] of arenes with organolithium reagents are unable to tolerate aryl bromides, nitriles, esters, and other metalation-sensitive heterocycles. Palladium-catalyzed Miyaura borylation[49] of aryl halides or borylative cyclization[50] of 2-alkynylanilines are also incompatible for the synthesis brominated indole 3-boronic esters due to the potential oxidative addition of Pd into Ar—Br bond.

Chart 1, Example 5. Aminoboration Scope of 3-Borylated Indoles[a] with Functional Groups Incompatible with Competing Metalation or Pd(0)-Catalyzed Technologies Shown in Blue

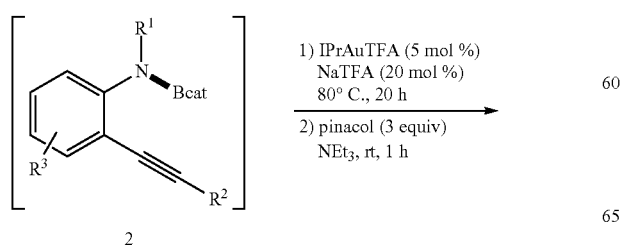

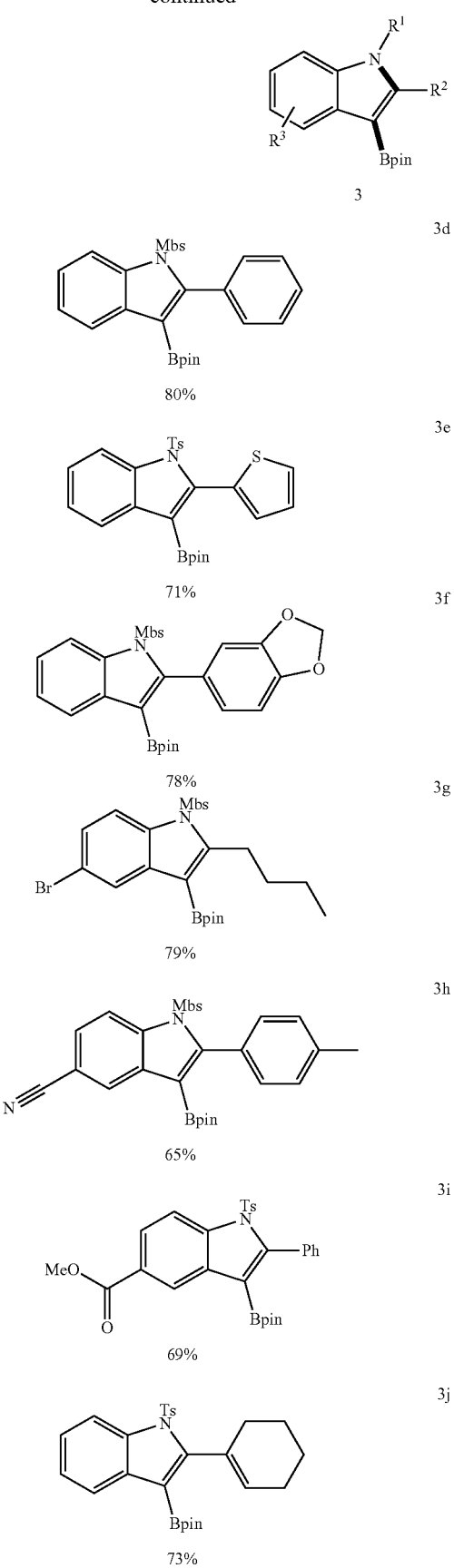

-continued

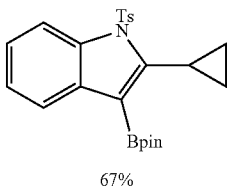

67%

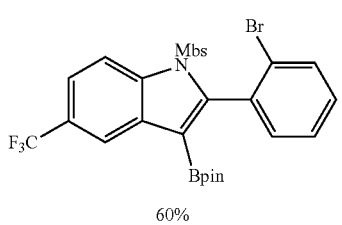

60%

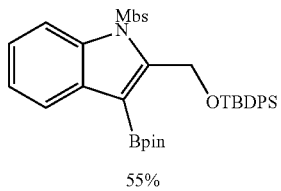

55%

[a]Isolated yield of the Bpin product. [b]110° c.

The aminoboration reaction is compatible with a variety of these potentially sensitive functional groups. Compounds with these functional groups are shown in blue in Chart 1. Pharmaceutically relevant thiophenes (3e), aryl bromides (3g and 3l), nitriles (3h), esters (3i) are tolerated by this method, as are alkenes (3j) and silyl-protected alcohols (3m). For bulkier substituents at $R^2$, o-substituted aryl (3l) and OTBDPS (3m), increased temperatures of 110° C. were required to induce the cyclization. Pharmaceutically relevant[51] 1,3-benzodioxoles (3f) also can be tolerated in this transformation.

Due to the challenge of achieving the required functional group tolerance with alternative metalation and palladium (0)-catalyzed methods, borylated bromoindoles previously were made via routes with highly toxic mercury acetate.[38,52] For example, in the total synthesis of dragmacidin D by Stoltz and coworkers, a tosylated bromoindole was borylated at the 3-position using mercuration with $Hg(OAc)_2$ followed by Hg/B exchange with $BH_3$.[52] Recent industrial pharmaceutical leads have also been synthesized by mercuration routes in order generate these borylated bromoindoles.[38] In contrast, the functional group tolerance of the aminoboration method provides a mercury-free route to the synthesis of borylated bromoindoles (e.g., 3g).

Scheme 5A, Example 5. Mercury-Free Synthesis of 3-Borylated Bromoindole 3g On 1 Gram Scale and Characterization by X-Ray Crystallography

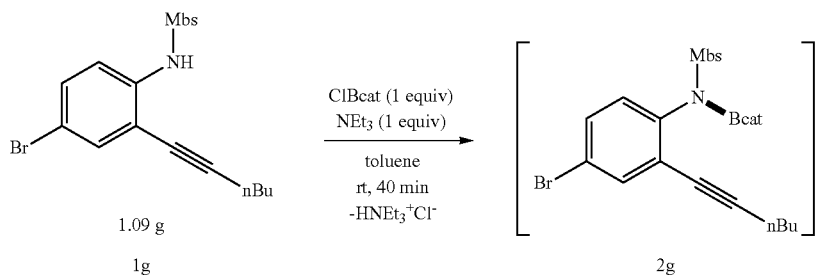

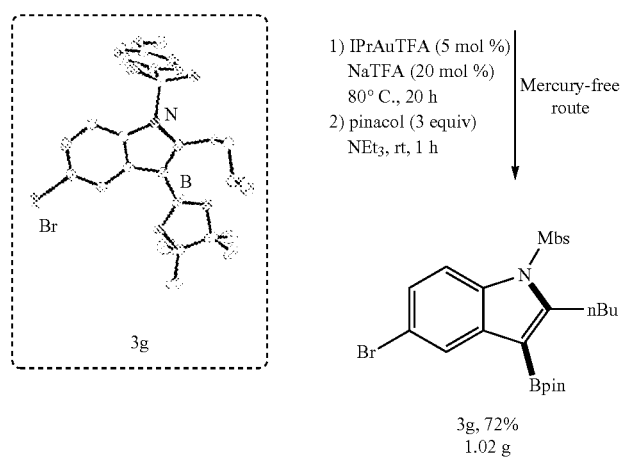

The aminoboration reaction of 2-alkynylanilines can be easily run on the gram scale (Scheme 5A, Example 5). The scalability of this halide-tolerant aminoboration transformation demonstrates its synthetic utility and allows for generation of quantities suitable for multistep synthesis for downstream manipulation of the C—Br and C—B bonds in cross-coupling reactions.[3,4] The solid-state molecular structure of 3g, obtained from single-crystal X-ray diffraction analysis, verifies the structure of the aminoborylated product arising from anti 1,2-addition of B—N bond across alkynes.

The employment of bromine-containing 3-borylated indole 3g in sequential Suzuki cross-coupling reactions highlights this downstream synthetic utility (Scheme 5B, Example 5). The C—B bond of 3g accesses a selective cross-coupling with an aryl iodide at room temperature to generate a new C—C bond,[52] while maintaining the C—Br bond intact, to afford functionalized indole 4. The Ar—Br bond of 4 is available for a second cross-coupling with organoboronic acid derivatives, and here we further demonstrate the synthetic utility of 3-borylated indole 3d as a building block for C—C bond formation to construct biindole 5. Biindole scaffolds have reported biological activities,[53-55] and this aminoboration facilitates access to such structures.

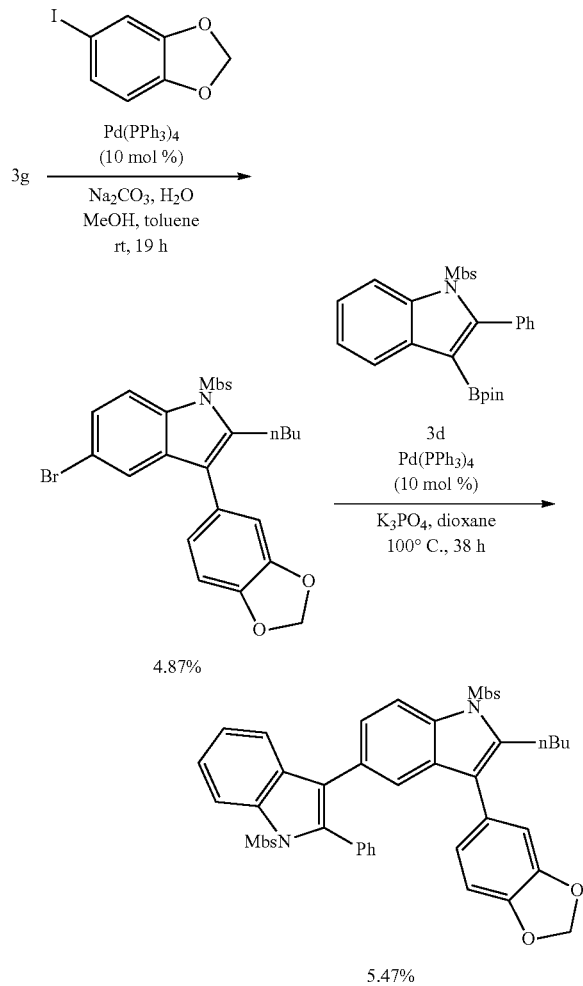

Scheme 5B, Example 5. Synthetic Versatility of Aminoboration Products

The synthetic utility of aminoboration is not limited to indole scaffolds and has potential for applications in the synthesis of other N-heterocyclic organoboron compounds (Scheme 5C, Example 5). When a simple amine 6, prepared from commercially available homopropargyl amine, is subjected to standard aminoboration conditions, 3-borylated dihydropyrrole 8a can be synthesized. The protodeborylated product 8b is the major byproduct, possibly due to a source of an acidic proton from the terminal alkyne of 7. This preliminary result demonstrates that a rigid backbone to aid cyclization and a gain of product aromaticity are not absolute requirements for the aminoboration reactivity.

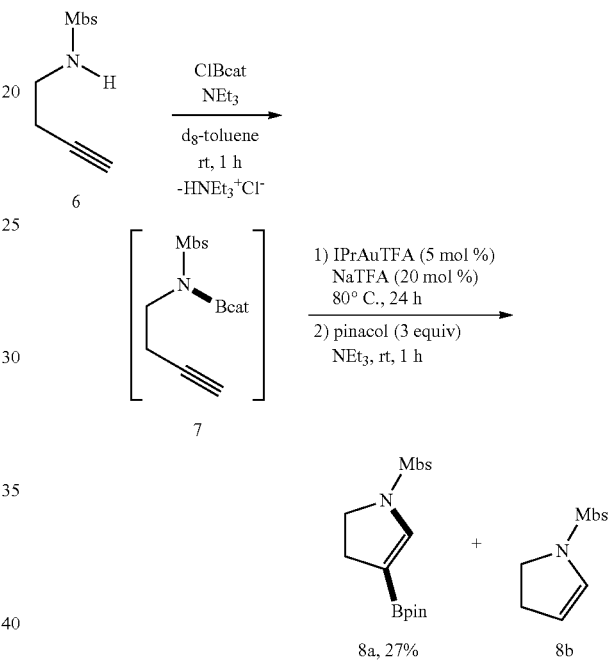

Scheme 5C, Example 5. Syntheis of 3-Borylated Dihydropyrrole

Numerous examples of Lewis acidic gold-mediated cyclization of 2-alkynylanilines exist for the synthesis of indole derivatives,[56] but not for the installation of boron on the indole backbone for downstream reactivity. Based on the known carbophilicity of gold[56,57] and our previous report on bifunctional catalysis on alkoxyboration of alkynes involving B—O bond activation,[58] we propose the catalytic cycle shown in Scheme 5D, Example 5. The potentially bifunctional Lewis acidic/basic catalyst IPrAuTFA and substrate 2d associate to generate intermediate 9 containing a tetracoordinate borate. Simultaneous B—N bond activation and cyclization of 9 releases organogold intermediate 10 and B-(trifluoroacetyl)catecholborane. The presence of proposed intermediates is supported by the detection of neutral organogold 10 in the reaction mixture by HRMS prior to completion of the reaction. Next, organogold species 10 and B-(trifluoroacetyl)catecholborane undergo Au-to-B transmetalation[59] to furnish the 3-borylated indole product 3d-Bcat and regenerate the IPrAuTFA catalyst. This reaction manifold is mechanistically distinct from the previous metal-catalyzed boron-element bond addition routes that proceed through metal-mediated breaking of the B-element bond through oxidative addition or σ bond metathesis.

Scheme 5D, Example 5. Postulated Mechanism of Aminoboration

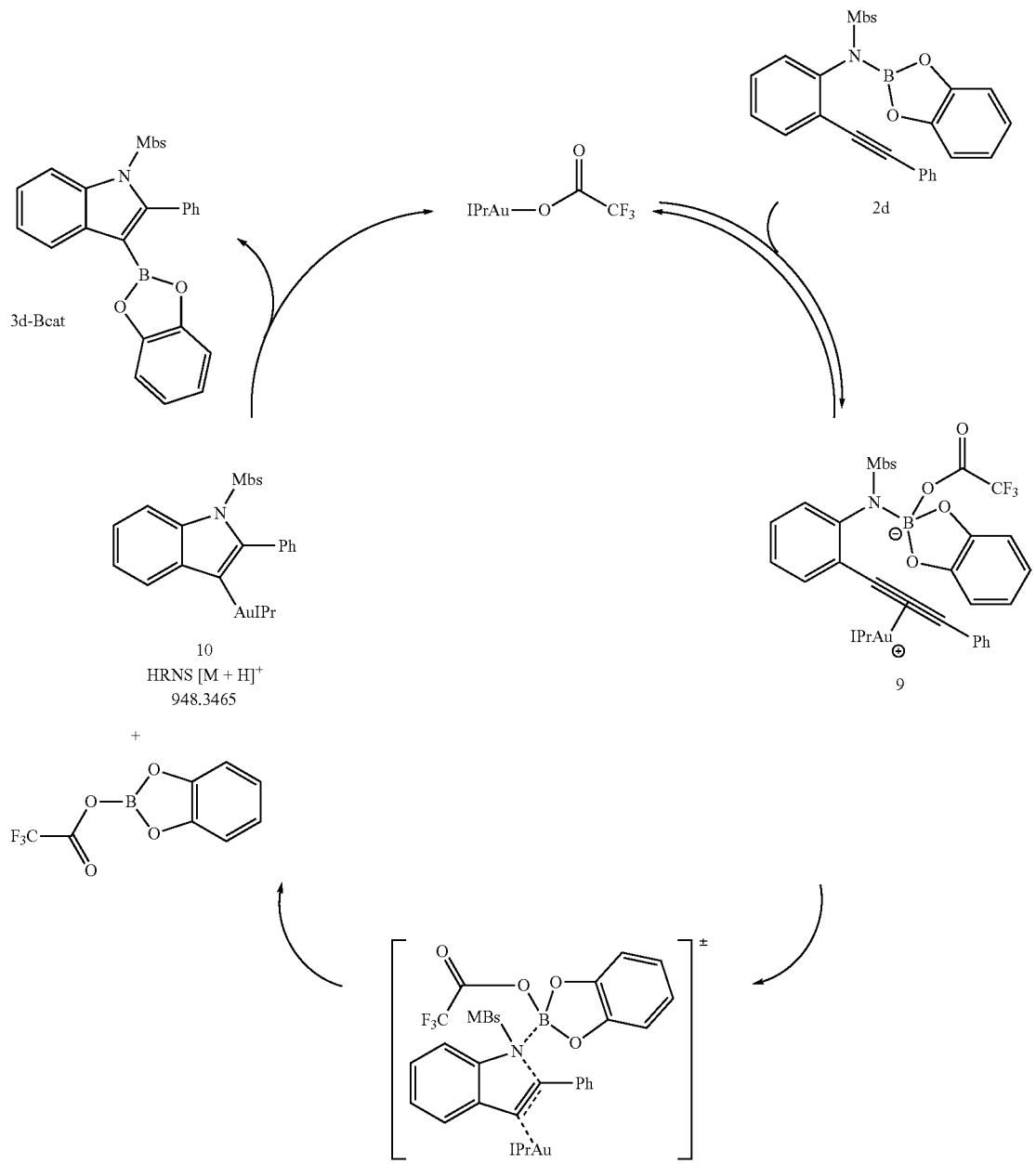

This reaction displays a notable dependence on the presence of the sodium trifluoroacetate additive. Optimal conditions occurred with 5 mol % IPrAuTFA catalyst and 20 mol % sodium trifluoroacetate additive (using eq 1, in Chart 1) and not simply with the IPrAuTFA catalyst alone (in Table 1). No reaction occurred when aminoboronic ester 2, generated from the route (eq 1) using ClBcat and $NEt_3$, was heated to 110° C. in $d_8$-toluene for 20 h using 2.5 mol % IPrAuTFA catalyst in the absence of added sodium trifluoroacetate. The added sodium trifluoroacetate may overcome catalyst inhibition from trace $HNEt_3Cl$ leftover during the preparation of 2 via the optimized chlorocatecholborate route.[60]

In summary, we have developed the first catalytic aminoboration reaction that adds B—N σ bonds across C—C π bonds. We have shown that the easily generated but rather unreactive B—N σ bond can be used for this addition reaction, thereby providing a new bond disconnection strategy for the efficient construction of indole building blocks for potential applications in drug discovery. The use of carbophilic gold catalyst and mildly basic trifluoroacetate provides tolerance of functional groups that are either incompatible with or difficult to access using existing methods. Ongoing work focuses on the development aminoboration reactivity for the synthesis other compound classes.

REFERENCES FOR EXAMPLE 5

(1) Hurd, D. T. *J. Am. Chem. Soc.* 1948, 70, 2053.
(2) Brown, H. C.; Rao, B. C. S. *J. Am. Chem. Soc.* 1956, 78, 5694.

(3) Miyaura, N.; Suzuki, A. *Chem. Rev.* 1995, 95, 2457.
(4) Qiao, J. X.; Lam, P. Y. S. *Synthesis* 2011, 829.
(5) Männig, D.; Nöth, H. *Angew. Chem., Int. Ed. Engl.* 1985, 24, 878.
(6) Crudden, C. M.; Edwards, D. *Eur. J. Org. Chem.* 2003, 4695.
(7) Carrol, A. M.; O'Sullivan, T. P.; Guiry, P. J. *Adv. Synth. Catal.* 2005, 347, 609.
(8) Miyaura, N. Hydroboration, Diboration, Silylboration, and Stannylboration. In *Catalytic Heterofunctionalization*; Togni, A.; Grützmacher, H., Eds.; Wiley-VCH: Weinheim, Germany, 2001; pp 1-45.
(9) Ishiyama, T.; Matsuda, N.; Miyaura, N.; Suzuki, A. *J. Am. Chem. Soc.* 1993, 115, 11018.
(10) Marder, T. B.; Norman, N. C. *Top. Catal.* 1998, 5, 63.
(11) Suginome, M.; Yamamoto, A.; Murakami, M. *J. Am. Chem. Soc.* 2003, 125, 6358.
(12) Suginome, M.; Shirakura, M.; Yamamoto, A. *J. Am. Chem. Soc.* 2009, 128, 14438.
(13) Suginome, M. *Chem. Rec.* 2010, 10, 348.
(14) Suginome, M.; Nakamura, H.; Ito, Y. *Chem. Commun.* 1996, 2777.
(15) Suginome, M.; Nakamura, H.; Ito, Y. *Angew. Chem., Int. Ed. Engl.* 1997, 36, 2516.
(16) Onozawa, S.; Hatanaka, Y.; Sakakura, T.; Shimada, S.; Tanaka, M. *Organometallics* 1996, 15, 5450.
(17) Ishiyama, T.; Nishijima, K.; Miyaura, N.; Suzuki, A. *J. Am. Chem. Soc.* 1993, 115, 7219.
(18) Lappert, M. F.; Prokai, B. *J. Organomet. Chem.* 1964, 1, 384.
(19) Hara, S.; Dojo, H.; Takinami, S.; Suzuki, A. *Tetrahedron Lett.* 1983, 24, 731.
(20) Semba, K.; Fujihara, T.; Terao, J.; Tsuji, Y. *Chem.—Eur. J.* 2012, 18, 4179.
(21) Bakus, R. C.; Atwood, D. A. Boron-Nitrogen Compounds. In *Encyclopedia of Inorganic Chemistry*; John Wiley & Sons, Ltd: 2006.
(22) Manning, M. J.; Griffin, T. S. Boron-Nitrogen Compounds, Organic. In *Kirk-Othmer Encyclopedia of Chemical Technology*; John Wiley & Sons, Inc.: 2000.
(23) Cragg, R. H.; Lappert, M. F.; Tilley, B. P. *J. Chem. Soc.* 1964, 2108.
(24) Cragg, R. H.; Miller, T. J. *J. Organomet. Chem.* 1983, 255, 143.
(25) Singaram, B. *Heteroat. Chem.* 1992, 3, 245.
(26) Jefferson, R.; Lappert, M. F.; Prokai, B.; Tilley, B. P. *J. Chem. Soc. A* 1966, 1584.
(27) Schreyer, P.; Paetzold, P.; Boese, R. *Chem. Ber.* 1988, 121, 195.
(28) Matsuda, N.; Hirano, K.; Satoh, T.; Miura, M. *J. Am. Chem. Soc.* 2013, 135, 4934.
(29) Hirano, K.; Miura, M. *Pure Appl. Chem.* 2014, 86, 291.
(30) Sakae, R.; Matsuda, N.; Hirano, K.; Satoh, T.; Miura, M. *Org. Lett.* 2014, 16, 1228.
(31) Sakae, R.; Hirano, K.; Satoh, T.; Miura, M. *Angew. Chem., Int. Ed.* 2015, 54, 613.
(32) Sakae, R.; Hirano, K.; Miura, M. *J. Am. Chem. Soc.* 2015, 137, 6460.
(33) Daley, E. N.; Vogels, C. M.; Geier, S. J.; Decken, A.; Doherty, S.; Westcott, S. A. *Angew. Chem., Int. Ed.* 2015, 54, 2121.
(34) Horton, D. A.; Bourne, G. T.; Smythe, M. L. *Chem. Rev.* 2003, 103, 893.
(35) Welsch, M. E.; Snyder, S. A.; Stockwell, B. R. *Curr. Opin. Chem. Biol.* 2010, 14, 347.
(36) Bandini, M.; Eichholzer, A. *Angew. Chem., Int. Ed.* 2009, 48, 9608.
(37) Zhang, M.-Z.; Chen, Q.; Yang, G.-F. *Eur. J. Med. Chem.* 2015, 89, 421.
(38) Tabart, M. Indolyldihydroimidazopyrimidinone Derivatives, Preparation Thereof and Therapeutic Use Thereof. International Patent PCT/EP2013/070581, Apr. 10, 2014.
(39) Wynberg, N. A.; Leger, L. J.; Conrad, M. L.; Vogels, C. M.; Decken, A.; Duffy, S. J.; Westcott, S. A. *Can. J. Chem.* 2005, 83, 661.
(40) IPrAuTFA was prepared from the salt metathesis reaction of commercially available IPrAuCl and AgTFA.
(41) Westcott, S. A.; Blom, H. P.; Marder, T. B.; Baker, R. T.; Calabrese, J. C. *Inorg. Chem.* 1993, 32, 2175.
(42) Gerrard, W.; Lappert, M. F.; Mountfield, B. A. *J. Chem. Soc.* 1959, 1529.
(43) Lappert, M. F.; Majumdar, M. K.; Tilley, B. P. *J. Chem. Soc. A* 1966, 1590.
(44) Robbins, D. W.; Hartwig, J. F. *Org. Lett.* 2012, 14, 4266.
(45) Paul, S.; Chotana, G. A.; Holmes, D.; Reichle, R. C.; Maleczka, R. E.; Smith, M. R. *J. Am. Chem. Soc.* 2006, 128, 15552.
(46) Robbins, D. W.; Boebel, T. A.; Hartwig, J. F. *J. Am. Chem. Soc.* 2010, 132, 4068.
(47) Wong, K.-T.; Chien, Y.-Y.; Liao, Y.-L.; Lin, C.-C.; Chou, M.-Y.; Leung, M.-K. *J. Org. Chem.* 2002, 67, 1041.
(48) Sharp, M. J.; Cheng, W.; Snieckus, V. *Tetrahedron Lett.* 1987, 28, 5093.
(49) Ishiyama, T.; Murata, M.; Miyaura, N. *J. Org. Chem.* 1995, 60, 7508.
(50) Huang, J.; Macdonald, S. J. F.; Harrity, J. P. A. *Chem. Commun.* 2010, 46, 8770.
(51) Murray, M. *Curr. Drug Metab.* 2000, 1, 67.
(52) Garg, N. K.; Sarpong, R.; Stoltz, B. M. *J. Am. Chem. Soc.* 2002, 124, 13179.
(53) Hu, B. Substituted Sulfonamide-Indoles. U.S. Pat. No. 7,442,805 B2, Oct. 28, 2008.
(54) Hiroyuki, W.; Osamu, K.; Naoki, T.; Takashi, Y.; Keisuke, H. Indole Compound and Application Thereof. Patent JP 2004149429 A, May 27, 2004.
(55) Gangloff, A. R.; Nowakowski, J.; Paraselli, B. R.; Stafford, J. A.; Tennant, M. G. Kinase Inhibitors. International Patent PCT/US2004/042631, Jul. 7, 2005.
(56) Abbiati, G.; Marinelli, F.; Rossi, E.; Arcadi, A. *Isr. J. Chem.* 2013, 53, 856.
(57) Fürstner, A.; Davies, P. W. *Angew. Chem., Int. Ed.* 2007, 46, 3410.
(58) Hirner, J. J.; Faizi, D. J.; Blum, S. A. *J. Am. Chem. Soc.* 2014, 136, 4740.
(59) Hirner, J. J.; Blum, S. A. *Tetrahedron* 2015, 71, 4445.
(60) Presumably trace chloride ions can compete with trifluoroacetate anion for binding to boron and/or gold.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A composition, comprising: a compound having a structure selected from the group consisting of:

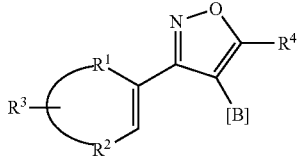

26

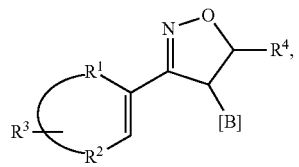

27

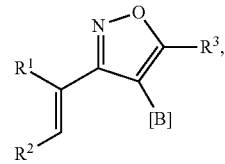

28

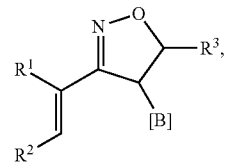

29

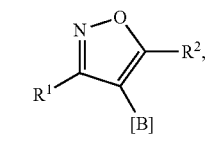

30

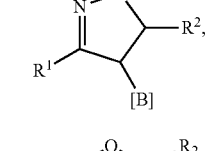

31

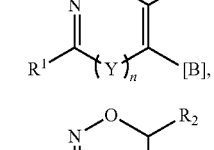

32

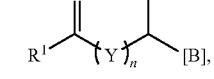

33

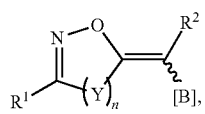

34

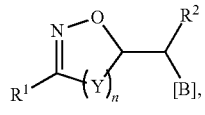

35

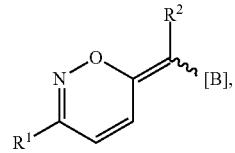

36

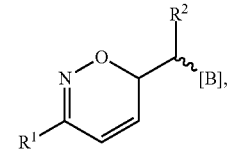

37

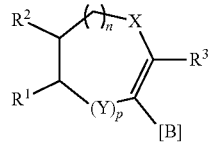

38

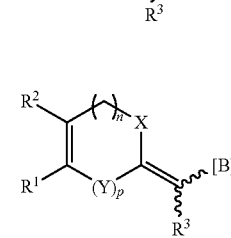

39

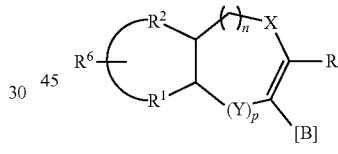

40

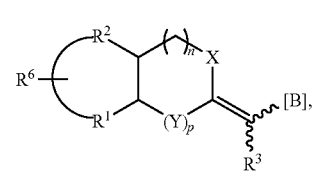

40

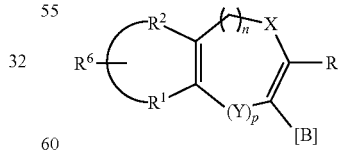

41

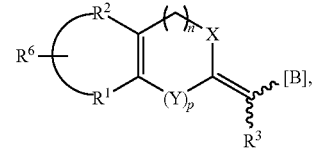

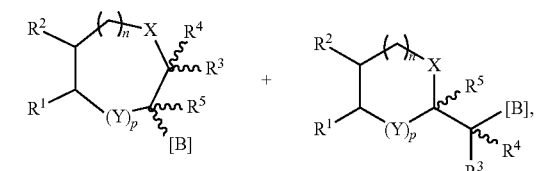
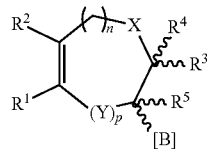
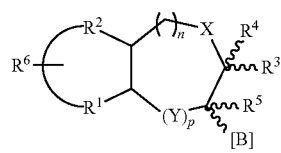
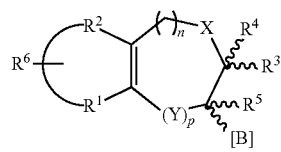
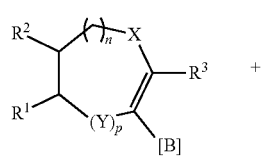
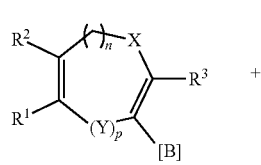
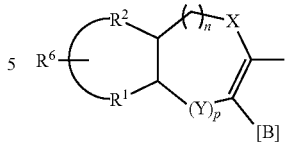
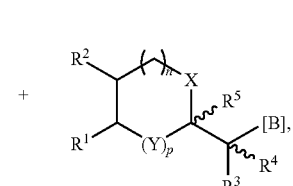
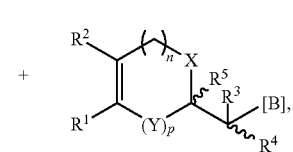
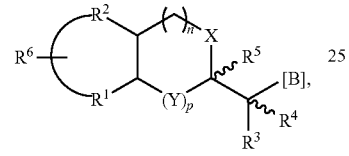
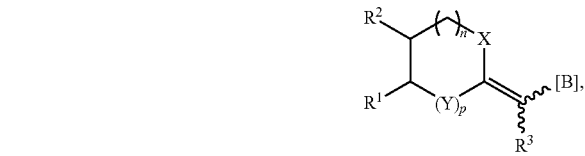
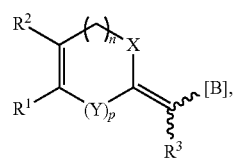

-continued

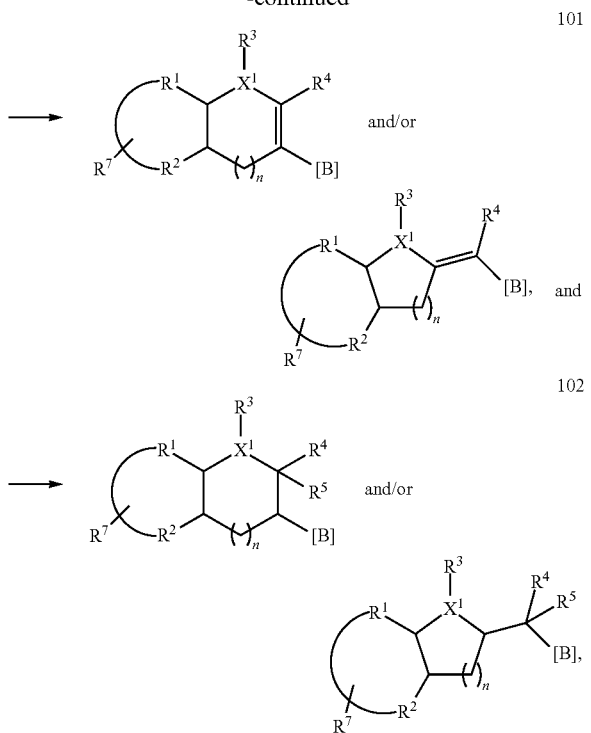

wherein [B] is $BX^2_{(1\ or\ 2)}$, where $X^2$ can independently selected from: catecholate, pinacolate, ethylene glycolate, 1,3-propanediolate, N-methyliminodiacetate, 2,2'-zanediyldiethanolate, fluoride, chloride, bromide, hydrogen, hydroxide, acetate, 9-Borabicyclo [3.3.1] nonane (9-BBN), diisopinocampheyl (Ipc), or 1,8-diaminonaphthalene, each of which can be substituted or unsubstituted;

wherein Y is selected from the group consisting of: $CH_2$, CRH, $CR_2$, NR, O, S, PR or $SiR_2$, where R is selected from the group consisting of H, a carbonyl functional group (substituted or unsubstituted), a carboxy functional group (substituted or unsubstituted), a carbocycle group (substituted or unsubstituted), a heterocycle (substituted or unsubstituted), a halide, or an alkyl group (substituted or unsubstituted);

wherein each of R, $R^1$, $R^2$, $R^3$, $R^4$, $R^5$, $R^6$, $R^7$, and $R^8$ is independently selected from: H, a carbonyl functional group (substituted or unsubstituted), a carbocycle group (substituted or unsubstituted), a heterocycle (substituted or unsubstituted), a halide, an alkyl group (cyclic or acyclic; substituted or unsubstituted), an alkenyl group (cyclic or acyclic; substituted or unsubstituted),$CF_3$, CN, $NO_2$, an aryl group (substituted or unsubstituted), a heteroaryl group (substituted or unsubstituted), a sulfonyl group, a boryl group, an ether group, a thioether group, a silyl group, an ester group, an amide group, an alkoxy group, a thiol group, an alcohol group, or an amine group;

wherein a "curved line" between R groups represents a carbon chain or a hetero carbon chain;

wherein X in all instances other than in compounds 38-41 are selected from the group consisting of: O, S, or —C(O)O—, and in compounds 38-41 X is S or —C(O)O—;

wherein Y is selected from the group consisting of: NR, O, S, or $CR^7R^8$; and wherein $X^1$ is selected from the group consisting of: O, NR, S, or $CR^1R^2$, where each of R, $R^1$, $R^2$ for $X^1$ is independently selected from: H, a carbonyl functional group, a carboxy group, a carbocycle group, a heterocycle, a halide, or an alkyl group, each of which is optionally substituted or unsubstituted.

2. A method of making an organoboron compound, comprising a reaction described by one of the following schemes:

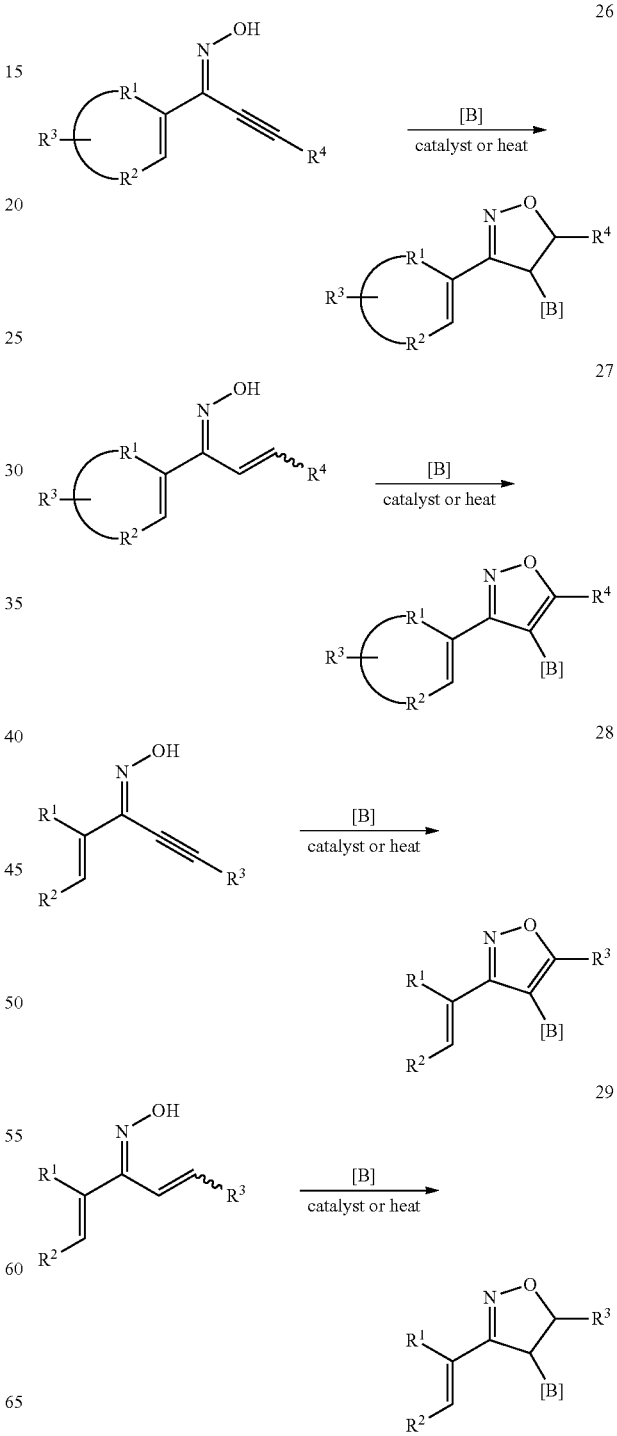

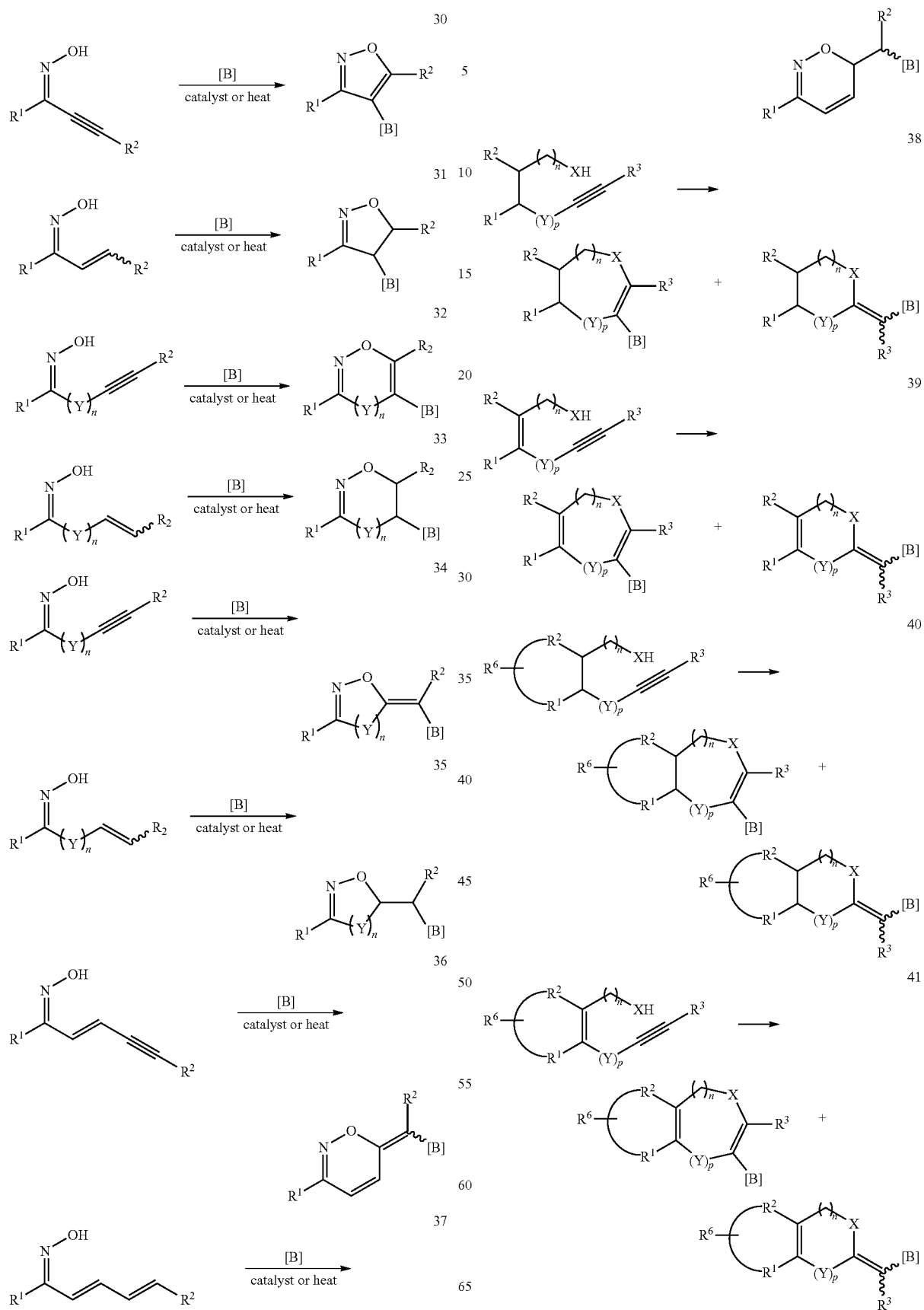

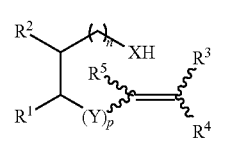
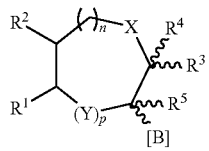
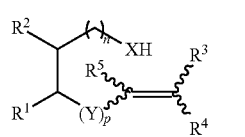
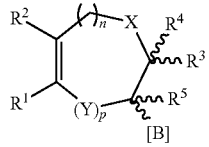
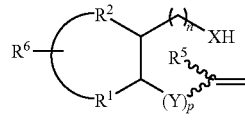
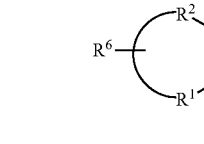
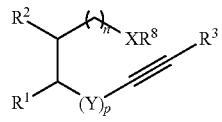
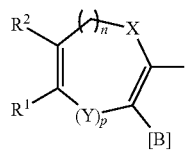
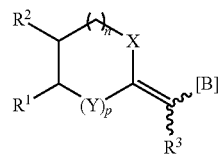
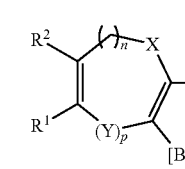
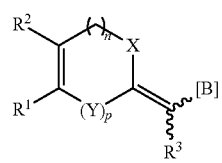
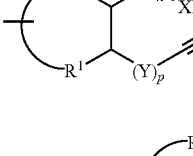
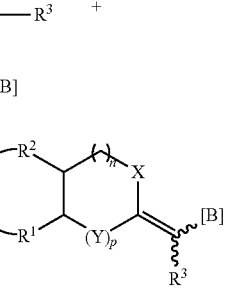
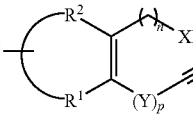
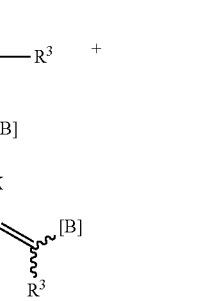
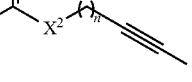

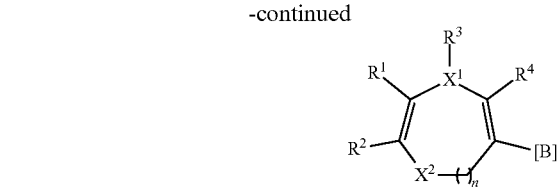
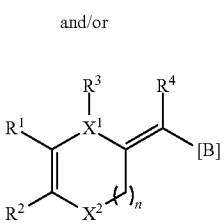
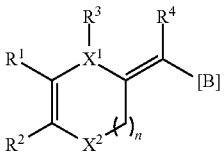
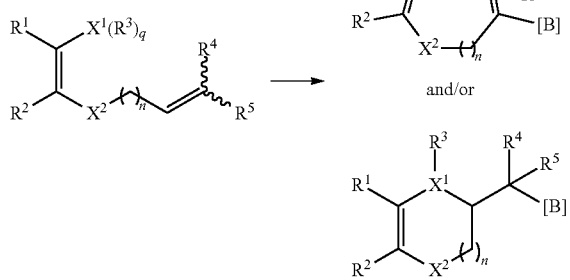
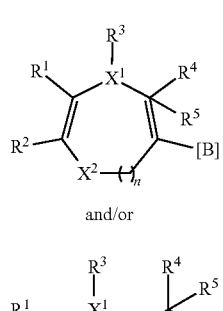
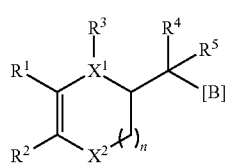
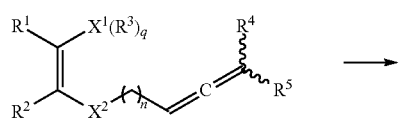
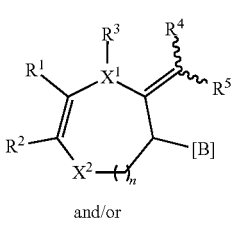
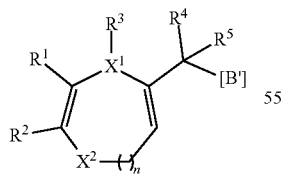
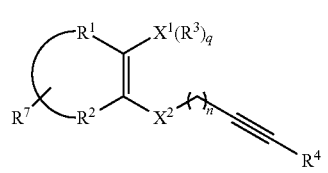
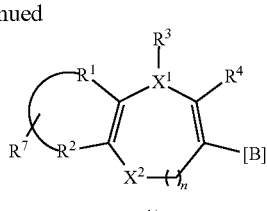
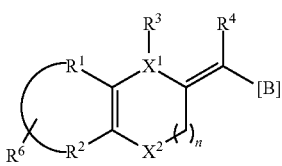
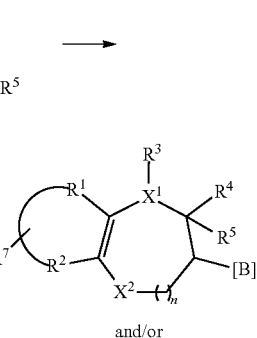
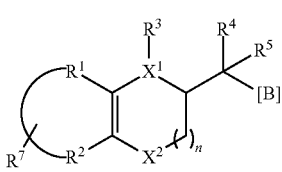
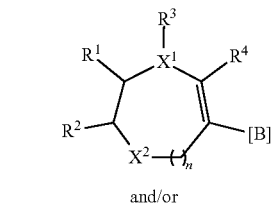
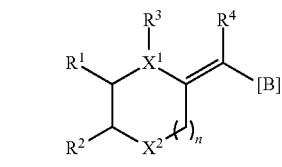

107
-continued
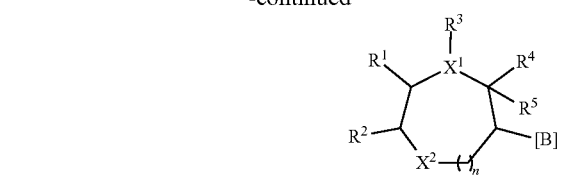
and/or
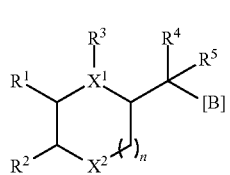
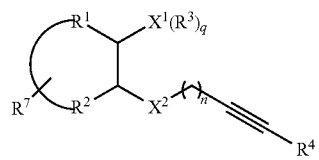
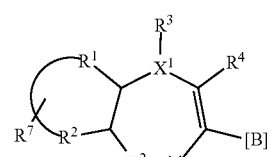
and/or
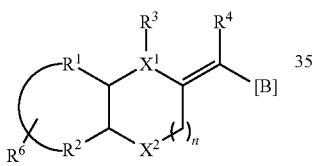
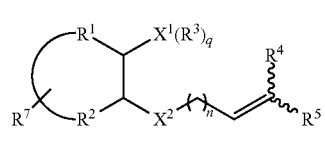
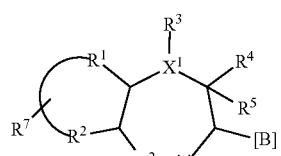
and/or
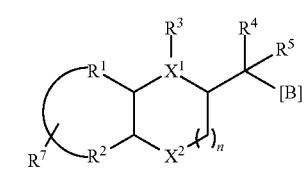
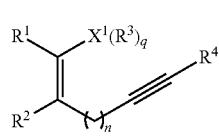
108
-continued
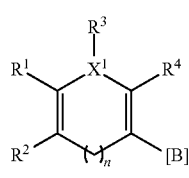
and/or
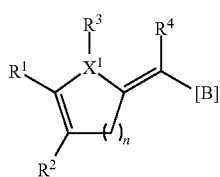
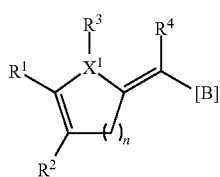
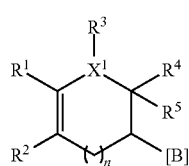
and/or
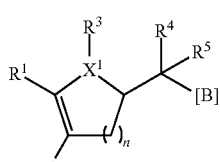
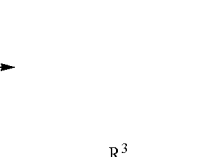
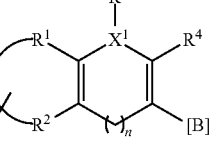
and/or
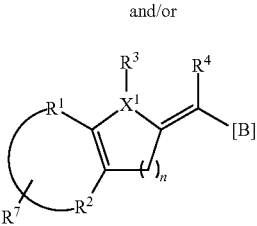

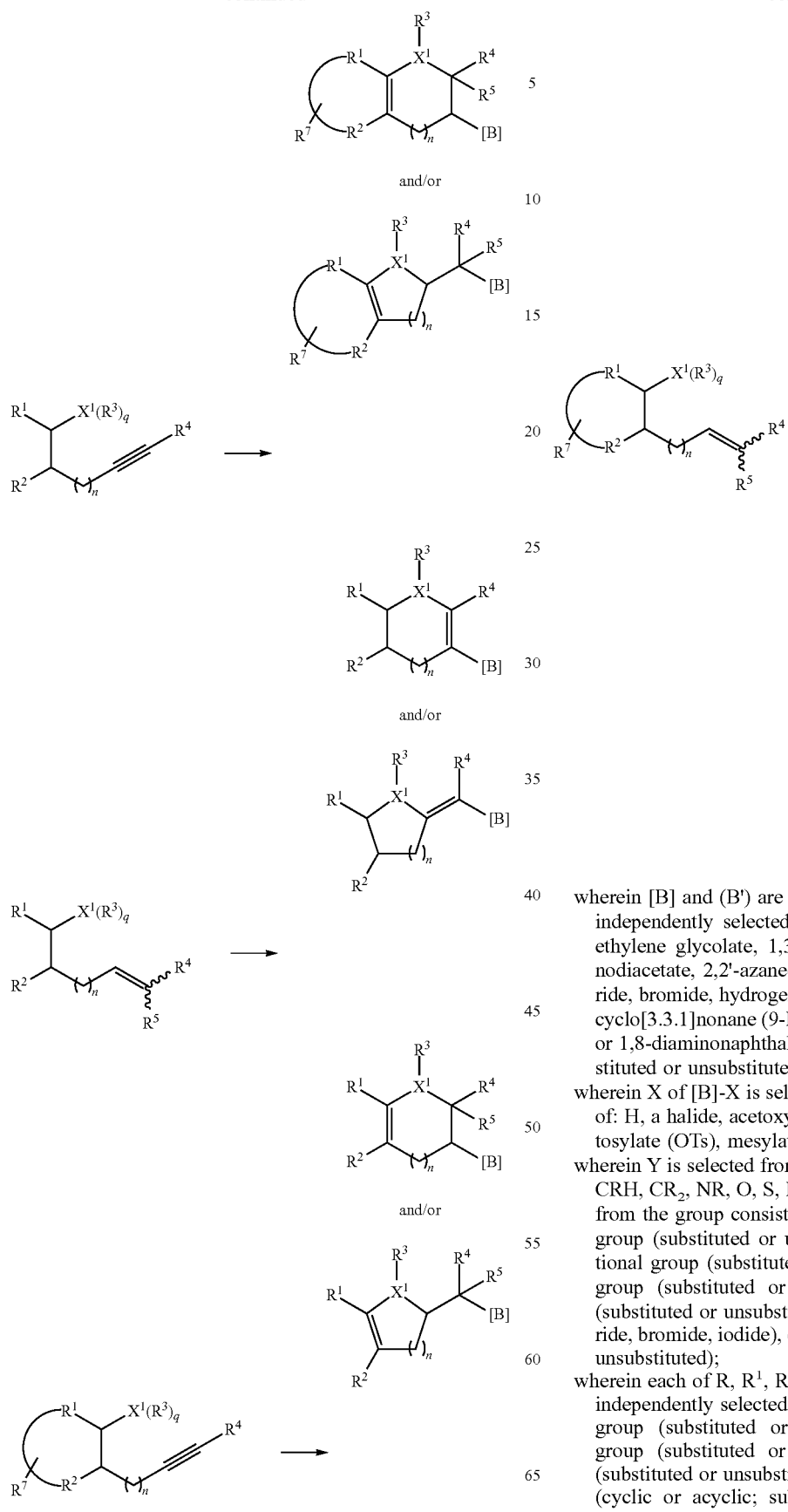

wherein [B] and (B') are each $BX^2_{(1\ or\ 2)}$, where $X^2$ can independently selected from: catecholate, pinacolate, ethylene glycolate, 1,3-propanediolate, N-methyliminodiacetate, 2,2'-azanediyldiethanolate, fluoride, chloride, bromide, hydrogen, hydroxide, acetate, 9-Borabicyclo[3.3.1]nonane (9-BBN), diisopinocampheyl (Ipc), or 1,8-diaminonaphthalene, each of which can be substituted or unsubstituted;

wherein X of [B]-X is selected from the group consisting of: H, a halide, acetoxy (OAc), trifluoroacetate (TFA), tosylate (OTs), mesylate (OMs), or triflate (OTf);

wherein Y is selected from the group consisting of: $CH_2$, CRH, $CR_2$, NR, O, S, PR or $SiR_2$, where R is selected from the group consisting of H, a carbonyl functional group (substituted or unsubstituted), a carboxy functional group (substituted or substituted), a carbocycle group (substituted or unsubstituted), a heterocycle (substituted or unsubstituted), a halide (fluoride, chloride, bromide, iodide), or an alkyl group (substituted or unsubstituted);

wherein each of R, $R^1$, $R^2$, $R^3$, $R^4$, $R^5$, $R^6$, $R^7$, and $R^8$ is independently selected from: H, a carbonyl functional group (substituted or unsubstituted), a carbocycle group (substituted or unsubstituted), a heterocycle (substituted or unsubstituted), a halide, an alkyl group (cyclic or acyclic; substituted or unsubstituted), an alkenyl group (cyclic or acyclic; substituted or unsubstituted),$CF_3$, CN, $NO_2$, an aryl group (substituted or unsubstituted), a heteroaryl group (substituted or unsubstituted), a sulfonyl group, a boryl group, an ether group, a thioether group, a silyl group, an ester group, an amide group, an alkoxy group, a thiol group, an alcohol group, or an amine group;

wherein a "curved line" between R groups represents a carbon chain or a hetero carbon chain;

wherein X in all instances other than in schemes 38-41 are selected from the group consisting of: O, S, or —C(O)O—, and in schemes 38-41 X is S or —C(O)O—;

wherein Y is selected from the group consisting of: NR, O, S, or $CR^7R^8$; and wherein $X^1$ is selected from the group consisting of: O, NR, S, or $CR^1R^2$, where each of R, $R^1$, $R^2$ for $X^1$ is independently selected from: H, a carbonyl functional group, a carboxy functional group, a carbocycle group, a heterocycle, a halide, or an alkyl group, each of which is optionally substituted or unsubstituted, wherein the reagent in each Scheme is reacted with a salt of $BX^2$ to form the organoboron compound(s) shown in each Scheme.

* * * * *